(12) United States Patent
Cherney

(10) Patent No.: US 7,776,884 B2
(45) Date of Patent: Aug. 17, 2010

(54) CYCLIC DERIVATIVES AS MODULATORS OF CHEMOKINE RECEPTORS ACTIVITY

(75) Inventor: Robert J. Cherney, Newark, DE (US)

(73) Assignee: Bristol-Myers Squibb Company, Princeton, NJ (US)

(*) Notice: Subject to any disclaimer, the term of this patent is extended or adjusted under 35 U.S.C. 154(b) by 1225 days.

(21) Appl. No.: 11/351,415

(22) Filed: Feb. 10, 2006

(65) Prior Publication Data

US 2006/0135503 A1 Jun. 22, 2006

Related U.S. Application Data

(62) Division of application No. 10/383,391, filed on Mar. 7, 2003, now Pat. No. 7,087,604.

(60) Provisional application No. 60/362,604, filed on Mar. 8, 2002.

(51) Int. Cl.
- A61K 31/4525 (2006.01)
- A61K 31/4535 (2006.01)
- C07D 211/32 (2006.01)
- C07D 401/12 (2006.01)
- C07D 405/12 (2006.01)

(52) U.S. Cl. ............ 514/315; 546/192; 546/201; 546/213; 546/214; 546/228; 546/245; 514/323; 514/326

(58) Field of Classification Search ............ 546/192, 546/201, 213, 214, 228, 245; 514/317, 315, 514/326, 323
See application file for complete search history.

(56) References Cited

U.S. PATENT DOCUMENTS

| | | | |
|---|---|---|---|
| 4,240,957 | A | 12/1980 | Hirai et al. |
| 6,706,712 | B2 | 3/2004 | Cherney |
| 2003/0060459 | A1 | 3/2003 | Carter et al. |
| 2004/0110736 | A1 | 6/2004 | Cherney |
| 2004/0186140 | A1 | 9/2004 | Cherney et al. |
| 2004/0186143 | A1 | 9/2004 | Carter et al. |
| 2004/0235835 | A1 | 11/2004 | Carter |
| 2004/0235836 | A1 | 11/2004 | Cherney |
| 2005/0043392 | A1 | 2/2005 | Carter |
| 2005/0054626 | A1 | 3/2005 | Carter et al. |
| 2005/0054627 | A1 | 3/2005 | Carter et al. |
| 2005/0065147 | A1 | 3/2005 | Carter et al. |

FOREIGN PATENT DOCUMENTS

| | | |
|---|---|---|
| DE | 4302051 | 1/1993 |
| DE | 4326344 | 8/1993 |
| EP | 0490450 | 12/1991 |
| EP | 0672656 | 3/1995 |
| EP | 0529737 | 10/1997 |
| WO | WO 93/09135 | 5/1993 |
| WO | WO 94/13695 | 6/1994 |
| WO | WO 94/20062 | 9/1994 |
| WO | WO 96/09297 | 3/1996 |
| WO | WO 96/09836 | 4/1996 |
| WO | WO 97/22618 | 6/1997 |
| WO | WO 98/08802 | 3/1998 |
| WO | WO 99/11657 | 3/1999 |
| WO | WO 99/11658 | 3/1999 |
| WO | WO 99/25686 | 5/1999 |
| WO | WO 99/26615 | 6/1999 |
| WO | WO 99/47545 | 9/1999 |
| WO | WO 00/14097 | 3/2000 |
| WO | WO 00/39115 | 7/2000 |
| WO | WO 00/55126 | 9/2000 |
| WO | WO 00/59881 | 10/2000 |
| WO | WO 00/69815 | 11/2000 |
| WO | WO 00/69820 | 11/2000 |
| WO | WO-00/69820 | * 11/2000 |
| WO | WO 00/69855 | 11/2000 |
| WO | WO-00/69855 | * 11/2000 |
| WO | WO 01/07436 | 2/2001 |
| WO | WO 01/19816 | 3/2001 |
| WO | WO 02/50019 | 6/2002 |
| WO | WO 0250019 | 6/2002 |
| WO | WO 02/060859 | 8/2002 |
| WO | WO 02060859 | 8/2002 |
| WO | WO 02/088106 | 11/2002 |
| WO | WO 03/075853 | 9/2003 |
| WO | WO 2004071449 | 8/2004 |
| WO | WO 2004071460 | 8/2004 |
| WO | WO 2004098512 | 11/2004 |
| WO | WO 2004098516 | 11/2004 |
| WO | WO 2005020899 | 3/2005 |
| WO | WO 2005021498 | 3/2005 |
| WO | WO 2005021499 | 3/2005 |
| WO | WO 2005021500 | 3/2005 |

OTHER PUBLICATIONS

U.S. Appl. No. 11/181,436, filed Jul. 14, 2005, Cherney et al.

* cited by examiner

*Primary Examiner*—Kamal A Saeed
*Assistant Examiner*—Janet L Coppins
(74) *Attorney, Agent, or Firm*—Terence J. Bogie; Laurelee A. Duncan

(57) ABSTRACT

The present application describes modulators of MCP-1 of formula (I):

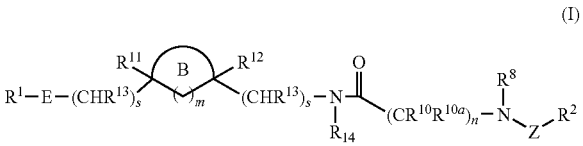

or pharmaceutically acceptable salt forms thereof, useful for the prevention of rheumatoid arthritis, multiple sclerosis, atherosclerosis, asthma, restinosis, organ transplantation, and cancer.

20 Claims, No Drawings

CYCLIC DERIVATIVES AS MODULATORS OF CHEMOKINE RECEPTORS ACTIVITY

This application is a divisional of U.S. Ser. No. 10/383,391 filed on Mar. 7, 2003 now U.S. Pat. No. 7,087,604, now allowed, which claims benefit to provisional application U.S. Ser. No. 60/362,604 filed Mar. 8, 2002.

FIELD OF THE INVENTION

This invention relates generally to modulators of chemokine receptor activity, pharmaceutical compositions containing the same, and methods of using the same as agents for treatment and prevention of inflammatory diseases, allergic and autoimmune diseases, and in particular, asthma, rheumatoid arthritis, atherosclerosis, and multiple sclerosis.

BACKGROUND OF THE INVENTION

Chemokines are chemotactic cytokines, of molecular weight 6-15 kDa, that are released by a wide variety of cells to attract and activate, among other cell types, macrophages, T and B lymphocytes, eosinophils, basophils and neutrophils (reviewed in: Luster, *New Eng. J. Med.* 1998, 338, 436-445 and Rollins, *Blood* 1997, 90, 909-928). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (−1 and −2) are chemotactic for, among other cell types, macrophages, T lymphocytes, eosinophils, dendritic cells, and basophils. There also exist the chemokines lymphotactin-1, lymphotactin-2 (both C chemokines), and fractalkine (a CXXXC chemokine) that do not fall into either of the major chemokine subfamilies.

The chemokines bind to specific cell-surface receptors belonging to the family of G-protein-coupled seven-transmembrane-domain proteins (reviewed in: Horuk, *Trends Pharm. Sci.* 1994, 15, 159-165) which are termed "chemokine receptors." On binding their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns: CCR-1 (or "CKR-1" or "CC-CKR-1") [MIP-1α, MCP-3, MCP-4, RANTES] (Ben-Barruch, et al., *Cell* 1993, 72, 415-425, and Luster, *New Eng. J. Med.* 1998, 338, 436-445); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo, et al., *Proc. Natl. Acad. Sci. USA* 1994, 91, 2752-2756, and Luster, *New Eng. J. Med.* 1998, 338, 436-445); CCR-3 (or "CKR-3" or "CC-CKR-3") [eotaxin-1, eotaxin-2, RANTES, MCP-3, MCP-4] (Combadiere, et al., *J. Biol. Chem.* 1995, 270, 16491-16494, and Luster, *New Eng. J. Med.* 1998, 338, 436-445); CCR-4 (or "CKR-4" or "CC-CKR-4") [TARC, MIP-1α, RANTES, MCP-1] (Power, et al., *J. Biol. Chem.* 1995, 270, 19495-19500, and Luster, *New Eng. J. Med.* 1998, 338, 436-445); CCR-5 (or "CKR-5" OR "CC-CKR-5") [MIP-1α, RANTES, MIP-1β] (Sanson, et al., *Biochemistry* 1996, 35, 3362-3367); CCR-6 (or "CKR-6" or "CC-CKR-6") [LARC] (Baba, et al., *J. Biol. Chem.* 1997, 272, 14893-14898); CCR-7 (or "CKR-7" or "CC-CKR-7") [ELC] (Yoshie et al., *J. Leukoc. Biol.* 1997, 62, 634-644); CCR-8 (or "CKR-8" or "CC-CKR-8") [1-309, TARC, MIP-1β] (Napolitano et al., *J. Immunol.*, 1996, 157, 2759-2763, and Bernardini, et al., *Eur. J. Immunol.* 1998, 28, 582-588); CCR-10 (or "CKR-10" or "CC-CKR-10") [MCP-1, MCP-3] (Bonini, et al., *DNA and Cell Biol.* 1997, 16, 1249-1256); and CCR-11 [MCP-1, MCP-2, and MCP-4] (Schweickert, et al., *J. Biol. Chem.* 2000, 275, 90550).

In addition to the mammalian chemokine receptors, mammalian cytomegaloviruses, herpesviruses and poxviruses have been shown to express, in infected cells, proteins with the binding properties of chemokine receptors (reviewed in: Wells and Schwartz, *Curr. Opin. Biotech.* 1997, 8, 741-748). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

The chemokines and their cognate receptors have been implicated as being important mediators of inflammatory, infectious, and immunoregulatory disorders and diseases, including asthma and allergic diseases, as well as autoimmune pathologies such as rheumatoid arthritis and atherosclerosis (reviewed in: Bharat K. Trivedi, et al, *Ann. Reports Med. Chem.* 2000, 35, 191; John Saunders and Christine M. Tarby, *Drug Disc. Today* 1999, 4, 80; Brett A. Premack and Thomas J. Schall, *Nature Medicine* 1996, 2, 1174). For example, the chemokine monocyte chemoattractant-1 (MCP-1) and its receptor CC Chemokine Receptor 2 (CCR-2) play a pivotal role in attracting leukocytes to sites of inflammation and in subsequently activating these cells. When the chemokine MCP-1 binds to CCR-2, it induces a rapid increase in intracellular calcium concentration, increased expression of cellular adhesion molecules, cellular degranulation, and the promotion of leukocyte migration. Demonstration of the importance of the MCP-1/CCR-2 interaction has been provided by experiments with genetically modified mice. MCP-1 −/− mice had normal numbers of leukocytes and macrophages, but were unable to recruit monocytes into sites of inflammation after several different types of immune challenge (Bao Lu, et al., *J. Exp. Med.* 1998, 187, 601). Likewise, CCR-2 −/− mice were unable to recruit monocytes or produce interferon-γ when challenged with various exogenous agents; moreover, the leukocytes of CCR-2 null mice did not migrate in response to MCP-1 (Landin Boring, et al., *J. Clin. Invest.* 1997, 100, 2552), thereby demonstrating the specificity of the MCP-1/CCR-2 interaction. Two other groups have independently reported equivalent results with different strains of CCR-2 −/− mice (William A. Kuziel, et al., *Proc. Natl. Acad. Sci. USA* 1997, 94, 12053, and Takao Kurihara, et al., *J. Exp. Med.* 1997, 186, 1757). The viability and generally normal health of the MCP-1 −/− and CCR-2 −/− animals is noteworthy, in that disruption of the MCP-1/CCR-2 interaction does not induce physiological crisis. Taken together, these data lead one to the conclusion that molecules that block the actions of MCP-1 would be useful in treating a number of inflammatory and autoimmune disorders. This hypothesis has now been validated in a number of different animal disease models, as described below.

Several studies have demonstrated the potential therapeutic value of antagonism of the MCP-1/CCR2 interaction in treating rheumatoid arthritis. A DNA vaccine encoding MCP-1 was shown recently to ameliorate chronic polyadjuvant-induced arthritis in rats (Sawsan Youssef, et al., *J. Clin. Invest.* 2000, 106, 361). Likewise, inflammatory disease symptoms could be controlled via direct administration of antibodies for MCP-1 to rats with collagen-induced arthritis (Hiroomi Ogata, et al., *J. Pathol.* 1997, 182, 106), or streptococcal cell wall-induced arthritis (Ralph C. Schimmer, et al., *J. Immunol.* 1998, 160, 1466). Perhaps most significantly, a peptide antagonist of MCP-1, MCP-1(9-76), was shown both to prevent disease onset and to reduce disease symptoms (depending on the time of administration) in the MRL-lpr mouse model of arthritis (Jiang-Hong Gong, et al., *J. Exp. Med.* 1997, 186, 131).

Three key studies have demonstrated the potential therapeutic value of antagonism of the MCP-1/CCR2 interaction in treating atherosclerosis. For example, when MCP-1 −/− mice are mated with LDL receptor-deficient mice, an 83% reduction in aortic lipid deposition was observed (Long Gu, et al., *Mol. Cell* 1998, 2, 275). Similarly, when MCP-1 was genetically ablated from mice which already overexpressed human apolipoprotein B, the resulting mice were protected from atherosclerotic lesion formation relative to the MCP-1+/+apoB control mice (Jennifa Gosling, et al., *J. Clin. Invest.* 1999, 103, 773). Likewise, when CCR-2 −/− mice are crossed with apolipoprotein E mice, a significant decrease in the incidence of atherosclerotic lesions was observed (Landin Boring, et al, *Nature* 1998, 394, 894).

Other studies have demonstrated the potential therapeutic value of antagonism of the MCP-1/CCR-2 interaction in treating multiple sclerosis; all of these studies have been demonstrated in experimental autoimmune encephalomyelitis (EAE), the standard animal model for multiple scelerosis. Administration of antibodies for MCP-1 to animals with EAE significantly diminished disease relapse (K. J. Kennedy, et al., *J. Neuroimmunol.* 1998, 92, 98). Furthermore, two recent reports have now shown that CCR-2 −/− mice are resistant to EAE (Brian T. Fife, et al., *J. Exp. Med.* 2000, 192, 899; Leonid Izikson, et al., *J. Exp. Med.* 2000, 192, 1075).

It is known that MCP-1 is upregulated in patients who develop bronchiolitis obliterans syndrome after lung transplantation (Martine Reynaud-Gaubert, et al., *J. of Heart and Lung Transplant.*, 2002, 21, 721-730; John Belperio, et al., *J. Clin. Invest.* 2001, 108, 547-556). In a murine model of bronchiolitis obliterans syndrome, administration of an antibody to MCP-1 led to attenuation of airway obliteration; likewise, CCR2 −/− mice were resistant to airway obliteration in this same model (John Belperio, et al., *J. Clin. Invest.* 2001, 108, 547-556). These data suggest that antagonism of MCP-1/CCR2 may be beneficial in treating rejection of organs following transplantation.

Other studies have demonstrated the potential therapeutic value of antagonism of the MCP-1/CCR2 interaction in treating asthma. Sequestration of MCP-1 with a neutralizing antibody in ovalbumin-challenged mice resulted in marked decrease in bronchial hyperresponsiveness and inflammation (Jose-Angel Gonzalo, et al., *J. Exp. Med.* 1998, 188, 157). It proved possible to reduce allergic airway inflammation in *Schistosoma mansoni* egg-challenged mice through the administration of antibodies for MCP-1 (Nicholas W. Lukacs, et al., *J. Immunol.* 1997, 158, 4398). Consistent with this, MCP-1 −/− mice displayed a reduced response to challenge with *Schistosoma mansoni* egg (Bao Lu, et al., *J. Exp. Med.* 1998, 187, 601).

Other studies have demonstrated the potential therapeutic value of antagonism of the MCP-1/CCR2 interaction in treating kidney disease. Administration of antibodies for MCP-1 in a murine model of glomerularnephritis resulted in a marked decrease in glomerular crescent formation and deposition of type I collagen (Clare M. Lloyd, et al., *J. Exp. Med.* 1997, 185, 1371). In addition, MCP-1 −/− mice with induced nephrotoxic serum nephritis showed significantly less tubular damage than their MCP-1 +/+ counterparts (Gregory H. Tesch, et al., *J. Clin. Invest.* 1999, 103, 73).

One study has demonstrated the potential therapeutic value of antagonism of the MCP-1/CCR2 interaction in treating systemic lupus erythematosus. Crossing of MCP-1 −/− mice with MRL-FAS$^{lpr}$ mice—the latter of which have a fatal autoimmune disease that is analogous to human systemic lupus erythematosus—results mice that have less disease and longer survival than the wildtype MRL-FAS$^{lpr}$ mice (Gregory H. Tesch, et al., *J. Exp. Med.* 1999, 190, 1813).

One study has demonstrated the potential therapeutic value of antagonism of the MCP-1/CCR2 interaction in treating colitis. CCR-2 −/− mice were protected from the effects of dextran sodium sulfate-induced colitis (Pietro G. Andres, et al., *J. Immunol.* 2000, 164, 6303).

One study has demonstrated the potential therapeutic value of antagonism of the MCP-1/CCR2 interaction in treating alveolitis. When rats with IgA immune complex lung injury were treated intravenously with antibodies raised against rat MCP-1 (JE), the symptoms of alveolitis were partially alleviated (Michael L. Jones, et al., *J. Immunol.* 1992, 149, 2147).

One study has demonstrated the potential therapeutic value of antagonism of the MCP-1/CCR2 interaction in treating colitis. CCR-2 −/− mice were protected from the effects of dextran sodium sulfate-induced colitis (Pietro G. Andres, et al., *J. Immunol.* 2000, 164, 6303).

One study has demonstrated the potential therapeutic value of antagonism of the MCP-1/CCR2 interaction in treating alveolitis. When rats with IgA immune complex lung injury were treated intravenously with antibodies raised against rat MCP-1 (JE), the symptoms of alveolitis were partially alleviated (Michael L. Jones, et al., *J. Immunol.* 1992, 149, 2147).

One study has demonstrated the potential therapeutic value of antagonism of the MCP-1/CCR2 interaction in treating cancer. When immunodeficient mice bearing human breast carcinoma cells were treated with an anti-MCP-1 antibody, inhibition of lung micrometastases and increases in survival were observed (Rosalba Salcedo, et al., *Blood* 2000, 96, 34-40).

One study has demonstrated the potential therapeutic value of antagonism of the MCP-1/CCR2 interaction in treating restinosis. Mice deficient in CCR2 showed reductions in the intimal area and in the intima/media ratio (relative to wildtype littermates) after injury of the femoral artery (Merce Roque, et al. *Arterioscler. Thromb. Vasc. Biol.* 2002, 22, 554-559).

Other studies have provided evidence that MCP-1 is overexpressed in various disease states not mentioned above. These reports provide strong correlative evidence that MCP-1 antagonists could be useful therapeutics for such diseases. Two reports described the overexpression of MCP-1 in the intestinal epithelial cells and bowel mucosa of patients with inflammatory bowel disease (H. C. Reinecker, et al., *Gastroenterology* 1995, 108, 40, and Michael C. Grimm, et al., *J. Leukoc. Biol.* 1996, 59, 804). Two reports describe the overexpression of MCP-1 rats with induced brain trauma (J. S. King, et al., *J. Neuroimmunol.* 1994, 56, 127, and Joan W. Berman, et al., *J. Immunol.* 1996, 156, 3017). Another study has demonstrated the overexpression of MCP-1 in rodent cardiac allografts, suggesting a role for MCP-1 in the pathogenesis of transplant arteriosclerosis(Mary E. Russell, et al. *Proc. Natl. Acad. Sci. USA* 1993, 90, 6086). The overexpression of MCP-1 has been noted in the lung endothelial cells of patients with idiopathic pulmonary fibrosis (Harry N. Antoniades, et al., *Proc. Natl. Acad. Sci. USA* 1992, 89, 5371). Similarly, the overexpression of MCP-1 has been noted in the skin from patients with psoriasis (M. Deleuran, et al., *J. Dermatol. Sci.* 1996, 13, 228, and R. Gillitzer, et al., *J. Invest. Dermatol.* 1993, 101, 127). Finally, a recent report has shown that MCP-1 is overexpressed in the brains and cerebrospinal fluid of patients with HIV-1-associated dementia (Alfredo Garzino-Demo, WO 99/46991).

It should also be noted that CCR-2 has been implicated as a co-receptor for some strains of HIV (B. J. Doranz, et al., *Cell* 1996, 85, 1149). It has also been determined that the use of CCR-2 as an HIV co-receptor can be correlated with disease progression (Ruth I. Connor, et al., *J. Exp. Med.* 1997, 185, 621). This finding is consistent with the recent finding that the presence of a CCR-2 mutant, CCR2-64I, is positively correlated with delayed onset of HIV in the human population (Michael W. Smith, et al., *Science* 1997, 277, 959). Although MCP-1 has not been implicated in these processes, it may be that MCP-1 antagonists that act via binding to CCR-2 may have beneficial therapeutic effects in delaying the disease progression to AIDS in HIV-infected patients.

Recently, a number of groups have described the development of small molecule antagonists of MCP-1 (reviewed in: Bharat K. Trivedi, et al, *Ann. Reports Med. Chem.* 2000, 35, 191). Workers at Teijen and Combichem reported the use of cyclic amines (A) as MCP-1 (Tatsuki Shiota, et al., WO 99/25686; Tatsuki Shiota, et al., WO 00/69815) and MIP-1α (Christine Tarby and Wilna Moree, WO 00/69820) antagonists. These compounds are distinguished from those of the present invention (I) by the requirement for the central cyclic amine grouping.

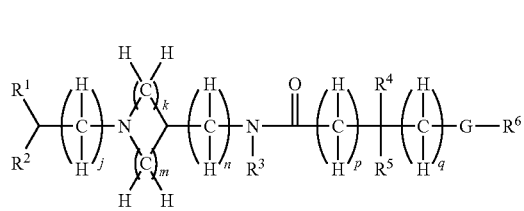

(A)

A number of other groups have also described the development of small molecule antagonists of the MCP-1/CCR-2 interaction. To date, indolopiperidines (Ian T. Forbes, et al., *Bioorg. Med. Chem. Lett.* 2000, 10, 1803), spiropiperidines (Tara Mirzadegan, et al., *J. Biol. Chem.* 2000, 275, 25562), quaternary amines (Masanori Baba, et al., *Proc. Natl. Acad. Sci.* 1999, 96, 5698), 2-substituted indoles (Alan Faull and Jason Kettle, WO 00/46196; Andrew John Barker, et al., WO 99/07351; Andrew John Barker, et al., WO 99/07678), pyrazolone derivatives (Janak Khimchand Padia, et al., U.S. Pat. No. 6,011,052, 2000), 2-substituted benzimidazoles (David Thomas Connor, et al., WO 98/06703), N,N-dialkylhomopiperazines (T. Shiota, et al., WO 97/44329), bicyclic pyrroles (Andrew J. Barker, et al., WO 99/40913 and Andrew J. Barker, et al., WO 99/40914), and 5-aryl pentadienamides (K. G. Carson, et al., Cambridge Health Tech Institute Chemokine Symposium, McLean, Va., USA, 1999) have all been reported as MCP-1 antagonists. The foregoing reference compounds are readily distinguished structurally from the present invention by virtue of substantial differences in the terminal functionality, the attachment functionality, or the core functionality. The prior art does not disclose nor suggest the unique combination of structural fragments that embody in the novel compounds described herein. Furthermore, the prior art does not disclose or suggest that the compounds of the present invention would be antagonists of MCP-1.

It should be noted that CCR-2 is also the receptor for the chemokines MCP-2, MCP-3, MCP-4, and MCP-5 (Luster, *New Eng. J. Med.* 1998, 338, 436-445). Since it is presumed that the new compounds of formula (I) described herein antagonize MCP-1 by binding to the CCR-2 receptor, it may be that these compounds of formula (I) are also effective antagonists of the actions of MCP-2, MCP-3, MCP-4, and MCP-5 that are mediated by CCR-2. Accordingly, when reference is made herein to "antagonism of MCP-1," it is to be assumed that this is equivalent to "antagonism of chemokine stimulation of CCR-2."

SUMMARY OF THE INVENTION

Accordingly, the present invention provides novel antagonists or partial agonists/antagonists of MCP-1 receptor activity, or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating rheumatoid arthritis, multiple sclerosis, and atherosclerosis, comprising administering to a host in need of such treatment a therapeutically effective amount of at least one of the compounds of the present invention or a pharmaceutically acceptable salt or prodrug form thereof.

The present invention provides a method for treating inflammatory diseases, comprising administering to a host in need of such treatment a therapeutically effective amount of at least one of the compounds of the present invention or a pharmaceutically acceptable salt or prodrug form thereof.

The present invention provides novel cyclic derivatives for use in therapy.

The present invention provides the use of novel cyclic derivatives for the manufacture of a medicament for the treatment of inflammatory diseases.

These and other features of the invention, which will become apparent during the following detailed description, have been achieved by the inventors' discovery that compounds of formula (I):

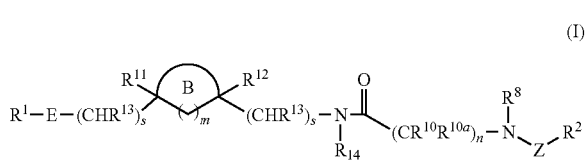

(I)

or stereoisomers or pharmaceutically acceptable salts thereof, wherein B, E, Z, m, n, p, s, $R^1$, $R^2$, $R^8$, $R^{10}$, $R^{10a}$, $R^{11}$, $R^{12}$, $R^{13}$, and $R^{14}$ are defined below, are effective modulators of chemokine activity.

DETAILED DESCRIPTION OF EMBODIMENTS OF THE PRESENT INVENTION

[1] Thus, in a first embodiment, the present invention provides novel compounds of formula (I):

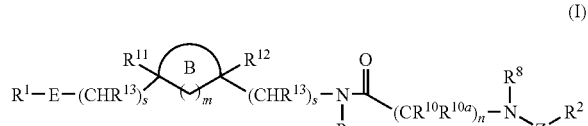

or a stereoisomer or a pharmaceutically acceptable salt thereof, wherein:

ring B is a cycloalkyl group of 3 to 8 carbon atoms wherein the cycloalkyl group is saturated or partially unsaturated; or a heterocycle of 3 to 7 atoms wherein the heterocycle is saturated or partially unsaturated, the heterocycle containing a heteroatom selected from —O—, —S—, —S(=O)—, —S(=O)$_2$—, and —N(R$^4$)—, the heterocycle optionally containing a —C(O)—; ring B being substituted with 0-2 R$^5$;

Z is selected from a bond, —C(O)—, —C(O)NH—, —C(S)NH—, —SO$_2$—, and —SO$_2$NH—;

E is selected from —S(O)$_p$(CHR$^{15}$)—, —C(O) (CHR$^{15}$)—, —OC(O)NH—, —NHC(O)O—, and —NHC(O)NH—;

R$^1$ is selected from a C$_{6-10}$ aryl group substituted with 0-5 R$^6$ and a 5-10 membered heteroaryl system containing 1-4 heteroatoms selected from N, O, and S, substituted with 0-3 R$^6$;

R$^2$ is selected from a C$_{6-10}$ aryl group substituted with 0-5 R$^7$ and a 5-10 membered heteroaryl system containing 1-4 heteroatoms selected from N, O, and S, substituted with 0-3 R$^7$;

R$^4$ is selected from H, C$_{1-6}$ alkyl, C$_{3-8}$ alkenyl, C$_{3-8}$ alkynyl, (CRR)$_t$OH, (CRR)$_t$SH, (CRR)$_t$OR$^{4d}$, (CHR)$_t$SR$^{4d}$, (CRR)$_t$NR$^{4a}$R$^{4a}$, (CRR)$_q$C(O)OH, (CRR)$_t$C(O)R$^{4b}$, (CRR)$_t$C(O)NR$^{4a}$R$^{4a}$, (CRR)$_t$OC(O)NR$^{4a}$R$^{4a}$, (CRR)$_t$NR$^{4a}$C(O)OR$^{4d}$, (CRR)$_t$NR$^{4a}$C(O)R$^{4b}$, (CRR)$_t$C(O)OR$^{4b}$, (CRR)$_t$OC(O)R$^{4b}$, (CRR)$_t$S(O)$_p$R$^{4b}$, (CRR)$_t$S(O)$_2$NR$^{4a}$R$^{4a}$, (CRR)$_t$NR$^{4a}$S(O)$_2$R$^{4b}$, C$_{1-6}$ haloalkyl, a (CRR)$_r$—C$_{3-10}$ carbocyclic residue substituted with 0-3 R$^{4e}$, and a (CHR)$_r$-4-10 membered heterocyclic system containing 1-4 heteroatoms selected from N, O, and S, substituted with 0-2 R$^{4e}$;

R$^{4a}$, at each occurrence, is independently selected from H, methyl substituted with 0-1 R$^{4c}$, C$_{2-6}$ alkyl substituted with 0-3 R$^{4e}$, C$_{3-8}$ alkenyl substituted with 0-3 R$^{4e}$, C$_{3-8}$ alkynyl substituted with 0-3 R$^{4e}$, a (CH$_2$)$_r$—C$_{3-10}$ carbocyclic residue substituted with 0-4 R$^{4e}$, and a (CHR)$_r$-4-10 membered heterocyclic system containing 1-4 heteroatoms selected from N, O, and S, substituted with 0-2 R$^{4e}$;

R$^{4b}$, at each occurrence, is selected from H, C$_{1-6}$ alkyl substituted with 0-3 R$^{4e}$, C$_{3-8}$ alkenyl substituted with 0-3 R$^{4e}$, C$_{3-8}$ alkynyl substituted with 0-3 R$^{4e}$, a (CH$_2$)$_r$—C$_{3-6}$ carbocyclic residue substituted with 0-2 R$^{4e}$, and a (CHR)$_r$-4-10 membered heterocyclic system containing 1-4 heteroatoms selected from N, O, and S, substituted with 0-2 R$^{4e}$;

R$^{4c}$ is independently selected from —C(O)R$^{4b}$, —C(O)OR$^{4d}$, —C(O)NR$^{4f}$R$^{4f}$, and (CH$_2$)$_r$phenyl;

R$^{4d}$, at each occurrence, is selected from methyl, CF$_3$, C$_{1-6}$ alkyl substituted with 0-3 R$^{4e}$, C$_{3-8}$ alkenyl substituted with 0-3 R$^{4e}$, C$_{3-8}$ alkynyl substituted with 0-3 R$^{4e}$, and a C$_{3-10}$ carbocyclic residue substituted with 0-3 R$^{4e}$;

R$^{4e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{4f}$R$^{4f}$, —C(O)R$^{4i}$, —C(O)OR$^{4j}$, —C(O)NR$^{4h}$R$^{4h}$, —OC(O)NR$^{4h}$R$^{4h}$, —NR$^{4h}$C(O)NR$^{4h}$R$^{4h}$, —NR$^{4h}$C(O)OR$^{4j}$, and (CH$_2$)$_r$phenyl;

R$^{4f}$, at each occurrence, is selected from H, C$_{1-6}$ alkyl, C$_{3-6}$ cycloalkyl, and phenyl;

R$^{4h}$, at each occurrence, is independently selected from H, C$_{1-6}$ alkyl, C$_{3-8}$ alkenyl, C$_{3-8}$ alkynyl, and a (CH$_2$)$_r$—C$_{3-10}$ carbocyclic;

R$^{4i}$, at each occurrence, is selected from H, C$_{1-6}$ alkyl, C$_{3-8}$ alkenyl, C$_{3-8}$ alkynyl, and a (CH$_2$)$_r$—C$_{3-6}$ carbocyclic residue;

R$^{4j}$, at each occurrence, is selected from CF$_3$, C$_{1-6}$ alkyl, C$_{3-8}$ alkenyl, C$_{3-8}$ alkynyl, and a C$_{3-10}$ carbocyclic residue;

R$^5$, at each occurrence, is independently selected from H, =O, C$_{1-6}$ alkyl, N$_3$, C$_{2-8}$ alkenyl, C$_{2-8}$ alkynyl, (CRR)$_r$OH, (CRR)$_r$SH, (CRR)$_r$OR$^{5d}$, (CRR)$_r$SR$^{5d}$, (CRR)$_r$NR$^{5a}$R$^{5a}$, (CRR)$_r$C(O)OH, (CRR)$_r$C(O)R$^{5b}$, (CRR)$_r$C(O)NR$^{5a}$R$^{5a}$, (CRR)$_r$NR$^{5a}$C(O)R$^{5b}$, (CRR)$_r$OC(O)NR$^{5a}$R$^{5a}$, (CRR)$_r$NR$^{5a}$C(O)OR$^{5d}$, (CRR)$_r$NR$^{5a}$C(O)NR$^{5a}$R$^{5a}$, (CRR)$_r$NR$^{5a}$C(O)H, (CRR)$_r$C(O)OR$^{5b}$, (CRR)$_r$OC(O)R$^{5b}$, (CRR)$_r$S(O)$_p$R$^{5b}$, (CRR)$_r$S(O)$_2$NR$^{5a}$R$^{5a}$, (CRR)$_r$NR$^{5a}$S(O)$_2$R$^{5b}$, (CRR)$_r$NR$^{5a}$S(O)$_2$NR$^{5a}$R$^{5a}$, (CRR)$_r$NR$^{5a}$C(=N)NR$^{5a}$R$^{5a}$, C$_{1-6}$ haloalkyl, a (CRR)$_r$—C$_{3-10}$ carbocyclic residue substituted with 0-3 R$^{5c}$, and a (CRR)$_r$-5-10 membered heterocyclic system containing 1-4 heteroatoms selected from N, O, and S, substituted with 0-2 R$^{5c}$;

R$^{5a}$, at each occurrence, is independently selected from H, methyl substituted with 0-1 R$^{5g}$, C$_{2-6}$ alkyl substituted with 0-2 R$^{5e}$, C$_{3-8}$ alkenyl substituted with 0-2 R$^{5e}$, C$_{3-8}$ alkynyl substituted with 0-2 R$^{5e}$, a (CH$_2$)$_r$—C$_{3-10}$ carbocyclic residue substituted with 0-5 R$^{5e}$, and a (CH$_2$)$_r$-5-10 membered heterocyclic system containing 1-4 heteroatoms selected from N, O, and S, substituted with 0-3 R$^{5e}$;

R$^{5b}$, at each occurrence, is selected from C$_{1-6}$ alkyl substituted with 0-3 R$^{5e}$, C$_{3-8}$ alkenyl substituted with 0-2 R$^{5e}$, C$_{3-8}$ alkynyl substituted with 0-2 R$^{5e}$, a (CH$_2$)$_r$—C$_{3-6}$ carbocyclic residue substituted with 0-2 R$^{5e}$, and a (CH$_2$)$_r$-5-6 membered heterocyclic system containing 1-4 heteroatoms selected from N, O, and S, substituted with 0-3 R$^{5e}$;

R$^{5c}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{5f}$R$^{5f}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{5b}$, (CH$_2$)$_r$C(O)NR$^{5f}$R$^{5f}$, (CH$_2$)$_r$NR$^{5f}$C(O)R$^{5b}$, (CH$_2$)$_r$C(O)OC$_{1-4}$ alkyl, (CH$_2$)$_r$OC(O)R$^{5b}$, (CH$_2$)$_r$C(=NR$^{5f}$)NR$^{5f}$R$^{5f}$, (CH$_2$)$_r$S(O)$_p$R$^{5b}$, (CH$_2$)$_r$NHC(=NR$^{5f}$)NR$^{5f}$R$^{5f}$, (CH$_2$)$_r$S(O)$_2$NR$^{5f}$R$^{5f}$, (CH$_2$)$_r$NR$^{5f}$S(O)$_2$R$^{5b}$, and (CH$_2$)$_r$phenyl substituted with 0-3 R$^{5e}$;

R$^{5d}$, at each occurrence, is selected from methyl, CF$_3$, C$_{2-6}$ alkyl substituted with 0-2 R$^{5e}$, C$_{3-8}$ alkenyl substituted with 0-2 R$^{5e}$, C$_{3-8}$ alkynyl substituted with 0-2 R$^{5e}$, and a C$_{3-10}$ carbocyclic residue substituted with 0-3 R$^{5e}$;

R$^{5e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{5f}$R$^{5f}$, and (CH$_2$)$_r$phenyl;

R$^{5f}$, at each occurrence, is selected from H, C$_{1-6}$ alkyl, and C$_{3-6}$ cycloalkyl;

R$^{5g}$ is independently selected from —C(O)R$^{5b}$, —C(O)OR$^{5d}$, —C(O)NR$^{5f}$R$^{5f}$, and (CH$_2$)$_r$phenyl;

R, at each occurrence, is selected from H, $C_{1-6}$ alkyl substituted with 0-3 $R^{5e}$, $C_{2-8}$ alkenyl, $C_{2-8}$ alkynyl, $(CH_2)_rC_{3-6}$ cycloalkyl, and $(CH_2)_r$phenyl substituted with $R^{5e}$;

$R^6$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CR'R')_rNR^{6a}R^{6a}$, $(CR'R')_rOH$, $(CR'R')_rO(CR'R')_rR^{6d}$, $(CR'R')_rSH$, $(CR'R')_rC(O)H$, $(CR'R')_rS(CR'R')_rR^{6d}$, $(CR'R')_rSC(O)(CR'R')_rR^{6b}$, $(CR'R')_rC(O)OH$, $(CR'R')_rC(O)(CR'R')_rR^{6b}$, $(CR'R')_rNR^{6a}R^{6a}$, $(CR'R')_rC(O)NR^{6a}R^{6a}$, $(CR'R')_rNR^{6f}C(O)(CR'R')_rR^{6b}$, $(CR'R')_rC(O)O(CR'R')_rR^{6d}$, $(CR'R')_rOC(O)(CR'R')_rR^{6b}$, $(CR'R')_rOC(O)NR^{6a}(CR'R')_rR^{6d}$, $(CR'R')_rNR^{6a}C(O)NR^{6a}(CR'R')_rR^{6d}$, $(CR'R')_rNR^{6a}C(S)NR^{6a}(CR'R')_rR^{6d}$, $(CR'R')_rNR^{6f}C(O)O(CR'R')_rR^{6b}$, $(CR'R')_rC(=NR^{6f})NR^{6a}R^{6a}$, $(CR'R')_rNHC(=NR^{6f})NR^{6f}R^{6f}$, $(CR'R')_rS(O)_p(CR'R')_rR^{6b}$, $(CR'R')_rS(O)_2NR^{6a}R^{6a}$, $(CR'R')_rNR^{6f}S(O)_2NR^{6a}R^{6a}$, $(CR'R')_rNR^{6f}S(O)_2(CR'R')_rR^{6b}$, $C_{1-6}$ haloalkyl, $C_{2-8}$ alkenyl substituted with 0-3 R', $C_{2-8}$ alkynyl substituted with 0-3 R', and $(CR'R')_r$phenyl substituted with 0-3 $R^{6e}$;

alternatively, two $R^6$ on adjacent atoms on $R^1$ may join to form a cyclic acetal;

$R^{6a}$, at each occurrence, is selected from H, methyl substituted with 0-1 $R^{6g}$, $C_{2-6}$ alkyl substituted with 0-2 $R^{6e}$, $C_{3-8}$ alkenyl substituted with 0-2 $R^{6e}$, $C_{3-8}$ alkynyl substituted with 0-2 $R^{6e}$, a $(CH_2)_r$—$C_{3-10}$ carbocyclic residue substituted with 0-5 $R^{6e}$, and a $(CH_2)_r$-5-10 membered heterocyclic system containing 1-4 heteroatoms selected from N, O, and S, substituted with 0-2 $R^{6e}$;

$R^{6b}$, at each occurrence, is selected from H, $C_{1-6}$ alkyl substituted with 0-2 $R^{6e}$, $C_{3-8}$ alkenyl substituted with 0-2 $R^{6e}$, $C_{3-8}$ alkynyl substituted with 0-2 $R^{6e}$, a $(CH_2)_rC_{3-6}$ carbocyclic residue substituted with 0-3 $R^{6e}$, and a $(CH_2)_r$-5-6 membered heterocyclic system containing 1-4 heteroatoms selected from N, O, and S, substituted with 0-2 $R^{6e}$;

$R^{6d}$, at each occurrence, is selected from $C_{3-8}$ alkenyl substituted with 0-2 $R^{6e}$, $C_{3-8}$ alkynyl substituted with 0-2 $R^{6e}$, methyl, $CF_3$, $C_{2-6}$ alkyl substituted with 0-3 $R^{6e}$, a $(CH_2)_r$—$C_{3-10}$ carbocyclic residue substituted with 0-3 $R^{6e}$, and a $(CH_2)_r$-5-6 membered heterocyclic system containing 1-4 heteroatoms selected from N, O, and S, substituted with 0-3 $R^{6e}$;

$R^{6e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{6f}R^{6f}$, and $(CH_2)_r$phenyl;

$R^{6f}$, at each occurrence, is selected from H, $C_{1-5}$ alkyl, and $C_{3-6}$ cycloalkyl, and phenyl;

$R^{6g}$ is independently selected from —$C(O)R^{6b}$, —$C(O)OR^{6d}$, —$C(O)NR^{6f}R^{6f}$, and $(CH_2)_r$phenyl;

$R^7$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CR'R')_rNR^{7a}R^{7a}$, $(CR'R')_rOH$, $(CR'R')_rO(CR'R')_rR^{7d}$, $(CR'R')_rSH$, $(CR'R')_rC(O)H$, $(CR'R')_rS(CR'R')_rR^{7d}$, $(CR'R')_rC(O)OH$, $(CR'R')_rC(O)(CR'R')_rR^{7b}$, $(CR'R')_rC(O)NR^{7a}R^{7a}$, $(CR'R')_rNR^{7f}C(O)(CR'R')_rR^{7b}$, $(CR'R')_rC(O)OCR'R')_rR^{7d}$, $(CR'R')_rOC(O)(CR'R')_rR^{7b}$, $(CR'R')_rOC(O)NR^{7a}(CR'R')_rR^{7a}$, $(CR'R')_rNR^{7a}C(O)NR^{7a}(CR'R')_rR^{7a}$, $(CR'R')_rNR^{7f}C(O)O(CR'R')_rR^{7b}$, $(CR'R')_rC(=NR^{7f})NR^{7a}R^{7a}$, $(CR'R')_rNHC(=NR^{7f})NR^{7f}R^{7f}$, $(CR'R')_rS(O)_p(CR'R')_rR^{7b}$, $(CR'R')_rS(O)_2NR^{7a}R^{7a}$, $(CR'R')_rNR^{7a}S(O)_2NR^{7a}R^{7a}$, $(CR'R')_rNR^{7f}S(O)_2(CR'R')_rR^{7b}$, $C_{1-6}$ haloalkyl, $C_{2-8}$ alkenyl substituted with 0-3 R', $C_{2-8}$ alkynyl substituted with 0-3 R', and $(CR'R')_r$phenyl substituted with 0-3 $R^{7e}$;

alternatively, two $R^7$ on adjacent atoms on $R^2$ may join to form a cyclic acetal;

$R^{7a}$, at each occurrence, is independently selected from H, methyl substituted with 0-1 $R^{7g}$, $C_{2-6}$ alkyl substituted with 0-2 $R^{7e}$, $C_{3-8}$ alkenyl substituted with 0-2 $R^{7e}$, $C_{3-8}$ alkynyl substituted with 0-2 $R^{7e}$, a $(CH_2)_r$—$C_{3-10}$ carbocyclic residue substituted with 0-5 $R^{7e}$, and a $(CH_2)_r$-5-10 membered heterocyclic system containing 1-4 heteroatoms selected from N, O, and S, substituted with 0-2 $R^{7e}$;

$R^{7b}$, at each occurrence, is selected from $C_{1-6}$ alkyl substituted with 0-3 $R^{7e}$, $C_{3-8}$ alkenyl substituted with 0-2 $R^{7e}$, $C_{3-8}$ alkynyl substituted with 0-2 $R^{7e}$, a $(CH_2)_rC_{3-6}$ carbocyclic residue substituted with 0-3 $R^{7e}$, and a $(CH_2)_r$-5-6 membered heterocyclic system containing 1-4 heteroatoms selected from N, O, and S, substituted with 0-2 $R^{7e}$;

$R^{7d}$, at each occurrence, is selected from $C_{3-8}$ alkenyl substituted with 0-2 $R^{7e}$, $C_{3-8}$ alkynyl substituted with 0-2 $R^{7e}$, methyl, $CF_3$, $C_{2-6}$ alkyl substituted with 0-3 $R^{7e}$, a $(CH_2)_r$—$C_{3-10}$ carbocyclic residue substituted with 0-3 $R^{7e}$, and a $(CH_2)_r$-5-6 membered heterocyclic system containing 1-4 heteroatoms selected from N, O, and S, substituted with 0-3 $R^{7e}$;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $C(O)OC_{1-5}$ alkyl, $(CH_2)_rSC_{1-5}$ alkyl, $(CH_2)_rNR^{7f}R^{7f}$, and $(CH_2)_r$phenyl;

$R^{7f}$, at each occurrence, is selected from H, $C_{1-5}$ alkyl, and $C_{3-6}$ cycloalkyl, and phenyl;

$R^{7g}$ is independently selected from —$C(O)R^{7b}$, —$C(O)OR^{7d}$, —$C(O)NR^{7f}R^{7f}$, and $(CH_2)_r$phenyl;

R', at each occurrence, is selected from H, $C_{1-6}$ alkyl substituted with 0-3 $R^{6e}$, $C_{2-8}$ alkenyl, $C_{2-8}$ alkynyl, $(CH_2)_rC_{3-6}$ cycloalkyl, and $(CH_2)_r$phenyl substituted with $R^{6e}$;

$R^8$ is selected from H, $C_{1-4}$ alkyl, and $C_{3-4}$ cycloalkyl;

$R^{10}$ and $R^{10a}$ are independently selected from H, and $C_{1-4}$ alkyl substituted with 0-1 $R^{10b}$, alternatively, $R^{10}$ and $R^{10a}$ can join to form a $C_{3-6}$ cycloalkyl;

$R^{10b}$, at each occurrence, is independently selected from —OH, —SH, $NR^{10c}R^{10c}$, —$C(O)NR^{10c}R^{10c}$, and —$NHC(O)R^{10c}$;

$R^{10c}$ is selected from H, $C_{1-4}$ alkyl and $C_{3-6}$ cycloalkyl;

$R^{11}$ is selected from H, $C_{1-4}$ alkyl, $(CHR)_qOH$, $(CHR)_qSH$, $(CHR)_qOR^{11d}$, $(CHR)_qS(O)_pR^{11d}$, $(CHR)_rC(O)R^{11b}$, $(CHR)_rNR^{11a}R^{11a}$, $(CHR)_rC(O)NR^{11a}R^{11a}$, $(CHR)_rC(O)NR^{11a}OR^{11d}$, $(CHR)_qNR^{11a}C(O)R^{11b}$, $(CHR)_qNR^{11a}C(O)OR^{11d}$, $(CHR)_qOC(O)NR^{11a}R^{11a}$, $(CHR)_rC(O)OR^{11d}$, a $(CHR)_r$—$C_{3-6}$ carbocyclic residue substituted with 0-5 $R^{11e}$, and a $(CHR)_r$-5-10 membered heterocyclic system containing 1-4 heteroatoms selected from N, O, and S, substituted with 0-3 $R^{11e}$;

$R^{11a}$, at each occurrence, is independently selected from H, $C_{1-4}$ alkyl, $C_{3-4}$ alkenyl, $C_{3-4}$ alkynyl, $(CH_2)_rC_{3-6}$ cycloalkyl, a $(CH_2)_r$—$C_{3-6}$ carbocyclic residue substituted with 0-5 $R^{11e}$, and a $(CH_2)_r$-5-6 membered heterocyclic system containing 1-4 heteroatoms selected from N, O, and S, substituted with 0-3 $R^{11e}$;

$R^{11b}$, at each occurrence, is independently selected from $C_{1-4}$ alkyl, $C_{2-4}$ alkenyl, $C_{2-4}$ alkynyl, a $(CH_2)_r$—$C_{3-6}$ carbocyclic residue substituted with 0-2 $R^{11e}$, and a $(CH_2)_r$-5-6 membered heterocyclic system containing 1-4 heteroatoms selected from N, O, and S, substituted with 0-3 $R^{11e}$;

$R^{11d}$, at each occurrence, is independently selected from H, methyl, —$CF_3$, $C_{2-4}$ alkyl, $C_{3-6}$ alkenyl, $C_{3-6}$ alkynyl, a $C_{3-6}$ carbocyclic residue substituted with 0-3 $R^{11e}$, and a $(CH_2)_r$-5-6 membered heterocyclic system containing 1-4 heteroatoms selected from N, O, and S, substituted with 0-3 $R^{11e}$;

$R^{11e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, NO$_2$, (CF$_2$)$_r$CF$_3$, (CH$_2$)$_r$OC$_{1-5}$ alkyl, OH, —O—C$_{1-6}$ alkyl, SH, (CH$_2$)$_r$SC$_{1-5}$ alkyl, (CH$_2$)$_r$NR$^{11f}$R$^{11f}$, and (CH$_2$)$_r$phenyl;

$R^{11f}$, at each occurrence, is selected from H, $C_{1-6}$ alkyl, and $C_{3-6}$ cycloalkyl;

$R^{12}$ is selected from H, $C_{1-4}$ alkyl, (CHR)$_q$OH, (CHR)$_q$SH, (CHR)$_q$OR$^{12d}$, (CHR)$_q$S(O)$_p$R$^{12d}$, (CHR)$_r$C(O)R$^{12b}$ (CHR)$_r$NR$^{12a}$R$^{12a}$, (CHR)$_r$C(O)NR$^{12a}$R$^{12a}$, (CHR)$_r$C(O)NR$^{12a}$OR$^{12d}$, (CHR)$_q$NR$^{12a}$C(O)R$^{12b}$, (CHR)$_q$NR$^{12a}$C(O)OR$^{12d}$, (CHR)$_q$OC(O)NR$^{12a}$R$^{12a}$, (CHR)$_r$C(O)OR$^{12d}$, a (CHR)$_r$—C$_{3-6}$ carbocyclic residue substituted with 0-5 R$^{12e}$, and a (CHR)$_r$-5-10 membered heterocyclic system containing 1-4 heteroatoms selected from N, O, and S, substituted with 0-3 R$^{12e}$;

$R^{12a}$, at each occurrence, is independently selected from H, $C_{1-4}$ alkyl, $C_{3-4}$ alkenyl, $C_{3-4}$ alkynyl, (CH$_2$)$_r$C$_{3-6}$ cycloalkyl, a (CH$_2$)$_r$—C$_{3-6}$ carbocyclic residue substituted with 0-5 R$^{12e}$, and a (CH$_2$)$_r$-5$^{-6}$ membered heterocyclic system containing 1-4 heteroatoms selected from N, O, and S, substituted with 0-3 R$^{12e}$;

$R^{12b}$, at each occurrence, is independently selected from $C_{1-4}$ alkyl, $C_{2-4}$ alkenyl, $C_{2-4}$ alkynyl, a (CH$_2$)$_r$—C$_{3-6}$ carbocyclic residue substituted with 0-2 R$^{12e}$, and a (CH$_2$)$_r$-5$^{-6}$ membered heterocyclic system containing 1-4 heteroatoms selected from N, O, and S, substituted with 0-3 R$^{12e}$;

$R^{12d}$, at each occurrence, is independently selected from H, methyl, —CF$_3$, $C_{2-4}$ alkyl, $C_{3-6}$ alkenyl, $C_{3-6}$ alkynyl, a $C_{3-6}$ carbocyclic residue substituted with 0-3 R$^{12e}$, and a (CH$_2$)$_r$-5$^{-6}$ membered heterocyclic system containing 1-4 heteroatoms selected from N, O, and S, substituted with 0-3 R$^{12e}$;

$R^{12e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, NO$_2$, (CF$_2$)$_r$CF$_3$, (CH$_2$)$_r$OC$_{1-5}$ alkyl, OH, —O—C$_{1-16}$ alkyl, SH, (CH$_2$)$_r$SC$_{1-5}$ alkyl, (CH$_2$)$_r$NR$^{12f}$R$^{12f}$, and (CH$_2$)$_r$phenyl;

$R^{12f}$, at each occurrence, is selected from H, $C_{1-6}$ alkyl, and $C_{3-6}$ cycloalkyl;

$R^{13}$, at each occurrence, is independently selected from methyl, $C_{2-4}$ alkyl substituted with 0-1 R$^{13b}$;

$R^{13b}$ is selected from —OH, —SH, —NR$^{13c}$R$^{13c}$, —C(O)NR$^{13c}$R$^{13c}$, and —NHC(O)R$^{13c}$;

$R^{13c}$ is selected from H, $C_{1-4}$ alkyl and $C_{3-6}$ cycloalkyl;

$R^{14}$ is selected from H, and $C_{1-3}$ alkyl;

$R^{15}$ is selected from H and $C_{1-3}$ alkyl;

n is selected from 1 and 2;

m is selected from 0 and 1;

p, at each occurrence, is independently selected from 0, 1, and 2;

q, at each occurrence, is independently selected from 1, 2, 3, and 4;

r, at each occurrence, is independently selected from 0, 1, 2, 3, and 4;

s, at each occurrence, is independently selected from 0 and 1; and t, at each occurrence, is independently selected from 2, 3, and 4.

[2] Thus, in a first embodiment, the present invention provides novel compounds of formula (Ia):

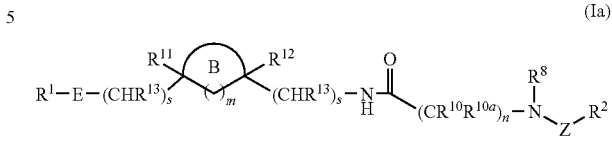

(Ia)

or a stereoisomer or a pharmaceutically acceptable salt thereof, wherein:

ring B is a cycloalkyl group of 3 to 8 carbon atoms wherein the cycloalkyl group is saturated or partially unsaturated; or a heterocycle of 3 to 7 atoms wherein the heterocycle is saturated or partially unsaturated, the heterocycle containing a heteroatom selected from —O—, —S—, —S(=O)—, —S(=O)$_2$—, and —N(R$^4$)—, the heterocycle optionally containing a —C(O)—; ring B being substituted with 0-2 R$^5$;

Z is selected from a bond, —C(O)—, —C(O)NH—, —C(S)NH—, —SO$_2$—, and —SO$_2$NH—;

E is selected from —S(O)$_p$—, —C(O)—, —OC(O)NH—, —NHC(O)O—, and —NHC(O)NH—;

$R^1$ is selected from a $C_{6-10}$ aryl group substituted with 0-5 R$^6$ and a 5-10 membered heteroaryl system containing 1-4 heteroatoms selected from N, O, and S, substituted with 0-3 R$^6$;

$R^2$ is selected from a $C_{6-10}$ aryl group substituted with 0-5 R$^7$ and a 5-10 membered heteroaryl system containing 1-4 heteroatoms selected from N, O, and S, substituted with 0-3 R$^7$;

$R^4$ is selected from H, $C_{1-6}$ alkyl, $C_{3-8}$ alkenyl, $C_{3-8}$ alkynyl, (CRR)$_q$OH, (CRR)$_r$SH, (CRR)$_r$OR$^{4d}$, (CHR)$_r$SR$^{4d}$, (CRR)$_r$NR$^{4a}$R$^{4a}$, (CRR)$_q$C(O)OH, (CRR)$_r$C(O)R$^{4b}$, (CRR)$_r$C(O)NR$^{4a}$R$^{4a}$, (CRR)$_r$OC(O)NR$^{4a}$R$^{4a}$, (CRR)$_t$NR$^{4a}$C(O)OR$^{4d}$, (CRR)$_t$NR$^{4a}$C(O)R$^{4b}$, (CRR)$_t$C(O)OR$^{4b}$, (CRR)$_t$OC(O)R$^{4b}$, (CRR)$_s$S(O)$_p$R$^{4b}$, (CRR)$_s$S(O)$_2$NR$^{4a}$R$^{4a}$, (CRR)$_t$NR$^{4a}$S(O)$_2$R$^{4b}$, $C_{1-6}$ haloalkyl, a (CRR)$_r$—C$_{3-10}$ carbocyclic residue substituted with 0-3 R$^{4e}$, and a (CHR)$_r$-4-10 membered heterocyclic system containing 1-4 heteroatoms selected from N, O, and S, substituted with 0-2 R$^{4e}$;

$R^{4a}$, at each occurrence, is independently selected from H, methyl substituted with 0-1 R$^{4c}$, $C_{2-6}$ alkyl substituted with 0-3 R$^{4e}$, $C_{3-8}$ alkenyl substituted with 0-3 R$^{4e}$, $C_{3-8}$ alkynyl substituted with 0-3 R$^{4e}$, a (CH$_2$)$_r$—C$_{3-10}$ carbocyclic residue substituted with 0-4 R$^{4e}$, and a (CHR)$_r$-4-10 membered heterocyclic system containing 1-4 heteroatoms selected from N, O, and S, substituted with 0-2 R$^{4e}$;

$R^{4b}$, at each occurrence, is selected from H, $C_{1-6}$ alkyl substituted with 0-3 R$^{4e}$, $C_{3-8}$ alkenyl substituted with 0-3 R$^{4e}$, $C_{3-8}$ alkynyl substituted with 0-3 R$^{4e}$, a (CH$_2$)$_r$—C$_{3-6}$ carbocyclic residue substituted with 0-2 R$^{4e}$, and a (CHR)$_r$-4-10 membered heterocyclic system containing 1-4 heteroatoms selected from N, O, and S, substituted with 0-2 R$^{4e}$;

$R^{4c}$ is independently selected from —C(O)R$^{4b}$, —C(O)OR$^{4d}$, —C(O)NR$^{4f}$R$^{4f}$, and (CH$_2$)$_r$phenyl;

$R^{4d}$, at each occurrence, is selected from methyl, CF$_3$, $C_{1-6}$ alkyl substituted with 0-3 R$^{4e}$, $C_{3-8}$ alkenyl substituted with 0-3 R$^{4e}$, $C_{3-8}$ alkynyl substituted with 0-3 R$^{4e}$, and a $C_{3-10}$ carbocyclic residue substituted with 0-3 R$^{4e}$;

$R^{4e}$, at each occurrence, is selected from $C_{1-6}$ alkyl, $C_{2-8}$ alkenyl, $C_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$ SC$_{1-5}$ alkyl, (CH$_2$)$_r$NR$^{4f}$R$^{4f}$, —C(O)R$^{4i}$, —C(O)OR$^{4j}$, —C(O)NR$^{4h}$R$^{4h}$, —OC(O)NR$^{4h}$R$^{4h}$, —NR$^{4h}$C(O) NR$^{4h}$R$^{4h}$, —NR$^{4h}$C(O)OR$^{4j}$, and (CH$_2$)$_r$phenyl;

R$^{4f}$, at each occurrence, is selected from H, C$_{1-6}$ alkyl, C$_{3-6}$ cycloalkyl, and phenyl;

R$^{4h}$, at each occurrence, is independently selected from H, C$_{1-6}$ alkyl, C$_{3-8}$ alkenyl, C$_{3-8}$ alkynyl, and a (CH$_2$)$_r$—C$_{3-10}$ carbocyclic;

R$^{4i}$, at each occurrence, is selected from H, C$_{1-6}$ alkyl, C$_{3-8}$ alkenyl, C$_{3-8}$ alkynyl, and a (CH$_2$)$_r$—C$_{3-6}$ carbocyclic residue;

R$^{4j}$, at each occurrence, is selected from CF$_3$, C$_{1-6}$ alkyl, C$_{3-8}$ alkenyl, C$_{3-8}$ alkynyl, and a C$_{3-10}$ carbocyclic residue;

R$^5$, at each occurrence, is independently selected from H, =O, C$_{1-6}$ alkyl, C$_{2-8}$ alkenyl, C$_{2-8}$ alkynyl, (CRR)$_r$OH, (CRR)$_r$SH, (CRR)$_r$OR$^{5d}$, (CRR)$_r$SR$^{5d}$, (CRR)$_r$NR$^{5a}$R$^{5a}$, (CRR)$_r$C(O)OH, (CRR)$_r$C(O)R$^{5b}$, (CRR)$_r$C(O)NR$^{5a}$R$^{5a}$, (CRR)$_r$NR$^{5a}$C(O)R$^{5b}$, (CRR)$_r$OC(O)NR$^{5a}$R$^{5a}$, (CRR)$_r$NR$^{5a}$C(O)OR$^{5d}$, (CRR)$_r$NR$^{5a}$C(O)NR$^{5a}$R$^{5a}$, (CRR)$_r$NR$^{5a}$C(O)H, (CRR)$_r$C(O)OR$^{5b}$, (CRR)$_r$OC(O)R$^{5b}$, (CRR)$_r$S(O)$_p$R$^{5b}$, (CRR)$_r$S(O)$_2$NR$^{5a}$R$^{5a}$, (CRR)$_r$NR$^{5a}$S (O)$_2$R$^{5b}$, (CRR)$_r$NR$^{5a}$S(O)$_2$ NR$^{5a}$R$^{5a}$, C$_{1-6}$ haloalkyl, a (CRR)$_r$—C$_{3-10}$ carbocyclic residue substituted with 0-3 R$^{5c}$, and a (CRR)$_r$-5-10 membered heterocyclic system containing 1-4 heteroatoms selected from N, O, and S, substituted with 0-2 R$^{5c}$;

R$^{5a}$, at each occurrence, is independently selected from H, methyl substituted with 0-1 R$^{5g}$, C$_{2-6}$ alkyl substituted with 0-2 R$^{5e}$, C$_{3-8}$ alkenyl substituted with 0-2 R$^{5e}$, C$_{3-8}$ alkynyl substituted with 0-2 R$^{5e}$, a (CH$_2$)$_r$—C$_{3-10}$ carbocyclic residue substituted with 0-5 R$^{5e}$, and a (CH$_2$)$_r$-5-10 membered heterocyclic system containing 1-4 heteroatoms selected from N, O, and S, substituted with 0-3 R$^{5e}$;

R$^{5b}$, at each occurrence, is selected from C$_{1-6}$ alkyl substituted with 0-3 R$^{5e}$, C$_{3-8}$ alkenyl substituted with 0-2 R$^{5e}$, C$_{3-8}$ alkynyl substituted with 0-2 R$^{5e}$, a (CH$_2$)$_r$—C$_{3-6}$ carbocyclic residue substituted with 0-2 R$^{5e}$, and a (CH$_2$)$_r$-5-6 membered heterocyclic system containing 1-4 heteroatoms selected from N, O, and S, substituted with 0-3 R$^{5e}$;

R$^{5c}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{5f}$R$^{5f}$, (CH$_2$)$_r$OH, (CH$_2$)$_r$ OC$_{1-4}$ alkyl, (CH$_2$)$_r$SC$_{1-4}$ alkyl, (CH$_2$)$_r$C(O)OH, (CH$_2$)$_r$C (O)R$^{5b}$, (CH$_2$)$_r$C(O)NR$^{5f}$R$^{5f}$, (CH$_2$)$_r$NR$^{5f}$C(O)R$^{5b}$, (CH$_2$)$_r$C(O)OC$_{1-4}$ alkyl, (CH$_2$)$_r$OC(O)R$^{5b}$, (CH$_2$)$_r$C (=NR$^{5f}$)NR$^{5f}$R$^{5f}$, (CH$_2$)$_r$S(O)$_p$R$^{5b}$, (CH$_2$)$_r$NHC(=NR$^{5f}$) NR$^{5f}$R$^{5f}$, (CH$_2$)$_r$S(O)$_2$NR$^{5f}$R$^{5f}$, (CH$_2$)$_r$NR$^{5f}$S(O)$_2$R$^{5b}$, and (CH$_2$)$_r$phenyl substituted with 0-3 R$^{5e}$;

R$^{5d}$, at each occurrence, is selected from methyl, CF$_3$, C$_{2-6}$ alkyl substituted with 0-2 R$^{5e}$, C$_{3-8}$ alkenyl substituted with 0-2 R$^{5e}$, C$_{3-8}$ alkynyl substituted with 0-2 R$^{5e}$, and a C$_{3-10}$ carbocyclic residue substituted with 0-3 R$^{5e}$;

R$^{5e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$ SC$_{1-5}$ alkyl, (CH$_2$)$_r$NR$^{5f}$R$^{5f}$, and (CH$_2$)$_r$phenyl;

R$^{5f}$, at each occurrence, is selected from H, C$_{1-6}$ alkyl, and C$_{3-6}$ cycloalkyl;

R$^{5g}$ is independently selected from —C(O)R$^{5b}$, —C(O) OR$^{5d}$, —C(O)NR$^{5f}$R$^{5f}$, and (CH$_2$)$_r$phenyl;

R, at each occurrence, is selected from H, C$_{1-6}$ alkyl substituted with R$^{5e}$, C$_{2-8}$ alkenyl, C$_{2-8}$ alkynyl, (CH$_2$)$_r$C$_{3-6}$ cycloalkyl, and (CH$_2$)$_r$phenyl substituted with R$^{5e}$;

R$^6$, at each occurrence, is selected from C$_{1-8}$ alkyl, C$_{2-8}$ alkenyl, C$_{2-8}$ alkynyl, (CH$_2$)$_r$C$_{3-6}$ cycloalkyl, Cl, Br, I, F, NO$_2$, CN, (CR'R')$_r$NR$^{6a}$R$^{6a}$, (CR'R')$_r$OH, (CR'R')$_r$O(CR'R')$_r$ R$^{6d}$, (CR'R')$_r$SH, (CR'R')$_r$C(O)H, (CR'R')$_r$S(CR'R')$_r$R$^{6d}$, (CR'R')$_r$SC(O) (CR'R)$_r$R$^{6b}$, (CR'R')$_r$C(O)OH, (CR'R')$_r$C (O) (CR'R')$_r$R$^{6b}$, (CR'R')$_r$NR$^{6a}$R$^{6a}$, (CR'R')$_r$C(O) NR$^{6a}$R$^{6a}$, (CR'R')$_r$NR$^{6f}$C(O) (CR'R')$_r$R$^{6b}$, (CR'R')$_r$C(O)O (CR'R')$_r$R$^{6d}$, (CR'R')$_r$OC(O) (CR'R')$_r$R$^{6b}$, (CR'R')$_r$OC(O) NR$^{6a}$(CR'R')$_r$R$^{6d}$, (CR'R')$_r$NR$^{6a}$C(O)NR$^{6a}$(CR'R')$_r$R$^{6d}$, (CR'R')$_r$NR$^{6a}$C(S)NR$^{6a}$(CR'R')$_r$R$^{6d}$, (CR'R')$_r$NR$^{6f}$C(O)O (CR'R')$_r$R$^{6b}$, (CR'R')$_r$C(=NR$^{6f}$)NR$^{6a}$R$^{6a}$, (CR'R')$_r$NHC (=NR$^{6f}$)NR$^{6f}$R$^{6f}$, (CR'R')$_r$S(O)$_p$(CR'R')$_r$R$^{6b}$, (CR'R')$_r$S (O)$_2$NR$^{6a}$R$^{6a}$, (CR'R')$_r$NR$^{6f}$S(O)$_2$NR$^{6a}$R$^{6a}$, (CR'R')$_r$ NR$^{6f}$S(O)$_2$(CR'R')$_r$R$^{6b}$, C$_{1-6}$ haloalkyl, C$_{2-8}$ alkenyl substituted with 0-3 R', C$_{2-8}$ alkynyl substituted with 0-3 R', and (CR'R')$_r$phenyl substituted with 0-3 R$^{6e}$;

alternatively, two R$^6$ on adjacent atoms on R$^1$ may join to form a cyclic acetal;

R$^{6a}$, at each occurrence, is selected from H, methyl substituted with 0-1 R$^{6g}$, C$_{2-6}$ alkyl substituted with 0-2 R$^{6e}$, C$_{3-8}$ alkenyl substituted with 0-2 R$^{6e}$, C$_{3-8}$ alkynyl substituted with 0-2 R$^{6e}$, a (CH$_2$)$_r$—C$_{3-10}$ carbocyclic residue substituted with 0-5 R$^{6e}$, and a (CH$_2$)$_r$-5-10 membered heterocyclic system containing 1-4 heteroatoms selected from N, O, and S, substituted with 0-2 R$^{6e}$; R$^{6b}$, at each occurrence, is selected from H, C$_{1-6}$ alkyl substituted with 0-2 R$^{6e}$, C$_{3-8}$ alkenyl substituted with 0-2 R$^{6e}$, C$_{3-8}$ alkynyl substituted with 0-2 R$^{6e}$, a (CH$_2$)$_r$C$_{3-6}$ carbocyclic residue substituted with 0-3 R$^{6e}$, and a (CH$_2$)$_r$-5-6 membered heterocyclic system containing 1-4 heteroatoms selected from N, O, and S, substituted with 0-2 R$^{6e}$;

R$^{6d}$, at each occurrence, is selected from C$_{3-8}$ alkenyl substituted with 0-2 R$^{6e}$, C$_{3-8}$ alkynyl substituted with 0-2 R$^{6e}$, methyl, CF$_3$, C$_{2-6}$ alkyl substituted with 0-3 R$^{6e}$, a (CH$_2$)$_r$—C$_{3-10}$ carbocyclic residue substituted with 0-3 R$^{6e}$, and a (CH$_2$)$_r$-5-6 membered heterocyclic system containing 1-4 heteroatoms selected from N, O, and S, substituted with 0-3 R$^{6e}$;

R$^{6e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$ SC$_{1-5}$ alkyl, (CH$_2$)$_r$NR$^{6f}$R$^{6f}$, and (CH$_2$)$_r$phenyl;

R$^{6f}$, at each occurrence, is selected from H, C$_{1-5}$ alkyl, and C$_{3-6}$ cycloalkyl, and phenyl;

R$^{6g}$ is independently selected from —C(O)R$^{6b}$, —C(O) OR$^{6d}$, —C(O)NR$^{6f}$R$^{6f}$, and (CH$_2$)$_r$phenyl;

R$^7$, at each occurrence, is selected from C$_{1-8}$ alkyl, C$_{2-8}$ alkenyl, C$_{2-8}$ alkynyl, (CH$_2$)$_r$C$_{3-6}$ cycloalkyl, Cl, Br, I, F, NO$_2$, CN, (CR'R')$_r$NR$^{7a}$R$^{7a}$, (CR'R')$_r$OH, (CR'R')$_r$O(CR'R')$_r$ R$^{7d}$, (CR'R')$_r$SH, (CR'R')$_r$C(O)H, (CR'R')$_r$S(CR'R')$_r$R$^{7d}$, (CR'R')$_r$C(O)OH, (CR'R')$_r$C(O) (CR'R')$_r$R$^{7b}$, (CR'R')$_r$C (O)NR$^{7a}$R$^{7a}$, (CR'R')$_r$NR$^{7f}$C(O) (CR'R')$_r$R$^{7b}$, (CR'R')$_r$C (O)O(CR'R')$_r$R$^{7d}$, (CR'R')$_r$OC(O) (CR'R')$_r$R$^{7b}$, (CR'R')$_r$ OC(O)NR$^{7a}$(CR'R')$_r$R$^{7a}$, (CR'R')$_r$NR$^{7a}$C(O)NR$^{7a}$ (CR'R')$_r$R$^{7a}$, (CR'R')$_r$NR$^{7f}$C(O)O(CR'R')$_r$R$^{7b}$, (CR'R')$_r$C (=NR$^{7f}$)NR$^{7a}$R$^{7a}$, (CR'R')$_r$NHC(=NR$^{7f}$)NR$^{7f}$R$^{7f}$, (CR'R')$_r$S(O)$_p$(CR'R')$_r$R$^{7b}$, (CR'R')$_r$S(O)$_2$NR$^{7a}$R$^{7a}$, (CR'R')$_r$NR$^{7a}$S(O)$_2$NR$^{7a}$R$^{7a}$, (CR'R')$_r$NR$^{7f}$S(O)$_2$(CR'R')$_r$ R$^{7b}$, C$_{1-6}$ haloalkyl, C$_{2-8}$ alkenyl substituted with 0-3 R', C$_{2-8}$ alkynyl substituted with 0-3 R', and (CR'R')$_r$phenyl substituted with 0-3 R$^{7e}$;

alternatively, two R$^7$ on adjacent atoms on R$^2$ may join to form a cyclic acetal;

R$^{7a}$, at each occurrence, is independently selected from H, methyl substituted with 0-1 R$^{7g}$, C$_{2-6}$ alkyl substituted with 0-2 R$^{7e}$, C$_{3-8}$ alkenyl substituted with 0-2 R$^{7e}$, C$_{3-8}$ alkynyl substituted with 0-2 R$^{7e}$, a (CH$_2$)$_r$—C$_{3-10}$ carbocyclic residue substituted with 0-5 R$^{7e}$, and a (CH$_2$)$_r$-5-10 membered heterocyclic system containing 1-4 heteroatoms selected from N, O, and S, substituted with 0-2 R$^{7e}$;

$R^{7b}$, at each occurrence, is selected from $C_{1-6}$ alkyl substituted with 0-2 $R^{7e}$, $C_{3-8}$ alkenyl substituted with 0-2 $R^{7e}$, $C_{3-8}$ alkynyl substituted with 0-2 $R^{7e}$, a $(CH_2)_r$-$C_{3-6}$ carbocyclic residue substituted with 0-3 $R^{7e}$, and a $(CH_2)_r$-$5^{-6}$ membered heterocyclic system containing 1-4 heteroatoms selected from N, O, and S, substituted with 0-2 $R^{7e}$;

$R^{7d}$, at each occurrence, is selected from $C_{3-8}$ alkenyl substituted with 0-2 $R^{7e}$, $C_{3-8}$ alkynyl substituted with 0-2 $R^{7e}$, methyl, $CF_3$, $C_{2-6}$ alkyl substituted with 0-3 $R^{7e}$, a $(CH_2)_r$-$C_{3-10}$ carbocyclic residue substituted with 0-3 $R^{7e}$, and a $(CH_2)_r$-$5^{-6}$ membered heterocyclic system containing 1-4 heteroatoms selected from N, O, and S, substituted with 0-3 $R^{7e}$;

$R^{7e}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, F, Br, I, CN, $NO_2$, $(CF_2)_r CF_3$, $(CH_2)_r OC_{1-5}$ alkyl, OH, SH, $C(O)OC_{1-5}$ alkyl, $(CH_2)_r SC_{1-5}$ alkyl, $(CH_2)_r NR^{7f}R^{7f}$, and $(CH_2)_r$phenyl;

$R^{7f}$, at each occurrence, is selected from H, $C_{1-5}$ alkyl, and $C_{3-6}$ cycloalkyl, and phenyl;

$R^{7g}$ is independently selected from $-C(O)R^{7b}$, $-C(O)OR^{7d}$, $-C(O)NR^{7f}R^{7f}$, and $(CH_2)_r$phenyl;

R', at each occurrence, is selected from H, $C_{1-6}$ alkyl substituted with $R^{6e}$, $C_{2-8}$ alkenyl, $C_{2-8}$ alkynyl, $(CH_2)_r C_{3-6}$ cycloalkyl, and $(CH_2)_r$phenyl substituted with $R^{6e}$;

$R^8$ is selected from H, $C_{1-4}$ alkyl, and $C_{3-4}$ cycloalkyl;

$R^{10}$ and $R^{10a}$ are independently selected from H, and $C_{1-4}$alkyl substituted with 0-1 $R^{10b}$, alternatively, $R^{10}$ and $R^{10a}$ can join to form a $C_{3-6}$ cycloalkyl;

$R^{10b}$, at each occurrence, is independently selected from $-OH$, $-SH$, $-NR^{10c}R^{10c}$, $-C(O)NR^{10c}R^{10c}$, and $-NHC(O)R^{10c}$;

$R^{10c}$ is selected from H, $C_{1-4}$ alkyl and $C_{3-6}$ cycloalkyl;

$R^{11}$ is selected from H, $C_{1-4}$ alkyl, $(CHR)_q OH$, $(CHR)_q SH$, $(CHR)_q OR^{11d}$, $(CHR)_q S(O)_p R^{11d}$, $(CHR)_r C(O)R^{11b}$, $(CHR)_r NR^{11a}R^{11a}$, $(CHR)_r C(O)NR^{11a}R^{11a}$, $(CHR)_r C(O)NR^{11a}OR^{11d}$, $(CHR)_q NR^{11a}C(O)R^{11b}$, $(CHR)_q NR^{11a}C(O)OR^{11d}$, $(CHR)_q OC(O)NR^{11a}R^{11a}$, $(CHR)_r C(O)OR^{11d}$, a $(CHR)_r$-$C_{3-6}$ carbocyclic residue substituted with 0-5 $R^{11e}$, and a $(CHR)_r$-5-10 membered heterocyclic system containing 1-4 heteroatoms selected from N, O, and S, substituted with 0-3 $R^{11e}$;

$R^{11a}$, at each occurrence, is independently selected from H, $C_{1-4}$ alkyl, $C_{3-4}$ alkenyl, $C_{3-4}$ alkynyl, $(CH_2)_r C_{3-6}$ cycloalkyl, a $(CH_2)_r$-$C_{3-6}$ carbocyclic residue substituted with 0-5 $R^{11e}$, and a $(CH_2)_r$-$5^{-6}$ membered heterocyclic system containing 1-4 heteroatoms selected from N, O, and S, substituted with 0-3 $R^{11e}$;

$R^{11b}$, at each occurrence, is independently selected from $C_{1-4}$ alkyl, $C_{2-4}$ alkenyl, $C_{2-4}$ alkynyl, a $(CH_2)_r$-$C_{3-6}$ carbocyclic residue substituted with 0-2 $R^{11e}$, and a $(CH_2)_r$-5-6 membered heterocyclic system containing 1-4 heteroatoms selected from N, O, and S, substituted with 0-3 $R^{11e}$;

$R^{11d}$, at each occurrence, is independently selected from H, methyl, $-CF_3$, $C_{2-4}$ alkyl, $C_{3-6}$ alkenyl, $C_{3-6}$ alkynyl, a $C_{3-6}$ carbocyclic residue substituted with 0-3 $R^{11e}$, and a $(CH_2)_r$-$5^{-6}$ membered heterocyclic system containing 1-4 heteroatoms selected from N, O, and S, substituted with 0-3 $R^{11e}$;

$R^{11e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_r CF_3$, $(CH_2)_r OC_{1-5}$ alkyl, OH, $-O-C_{1-6}$ alkyl, SH, $(CH_2)_r SC_{1-5}$ alkyl, $(CH_2)_r NR^{11f}R^{11f}$, and $(CH_2)_r$phenyl;

$R^{11f}$, at each occurrence, is selected from H, $C_{1-6}$ alkyl, and $C_{3-6}$ cycloalkyl;

$R^{12}$ is selected from H, $C_{1-4}$ alkyl, $(CHR)_q OH$, $(CHR)_q SH$, $(CHR)_q OR^{12d}$, $(CHR)_q S(O)_p R^{12d}$, $(CHR)_r C(O)R^{12b}$, $(CHR)_r NR^{12a}R^{12a}$, $(CHR)_r C(O)NR^{12a}R^{12a}$, $(CHR)_r C(O)NR^{12a}OR^{12d}$, $(CHR)_q NR^{12a}C(O)R^{12b}$, $(CHR)_q NR^{12a}C(O)OR^{12d}$, $(CHR)_q OC(O)NR^{12a}R^{12a}$, $(CHR)_r C(O)OR^{12d}$, a $(CHR)_r$-$C_{3-6}$ carbocyclic residue substituted with 0-5 $R^{12e}$, and a $(CHR)_r$-5-10 membered heterocyclic system containing 1-4 heteroatoms selected from N, O, and S, substituted with 0-3 $R^{12e}$;

$R^{12a}$, at each occurrence, is independently selected from H, $C_{1-4}$ alkyl, $C_{3-4}$ alkenyl, $C_{3-4}$ alkynyl, $(CH_2)_r C_{3-6}$ cycloalkyl, a $(CH_2)_r$-$C_{3-6}$ carbocyclic residue substituted with 0-5 $R^{12e}$, and a $(CH_2)_r$-$5^{-6}$ membered heterocyclic system containing 1-4 heteroatoms selected from N, O, and S, substituted with 0-3 $R^{12e}$;

$R^{12b}$, at each occurrence, is independently selected from $C_{1-4}$ alkyl, $C_{2-4}$ alkenyl, $C_{2-4}$ alkynyl, a $(CH_2)_r$-$C_{3-6}$ carbocyclic residue substituted with 0-2 $R^{12e}$, and a $(CH_2)_r$-$5^{-6}$ membered heterocyclic system containing 1-4 heteroatoms selected from N, O, and S, substituted with 0-3 $R^{12e}$;

$R^{12d}$, at each occurrence, is independently selected from H, methyl, $-CF_3$, $C_{2-4}$ alkyl, $C_{3-6}$ alkenyl, $C_{3-6}$ alkynyl, a $C_{3-6}$ carbocyclic residue substituted with 0-3 $R^{12e}$, and a $(CH_2)_r$-$5^{-6}$ membered heterocyclic system containing 1-4 heteroatoms selected from N, O, and S, substituted with 0-3 $R^{12e}$;

$R^{12e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_r CF_3$, $(CH_2)_r OC_{1-5}$ alkyl, OH, $-O-C_{1-16}$ alkyl, SH, $(CH_2)_r SC_{1-5}$ alkyl, $(CH_2)_r NR^{12f}R^{12f}$, and $(CH_2)_r$phenyl;

$R^{12f}$, at each occurrence, is selected from H, $C_{1-6}$ alkyl, and $C_{3-6}$ cycloalkyl;

$R^{13}$, at each occurrence, is independently selected from H, methyl, $C_{2-4}$ alkyl substituted with 0-1 $R^{13b}$;

$R^{13b}$ is selected from $-OH$, $-SH$, $-NR^{13c}R^{13c}$, $-C(O)NR^{13c}R^{13c}$, and $-NHC(O)R^{13}C$;

$R^{13c}$ is selected from H, $C_{1-4}$ alkyl and $C_{3-6}$ cycloalkyl;

n is selected from 1 and 2;

m is selected from 0 and 1;

p, at each occurrence, is independently selected from 0, 1, and 2;

q, at each occurrence, is independently selected from 1, 2, 3, and 4;

r, at each occurrence, is independently selected from 0, 1, 2, 3, and 4;

s, at each occurrence, is independently selected from 0 and 1; and t, at each occurrence, is independently selected from 2, 3, and 4.

[3] In another embodiment, the present invention provides novel compounds of formula (Ia), wherein:

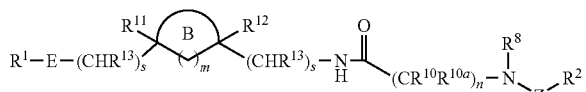

(Ia)

$R^4$ is selected from H, $C_{1-6}$ alkyl, $C_{3-8}$ alkenyl, $C_{3-8}$ alkynyl, $(CRR)_t OH$, $(CRR)_t SH$, $(CRR)_t OR^{4d}$, $(CHR)_t SR^{4d}$, $(CRR)_t NR^{4a}R^{4a}$, $(CRR)_q C(O)OH$, $(CRR)_t C(O)R^{4b}$, $(CRR)_t C(O)NR^{4a}R^{4a}$, $(CRR)_t OC(O)NR^{4a}R^{4a}$, $(CRR)_t NR^{4a}C(O)OR^{4d}$, $(CRR)_t NR^{4a}C(O)R^{4b}$, $(CRR)_t C(O)OR^{4b}$, $(CRR)_t OC(O)R^{4b}$, $(CRR)_r S(O)_p R^{4b}$, $(CRR)_r S(O)_2 NR^{4a}R^{4a}$, (CRR)$_r$NR$^{4a}$S(O)$_2$R$^{4b}$, C$_{1-6}$ haloalkyl, a (CRR)$_r$—C$_{3-10}$ carbocyclic residue substituted with 0-3 R$^{4e}$, and a (CHR)$_r$-4-10 membered heterocyclic system containing 1-4 heteroatoms selected from N, O, and S, substituted with 0-2 R$^{4e}$;

R$^5$, at each occurrence, is independently selected from H, =O, C$_{1-6}$ alkyl, C$_{2-8}$ alkenyl, C$_{2-8}$ alkynyl, (CRR)$_r$OH, (CRR)$_r$SH, (CRR)$_r$OR$^{5d}$, (CRR)$_r$SR$^{5d}$, (CRR)$_r$NR$^{5a}$R$^{5a}$, (CRR)$_r$C(O)OH, (CRR)$_r$C(O)R$^{5b}$, (CRR)$_r$C(O)NR$^{5a}$R$^{5a}$, (CRR)$_r$NR$^{5a}$C(O)R$^{5b}$, (CRR)$_r$OC(O)NR$^{5a}$R$^{5a}$, (CRR)$_r$NR$^{5a}$C(O)OR$^{5d}$, (CRR)$_r$NR$^{5a}$C(O)NR$^{5a}$R$^{5a}$, (CRR)$_r$NR$^{5a}$C(O)H, (CRR)$_r$C(O)OR$^{5b}$, (CRR)$_r$OC(O)R$^{5b}$, (CRR)$_r$S(O)$_p$R$^{5b}$, (CRR)$_r$S(O)$_2$NR$^{5a}$R$^{5a}$, (CRR)$_r$NR$^{5a}$S(O)$_2$R$^{5b}$, (CRR)$_r$NR$^{5a}$S(O)$_2$ NR$^{5a}$R$^{5a}$, C$_{1-6}$ haloalkyl, a (CRR)$_r$—C$_{3-10}$ carbocyclic residue substituted with 0-3 R$^{5c}$, and a (CRR)$_r$-5-10 membered heterocyclic system containing 1-4 heteroatoms selected from N, O, and S, substituted with 0-2 R$^{5c}$;

R, at each occurrence, is selected from H, C$_{1-6}$ alkyl substituted with 0-3 R$^{5e}$, C$_{2-8}$ alkenyl, C$_{2-8}$ alkynyl, (CH$_2$)$_r$C$_{3-6}$ cycloalkyl, and (CH$_2$)$_r$phenyl substituted with R$^{5e}$;

R$^{7b}$, at each occurrence, is selected from C$_{1-6}$ alkyl substituted with 0-2 R$^{7e}$, C$_{3-8}$ alkenyl substituted with 0-2 R$^{7e}$, C$_{3-8}$ alkynyl substituted with 0-2 R$^{7e}$, a (CH$_2$)$_r$C$_{3-6}$ carbocyclic residue substituted with 0-3 R$^{7e}$, and a (CH$_2$)$_r$-5-6 membered heterocyclic system containing 1-4 heteroatoms selected from N, O, and S, substituted with 0-2 R$^{7e}$;

R', at each occurrence, is selected from H, C$_{1-6}$ alkyl substituted with 0-3 R$^{6e}$, C$_{2-8}$ alkenyl, C$_{2-8}$ alkynyl, (CH$_2$)$_r$C$_{3-6}$ cycloalkyl, and (CH$_2$)$_r$phenyl substituted with R$^{6e}$.

Thus, in a another embodiment, the present invention provides novel compounds of formula (I) or (Ia):
R$^{10}$ and R$^{10a}$ are H; and
n is 1.

[3] In another embodiment, the present invention provides novel compounds of formula (I) or (Ia), wherein:
ring B is selected from

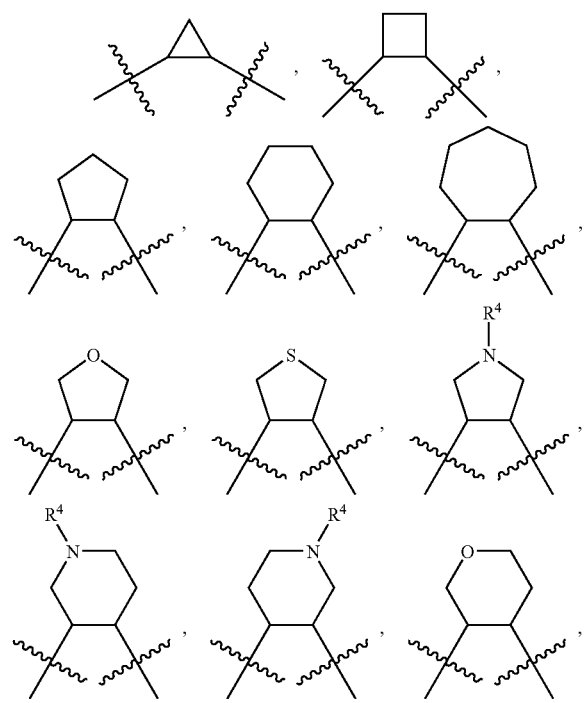

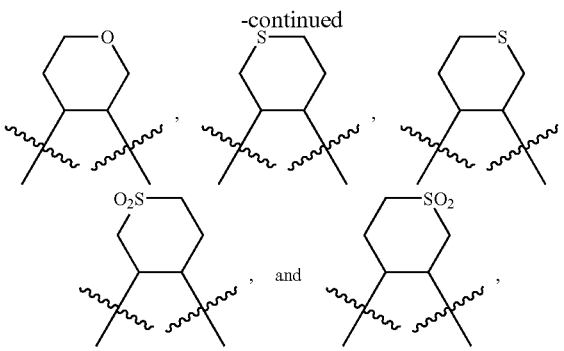

ring B being optionally substituted with 0-1 R$^5$; and
R$^{11}$ and R$^{12}$ are H.

[4] In another embodiment, the present invention provides novel compounds of formula (I) or (Ia), wherein:
R$^5$, at each occurrence, is independently selected from H, C$_{1-6}$ alkyl, C$_{2-8}$ alkenyl, C$_{2-8}$ alkynyl, (CRR)$_r$OH, (CRR)$_r$SH, (CRR)$_r$OR$^{5d}$, (CRR)$_r$SR$^{5d}$, (CRR)$_r$NR$^{5a}$R$^{5a}$, (CRR)$_r$C(O)OH, (CRR)$_r$C(O)R$^{5b}$, (CRR)$_r$C(O)NR$^{5a}$R$^{5a}$, (CRR)$_r$NR$^{5a}$C(O)R$^{5b}$, (CRR)$_r$NR$^{5a}$C(O)OR$^{5d}$, (CRR)$_r$OC(O)NR$^{5a}$R$^{5a}$, (CHR)$_r$NR$^{5a}$C(O)NR$^{5a}$R$^{5a}$, CRR(CRR)$_r$NR$^{5a}$C(O)H, (CRR)$_r$C(O)OR$^{5b}$, (CRR)$_r$OC(O)R$^{5b}$, (CRR)$_r$S(O)$_p$R$^{5b}$, (CRR)$_r$S(O)$_2$NR$^{5a}$R$^{5a}$, (CRR)$_r$NR$^{5a}$S(O)$_2$R$^{5b}$, and C$_{1-6}$ haloalkyl;

R$^{5a}$, at each occurrence, is independently selected from H, methyl, C$_{1-6}$ alkyl substituted with 0-2 R$^{5e}$ wherein the alkyl is selected from ethyl, propyl, i-propyl, butyl, i-butyl, pentyl, hexyl, C$_3$ alkenyl substituted with 0-1 R$^{5e}$, wherein the alkenyl is selected from allyl, C$_3$ alkynyl substituted with 0-1 R$^{5e}$ wherein the alkynyl is selected from propynyl, and a (CH$_2$)$_r$—C$_{3-4}$ carbocyclic residue substituted with 0-5 R$^{5e}$, wherein the carbocyclic residue is selected from cyclopropyl, and cyclobutyl;

R$^{5b}$, at each occurrence, is selected from C$_{1-6}$ alkyl substituted with 0-2 R$^{5e}$, wherein the alkyl is selected from methyl, ethyl, propyl, i-propyl, butyl, i-butyl, pentyl, and hexyl, a (CH$_2$)$_r$—C$_{3-4}$ carbocyclic residue substituted with 0-2 R$^{5e}$, wherein the carbocyclic residue is selected from cyclopropyl, and cyclobutyl; and R$^{5d}$, at each occurrence, is selected from methyl, CF$_3$, C$_{2-6}$ alkyl substituted with 0-2 R$^{5e}$, wherein the alkyl is selected from methyl, ethyl, propyl, i-propyl, butyl, i-butyl, pentyl, and hexyl, C$_{3-8}$ alkenyl, C$_{3-8}$ alkynyl, and a C$_{3-10}$ carbocyclic residue substituted with 0-3 R$^{5e}$.

[5] In another embodiment, the present invention provides novel compounds of formula (I) or (Ia), wherein:
R$^4$ is selected from H, C$_{1-6}$ alkyl, C$_{3-8}$ alkenyl, C$_{3-8}$ alkynyl, (CRR)$_r$OH, (CRR)$_r$SH, (CRR)$_r$OR$^{4d}$, (CRR)$_r$SR$^{4d}$, (CRR)$_t$NR$^{4a}$R$^{4a}$, (CRR)$_q$C(O)OH, (CRR)$_r$C(O)R$^{4b}$, (CRR)$_r$C(O)NR$^{4a}$R$^{4a}$, (CRR)$_r$NR$^{4a}$C(O)R$^{4b}$, (CRR)$_r$OC(O)NR$^{4a}$R$^{4a}$, (CRR)$_r$NR$^{4a}$C(O)OR$^{4d}$, (CRR)$_r$NR$^{4a}$C(O)R$^{4b}$, (CRR)$_r$C(O)OR$^{4b}$, (CRR)$_r$OC(O)R$^{4b}$, (CRR)$_r$S(O)$_p$R$^{4b}$, (CRR)$_r$S(O)$_2$NR$^{4a}$R$^{4a}$, (CRR)$_r$NR$^{4a}$S(O)$_2$R$^{4b}$;

R, at each occurrence, is independently selected from H, C$_{1-6}$ alkyl substituted with 0-3 R$^{5e}$, wherein the C$_{1-6}$ alkyl is selected from methyl, ethyl, propyl, allyl, propynyl, (CH$_2$)$_r$C$_{3-6}$ cycloalkyl, and (CH$_2$)$_r$phenyl substituted with R$^{6e}$;

R$^5$, at each occurrence, is independently selected from H, methyl, ethyl, propyl, i-propyl, butyl, i-butyl, allyl, propynyl, (CH$_2$)$_r$OH, (CH$_2$)$_r$OR$^{5d}$, (CH$_2$)$_r$NR$^{5a}$R$^{5a}$, (CH$_2$)$_r$C(O)OH, (CH$_2$)$_r$C(O)R$^{5b}$, (CH$_2$)$_r$C(O)NR$^{5a}$R$^{5a}$, (CH$_2$)$_r$ NR$^{5a}$C(O)R$^{5b}$, (CH$_2$)$_r$OC(O)NR$^{5a}$R$^{5a}$, (CH$_2$)$_r$NR$^{5a}$C(O)OR$^{5d}$, (CH$_2$)$_r$NR$^{5a}$C(O)R$^{5b}$, (CH$_2$)$_r$C(O)OR$^{5b}$, (CH$_2$)$_r$OC(O)R$^{5b}$, (CH$_2$)$_r$NR$^{5a}$S(O)$_2$R$^{5b}$, and C$_{1-6}$ haloalkyl;

R$^{5a}$, at each occurrence, is independently selected from H, methyl, ethyl, propyl, i-propyl, butyl, i-butyl, pentyl, hexyl, cyclopropyl, cyclobutyl phenyl, and benzyl; and r, at each occurrence, is selected from 0, 1, and 2.

[6] In another embodiment, the present invention provides novel compounds of formula (I) or (Ia), wherein:

R$^1$ is selected from phenyl substituted with 0-2 R$^6$, naphthyl substituted with 0-2R$^6$, and a 5-10 membered heteroaryl system containing 1-4 heteroatoms selected from N, O, and S, substituted with 0-3 R$^6$ wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl;

R$^2$ is selected from phenyl substituted with 0-2 R$^7$, and a 5-10 membered heteroaryl system containing 1-4 heteroatoms selected from N, O, and S, substituted with 0-3 R$^7$ wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, phthalazinyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl;

R$^4$ is selected from H, methyl, ethyl, propyl, i-propyl, butyl, i-butyl, allyl, propynyl, (CRR)$_t$OH, (CRR)$_t$SH, (CRR)$_t$OR$^{4d}$, (CRR)$_t$SR$^{4d}$, (CRR)$_t$NR$^{4a}$R$^{4a}$, (CRR)$_q$C(O)OH, (CRR)$_r$C(O)R$^{4b}$, (CRR)$_r$C(O)NR$^{4a}$R$^{4a}$, (CRR)$_r$NR$^{4a}$C(O)R$^{4b}$, (CRR)$_r$OC(O)NR$^{4a}$R$^{4a}$, (CRR)$_r$NR$^{4a}$C(O)OR$^{4d}$, (CRR)$_t$NR$^{4a}$C(O)R$^{4b}$, (CRR)$_r$C(O)OR$^{4b}$, (CRR)$_r$OC(O)R$^{4b}$, (CRR)$_r$S(O)$_p$R$^{4b}$, (CRR)$_r$S(O)$_2$NR$^{4a}$R$^{4a}$, (CRR)$_r$NR$^{4a}$S(O)$_2$R$^{4b}$;

R$^{4a}$, at each occurrence, is independently selected from H, methyl substituted with 0-1 R$^{4c}$, C$_{2-6}$ alkyl substituted with 0-3 R$^{4e}$ wherein C$_{2-6}$ is selected from ethyl, propyl, i-propyl, butyl, i-butyl, t-butyl, pentyl and hexyl, and a (CH$_2$)$_r$—C$_{3-6}$ carbocyclic residue substituted with 0-4 R$^{4e}$ wherein the carbocyclic residue is selected from cyclopropyl, cyclohexyl, and phenyl;

R$^{4b}$ is selected from H, methyl, ethyl, propyl, i-propyl, butyl, i-butyl, t-butyl, pentyl, and cyclopropyl;

R$^{4d}$ is selected from methyl, ethyl, propyl, i-propyl, butyl, i-butyl, t-butyl, pentyl, and cyclopropyl; and R$^8$ is selected from H, methyl, ethyl, propyl, i-propyl, and cyclopropyl.

[7] In another embodiment, the present invention provides novel compounds of formula (I) or (Ia), wherein:

R$^6$, at each occurrence, is selected from C$_{1-8}$ alkyl, C$_{2-8}$ alkenyl, C$_{2-8}$ alkynyl, (CR'R')$_r$C$_{3-6}$ cycloalkyl, Cl, Br, I, F, NO$_2$, CN, (CR'R')$_r$NR$^{6a}$R$^{6a}$, (CR'R')$_r$OH, (CR'R')$_r$O(CR'R')$_r$R$^{6d}$, (CR'R')$_r$SH, (CR'R')$_r$C(O)H, (CR'R')$_r$S(CR'R')$_r$R$^{6d}$, (CR'R')$_r$C(O)OH, (CR'R')$_r$C(O)(CR'R')$_r$R$^{6b}$, (CR'R')$_r$C(O)NR$^{6a}$R$^{6a}$, (CR'R')$_r$NR$^{6f}$C(O)(CR'R')$_r$R$^{6b}$, (CR'R')$_r$C(O)O(CR'R')$_r$R$^{6d}$, (CR'R')$_r$NR$^{6a}$C(O)NR$^{6a}$R$^{6a}$, (CR'R')$_r$NR$^{6a}$C(S)NR$^{6a}$R$^{6a}$, (CR'R')$_r$OC(O) (CR'R')$_r$R$^{6b}$, (CR'R')$_r$S(O)$_p$(CR'R')$_r$R$^{6b}$, (CR'R')$_r$S(O)$_2$NR$^{6a}$R$^{6a}$, (CR'R')$_r$NR$^{6f}$S(O)$_2$(CR'R')$_r$R$^{6b}$, (CR'R')$_r$NR$^{6f}$S(O)$_2$NR$^{6a}$R$^{6a}$, C$_{1-6}$ haloalkyl, and (CR'R')$_r$phenyl substituted with 0-3 R$^{6e}$; R$^{6a}$, at each occurrence, is independently selected from H, methyl, ethyl, propyl, i-propyl, butyl, i-butyl, t-butyl, pentyl, hexyl, cyclopropyl and phenyl;

R$^{6b}$, at each occurrence, is selected from methyl, ethyl, propyl, i-propyl, butyl, i-butyl, t-butyl, pentyl, hexyl, cyclopropyl, and phenyl;

R$^{6d}$, at each occurrence, is selected from methyl, CF$_3$, ethyl, propyl, i-propyl, butyl, i-butyl, t-butyl, pentyl, hexyl, cyclopropyl, and phenyl;

R$^{6e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{6f}$R$^{6f}$, and (CH$_2$)$_r$phenyl;

R$^{6f}$, at each occurrence, is selected from H, methyl, ethyl, propyl, i-propyl, butyl, i-butyl, t-butyl, pentyl, hexyl, cyclopropyl, and phenyl;

R$^7$ is selected from methyl, ethyl, propyl, i-propyl, butyl, i-butyl, s-butyl, t-butyl, pentyl, hexyl, (CR'R')$_r$C$_{3-6}$ cycloalkyl, Cl, Br, I, F, NO$_2$, CN, (CR'R')$_r$NR$^{7a}$R$^{7a}$, (CR'R')$_r$OH, (CR'R')$_r$O(CH)$_r$R$^{7d}$, (CR'R')$_r$SH, (CR'R')$_r$C(O)H, (CR'R')$_r$S(CR'R')$_r$R$^{7d}$, (CR'R')$_r$C(O)OH, (CR'R')$_r$C(O) (CR'R')$_r$R$^{7b}$, (CR'R')$_r$C(O)NR$^{7a}$R$^{7a}$, (CR'R')$_r$NR$^{7f}$C(O) (CR'R')$_r$R$^{7b}$, (CR'R')$_r$C(O)O(CR'R')$_r$R$^{7d}$, (CR'R')$_r$OC(O) CR'R')$_r$R$^{7b}$, (CR'R')$_r$NR$^{7a}$C(O)NR$^{7a}$R$^{7a}$, (CR'R')$_r$NR$^{7a}$C(O)O(CR'R')$_r$R$^{7d}$, (CR'R')$_r$S(O)$_p$(CR'R')$_r$R$^{7b}$, (CR'R')$_r$S(O)$_2$NR$^{7a}$R$^{7a}$, CR'R')$_r$NR$^{7f}$S(O)$_2$(CR'R')$_r$R$^{7b}$, C$_{1-6}$ haloalkyl, and (CR'R')$_r$phenyl substituted with 0-3 R$^{7e}$;

R$^{7a}$, at each occurrence, is selected from H, methyl, ethyl, propyl, i-propyl, butyl, i-butyl, t-butyl, pentyl, hexyl, prop-2-enyl, 2-methyl-2-propenyl, cyclopropyl, cyclobutyl, cyclopentyl, cyclohexyl, CH$_2$cyclopropyl, and benzyl;

R$^{7b}$, at each occurrence, is selected from methyl, ethyl, propyl, i-propyl, butyl, i-butyl, t-butyl, pentyl, hexyl, cyclopropyl, cyclopentyl, CH$_2$-cyclopentyl, cyclohexyl, CH$_2$-cyclohexyl, CF$_3$, pyrrolidinyl, morpholinyl, piperizenyl substituted with 0-1 R$^{7e}$, and azetidinyl;

R$^{7d}$, at each occurrence, is selected from methyl, CF$_3$, ethyl, propyl, i-propyl, butyl, i-butyl, t-butyl, pentyl, hexyl, and cyclopropyl;

R$^{7e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, C(O) OC$_{1-5}$ alkyl, (CH$_2$)$_r$SC$_{1-5}$ alkyl, (CH$_2$)$_r$NR$^{7f}$R$^{7f}$, and (CH$_2$)$_r$phenyl;

R$^{7f}$, at each occurrence, is selected from H, methyl, ethyl, propyl, i-propyl, butyl, i-butyl, t-butyl, pentyl, hexyl, cyclopropyl, and phenyl; and r is 0 or 1.

[8] In another embodiment, the present invention provides novel compounds of formula (I) or (Ia), wherein:

R$^7$ is selected from methyl, ethyl, propyl, i-propyl, butyl, i-butyl, s-butyl, pentyl, hexyl, Cl, Br, I, F, NO$_2$, NR$^{7a}$R$^{7a}$, NHC(O)NHR$^{7a}$, NR$^{7a}$C(O)R$^{7b}$, NR$^{7a}$C(O)OR$^{7d}$, CF$_3$, OCF$_3$, C(O)R$^{7b}$, C(O)OR$^{7d}$, NR$^{7f}$C(O)NR$^{7a}$R$^{7a}$, NHS(O)$_2$R$^{7b}$,

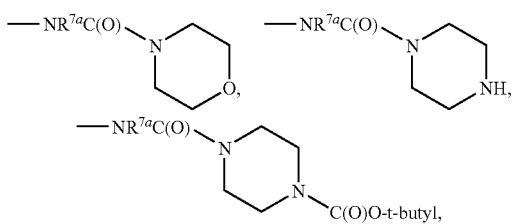

-continued

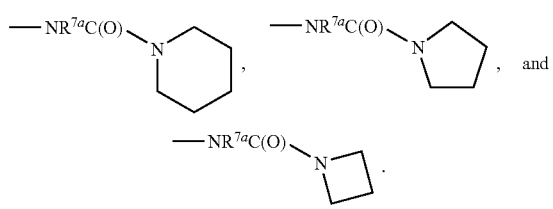

[9] In another embodiment, the present invention provides novel compounds of formula (I) or (Ia), wherein:
ring B is selected from

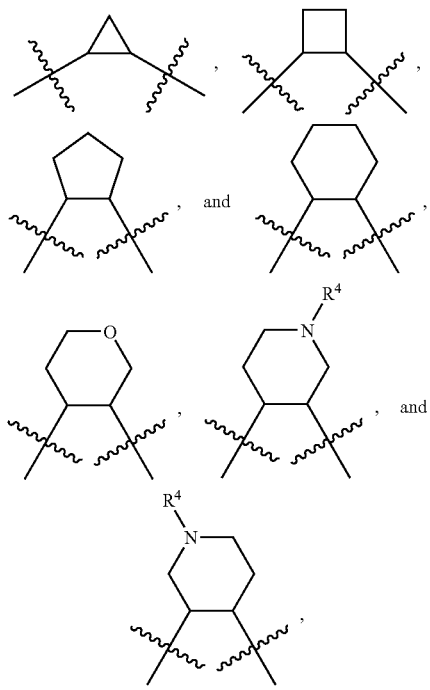

ring B being optionally substituted with 0-1 $R^5$;
Z is —C(O)—;
$R^1$ is selected from a $C_{6-10}$ aryl group substituted with 0-3 $R^6$ wherein the aryl group is selected from phenyl and naphthyl, and a 5-10 membered heteroaryl system containing 1-4 heteroatoms selected from N and O, substituted with 0-3 $R^6$ wherein the heteroaryl system is selected from indolyl and pyridinyl;
$R^2$ is phenyl substituted with 0-2 $R^7$;
$R^4$ is selected from H, methyl, ethyl, propyl, i-propyl, butyl, i-butyl, t-butyl, pentyl, hexyl, and $(CH_2)_r C(O)R^{4b}$;
$R^6$ is selected from methyl, ethyl, propyl, i-propyl, butyl, F, Cl, Br, I, $NO_2$, CN, $O(CH_2)_r R^{6d}$, C(O)H, $SR^{6d}$, $NR^{6a}R^{6a}$, $NC(O)R^{6b}$, $OC(O)R^{6b}$, $S(O)_p R^{6b}$, $(CHR')_r S(O)_2 NR^{6a}R^{6a}$, $CF_3$;
$R^{6a}$ is H, methyl, or ethyl;
$R^{6b}$ is H, or methyl;
$R^{6d}$ is methyl, phenyl, $CF_3$, and $(CH_2)$-phenyl; and
r is 0 or 1.

[10] In another embodiment, the present invention provides novel compounds of formula (I) or (Ia), wherein:
ring B is selected from

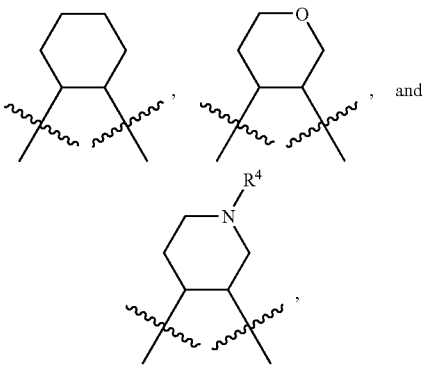

ring B being substituted with 0-1 $R^5$;
$R^1$ is selected from a $C_{6-10}$ aryl group substituted with 0-3 $R^6$ wherein the aryl group is selected from phenyl, and a 5-10 membered heteroaryl system containing 1-4 heteroatoms selected from N and O, substituted with 0-3 $R^6$ wherein the heteroaryl system is selected from indolyl and pyridinyl;
$R^4$ is selected from H, methyl, ethyl, propyl, i-propyl, butyl, i-butyl, t-butyl, pentyl, hexyl, allyl and $(CH_2)_r C(O)R^{4b}$;
$R^5$ is selected from H. OH, $OCH_3$, and $NR^{5a}R^{5a}$;
$R^{5a}$ is selected from H, methyl, ethyl, propyl, i-propyl, butyl, s-butyl, i-butyl, t-butyl, pentyl, hexyl, allyl cyclopropyl, cyclopropylmethyl, acetyl, methysulfonyl, —C(O)$CF_3$, C(=N)$NH_2$, benzyl, and —C(O)O-t-butyl;
$R^6$ is selected from methyl, ethyl, propyl, i-propyl, butyl, vinyl, F, Cl, Br, I, C(O)H, $SR^{6d}$, $S(O)_p R^{6d}$, $CF_3$, and $CH_2OH$;
$R^{6d}$ is methyl;
$R^7$ is selected from methyl, ethyl, propyl, i-propyl, butyl, i-butyl, s-butyl, pentyl, hexyl, Cl, Br, I, F, $NO_2$, $NR^{7a}R^{7a}$, $NHC(O)NHR^{7a}$, $NR^{7a}C(O)R^{7b}$, $NR^{7a}C(O)OR^{7d}$, $CF_3$, $OCF_3$, $C(O)OR^{7d}$, $C(O)R^{7b}$, $NR^{7f}C(O)NR^{7a}R^{7a}$, $NHS(O)_2 R^{7b}$,

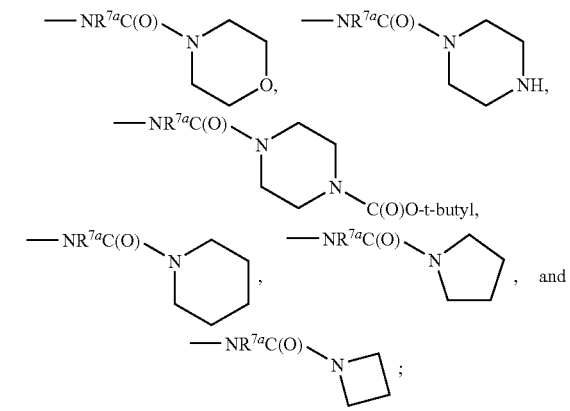

$R^{7a}$ is selected from H, methyl, ethyl, propyl, i-propyl, butyl, i-butyl, t-butyl, pentyl, neo-pentyl, cyclopropyl, cyclobutyl, cyclopentyl, and cyclohexyl;
$R^{7b}$ is selected from cyclohexyl and $CF_3$; and
$R^{7d}$ is selected from methyl, ethyl, propyl, i-propyl, butyl, i-butyl, and t-butyl.

[11] In another embodiment, the present invention provides novel compounds of formula (I) or (Ia), wherein:
E is —S(O)$_p$—.

[12] In another embodiment, the present invention provides novel compounds of formula (I) or (Ia), wherein:
E is —NHC(O)NH—.

[13] In another embodiment, the present invention provides novel compounds of formula (I) or (Ia), wherein:
Z is a bond; and
$R^2$ is a 5-10 membered heteroaryl system containing 1-4 heteroatoms selected from N, O, and S, substituted with 0-3 $R^7$ wherein the heteroaryl is selected from indolyl, naphthalenyl, phthalazinyl, cinnolinyl, quinolinyl, isoquinolinyl, indazolyl, and quinazolinyl, benzimidazolyl, benzofuranyl, benzothiofuranyl, benzoxazolyl, benzthiazolyl, benzisoxazolyl, and benzisothiazolyl.

[14] In another embodiment, the present invention provides novel compounds of formula (I) or (Ia), wherein
$R^5$, at each occurrence, is independently selected from H, $C_{1-6}$ alkyl, $N_3$, $C_{2-8}$ alkenyl, $C_{2-8}$ alkynyl, (CRR)$_r$OH, (CRR)$_r$SH, (CRR)$_r$OR$^{5d}$, (CRR)$_r$SR$^{5d}$, (CRR)$_r$NR$^{5a}$R$^{5a}$, (CRR)$_r$C(O)OH, (CRR)$_r$C(O)R$^{5b}$, (CRR)$_r$C(O)NR$^{5a}$R$^{5a}$, (CRR)$_r$NR$^{5a}$C(O)R$^{5b}$, (CRR)$_r$NR$^{5a}$C(O)OR$^{5d}$, (CRR)$_r$OC(O)NR$^{5a}$R$^{5a}$, (CHR)$_r$NR$^{5a}$C(O)NR$^{5a}$R$^{5a}$, CRR (CRR)$_r$NR$^{5a}$C(O)H, (CRR)$_r$C(O)OR$^{5b}$, (CRR)$_r$OC(O)R$^{5b}$, (CRR)$_r$S(O)$_p$R$^{5b}$, (CRR)$_r$S(O)$_2$NR$^{5a}$R$^{5a}$, (CRR)$_r$NR$^{5a}$S(O)$_2$R$^{5b}$, (CRR)$_r$NR$^{5a}$C(=N)NR$^{5a}$R$^{5a}$, and $C_{1-6}$ haloalkyl, and a (CH$_2$)$_r$-5-10 membered heterocyclic system containing 1-4 heteroatoms selected from N, O, and S, substituted with 0-2 $R^{5c}$, wherein the heterocyclic system is selected from piperidinyl;

$R^{5a}$, at each occurrence, is independently selected from H, methyl, $C_{2-6}$ alkyl substituted with 0-2 $R^{5e}$ wherein the alkyl is selected from ethyl, propyl, i-propyl, butyl, i-butyl, pentyl, hexyl, $C_3$ alkenyl substituted with 0-1 $R^{5e}$, wherein the alkenyl is selected from allyl, $C_3$ alkynyl substituted with 0-1 $R^{5e}$ wherein the alkynyl is selected from propynyl, and a (CH$_2$)$_r$—C$_{3-4}$ carbocyclic residue substituted with 0-5 $R^{5e}$, wherein the carbocyclic residue is selected from cyclopropyl, cyclobutyl, cyclopentyl, cyclohexyl, and phenyl;

$R^{5b}$, at each occurrence, is selected from $C_{1-6}$ alkyl substituted with 0-3 $R^{5e}$, wherein the alkyl is selected from methyl, ethyl, propyl, i-propyl, butyl, i-butyl, pentyl, and hexyl, a (CH$_2$)$_r$—C$_{3-4}$ carbocyclic residue substituted with 0-2 $R^{5e}$, wherein the carbocyclic residue is selected from cyclopropyl, and cyclobutyl; and $R^{5d}$, at each occurrence, is selected from methyl, CF$_3$, $C_{2-6}$ alkyl substituted with 0-2 $R^{5e}$, wherein the alkyl is selected from methyl, ethyl, propyl, i-propyl, butyl, i-butyl, pentyl, and hexyl, $C_{3-8}$ alkenyl, $C_{3-8}$ alkynyl, and a $C_{3-10}$ carbocyclic residue substituted with 0-3 $R^{5e}$.

[15] In another embodiment, the present invention provides novel compounds of formula (I) or (Ia), wherein
$R^4$ is selected from H, $C_{1-6}$ alkyl, $C_{3-8}$ alkenyl, $C_{3-8}$ alkynyl, (CRR)$_t$OH, (CRR)$_t$SH, (CRR)$_t$OR$^{4d}$, (CRR)$_t$SR$^{4d}$, (CRR)$_t$NR$^{4a}$R$^{4a}$, (CRR)$_q$C(O)OH, (CRR)$_t$C(O)R$^{4b}$, (CRR)$_t$C(O)NR$^{4a}$R$^{4a}$, (CRR)$_t$NR$^{4a}$C(O)R$^{4b}$, (CRR)$_t$OC(O)NR$^{4a}$R$^{4a}$, (CRR)$_t$NR$^{4a}$C(O)OR$^{4d}$, (CRR)$_t$NR$^{4a}$C(O)R$^{4b}$, (CRR)$_t$C(O)OR$^{4b}$, (CRR)$_t$OC(O)R$^{4b}$, (CRR)$_t$S(O)$_p$R$^{4b}$, (CRR)$_t$S(O)$_2$NR$^{4a}$R$^{4a}$, (CRR)$_t$NR$^{4a}$S(O)$_2$R$^{4b}$;
R, at each occurrence, is independently selected from H, $C_{1-6}$ alkyl substituted with 0-3 $R^{5e}$, wherein the $C_{1-6}$ alkyl is selected from methyl, ethyl, propyl, allyl, propynyl, (CH$_2$)$_r$C$_{3-6}$ cycloalkyl, and (CH$_2$)$_r$phenyl substituted with $R^{6e}$;

$R^5$, at each occurrence, is independently selected from H, methyl, ethyl, propyl, i-propyl, butyl, i-butyl, allyl, propynyl, $N_3$, (CH$_2$)$_r$OH, (CH$_2$)$_r$OR$^{5d}$, (CH$_2$)$_r$NR$^{5a}$R$^{5a}$, (CH$_2$)$_r$C(O)OH, (CH$_2$)$_r$C(O)R$^{5b}$, (CH$_2$)$_r$C(O)NR$^{5a}$R$^{5a}$, (CH$_2$)$_r$NR$^{5a}$C(O)R$^{5b}$, (CH$_2$)$_r$OC(O)NR$^{5a}$R$^{5a}$, (CH$_2$)$_r$NR$^{5a}$C(O)OR$^{5d}$, (CH$_2$)$_r$NR$^{5a}$C(O)R$^{5b}$, (CH$_2$)$_r$C(O)OR$^{5b}$, (CH$_2$)$_r$OC(O)R$^{5b}$, (CH$_2$)$_r$NR$^{5a}$S(O)$_2$R$^{5b}$, (CH$_2$)$_r$NR$^{5a}$C(=N)NR$^{5a}$R$^{5a}$, and $C_{1-6}$ haloalkyl, and a (CH$_2$)$_r$-5-10 membered heterocyclic system containing 1-4 heteroatoms selected from N, O, and S, substituted with 0-2 $R^{5c}$, wherein the heterocyclic system is selected from piperidinyl;

$R^{5a}$, at each occurrence, is independently selected from H, methyl, ethyl, propyl, i-propyl, butyl, i-butyl, pentyl, hexyl, cyclopropyl, and cyclobutyl; and r, at each occurrence, is selected from 0, 1, and 2.

[16] In another embodiment, the present invention provides novel compounds of formula (I) or (Ia), wherein $R^6$, at each occurrence, is selected from $C_{1-8}$ alkyl, $C_{2-8}$ alkenyl, $C_{2-8}$ alkynyl, (CHR')$_r$C$_{3-6}$ cycloalkyl, Cl, Br, I, F, NO$_2$, CN, (CHR')$_r$NR$^{6a}$R$^{6a}$, (CHR')$_r$OH, (CHR')$_r$OR$^{6d}$, (CHR')$_r$SH, (CHR')$_r$C(O)H, (CHR')$_r$SR$^{6d}$, (CHR')$_r$C(O)OH, (CHR')$_r$C(O)R$^{6b}$, (CHR')$_r$C(O)NR$^{6a}$R$^{6a}$, (CHR')$_r$NR$^{6f}$C(O)R$^{6b}$, (CHR')$_r$C(O)OR$^{6d}$, (CHR')$_r$NR$^{6a}$C(O)NR$^{6a}$R$^{6a}$, (CHR')$_r$NR$^{6a}$C(S)NR$^{6a}$R$^{6a}$, (CHR')$_r$OC(O)R$^{6b}$, (CHR')$_r$S(O)$_p$R$^{6b}$, (CHR')$_r$S(O)$_2$NR$^{6a}$R$^{6a}$, (CHR')$_r$NR$^{6f}$S(O)$_2$R$^{6b}$, (CHR')$_r$NR$^{6f}$S(O)$_2$ NR$^{6a}$R$^{6a}$, $C_{1-6}$ haloalkyl, and (CHR')$_r$phenyl substituted with 0-3 $R^{6e}$;

$R^{6a}$, at each occurrence, is independently selected from H, methyl, ethyl, propyl, i-propyl, butyl, i-butyl, t-butyl, pentyl, hexyl, cyclopropyl and phenyl;

$R^{6b}$, at each occurrence, is selected from methyl, ethyl, propyl, i-propyl, butyl, i-butyl, t-butyl, pentyl, hexyl, —(CH$_2$)$_r$-cyclopropyl, and —(CH$_2$)$_r$-phenyl;

$R^{6d}$, at each occurrence, is selected from methyl, CF$_3$, ethyl, propyl, i-propyl, butyl, i-butyl, t-butyl, pentyl, hexyl, —(CH$_2$)$_r$-cyclopropyl, and —(CH$_2$)$_r$-phenyl;

$R^{6e}$, at each occurrence, is selected from $C_{1-6}$ alkyl, $C_{2-8}$ alkenyl, $C_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{6f}$R$^{6f}$, and (CH$_2$)$_r$phenyl;

$R^{6f}$, at each occurrence, is selected from H, methyl, ethyl, propyl, i-propyl, butyl, i-butyl, t-butyl, pentyl, hexyl, cyclopropyl, and phenyl;

$R^7$ is selected from methyl, ethyl, propyl, i-propyl, butyl, i-butyl, s-butyl, t-butyl, pentyl, hexyl, (CRR)$_r$C$_{3-6}$ cycloalkyl, Cl, Br, I, F, NO$_2$, CN, (CHR')$_r$NR$^{7a}$R$^{7a}$, (CHR')$_r$OH, (CHR')$_r$O(CH)$_r$R$^{7d}$, (CHR')$_r$SH, (CHR')$_r$C(O)H, (CHR')$_r$SR$^{7d}$, (CHR')$_r$C(O)OH, (CHR')$_r$C(O)R$^{7b}$, (CHR')$_r$C(O)NR$^{7a}$R$^{7a}$, (CHR')$_r$NR$^{7f}$C(O)R$^{7b}$, (CHR')$_r$C(O)O(CRR)$_r$R$^{7d}$, (CHR')$_r$OC(O)R$^{7b}$, (CHR')$_r$NR$^{7a}$C(O)NR$^{7a}$R$^{7a}$, (CHR')$_r$NR$^{7a}$C(O)OR$^{7d}$, (CHR')$_r$S(O)$_p$(CRR)$_r$R$^{7b}$, (CHR')$_r$S(O)$_2$NR$^{7a}$R$^{7a}$, (CHR')$_r$NR$^{7f}$S(O)$_2$(CRR)$_r$R$^{7b}$, $C_{1-6}$ haloalkyl, and (CHR')$_r$phenyl substituted with 0-3 $R^{7e}$;

$R^{7a}$, at each occurrence, is selected from H, methyl, ethyl, propyl, i-propyl, butyl, i-butyl, t-butyl, pentyl, hexyl, prop-2-enyl, 2-methyl-2-propenyl, cyclopropyl, cyclobutyl, cyclopentyl, cyclohexyl, CH$_2$cyclopropyl, phenyl, and benzyl;

$R^{7b}$, at each occurrence, is selected from methyl, ethyl, propyl, i-propyl, butyl, i-butyl, t-butyl, pentyl, hexyl, cyclopropyl, cyclopentyl, CH$_2$-cyclopentyl, cyclohexyl, CH$_2$-cyclohexyl, CF$_3$, pyrrolidinyl, morpholinyl, piperizenyl substituted with 0-1 $R^{7e}$, and azetidinyl;

$R^{7d}$, at each occurrence, is selected from methyl, CF$_3$, ethyl, propyl, i-propyl, butyl, i-butyl, t-butyl, pentyl, hexyl, and cyclopropyl; $R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $C(O)OC_{1-5}$ alkyl, $(CH_2)_rSC_{1-5}$ alkyl, $(CH_2)_rNR^{7f}R^{7f}$, and $(CH_2)_r$phenyl; $R^{7f}$, at each occurrence, is selected from H, methyl, ethyl, propyl, i-propyl, butyl, i-butyl, t-butyl, pentyl, hexyl, cyclopropyl, and phenyl; and r is 0 or 1.

[17] In another embodiment, the present invention provides novel compounds of formula (I) or (Ia), wherein ring B is selected from

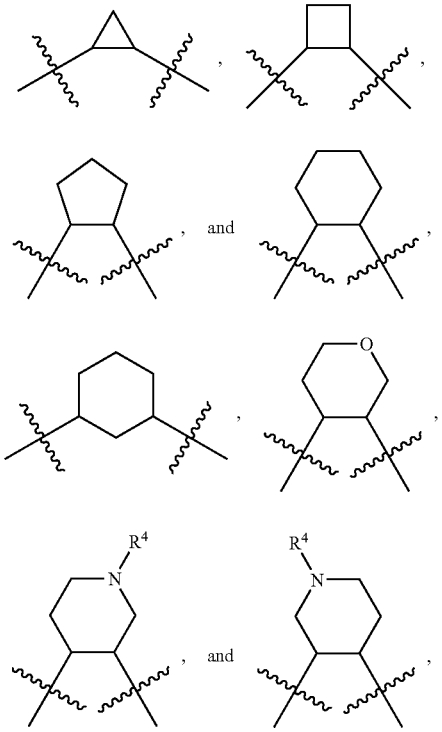

ring B being optionally substituted with 0-1 $R^5$;

Z is —C(O)—;

$R^1$ is selected from a $C_{6-10}$ aryl group substituted with 0-3 $R^6$ wherein the aryl group is selected from phenyl and naphthyl, and a 5-10 membered heteroaryl system containing 1-4 heteroatoms selected from N and O, substituted with 0-3 $R^6$ wherein the heteroaryl system is selected from benzothiazolyl, indolyl and pyridinyl;

$R^2$ is selected from phenyl substituted with 0-2 $R^7$, and indazolyl substituted with 0-2 $R^7$;

$R^4$ is selected from H, methyl, ethyl, propyl, i-propyl, butyl, i-butyl, t-butyl, pentyl, hexyl, allyl, OH, $C(O)OR^{4d}$, and $(CH_2)_rC(O)R^{4b}$;

$R^6$ is selected from methyl, ethyl, propyl, i-propyl, butyl, vinyl, F, Cl, Br, I, $NO_2$, CN, $O(CH_2)_rR^{6d}$, $C(O)H$, $(CH_2)$ OH, —CHOH—$CH_2$OH $SR^{6d}$, $C(O)R^{6b}$, $NR^{6a}R^{6a}$, $NC(O)R^{6b}OC(O)R^{6b}$, $S(O)_pR^{6b}$, $(CHR')_rS(O)_2NR^{6a}R^{6a}$, $CF_3$;

$R^{6a}$ is H, methyl, or ethyl;

$R^{6b}$ is H, or methyl;

$R^{6d}$ is methyl, phenyl, $CF_3$, and $(CH_2)$-phenyl; and r is 0 or 1.

[18] In another embodiment, the present invention provides novel compounds of formula (I) or (Ia), wherein ring B is selected from

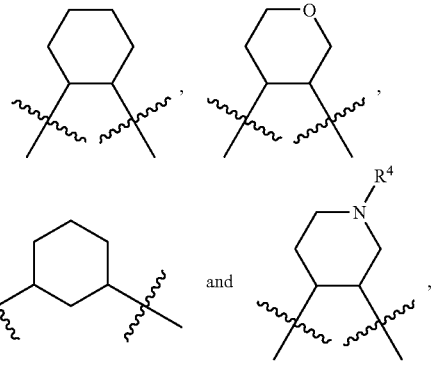

ring B being substituted with 0-1 $R^5$;

$R^1$ is selected from a $C_{6-10}$ aryl group substituted with 0-3 $R^6$ wherein the aryl group is selected from phenyl, and a 5-10 membered heteroaryl system containing 1-4 heteroatoms selected from N and O, substituted with 0-3 $R^6$ wherein the heteroaryl system is selected from benzothiazolyl;

$R^4$ is selected from H, methyl, ethyl, propyl, i-propyl, butyl, i-butyl, t-butyl, pentyl, hexyl, allyl and $(CH_2)_rC(O)R^{4b}$;

$R^5$ is selected from H, OH, $OCH_3$, $N_3$, $NHC(=NH)NH_2$, $NR^{5a}R^{5a}$, and piperidinyl;

$R^{5a}$ is selected from H, methyl, ethyl, propyl, i-propyl, butyl, s-butyl, i-butyl, t-butyl, pentyl, hexyl, allyl, propargyl, cyclopropyl, cyclopropylmethyl, acetyl, methysulfonyl, —$C(O)CF_3$, $C(=N)NH_2$, benzyl, and —C(O)O-t-butyl;

$R^7$ is selected from methyl, ethyl, propyl, i-propyl, butyl, i-butyl, s-butyl, pentyl, hexyl, Cl, Br, I, F, $NO_2$, $NR^{7a}R^{7a}$, $NHC(O)NHR^{7a}$, $NR^{7a}C(O)R^{7b}$, $NR^{7a}C(O)OR^{7d}$, $CF_3$, $OCF_3$, $C(O)OR^{7d}$, $C(O)R^{7b}$, $NR^{7f}C(O)NR^{7a}R^{7a}$, $NHS(O)_2R^{7b}$,

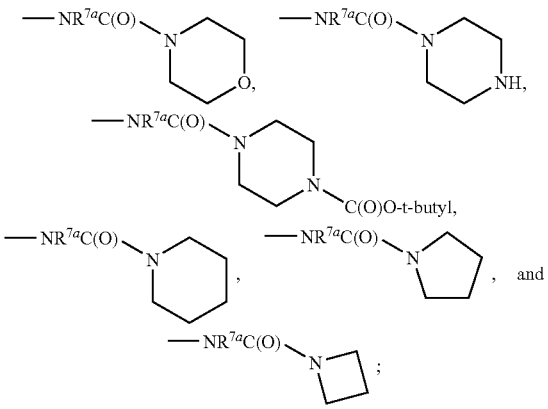

$R^{7a}$ is selected from H, methyl, ethyl, propyl, i-propyl, butyl, i-butyl, t-butyl, pentyl, neo-pentyl, cyclopropyl, cyclobutyl, cyclopentyl, and cyclohexyl;

$R^{7b}$ is selected from methyl, ethyl, propyl, i-propyl, butyl, cyclohexyl and $CF_3$;

$R^{7d}$ is selected from methyl, ethyl, propyl, i-propyl, butyl, i-butyl, and t-butyl; and $R^{14}$ is selected from H and methyl.

[19] In another embodiment, the present invention provides novel compounds of formula (I) or (Ia), wherein
Z is a bond; and
R² is a 5-10 membered heteroaryl system containing 1-4 heteroatoms selected from N, O, and S, substituted with 0-3 R⁷ wherein the heteroaryl is selected from indolyl, naphthalenyl, phthalazinyl, cinnolinyl, quinolinyl, isoquinolinyl, indazolyl, and quinazolinyl, benzimidazolyl, benzofuranyl, benzothiofuranyl, benzoxazolyl, benzthiazolyl, benzisoxazolyl, and benzisothiazolyl.

[20] In another embodiment, the present invention provides novel compounds of formula (I) or (Ia), wherein
R² is indazolyl.

[21] In another embodiment, the present invention provides novel compounds of formula (I), wherein the compound is selected from
(±)tert-Butyl 2-({[2-({(1S*,2R*)-2-[(phenylthio)methyl]cyclohexyl}amino)-2-oxoethyl]amino}carbonyl)-4-(trifluoromethyl)phenylcarbamate;
(±)tert-Butyl 2-({[2-({(1S*,2R*)-2-[(phenylsulfonyl)methyl]cyclohexyl}amino)-2-oxoethyl]amino}carbonyl)-4-(trifluoromethyl)phenylcarbamate;
(±)tert-Butyl 2-({[2-({(1S*,2R*)-2-[(1,3-benzothiazol-2-ylthio)methyl]cyclohexyl}amino)-2-oxoethyl]amino}carbonyl)-4-(trifluoromethyl)phenylcarbamate;
(±)tert-Butyl 2-({[2-({(1S*,2R*)-2-[(4-methylphenylthio)methyl]cyclohexyl}amino)-2-oxoethyl]amino}carbonyl)-4-(trifluoromethyl)phenylcarbamate;
(±)2-Amino-N-{2-[((1S*,2R*)-2-{[(4-methylphenyl)thio]methyl}cyclohexyl)amino]-2-oxoethyl}-5-(trifluoromethyl)benzamide;
(±)tert-Butyl 2-({[2-({(1S*,2R*)-2-[(4-methylphenylsulfonyl)methyl]cyclohexyl}amino)-2-oxoethyl]amino}carbonyl)-4-(trifluoromethyl)phenylcarbamate;
(±)2-Amino-N-{2-[((1S*,2R*)-2-{[(4-methylphenyl)sulfonyl]methyl}cyclohexyl)amino]-2-oxoethyl}-5-(trifluoromethyl)benzamide;
(±)2-Amino-N-{2-[((1S*,2R*)-2-{[1,3-benzothiazol-2-ylthio]methyl}cyclohexyl)amino]-2-oxoethyl}-5-(trifluoromethyl)benzamide;
(±)N-{2-[((1S*,2R*)-2-{[(4-methylphenyl)thio]methyl}cyclohexyl)amino]-2-oxoethyl}-2-[(trifluoroacetyl)amino]-5-(trifluoromethyl)benzamide;
(±)N-{2-[((1S*,2R*)-2-{[(4-methylphenyl)sulfonyl]methyl}cyclohexyl)amino]-2-oxoethyl}-2-[(trifluoroacetyl)amino]-5-(trifluoromethyl)benzamide;
(±)tert-Butyl 2-({[2-({(1S*,2R*)-2-[(4-ethylphenylsulfonyl)methyl]cyclohexyl}amino)-2-oxoethyl]amino}carbonyl)-4-(trifluoromethyl)phenylcarbamate;
(±)tert-Butyl 2-({[2-({(1S*,2R*)-2-[(4-bromophenylsulfonyl)methyl]cyclohexyl}amino)-2-oxoethyl]amino}carbonyl)-4-(trifluoromethyl)phenylcarbamate;
(±)2-Amino-N-{2-[((1S*,2R*)-2-{[(4-ethylphenyl)sulfonyl]methyl}cyclohexyl)amino]-2-oxoethyl}-5-(trifluoromethyl)benzamide;
(±)2-Amino-N-{2-[((1S*,2R*)-2-{[(4-bromophenyl)sulfonyl]methyl}cyclohexyl)amino]-2-oxoethyl}-5-(trifluoromethyl)benzamide;
(±)tert-Butyl 2-({[2-({(1S*,2R*)-2-[(4-vinylphenylsulfonyl)methyl]cyclohexyl}amino)-2-oxoethyl]amino}carbonyl)-4-(trifluoromethyl)phenylcarbamate;
(±)tert-butyl 2-{[(2-{[(1S*,2R*)-2-({[4-(1,2-dihydroxyethyl)phenyl]sulfonyl}methyl)cyclohexyl]amino}-2-oxoethyl)amino]carbonyl}-4-(trifluoromethyl)phenylcarbamate;
(±)tert-butyl 2-{[(2-{[(1S*,2R*)-2-({[4-formylphenyl]sulfonyl}methyl)cyclohexyl]amino}-2-oxoethyl)amino]carbonyl}-4-(trifluoromethyl)phenylcarbamate;
(±)tert-butyl 2-{[(2-{[(1S*,2R*)-2-({[4-(methylthio)phenyl]sulfonyl}methyl)cyclohexyl]amino}-2-oxoethyl)amino]carbonyl}-4-(trifluoromethyl)phenylcarbamate;
(±)2-Amino-N-{2-[((1S*,2R*)-2-{[(4-(methylthio)phenyl)sulfonyl]methyl}cyclohexyl)amino]-2-oxoethyl}-5-(trifluoromethyl)benzamide;
(±)2-Amino-N-{2-[((1S*,2R*)-2-{[(4-vinylphenyl)sulfonyl]methyl}cyclohexyl)amino]-2-oxoethyl}-5-(trifluoromethyl)benzamide;
(±)tert-butyl 2-{[(2-{[(1S*,2R*)-2-({[4-(hydroxymethyl)phenyl]sulfonyl}methyl)cyclohexyl]amino}-2-oxoethyl)amino]carbonyl}-4-(trifluoromethyl)phenylcarbamate;
(±)[iso-propyl 2-{[(2-{[(1S*,2R*)-2-({[4-(methylthio)phenyl]sulfonyl}methyl)cyclohexyl]amino}-2-oxoethyl)amino]carbonyl}-4-(trifluoromethyl)phenylcarbamate;
(±)2-{[(Isopropylamino)carbonyl]amino}-N-(2-{[(1S*,2R*)-2-({[4-(methylthio)phenyl]sulfonyl}methyl)cyclohexyl]amino}-2-oxoethyl)-5-(trifluoromethyl)benzamide;
(±)2-[(cyclohexylcarbonyl)amino]-N-(2-{[(1S*,2R*)-2-({[4-(methylthio)phenyl]sulfonyl}methyl)cyclohexyl]amino}-2-oxoethyl)-5-(trifluoromethyl)benzamide;
(±)2-{[(cyclopentylamino)carbonyl]amino}-N-(2-{[(1S*,2R*)-2-({[4-(methylthio)phenyl]sulfonyl}methyl)cyclohexyl]amino}-2-oxoethyl)-5-(trifluoromethyl)benzamide;
(±)2-{[(Isobutylamino)carbonyl]amino}-N-(2-{[(1S*,2R*)-2-({[4-(methylthio)phenyl]sulfonyl}methyl)cyclohexyl]amino}-2-oxoethyl)-5-(trifluoromethyl)benzamide;
(±)2-{[(Ethylamino)carbonyl]amino}-N-(2-{[(1S*,2R*)-2-({[4-(methylthio)phenyl]sulfonyl}methyl)cyclohexyl]amino}-2-oxoethyl)-5-(trifluoromethyl)benzamide;
(±)2-{[(Dimethylamino)carbonyl]amino}-N-(2-{[(1S*,2R*)-2-({[4-(methylthio)phenyl]sulfonyl}methyl)cyclohexyl]amino}-2-oxoethyl)-5-(trifluoromethyl)benzamide;
(±)2-{[(Diethylamino)carbonyl]amino}-N-(2-{[(1S*,2R*)-2-({[4-(methylthio)phenyl]sulfonyl}methyl)cyclohexyl]amino}-2-oxoethyl)-5-(trifluoromethyl)benzamide;
(±)N-[2-{[(2-{[(1S*,2R*)-2-({[4-(methylthio)phenyl]sulfonyl}methyl)cyclohexyl]amino}-2-oxoethyl)amino]carbonyl}-4-(trifluoromethyl)phenyl]-1-pyrrolidinecarboxamide;
(±)tert-Butyl 2-{[(2-{[(1S*,2R*,5S*)-5-hydroxy-2-({[4-(methylthio)phenyl]sulfonyl}methyl)cyclohexyl]amino}-2-oxoethyl)amino]carbonyl}-4-(trifluoromethyl)phenylcarbamate;
(±)N-[2-{[(2-{[(1S*,2R*,5S*)-5-hydroxy-2-({[4-(methylthio)phenyl]sulfonyl}methyl)cyclohexyl]amino}-2-oxoethyl)amino]carbonyl}-4-(trifluoromethyl)phenyl]-1-pyrrolidinecarboxamide;
(±)2-{[(ethylamino)carbonyl]amino}-N-(2-{[(1S*,2R*,5S*)-5-hydroxy-2-({[4-(methylthio)phenyl]sulfonyl}methyl)cyclohexyl]amino}-2-oxoethyl)-5-(trifluoromethyl)benzamide;
(±)2-Amino-N-(2-{[(1S*,2R*,5S*)-5-hydroxy-2-({[4-(methylthio)phenyl]sulfonyl}methyl)cyclohexyl]amino}-2-oxoethyl)-5-(trifluoromethyl)benzamide;
(±)2-Isopropylamino-N-(2-{[(1S*,2R*,5S*)-5-hydroxy-2-({[4-(methylthio)phenyl]sulfonyl}methyl)cyclohexyl]amino}-2-oxoethyl)-5-(trifluoromethyl)benzamide;
N-[2-{[(2-{[(1S,2R)-2-({[4-(methylthio)phenyl]sulfonyl}methyl)cyclohexyl]amino}-2-oxoethyl)amino]carbonyl}-4-(trifluoromethyl)phenyl]-1-pyrrolidinecarboxamide;

N-[2-{[(2-{[(1R,2S)-2-({[4-(methylthio)phenyl]sulfonyl}methyl)cyclohexyl]amino}-2-oxoethyl)amino]carbonyl}-4-(trifluoromethyl)phenyl]-1-pyrrolidinecarboxamide;

(±)N-[2-{[(2-{[(1S*,2R*,5S*)-5-methoxy-2-({[4-(methylthio)phenyl]sulfonyl}methyl)cyclohexyl]amino}-2-oxoethyl)amino]carbonyl}-4-(trifluoromethyl)phenyl]-1-pyrrolidinecarboxamide;

(±)2-{[(Ethylamino)carbonyl]amino}-N-(2-{[(1S*,2R*,5S*)-5-methoxy-2-({[4-(methylthio)phenyl]sulfonyl}methyl)cyclohexyl]amino}-2-oxoethyl)-5-(trifluoromethyl)benzamide;

(±)N-[2-{[(2-{[(1S*,2R*)-2-({[4-(methylthio)phenyl]sulfonyl}methyl)cyclohexyl]amino}-2-oxoethyl)amino]carbonyl}-4-(trifluoromethyl)phenyl]-1-azetidinecarboxamide;

(±)N-[2-{[(2-{[(1S*,2R*)-2-({[4-(methylthio)phenyl]sulfonyl}methyl)cyclohexyl]amino}-2-oxoethyl)amino]carbonyl}-4-(trifluoromethyl)phenyl]-4-morpholinecarboxamide;

(±)N-[2-{[(2-{[(1S*,2R*,5S*)-5-hydroxy-2-({[4-(methylthio)phenyl]sulfonyl}methyl)cyclohexyl]amino}-2-oxoethyl)amino]carbonyl}-4-(trifluoromethyl)phenyl]-1-azetidinecarboxamide;

(±)N-[2-{[(2-{[(1S,2R,5S)-5-hydroxy-2-({[4-(methylthio)phenyl]sulfonyl}methyl)cyclohexyl]amino}-2-oxoethyl)amino]carbonyl}-4-(trifluoromethyl)phenyl]-4-morpholinecarboxamide;

(±)tert-Butyl 4-({[2-{[(2-{[(1S*,2R*,5S*)-5-hydroxy-2-({[4-(methylthio)phenyl]sulfonyl}methyl)cyclohexyl]amino}-2-oxoethyl)amino]carbonyl}-4-(trifluoromethyl)phenyl]amino}carbonyl)-1-piperazinecarboxylate;

(±)N-[2-{[(2-{[(1S*,2R*,5S*)-5-hydroxy-2-({[4-(methylthio)phenyl]sulfonyl}methyl)cyclohexyl]amino}-2-oxoethyl)amino]carbonyl}-4-(trifluoromethyl)phenyl]-1-piperazinecarboxamide;

(±)tert-Butyl 4-({[2-{[(2-{[(1S*,2R*)-2-({[4-(methylthio)phenyl]sulfonyl}methyl)cyclohexyl]amino}-2-oxoethyl)amino]carbonyl}-4-(trifluoromethyl)phenyl]amino}carbonyl)-1-piperazinecarboxylate;

(±)N-[2-{[(2-{[(1S*,2R*)-2-({[4-(methylthio)phenyl]sulfonyl}methyl)cyclohexyl]amino}-2-oxoethyl)amino]carbonyl}-4-(trifluoromethyl)phenyl]-1-piperazinecarboxamide;

(±)2-Isobutylamino-N-(2-{[(1S*,2R*)-2-({[4-(methylthio)phenyl]sulfonyl}methyl)cyclohexyl]amino}-2-oxoethyl)-5-(trifluoromethyl)benzamide;

(±)2-Neopentylamino-N-(2-{[(1S*,2R*)-2-({[4-(methylthio)phenyl]sulfonyl}methyl)cyclohexyl]amino}-2-oxoethyl)-5-(trifluoromethyl)benzamide;

(±)N-(2-{[(1S*,2R*,4R*)-4-Amino-2-({[4-(methylthio)phenyl]sulfonyl}methyl)cyclohexyl]amino}-2-oxoethyl)-3-(trifluoromethyl)benzamide;

(±)N-(2-{[(1S*,2R*,4R*)-4-Amino-2-({phenylsulfonyl}methyl)cyclohexyl]amino}-2-oxoethyl)-3-(trifluoromethyl)benzamide;

(±)N-(2-{[(1S*,2R*,4R*)-4-(dimethylamino)-2-({[4-(methylthio)phenyl]sulfonyl}methyl)cyclohexyl]amino}-2-oxoethyl)-3-(trifluoromethyl)benzamide;

(±)N-(2-{[(1S*,2R*,4R*)-4-(isopropylamino)-2-({[4-(methylthio)phenyl]sulfonyl}methyl)cyclohexyl]amino}-2-oxoethyl)-3-(trifluoromethyl)benzamide;

(±)N-(2-{[(1S*,2R*,4R*)-4-(cyclobutylamino)-2-({[4-(methylthio)phenyl]sulfonyl}methyl)cyclohexyl]amino}-2-oxoethyl)-3-(trifluoromethyl)benzamide;

(±)N-(2-{[(1S*,2R*,4R*)-4-(diethylamino)-2-({[4-(methylthio)phenyl]sulfonyl}methyl)cyclohexyl]amino}-2-oxoethyl)-3-(trifluoromethyl)benzamide;

(±)N-(2-{[(1S*,2R*,4R*)-4-(dipropylamino)-2-({[4-(methylthio)phenyl]sulfonyl}methyl)cyclohexyl]amino}-2-oxoethyl)-3-(trifluoromethyl)benzamide;

(±)N-(2-{[(1S*,2R*,4R*)-4-(benzylamino)-2-({[4-(methylthio)phenyl]sulfonyl}methyl)cyclohexyl]amino}-2-oxoethyl)-3-(trifluoromethyl)benzamide;

(±)N-(2-{[(1S*,2R*,4R*)-4-(Bis-cyclopropylmethylamino)-2-({[4-(methylthio)phenyl]sulfonyl}methyl)cyclohexyl]amino}-2-oxoethyl)-3-(trifluoromethyl)benzamide;

(±)N-(2-{[(1S*,2R*,4R*)-4-(dibutylamino)-2-({[4-(methylthio)phenyl]sulfonyl}methyl)cyclohexyl]amino}-2-oxoethyl)-3-(trifluoromethyl)benzamide;

(±)N-(2-{[(1S*,2R*,4R*)-4-(N-isopropyl-N-methylamino)-2-({[4-(methylthio)phenyl]sulfonyl}methyl)cyclohexyl]amino}-2-oxoethyl)-3-(trifluoromethyl)benzamide;

(±)N-(2-{[(1S*,2R*,4R*)-4-(acetylamino)-2-({[4-(methylthio)phenyl]sulfonyl}methyl)cyclohexyl]amino}-2-oxoethyl)-3-(trifluoromethyl)benzamide;

(±)N-(2-{[(1S*,2R*,4R*)-4-[(methylsulfonyl)amino]-2-({[4-(methylthio)phenyl]sulfonyl}methyl)cyclohexyl]amino}-2-oxoethyl)-3-(trifluoromethyl)benzamide;

(±)N-[2-({[(1S*,2R*,4R*)-2-({[4-(methylthio)phenyl]sulfonyl}methyl)-4-[(trifluoroacetyl)amino]cyclohexyl}amino)-2-oxoethyl]-3-(trifluoromethyl)benzamide;

(±)N-(2-{[(1S*,2R*,4R*)-4-(methylamino)-2-({[4-(methylthio)phenyl]sulfonyl}methyl)cyclohexyl]amino}-2-oxoethyl)-3-(trifluoromethyl)benzamide;

(±)N-(2-{[(1S*,2R*,4R*)-4-{[amino(imino)methyl]amino}-2-({[4-(methylthio)phenyl]sulfonyl}methyl)cyclohexyl]amino}-2-oxoethyl)-3-(trifluoromethyl)benzamide;

(±)N-(2-{[(1S*,2R*,5R*)-5-amino-2-({[4-(methylthio)phenyl]sulfonyl}methyl)cyclohexyl]amino}-2-oxoethyl)-3-(trifluoromethyl)benzamide;

(±)N-(2-{[(1S*,2R*,5R*)-5-(isopropylamino)-2-({[4-(methylthio)phenyl]sulfonyl}methyl)cyclohexyl]amino}-2-oxoethyl)-3-(trifluoromethyl)benzamide;

(±)N-(2-{[(1S*,2R*,5R*)-5-((bis-isobutyl)amino)-2-({[4-(methylthio)phenyl]sulfonyl}methyl)cyclohexyl]amino}-2-oxoethyl)-3-(trifluoromethyl)benzamide;

(±)N-(2-{[(1S*,2R*,5R*)-5-(acetylamino)-2-({[4-(methylthio)phenyl]sulfonyl}methyl)cyclohexyl]amino}-2-oxoethyl)-3-(trifluoromethyl)benzamide;

(±)N-(2-{[(1S*,2R*,5R*)-5-[(methylsulfonyl)amino]-2-({[4-(methylthio)phenyl]sulfonyl}methyl)cyclohexyl]amino}-2-oxoethyl)-3-(trifluoromethyl)benzamide;

(±)tert-Butyl 2-{[(2-{[(1S*,2R*,5R*)-5-amino-2-({[4-(methylthio)phenyl]sulfonyl}methyl)cyclohexyl]amino}-2-oxoethyl)amino]carbonyl}-4-(trifluoromethyl)phenylcarbamate;

(±)2-Amino-N-(2-{[(1S*,2R*,5R*)-5-amino-2-({[4-(methylthio)phenyl]sulfonyl}methyl)cyclohexyl]amino}-2-oxoethyl)-5-(trifluoromethyl)benzamide;

(±)2-Amino-N-(2-{[(1S*,2R*,5R*)-5-isopropylamino-2-({[4-(methylthio)phenyl]sulfonyl}methyl)cyclohexyl]amino}-2-oxoethyl)-5-(trifluoromethyl)benzamide;

(±)tert-Butyl 2-{[(2-{[(1S*,2R*,5R*)-5-amino-2-({[4-(methylthio)phenyl]sulfonyl}methyl)cyclohexyl]amino}-2-oxoethyl)amino]carbonyl}-4-(trifluoromethoxy)phenylcarbamate;

(±)2-Amino-N-(2-{[(1S*,2R*,5R*)-5-amino-2-({[4-(methylthio)phenyl]sulfonyl}methyl)cyclohexyl]amino}-2-oxoethyl)-5-(trifluoromethoxy)benzamide;

(±)N-[2-{[(2-{[(3R*,4R*)-4-({[4-(methylthio)phenyl]sulfonyl}methyl)tetrahydro-2H-pyran-3-yl]amino}-2-oxoethyl)amino]carbonyl}-4-(trifluoromethyl)phenyl]-1-pyrrolidinecarboxamide;

N-[2-{[(2-{[(3R,4R)-4-({[4-(methylthio)phenyl]sulfonyl}methyl)tetrahydro-2H-pyran-3-yl]amino}-2-oxoethyl)amino]carbonyl}-4-(trifluoromethyl)phenyl]-1-pyrrolidinecarboxamide;

N-[2-{[(2-{[(3S,4S)-4-({[4-(methylthio)phenyl]sulfonyl}methyl)tetrahydro-2H-pyran-3-yl]amino}-2-oxoethyl)amino]carbonyl}-4-(trifluoromethyl)phenyl]-1-pyrrolidinecarboxamide;

(±)2-{[(Ethylamino)carbonyl]amino}-N-(2-{[(3R*,4R*)-4-({[4-(methylthio)phenyl]sulfonyl}methyl)tetrahydro-2H-pyran-3-yl]amino}-2-oxoethyl)-5-(trifluoromethyl)benzamide;

(±)2-{[(ethylamino)carbonyl]amino}-N-(2-{[(3R*,4R*)-4-({phenylsulfonyl}methyl)tetrahydro-2H-pyran-3-yl]amino}-2-oxoethyl)-5-(trifluoromethyl)benzamide;

(±)N-[2-{[(2-{[(3R*,4R*)-4-({[4-(methylthio)phenyl]sulfonyl}methyl)tetrahydro-2H-pyran-3-yl]amino}-2-oxoethyl)amino]carbonyl}-4-(trifluoromethyl)phenyl]-4-morpholinecarboxamide;

(±)2-{[(Methylamino)carbonyl]amino}-N-(2-{[(3R*,4R*)-4-({[4-(methylthio)phenyl]sulfonyl}methyl)tetrahydro-2H-pyran-3-yl]amino}-2-oxoethyl)-5-(trifluoromethyl)benzamide;

(±)N-[2-{[(2-{[(3R*,4R*)-4-({[4-(methylthio)phenyl]sulfonyl}methyl)tetrahydro-2H-pyran-3-yl]amino}-2-oxoethyl)amino]carbonyl}-4-(trifluoromethyl)phenyl]-1-azetidinecarboxamide;

(±)2-{[(Isopropylamino)carbonyl]amino}-N-(2-{[(3R*,4R*)-4-({[4-(methylthio)phenyl]sulfonyl}methyl)tetrahydro-2H-pyran-3-yl]amino}-2-oxoethyl)-5-(trifluoromethyl)benzamide;

(±)Isopropyl 2-{[(2-{[(3R*,4R*)-4-({[4-(methylthio)phenyl]sulfonyl}methyl)tetrahydro-2H-pyran-3-yl]amino}-2-oxoethyl)amino]carbonyl}-4-(trifluoromethyl)phenylcarbamate;

(±)Ethyl 2-{[(2-{[(3R*,4R*)-4-({[4-(methylthio)phenyl]sulfonyl}methyl)tetrahydro-2H-pyran-3-yl]amino}-2-oxoethyl)amino]carbonyl}-4-(trifluoromethyl)phenylcarbamate;

(±)tert-Butyl (3R*,4R*)-3-{1-({[2-[(tert-butoxycarbonyl)amino]-5-(trifluoromethyl)benzoyl]amino}methyl)carbonyl]amino}-4-({[4-(methylthio)phenyl]sulfonyl}methyl)-1-piperidinecarboxylate;

(±)2-Amino-N-(2-{[(3R*,4R*)-4-({[4-(methylthio)phenyl]sulfonyl}methyl)-3-piperidinyl]amino}-2-oxoethyl)-5-(trifluoromethyl)benzamide;

(±)N-(2-{[(3R*,4R*)-1-allyl-4-({[4-(methylthio)phenyl]sulfonyl}methyl)-3-piperidinyl]amino}-2-oxoethyl)-2-amino-5-(trifluoromethyl)benzamide;

(±)tert-Butyl (3R*,4R*)-4-({[4-(methylthio)phenyl]sulfonyl}methyl)-3-{[1-({[2-[(1-pyrrolidinylcarbonyl)amino]-5-(trifluoromethyl)benzoyl]amino}methyl)carbonyl]amino}-1-piperidinecarboxylate;

(±)tert-Butyl (3R*,4R*)-3-{[1-({[2-{[(methylamino)arbonylcamamino}-5-(trifluoromethyl)benzoyl]amino}methyl)carbonyl]amino}-4-({[4-(methylthio)phenyl]sulfonyl}methyl)-1-piperidinecarboxylate;

(±)N-[2-{[(2-{(3R*,4R*)-4-({[4-(methylthio)phenyl]sulfonyl}methyl)-3-piperidinyl]amino}-2-oxoethyl)amino]carbonyl}-4-(trifluoromethyl)phenyl]-1-pyrrolidinecarboxamide;

(±)2-{[(Methylamino)carbonyl]amino}-N-(2-{[(3R*,4R*)-4-({[4-(methylthio)phenyl]sulfonyl}methyl)-3-piperidinyl]amino}-2-oxoethyl)-5-(trifluoromethyl)benzamide;

(±)tert-Butyl (3R*,4R*)-4-({[4-(methylthio)phenyl]sulfonyl}methyl)-3-{[1-({[2-[(1-azetidinecarbonyl)amino]-5-(trifluoromethyl)benzoyl]amino}methyl)carbonyl]amino}-1-piperidinecarboxylate;

(±)N-[2-{[(2-{[(3R*,4R*)-4-({[4-(methylthio)phenyl]sulfonyl}methyl)-3-piperidinyl]amino}-2-oxoethyl)amino]carbonyl}-4-(trifluoromethyl)phenyl]-1-azetidinecarboxamide;

(±)N-[2-{[(2-{[(3R*,4R*)-4-({[4-(methylthio)phenyl]sulfonyl}methyl)-1-propyl-3-piperidinyl]amino}-2-oxoethyl)amino]carbonyl}-4-(trifluoromethyl)phenyl]-1-azetidinecarboxamide;

(±)tert-Butyl (3R*,4R*)-4-({[4-(methylthio)phenyl]sulfonyl}methyl)-3-{[1-({[2-[(4-morpholinecarbonyl)amino]-5-(trifluoromethyl)benzoyl]amino}methyl)carbonyl]amino}-1-piperidinecarboxylate;

(±)N-[2-{[(2-{[(3R*,4R*)-4-({[4-(methylthio)phenyl]sulfonyl}methyl)-3-piperidinyl]amino}-2-oxoethyl)amino]carbonyl}-4-(trifluoromethyl)phenyl]-4-morpholinecarboxamide;

(±)N-[2-{[(2-{[(3R*,4R*)-4-({[4-(methylthio)phenyl]sulfonyl}methyl)-1-propyl-3-piperidinyl]amino}-2-oxoethyl)amino]carbonyl}-4-(trifluoromethyl)phenyl]-4-morpholinecarboxamide;

(±)N-[2-{[(2-{[(3R*,4R*)-4-({[4-(methylthio)phenyl]sulfonyl}methyl)-1-propyl-3-piperidinyl]amino}-2-oxoethyl)amino]carbonyl}-4-(trifluoromethyl)phenyl]-1-pyrrolidinecarboxamide;

(±)2-amino-N-(2-{[(1S*,2R*)-2-({[4-bromophenyl]thio}methyl)cyclohexyl]amino}-2-oxoethyl)-5-(trifluoromethyl)benzamide;

(±)2-amino-N-(2-{[(1S*,2R*)-2-({[4-chlorophenyl]thio}methyl)cyclohexyl]amino}-2-oxoethyl)-5-(trifluoromethyl)benzamide;

(±)2-amino-N-(2-{[(1S*,2R*)-2-({[4-(methylthio)phenyl]thio}methyl)cyclohexyl]amino}-2-oxoethyl)-5-(trifluoromethyl)benzamide;

(±)N-{2-[((1S*,2R*)-2-{[(4-bromophenyl)thio]methyl}cyclohexyl)amino]-2-oxoethyl}-2-{[(isopropylamino)carbonyl]amino}-5-(trifluoromethyl)benzamide;

(±)2-amino-N-[2-({(1S*,2R*)-2-[({[4-(methylthio)phenyl]amino}carbonyl)amino]cyclohexyl}amino)-2-oxoethyl]-5-(trifluoromethyl)benzamide;

(±)tert-Butyl 2-({[2-({(1S*,2R*)-2-[({[4-(methylsulfonyl)phenyl]amino}carbonyl)amino]cyclohexyl}amino)-2-oxoethyl]amino}carbonyl)-4-(trifluoromethyl)phenylcarbamate;

(±)N-(2-{[(1S*,2R*,5S*)-5-amino-2-({[4-(methylthio)phenyl]sulfonyl}methyl)cyclohexyl]amino}-2-oxoethyl)-3-(trifluoromethyl)benzamide;

(1S,2R,4S/4R)-N-{[4-Dimethylamino-2-(4-methylsulfanyl-benzenesulfonylmethyl)-cyclohexylcarbamoyl]-methyl}-3-trifluoromethyl-benzamide;

(1S,2S,4S)-N-{[4-Dimethylamino-2-(4-methylsulfanyl-benzenesulfonylmethyl)-cyclohexylcarbamoyl]-methyl}-3-trifluoromethyl-benzamide;

(1S,2R,4R)-N-{[4-Dimethylamino-2-(4-methylsulfanyl-benzenesulfonylmethyl)-cyclohexylcarbamoyl]-methyl}-3-trifluoromethyl-benzamide;

±(1S*,2R*,4S*)-N-{[4-Hydroxy-2-(4-methylsulfanyl-benzenesulfonylmethyl)-cyclohexylcarbamoyl]-methyl}-3-trifluoromethyl-benzamide;

±(1S*,2R*,4S*)-[2-{[4-Hydroxy-2-(4-methylsulfanyl-benzenesulfonylmethyl)-cyclohexylcarbamoyl]-methyl}-carbamoyl)-4-trifluoromethyl-phenyl]-carbamic acid tert-butyl ester;

(1S,2R,4R)-N-{[2-(4-Bromo-benzenesulfonylmethyl)-4-(isopropyl-methyl-amino)-cyclohexylcarbamoyl]-methyl}-3-trifluoromethyl-benzamide;

(1S,2R,4R)-N-{[2-(4-Bromo-benzenesulfonylmethyl)-4-(isopropyl-methyl-amino)-cyclohexylcarbamoyl]-methyl}-3-trifluoromethyl-benzamide;

(1S,2R,4R)-N-{[4-(Isopropyl-methyl-amino)-2-(toluene-4-sulfonylmethyl)-cyclohexylcarbamoyl]-methyl}-3-trifluoromethyl-benzamide;

(1S,2R,4R)-N-{[2-(4-Ethyl-benzenesulfonylmethyl)-4-(isopropyl-methyl-amino)-cyclohexylcarbamoyl]-methyl}-3-trifluoromethyl-benzamide;

±(1S*,2R*,4R*)-N-[4-Dimethylamino-2-(4-methylsulfanyl-benzenesulfonylmethyl)-cyclohexyl]-2-(5-trifluoromethyl-1H-indazol-3-ylamino)-acetamide;

±(1S*,2R*,4R*)-N-[4-(Isopropyl-methyl-amino)-2-(4-methylsulfanyl-benzenesulfonylmethyl)-cyclohexyl]-2-(5-trifluoromethyl-1H-indazol-3-ylamino)-acetamide;

±(1S*,2R*,4R*)-N-[4-(Isopropyl-methyl-amino)-2-(4-methylsulfanyl-benzenesulfonylmethyl)-cyclohexyl]-2-(1-methyl-5-trifluoromethyl-1H-indazol-3-ylamino)-acetamide;

±(1S*,2R*,4R*)-[2-({[4-Isopropylamino-2-(4-methylsulfanyl-benzenesulfonylmethyl)-cyclohexylcarbamoyl]-methyl}-carbamoyl)-4-trifluoromethyl-phenyl]-carbamic acid tertbutylester;

±(1S*,2R*,4R*)-2-Amino-N-{[4-isopropylamino-2-(4-methylsulfanyl-benzenesulfonylmethyl)-cyclohexylcarbamoyl]-methyl}-5-trifluoromethyl-benzamide;

±(1S*,2R*,4R*)-[2-({[4-(Isopropyl-methyl-amino)-2-(4-methylsulfanyl-benzenesulfonylmethyl)-cyclohexylcarbamoyl]-methyl}-carbamoyl)-4-trifluoromethyl-phenyl]-carbamic acid tert-butyl ester;

±(1S*,2R*,4R*)-2-Amino-N-{[4-(isopropyl-methyl-amino)-2-(4-methylsulfanyl-benzenesulfonylmethyl)-cyclohexylcarbamoyl]-methyl}-5-trifluoromethyl-benzamide;

±(1S*,2R*,4R*)-N-{[4-(Isopropyl-propyl-amino)-2-(4-methylsulfanyl-benzenesulfonylmethyl)-cyclohexylcarbamoyl]-methyl}-3-trifluoromethyl-benzamide;

±(1S*,2R*,4R*)-N-{[4-(Cyclopropylmethyl-isopropyl-amino)-2-(4-methylsulfanyl-benzenesulfonylmethyl)-cyclohexylcarbamoyl]-methyl}-3-trifluoromethyl-benzamide;

±(1S*,2R*,4R*)-N-{[4-(Ethyl-isopropyl-amino)-2-(4-methylsulfanyl-benzenesulfonylmethyl)-cyclohexylcarbamoyl]-methyl}-3-trifluoromethyl-benzamide;

±(1S*,2R*,4R*)-N-{[4-(Isobutyl-isopropyl-amino)-2-(4-methylsulfanyl-benzenesulfonylmethyl)-cyclohexylcarbamoyl]-methyl}-3-trifluoromethyl-benzamide;

±(1S*,2R*,4R*)-N-{[4-(Isopropyl-prop-2-ynyl-amino)-2-(4-methylsulfanyl-benzenesulfonylmethyl)-cyclohexylcarbamoyl]-methyl}-3-trifluoromethyl-benzamide;

±(1S*,2R*,4R*)-N-({[4-Azido-2-(4-methylsulfanyl-benzenesulfonylmethyl)-cyclohexyl]-methyl-carbamoyl}-methyl)-3-trifluoromethyl-benzamide;

±(1S*,2R*,4R*)-N-({[4-Amino-2-(4-methylsulfanyl-benzenesulfonylmethyl)-cyclohexyl]-methyl-carbamoyl}-methyl)-3-trifluoromethyl-benzamide;

±(1S*,2R*,4R*)-N-({[4-Isopropylamino-2-(4-methylsulfanyl-benzenesulfonylmethyl)-cyclohexyl]-methyl-carbamoyl}-methyl)-3-trifluoromethyl-benzamide;

N-{1(R)-[(1S*,2R*,4R*)-4-Azido-2-(4-methylsulfanyl-benzenesulfonylmethyl)-cyclohexylcarbamoyl]-ethyl}-3-trifluoromethyl-benzamide;

N-{1(R)-[(1S*,2R*,4R*)-4-Amino-2-(4-methylsulfanyl-benzenesulfonylmethyl)-cyclohexylcarbamoyl]-ethyl}-3-trifluoromethyl-benzamide;

N-{1(R)-[(1S*,2R*,4R*)-4-Isopropylamino-2-(4-methylsulfanyl-benzenesulfonylmethyl)-cyclohexylcarbamoyl]-ethyl}-3-trifluoromethyl-benzamide;

N-{1(R)-[(1S*,2R*,4R*)-4-(Isopropyl-methyl-amino)-2-(4-methylsulfanyl-benzenesulfonylmethyl)-cyclohexylcarbamoyl]-ethyl}-3-trifluoromethyl-benzamide;

N-{1(S)-[(1S*,2R*,4R*)-4-(Isopropyl-methyl-amino)-2-(4-methylsulfanyl-benzenesulfonylmethyl)-cyclohexylcarbamoyl]-ethyl}-3-trifluoromethyl-benzamide;

±(1S*,2R*,5R*)-2-Amino-N-{[5-dimethylamino-2-(4-methylsulfanyl-benzenesulfonylmethyl)-cyclohexylcarbamoyl]-methyl}-5-trifluoromethyl-benzamide;

±(1S*,2R*,5R*)-N-{[5-Dimethylamino-2-(4-methylsulfanyl-benzenesulfonylmethyl)-cyclohexylcarbamoyl]-methyl}-2-methylamino-5-trifluoromethoxy-benzamide;

±(1S*,2R*,5R*)-2-Amino-N-{[5-isopropylamino-2-(4-methylsulfanyl-benzenesulfonylmethyl)-cyclohexylcarbamoyl]-methyl}-5-trifluoromethoxy-benzamide;

±(1R*,3R*,4S*)-N-[(3-Benzenesulfonylmethyl-4-amino-cyclohexylcarbamoyl)-methyl]-3-trifluoromethyl-benzamide;

±(1R*,3R*,4S*)-N-[(3-Benzenesulfonylmethyl-4-isopropylamino-cyclohexylcarbamoyl)-methyl]-3-trifluoromethyl-benzamide; and ±(1R*,3R*,4S*)-N-[(3-Benzenesulfonylmethyl-4-piperidin-1-yl-cyclohexylcarbamoyl)-methyl]-3-trifluoromethyl-benzamide.

In another embodiment, the present invention is directed to a pharmaceutical composition, comprising a pharmaceutically acceptable carrier and a therapeutically effective amount of a compound of Formula (I) or (Ia).

In another embodiment, the present invention is directed to a method for modulation of chemokine or chemokine receptor activity comprising administering to a patient in need thereof a therapeutically effective amount of a compound of Formula (I) or (Ia).

In another embodiment, the present invention is directed to a method for modulation of MCP-1, MCP-2, MCP-3 and MCP-4, and MCP-5 activity that is mediated by the CCR2 receptor comprising administering to a patient in need thereof a therapeutically effective amount of a compound of Formula (I) or (Ia).

In another embodiment, the present invention is directed to a method for modulation of MCP-1 activity comprising administering to a patient in need thereof a therapeutically effective amount of a compound of Formula (I) or (Ia).

In another embodiment, the present invention is directed to a method for treating disorders, comprising administering to a patient in need thereof a therapeutically effective amount of a compound of Formula (I) or (Ia), said disorders being selected from osteoarthritis, aneurism, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, rheumatoid arthritis, restinosis, organ transplantation, and cancer.

In another embodiment, the present invention is directed to a method for treating disorders, of Formula (I) or (Ia), wherein said disorders being selected from psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artheroscleросis, rheumatoid arthritis, restinosis, organ transplantation, and cancer.

In another embodiment, the present invention is directed to a method for treating disorders, of Formula (I) or (Ia), wherein said disorders being selected from alveolitis, colitis, systemic lupus erythematosus, nephrotoxic serum nephritis, glomerularnephritis, asthma, multiple sclerosis, artherosclerosis, rheumatoid arthritis, restinosis, organ transplantation, and cancer.

In another embodiment, the present invention is directed to a method for treating disorders, of Formula (I) or (Ia), wherein said disorders being selected from asthma, multiple sclerosis, artherosclerosis, rheumatoid arthritis, restinosis, organ transplantation.

In another embodiment, the present invention is directed to a method for treating or preventing rheumatoid arthritis, comprising administering to a patient in need thereof a therapeutically effective amount of a compound of Formula (I) or (Ia).

In another embodiment, the present invention is directed to a method for treating or preventing multiple sclerosis, comprising administering to a patient in need thereof a therapeutically effective amount of a compound of Formula (I) or (Ia).

In another embodiment, the present invention is directed to a method for treating or preventing atherosclerosis, comprising administering to a patient in need thereof a therapeutically effective amount of a compound of Formula (I) or (Ia).

In another embodiment, the present invention is directed to a method for treating or preventing asthma, comprising administering to a patient in need thereof a therapeutically effective amount of a compound of Formula (I) or (Ia).

In another embodiment, the present invention is directed to a method for treating restinosis, comprising administering to a patient in need thereof a therapeutically effective amount of a compound of Formula (I) or (Ia).

In another embodiment, the present invention is directed to a method for treating organ transplatation, comprising administering to a patient in need thereof a therapeutically effective amount of a compound of Formula (I) or (Ia).

In another embodiment, the present invention is directed to a method for treating cancer, comprising administering to a patient in need thereof a therapeutically effective amount of a compound of Formula (I) or (Ia).

In another embodiment, the present invention is directed to a method for treating or preventing inflammatory diseases, comprising administering to a patient in need thereof a therapeutically effective amount of a compound of Formula (I) or (Ia).

In another embodiment, the present invention is directed to a method for modulation of CCR2 activity comprising administering to a patient in need thereof a therapeutically effective amount of a compound of Formula (I) or (Ia).

In another embodiment, the present invention is directed to compounds of Formula (I) or (Ia) for use in therapy.

In another embodiment, the present invention is directed the use of a compound of Formula (I) or (Ia) in the preparation of a medicament for the treatment of osteoarthritis, aneurism, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, rheumatoid arthritis, restinosis, organ transplantation, and cancer.

In another embodiment, ring B is selected from

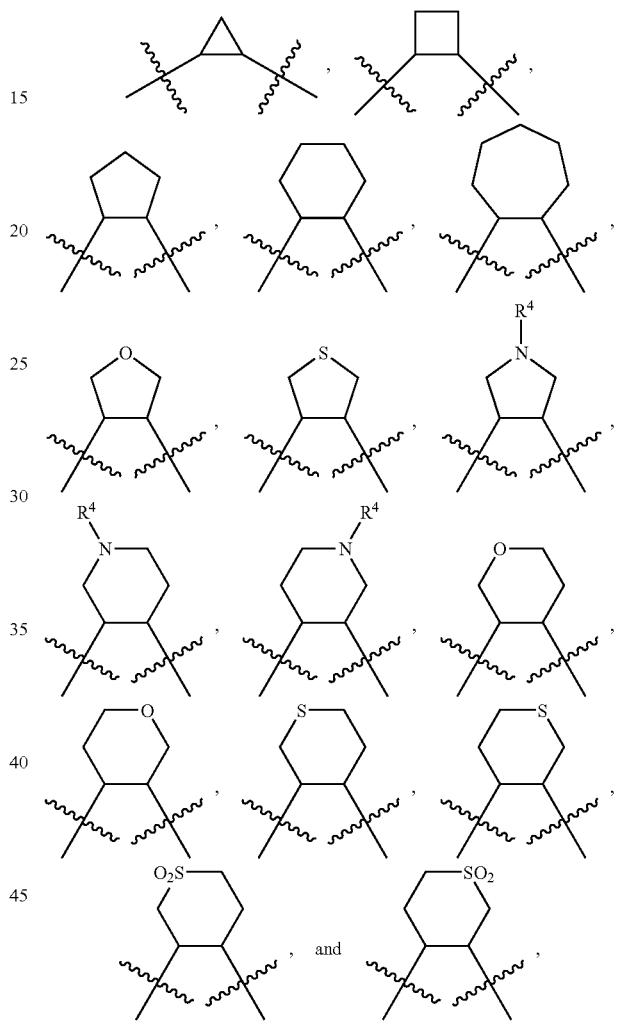

ring B being optionally substituted with 0-1 $R^5$.

In another embodiment, ring B is selected from

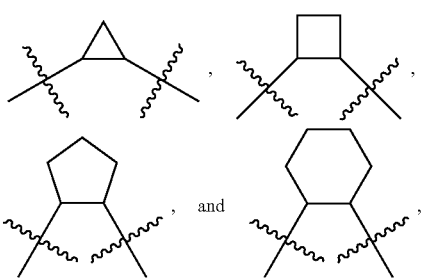

-continued

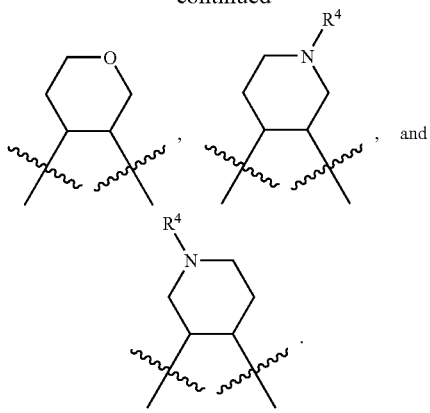

In another embodiment, ring B is selected from

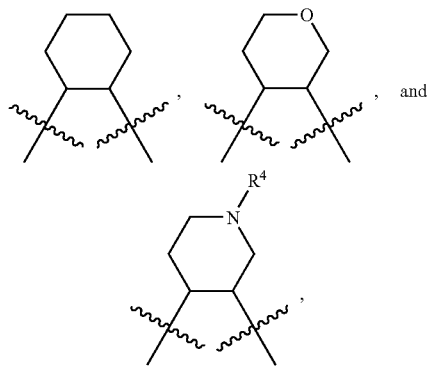

ring B being substituted with 0-1 $R^5$.
In another embodiment, ring B is selected from

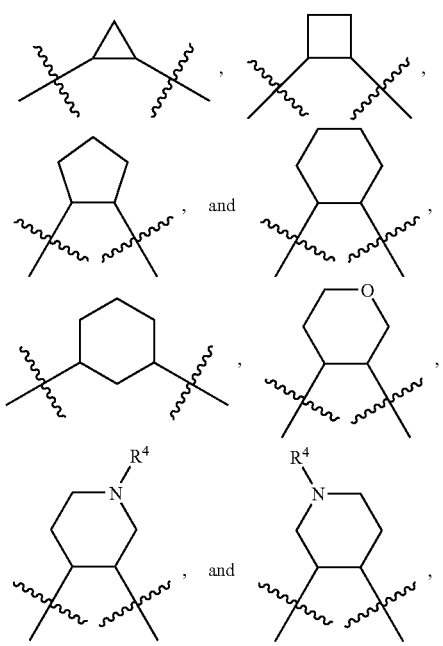

ring B being optionally substituted with 0-1 $R^5$.
In another embodiment, ring B is selected from

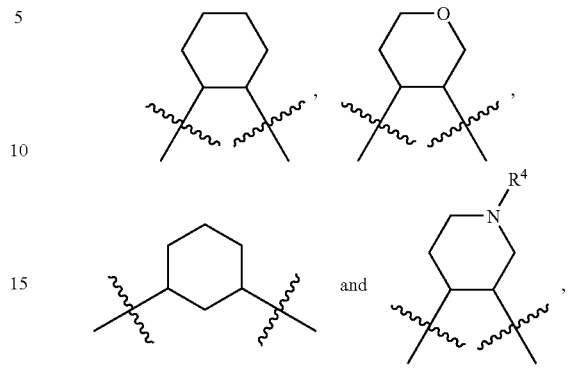

ring B being substituted with 0-1 $R^5$.

In another embodiment, E is —S(O)$_p$(CHR$^{15}$)—.

In another embodiment, E is —NHC(O)NH—.

In another embodiment, Z is selected from —OC(O)NH— and —NHC(O)O—.

In another embodiment, Z is a bond.

In another embodiment, Z is —C(O)—.

In another embodiment, $R^4$ is selected from H, $C_{1-6}$ alkyl, $C_{3-8}$ alkenyl, $C_{3-8}$ alkynyl, (CRR)$_q$OH, (CHR)$_s$SH, (CRR)$_t$OR$^{4d}$, (CHR)$_t$SR$^{4d}$, (CHR)$_t$NR$^{4a}$R$^{4a}$, (CHR)$_q$C(O)OH, (CHR)$_r$C(O)R$^{4b}$, (CHR)$_r$C(O)NR$^{4a}$R$^{4a}$, (CHR)$_t$NR$^{4a}$C(O)R$^{4b}$, (CHR)$_t$OC(O)NR$^{4a}$R$^{4a}$, (CHR)$_t$NR$^{4a}$C(O)OR$^{4d}$, (CHR)$_t$NR$^{4a}$C(O)R$^{4b}$, (CHR)$_r$C(O)OR$^{4b}$, (CHR)$_t$OC(O)R$^{4b}$, (CHR)$_r$S(O)$_p$R$^{4b}$, (CHR)$_r$S(O)$_2$NR$^{4a}$R$^{4a}$, (CHR)$_r$NR$^{4a}$S(O)$_2$R$^{4b}$; and R, at each occurrence, is independently selected from H, methyl, ethyl, propyl, allyl, propynyl, (CH$_2$)$_r$C$_{3-6}$ cycloalkyl, and (CH$_2$)$_r$phenyl substituted with R$^{6e}$.

In another embodiment, $R^4$ is selected from H, $C_{1-6}$ alkyl, $C_{3-8}$ alkenyl, $C_{3-8}$ alkynyl, (CRR)$_q$OH, (CRR)$_s$SH, (CRR)$_t$OR$^{4d}$, (CRR)$_t$SR$^{4d}$, (CRR)$_t$NR$^{4a}$R$^{4a}$, (CRR)$_q$C(O)OH, (CRR)$_r$C(O)R$^{4b}$, (CRR)$_r$C(O)NR$^{4a}$R$^{4a}$, (CRR)$_t$NR$^{4a}$C(O)R$^{4b}$, (CRR)$_t$OC(O)NR$^{4a}$R$^{4a}$, (CRR)$_t$NR$^{4a}$C(O)OR$^{4d}$, (CRR)$_t$NR$^{4a}$C(O)R$^{4b}$, (CRR)$_r$C(O)OR$^{4b}$, (CRR)$_t$OC(O)R$^{4b}$, (CRR)$_r$S(O)$_p$R$^{4b}$, (CRR)$_r$S(O)$_2$NR$^{4a}$R$^{4a}$, (CRR)$_r$NR$^{4a}$S(O)$_2$R$^{4b}$.

In another embodiment, $R^4$ is selected from H, methyl, ethyl, propyl, i-propyl, butyl, i-butyl, allyl, propynyl, (CRR)$_q$OH, (CRR)$_s$SH, (CRR)$_t$OR$^{4d}$, (CRR)$_t$SR$^{4d}$, (CRR)$_t$NR$^{4a}$R$^{4a}$, (CRR)$_q$C(O)OH, (CRR)$_r$C(O)R$^{4b}$, (CRR)$_r$C(O)NR$^{4a}$R$^{4a}$, (CRR)$_t$NR$^{4a}$C(O)R$^{4b}$, (CRR)$_t$OC(O)NR$^{4a}$R$^{4a}$, (CRR)$_t$NR$^{4a}$C(O)OR$^{4d}$, (CRR)$_t$NR$^{4a}$C(O)R$^{4b}$, (CRR)$_r$C(O)OR$^{4b}$, (CRR)$_t$OC(O)R$^{4b}$, (CRR)$_r$S(O)$_p$R$^{4b}$, (CRR)$_r$S(O)$_2$NR$^{4a}$R$^{4a}$, (CRR)$_r$NR$^{4a}$S(O)$_2$R$^{4b}$.

$R^{4b}$ is selected from H, methyl, ethyl, propyl, i-propyl, butyl, i-butyl, t-butyl, pentyl, and cyclopropyl; and $R^{4d}$ is selected from methyl, ethyl, propyl, i-propyl, butyl, i-butyl, t-butyl, pentyl, and cyclopropyl.

In another embodiment, $R^4$ is selected from H, methyl, ethyl, propyl, i-propyl, butyl, i-butyl, allyl, propynyl, (CH$_2$)$_r$C(O)R$^{4b}$.

In another embodiment, $R^4$ is selected from H, methyl, ethyl, propyl, i-propyl, butyl, i-butyl, t-butyl, pentyl, hexyl, allyl, OH, C(O)OR$^{4d}$, and (CH$_2$)$_r$ C(O)R$^{4b}$.

In another embodiment, $R^5$, at each occurrence, is independently selected from H, methyl, ethyl, propyl, i-propyl, butyl, i-butyl, allyl, propynyl, (CH$_2$)$_r$OH, (CH$_2$)$_r$OR$^{5d}$, $(CH_2)_rNR^{5a}R^{5a}$, $(CH_2)_rC(O)OH$, $(CH_2)_rC(O)R^{5b}$, $(CH_2)_rC(O)NR^{5a}R^{5a}$, $(CH_2)_rNR^{5a}C(O)R^{5b}$, $(CH_2)_rOC(O)NR^{5a}R^{5a}$, $(CH_2)_rNR^{5a}C(O)OR^{5d}$, $(CH_2)_rNR^{5a}C(O)R^{5b}$, $(CH_2)_rC(O)OR^{5b}$, $(CH_2)_rOC(O)R^{5b}$, $(CH_2)_rNR^{5a}S(O)_2R^{5b}$, and $C_{1-6}$ haloalkyl; and $R^{5a}$, at each occurrence, is independently selected from H, methyl, ethyl, propyl, i-propyl, butyl, i-butyl, pentyl, hexyl, cyclopropyl, and cyclobutyl.

In another embodiment, $R^5$, at each occurrence, is independently selected from H, $C_{1-6}$ alkyl, $N_3$, $C_{2-8}$ alkenyl, $C_{2-8}$ alkynyl, $(CRR)_rOH$, $(CRR)_rSH$, $(CRR)_rOR^{5d}$, $(CRR)_rSR^{5d}$, $(CRR)_rNR^{5a}R^{5a}$, $(CRR)_rC(O)OH$, $(CRR)_rC(O)R^{5b}$, $(CRR)_rC(O)NR^{5a}R^{5a}$, $(CRR)_rNR^{5a}C(O)R^{5b}$, $(CRR)_rNR^{5a}C(O)OR^{5d}$, $(CRR)_rOC(O)NR^{5a}R^{5a}$, $(CHR)_rNR^{5a}C(O)NR^{5a}R^{5a}$, $CRR(CRR)_rNR^{5a}C(O)H$, $(CRR)_rC(O)OR^{5b}$, $(CRR)_rOC(O)R^{5b}$, $(CRR)_rS(O)_pR^{5b}$, $(CRR)_rS(O)_2NR^{5a}R^{5a}$, $(CRR)_rNR^{5a}S(O)_2R^{5b}$, $(CRR)_rNR^{5a}C(=N)NR^{5a}R^{5a}$, and $C_{1-6}$ haloalkyl, and a $(CH_2)_r$-5-10 membered heterocyclic system containing 1-4 heteroatoms selected from N, O, and S, substituted with 0-2 $R^{5c}$, wherein the heterocyclic system is selected from piperidinyl.

In another embodiment, $R^5$, at each occurrence, is independently selected from H, OH, $OR^{5d}$, $(CH_2)_rNR^{5a}R^{5a}$, $(CH_2)_rNR^{5a}C(O)R^{5b}$, and $(CH_2)_rNR^{5a}C(O)OR^{5d}$.

In another embodiment, $R^5$ is selected from H, OH, $OCH_3$, $N_3$, $NHC(=NH)NH_2$, $NR^{5a}R^{5a}$, and piperidinyl.

In another embodiment, $R^1$ is selected from phenyl substituted with 0-2 $R^6$, naphthyl substituted with 0-2 $R^6$, and a 5-10 membered heteroaryl system containing 1-4 heteroatoms selected from N, O, and S, substituted with 0-3 $R^6$ wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl.

In another embodiment, $R^1$ is selected from a $C_{6-10}$ aryl group substituted with 0-3 $R^6$ wherein the aryl group is selected from phenyl and naphthyl, and a 5-10 membered heteroaryl system containing 1-4 heteroatoms selected from N and O, substituted with 0-3 $R^6$ wherein the heteroaryl system is selected from furyl, indolyl, benzothiazolyl, and benzotriazolyl.

In another embodiment, $R^2$ is selected from phenyl substituted with 0-2 $R^7$, and a 5-10 membered heteroaryl system containing 1-4 heteroatoms selected from N, O, and S, substituted with 0-3 $R^7$ wherein the heteroaryl is selected from benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl.

In another embodiment, $R^1$ is selected from a $C_{6-10}$ aryl group substituted with 0-3 $R^6$ wherein the aryl group is selected from phenyl and naphthyl, and a 5-10 membered heteroaryl system containing 1-4 heteroatoms selected from N and O, substituted with 0-3 $R^6$ wherein the heteroaryl system is selected from benzothiazolyl, indolyl and pyridinyl.

In another embodiment, $R^1$ is selected from a $C_{6-10}$ aryl group substituted with 0-3 $R^6$ wherein the aryl group is selected from phenyl and a 5-10 membered heteroaryl system containing 1-4 heteroatoms selected from N and O, substituted with 0-3 $R^6$ wherein the heteroaryl system is selected from benzothiazolyl.

In another embodiment, $R^2$ is phenyl substituted with 0-2 $R^7$.

In another embodiment, $R^2$ is indazolyl substituted with 0-2 $R^7$.

In another embodiment, $R^2$ is selected from phenyl substituted with 0-2 $R^7$, and a 5-10 membered heteroaryl system containing 1-4 heteroatoms selected from N, O, and S, substituted with 0-3 $R^7$ wherein the heteroaryl is selected from indolyl, naphthalenyl, phthalazinyl, cinnolinyl, quinolinyl, isoquinolinyl, indazolyl, and quinazolinyl, benzimidazolyl, benzofuranyl, benzothiofuranyl, benzoxazolyl, benzthiazolyl, benzisoxazolyl, and benzisothiazolyl.

In another embodiment, Z is a bond and $R^2$ is selected from a 5-10 membered heteroaryl system containing 1-4 heteroatoms selected from N, O, and S, substituted with 0-3 $R^7$ wherein the heteroaryl is selected from indolyl, naphthalenyl, phthalazinyl, cinnolinyl, quinolinyl, isoquinolinyl, indazolyl, and quinazolinyl, benzimidazolyl, benzofuranyl, benzothiofuranyl, benzoxazolyl, benzthiazolyl, benzisoxazolyl, and benzisothiazolyl.

In another embodiment, $R^6$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CH_2)_rNR^{6a}R^{6a}$, $(CH_2)_rOH$, $(CH_2)_rO(CH_2)_rR^{6d}$, $(CH_2)_rSH$, $(CH_2)_rC(O)H$, $(CH_2)_rS(CH_2)_rR^{6d}$, $(CH_2)_rC(O)OH$, $(CH_2)_rC(O)$ $(CH_2)_rR^{6b}$, $(CH_2)_rC(O)NR^{6a}R^{6a}$, $(CH_2)_rNR^{6f}C(O)$ $(CH_2)_rR^{6b}$, $(CH_2)_rC(O)O(CH_2)_rR^{6d}$, $(CH_2)_rOC(O)$ $(CH_2)_rR^{6b}$, $(CH_2)_rS(O)_p(CH_2)_rR^{6b}$, $(CH_2)_rS(O)_2NR^{6a}R^{6a}$, $(CH_2)_rNR^{6f}S(O)_2(CH_2)_rR^{6b}$, $(CH_2)_rNR^{6f}S(O)_2$ $NR^{6a}R^{6a}$, $C_{1-6}$ haloalkyl, and $(CH_2)_r$phenyl substituted with 0-3 $R^{6e}$;

$R^{6a}$, at each occurrence, is independently selected from H, methyl, ethyl, propyl, i-propyl, butyl, i-butyl, t-butyl, pentyl, hexyl, cyclopropyl and phenyl;

$R^{6b}$, at each occurrence, is selected from methyl, ethyl, propyl, i-propyl, butyl, i-butyl, t-butyl, pentyl, hexyl, cyclopropyl, and phenyl;

$R^{6d}$, at each occurrence, is selected from methyl, $CF_3$, ethyl, propyl, i-propyl, butyl, i-butyl, t-butyl, pentyl, hexyl, cyclopropyl, and phenyl;

$R^{6e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{6f}R^{6f}$, and $(CH_2)_r$phenyl; and $R^{6f}$, at each occurrence, is selected from H, methyl, ethyl, propyl, i-propyl, butyl, i-butyl, t-butyl, pentyl, hexyl, cyclopropyl, and phenyl.

In another embodiment, $R^6$ is selected from methyl, ethyl, propyl, i-propyl, butyl, F, Cl, Br, I, $NO_2$, CN, $O(CH_2)_rR^{6d}$, $C(O)H$, $SR^{6d}$, $NR^{6a}R^{6a}$, $OC(O)R^{6b}$, $S(O)_pR^{6b}$, $(CHR')_rS(O)_2NR^{6a}R^{6a}$, $CF_3$;

$R^{6a}$ is H, methyl, or ethyl;

$R^{6b}$ is H or methyl; and $R^{6d}$ is methyl, phenyl, $CF_3$, and $(CH_2)$-phenyl.

In another embodiment, $R^6$ is selected from methyl, ethyl, propyl, i-propyl, butyl, vinyl, F, Cl, Br, I, $NO_2$, CN, $O(CH_2)_rR^{6d}$, $C(O)H$, $(CH_2)OH$, $-CHOH-CH_2OH$ $SR^{6d}$, $C(O)R^{6b}$, $NR^{6a}R^{6a}$, $NC(O)R^{6b}$, $OC(O)R^{6b}$, $S(O)_p R^{6b}$, $(CHR')_rS(O)_2NR^{6a}R^{6a}$, $CF_3$;

$R^{6a}$ is H, methyl, or ethyl;

$R^{6b}$ is H, or methyl;

$R^{6d}$ is methyl, phenyl, $CF_3$, and $(CH_2)$-phenyl.

In another embodiment, $R^7$ is selected from methyl, ethyl, propyl, i-propyl, butyl, i-butyl, s-butyl, t-butyl, pentyl, hexyl, $(CH_2)_rC_{3-6}$ cycloalkyl, Cl, Br, I, F, $NO_2$, CN, $(CH_2)_r$ $NR^{7a}R^{7a}$, $(CH_2)_rOH$, $(CH_2)_rO(CH)_rR^{7d}$, $(CH_2)_rSH$, $(CH_2)_rC(O)H$, $(CH_2)_rS(CH_2)_rR^{7d}$, $(CH_2)_rC(O)OH$, $(CH_2)_rC(O)(CH_2)_rR^{7b}$, $(CH_2)_rC(O)NR^{7a}R^{7a}$, $(CH_2)_rNR^{7f}C(O)(CH_2)_rR^{7b}$, $(CH_2)_rC(O)O(CH_2)_rR^{7d}$, $(CH_2)_rOC(O)(CH_2)_rR^{7b}$, $(CH_2)_rNR^{7a}C(O)NR^{7a}R^{7a}$, $(CH_2)_rNR^{7a}C(O)O(CH_2)_rR^{7d}$, $(CH_2)_rS(O)p(CH_2)_rR^{7b}$, $(CH_2)_rS(O)_2NR^{7a}R^{7a}$, $(CH_2)_rNR^{7f}S(O)_2(CH_2)_rR^{7b}$, $C_{1-6}$ haloalkyl, and $(CH_2)_r$phenyl substituted with 0-3 $R^{7e}$;

$R^{7a}$, at each occurrence, is selected from H, methyl, ethyl, propyl, i-propyl, butyl, i-butyl, t-butyl, pentyl, hexyl, and cyclopropyl;

$R^{7b}$, at each occurrence, is selected from methyl, ethyl, propyl, i-propyl, butyl, i-butyl, t-butyl, pentyl, hexyl, and cyclopropyl;

$R^{7d}$, at each occurrence, is selected from methyl, $CF_3$, ethyl, propyl, i-propyl, butyl, i-butyl, t-butyl, pentyl, hexyl, and cyclopropyl;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-15}$ alkyl, $(CH_2)_rNR^{7f}R^{7f}$, and $(CH_2)_r$phenyl; and $R^{7f}$, at each occurrence, is selected from H, methyl, ethyl, propyl, i-propyl, butyl, i-butyl, t-butyl, pentyl, hexyl, cyclopropyl, and phenyl.

In another embodiment, $R^7$ is selected from methyl, ethyl, propyl, i-propyl, butyl, i-butyl, s-butyl, pentyl, hexyl, Cl, Br, I, F, $NO_2$, $NR^{7a}R^{7a}$, $NHC(O)NHR^{7a}$, $NR^{7a}C(O)R^{7b}$, $NR^{7a}C(O)OR^{7d}$, $CF_3$, $OCF_3$, $C(O)R^{7b}$, $NR^{7f}C(O)NHR^{7a}$, and $NHS(°)_2R^{7b}$.

In another embodiment, $R^7$ is selected from methyl, ethyl, propyl, i-propyl, butyl, i-butyl, s-butyl, pentyl, hexyl, Cl, Br, I, F, $NO_2$, $NR^{7a}R^{7a}$, $NHC(O)NHR^{7a}$, $NR^{7a}C(O)R^{7b}$, $NR^{7a}C(O)OR^{7d}$, $CF_3$, $OCF_3$, $C(O)OR^{7d}$, $C(O)R^{7b}$, $NR^{7f}C(O)NR^{7a}R^{7a}$, $NHS(°)_2R^{7b}$,

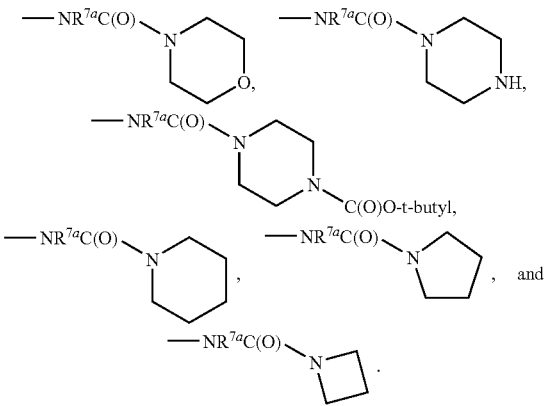

In another embodiment, $R^{7a}$ is selected from H, methyl, ethyl, propyl, i-propyl, butyl, i-butyl, t-butyl, pentyl, neo-pentyl, cyclopropyl, cyclobutyl, cyclopentyl, and cyclohexyl;

$R^{7b}$ is selected from cyclohexyl and $CF_3$; and $R^{7d}$ is selected from methyl, ethyl, propyl, i-propyl, butyl, i-butyl, and t-butyl.

In another embodiment, $R^7$ is selected from methyl, ethyl, propyl, i-propyl, butyl, i-butyl, s-butyl, pentyl, hexyl, Cl, Br, I, F, $NO_2$, $NR^{7a}R^{7a}$, $NHC(O)NHR^{7a}$, $NR^{7a}C(O)R^{7b}$, $NR^{7a}C(O)OR^{7d}$, $CF_3$, $OCF_3$, $C(O)OR^{7d}$, $C(O)R^{7b}$, $NR^{7f}C(O)NR^{7a}R^{7a}$, $NHS(°)_2R^{7b}$,

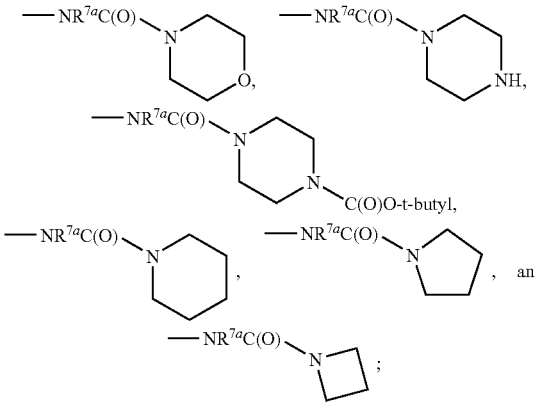

$R^{7a}$ is selected from H, methyl, ethyl, propyl, i-propyl, butyl, i-butyl, t-butyl, pentyl, neo-pentyl, cyclopropyl, cyclobutyl, cyclopentyl, and cyclohexyl;

$R^{7b}$ is selected from methyl, ethyl, propyl, i-propyl, butyl, cyclohexyl and $CF_3$;

$R^{7d}$ is selected from methyl, ethyl, propyl, i-propyl, butyl, i-butyl, and t-butyl.

In another embodiment, $R^8$ is H.

In another embodiment, $R^{11}$ and $R^{12}$ are H.

In another embodiment, $R^{14}$ is selected from H and methyl.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substitent is keto (i.e., =O), then 2 hydrogens on the atom are replaced.

When any variable (e.g., $R^a$) occurs more than one time in any constituent or formula for a compound, its definition at each occurrence is independent of its definition at every other occurrence. Thus, for example, if a group is shown to be substituted with 0-2 $R^a$, then said group may optionally be substituted with up to two $R^a$ groups and $R^a$ at each occurrence is selected independently from the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-8}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl. $C_{1-8}$ alkyl, is intended to include $C_1$, $C_2$, $C_3$, $C_4$, $C_5$, $C_6$, $C_7$, and $C_8$ alkyl groups. "Alkenyl" is intended to include hydrocarbon chains of either a straight or branched configuration and one or more unsaturated carbon-carbon bonds which may occur in any stable point along the chain, such as ethenyl, propenyl, and the like. "Alkynyl" is intended to include hydrocarbon chains of either a straight or branched configuration and one or more unsaturated triple carbon-carbon bonds which may occur in any stable point along the chain, such as ethynyl, propynyl, and the like. "$C_{3-6}$ cycloalkyl" is intended to include saturated ring groups having the specified number of carbon atoms in the ring, including mono-, bi-, or poly-cyclic ring systems, such as cyclopropyl, cyclobutyl, cyclopentyl, cyclohexyl, and cycloheptyl in the case of $C_7$ cycloalkyl. $C_{3-6}$ cycloalkyl, is intended to include $C_3$, $C_4$, $C_5$, and $C_6$ cycloalkyl groups.

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

As used herein, the term "5-6-membered cyclic ketal" is intended to mean 2,2-disubstituted 1,3-dioxolane or 2,2-disubstituted 1,3-dioxane and their derivatives.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl; [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl", is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S and is aromatic in nature.

Examples of heterocycles include, but are not limited to, 1H-indazole, 2-pyrrolidonyl, 2H,6H-1,5,2-dithiazinyl, 2H-pyrrolyl, 1H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, the heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or in combination with other active ingredients effective to inhibit MCP-1 or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Methods include, but are not limited to, those described below. All references cited herein are hereby incorporated in their entirety herein by reference.

ible with the reagents and reactions proposed. Such restrictions to the substituents which are compatible with the reaction conditions will be readily apparent to one skilled in the art and alternate methods must then be used.

A series of compounds of formula 7 are synthesized as shown in Scheme 1. A cyclic epoxide 1 can be opened (Marczak et al., *Syn. Comm.* 1990, 20, 1511 and Keehn et al., *Syn. Comm.* 1986, 16, 309) with a metallated sulfone to give the alcohol 2. This alcohol can be mesylated and displaced with azide before reduction gives the amine 3. The rest of the molecule can be assembled stepwise (through intermediate 4) or via a single coupling (using 8). These are very common amide bond couplings and give the target compound 7.

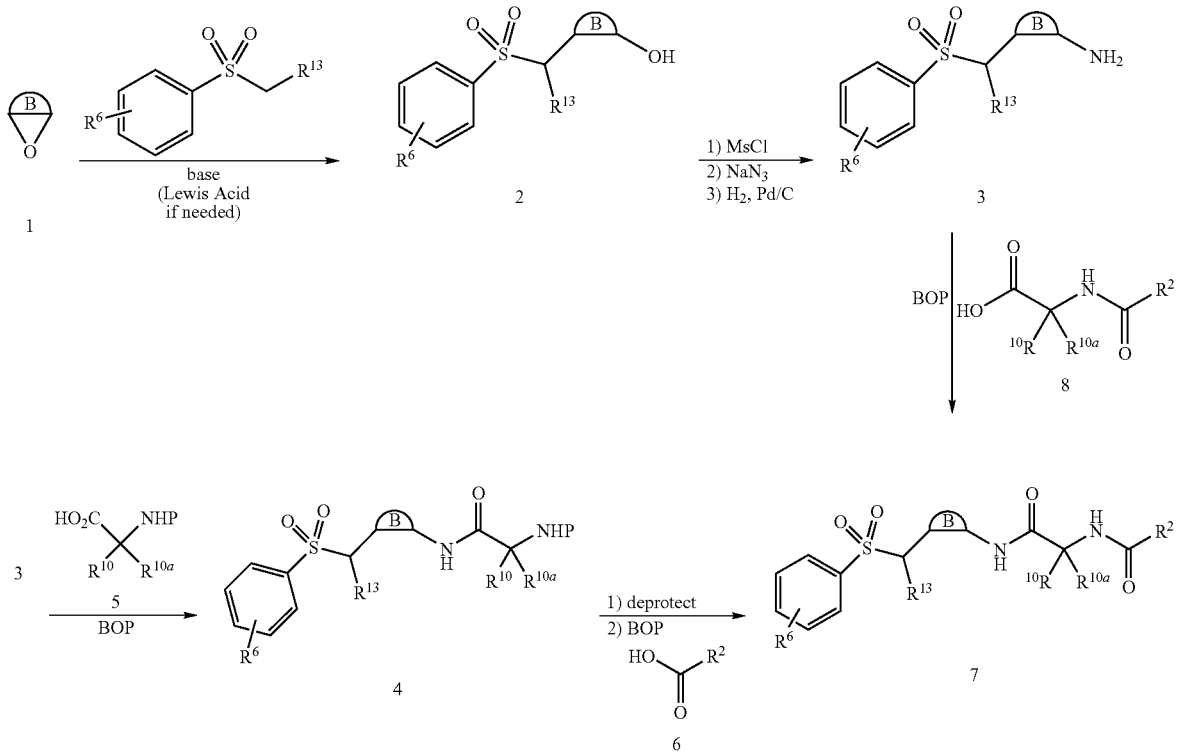

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compat- A series of compounds with formulas 14 and 7 can be synthesized by the methods shown in Scheme 2. Many amino esters 9 are available and can be N-protected (Boc or Cbz for example) to give 10. The ester of 10 can be reduced by LiBH$_4$ (or several other suitable reagents) to give the alcohol 11. There are several ways the alcohol 11 can be converted into the sulfide 12. One method (Nakagawa et al., *Tetrahedron. Lett.* 1975, 1409) uses the disulfide and Bu$_3$P. Another classical way is through the mesylate which can be displaced with a thiophenol anion. With 12 in hand, one can deprotect the amine to 13 prior to a BOP coupling to give the target compound 14. Compound 12 can also be oxidized to the sulfone 15 before deprotection gives amine 3 (see Scheme 1). This can be coupled directly with 8 to give the target compound 7.

Scheme 2
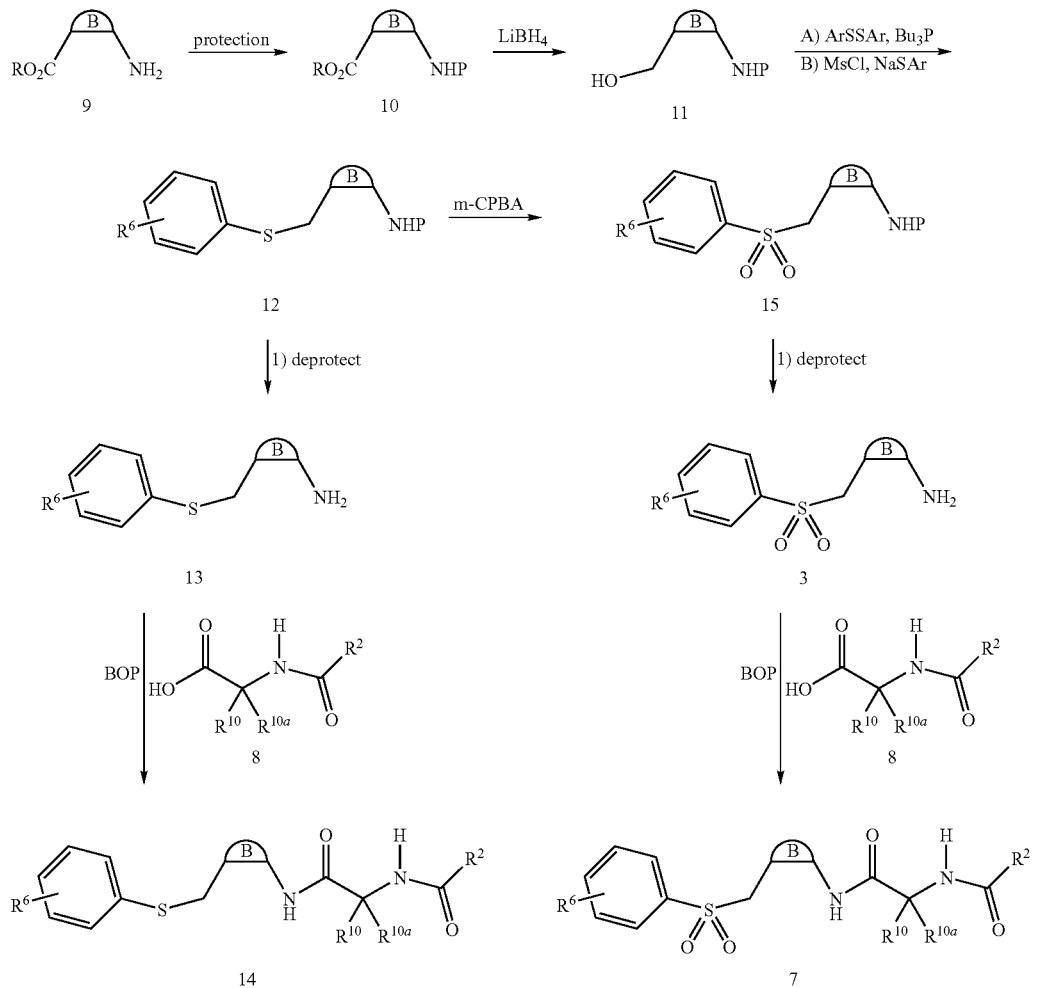
A series of compounds of formula 19 are synthesized as shown in Scheme 3. Intermediate 11, from above, can be used as a starting point to give the azide 16 through a Mitsunobu reaction. Reduction of 16 to the amine 17 allows for urea formation via the isocyanate. The resulting urea 18 can be deprotected and coupled to acid 8 to give the target 19.
Scheme 3
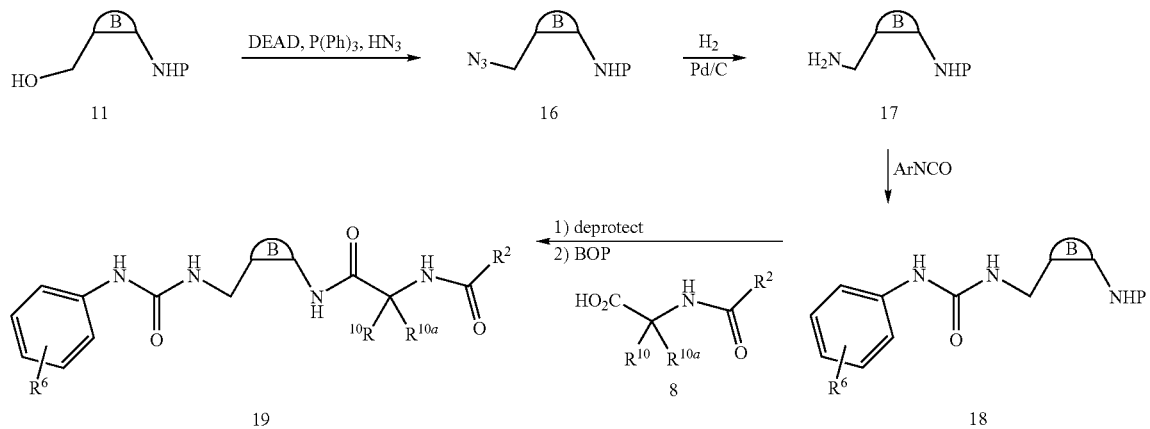

A series of compounds of formula 24 can be synthesized as shown in Scheme 4. An appropriate aryl or heterocyclic amine H$_2$NR$^2$ can undergo a reductive amination with a glyoxylate derivative to give 21. If the ester is used, then hydrolysis provides the carboxylate 22. This can be coupled with a core amine 23 to give the target 24.

Scheme 4

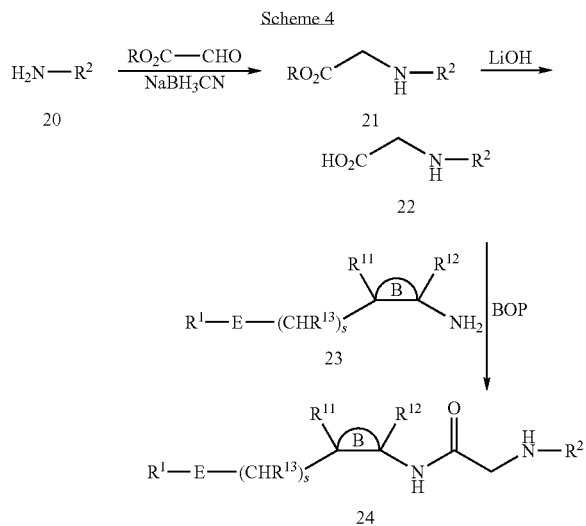

When required, separation of the racemic material can be achieved by HPLC using a chiral column or by a resolution using a resolving agent such as camphonic chloride as in Steven D. Young, et al, *Antimicrobial Agents and Chemotheraphy*, 1995, 2602-2605.

Other features of the invention will become apparent in the course of the following descriptions of exemplary embodiments which are given for illustration of the invention and are not intended to be limiting thereof.

EXAMPLES

Abbreviations used in the Examples are defined as follows: "1 x" for once, "2 x" for twice, "3 x" for thrice, "° C." for degrees Celsius, "g" for gram or grams, "mg" for milligram or milligrams, "mL" for milliliter or milliliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v", for volume to volume ratio, "aq" for aqueous solutions. "R" and "S" are stereochemical designations familiar to those skilled in the art.

Example 1

(±)tert-Butyl 2-({[2-({(1S*,2R*)-2-[(phenylthio) methyl]cyclohexyl}amino)-2-oxoethyl] amino}carbonyl)-4-(trifluoromethyl)phenylcarbamate (1a) (±)-cis-2-Hydroxymethyl-1-cyclohexylamine hydrochloride (3.3 g) was dissolved in THF (60 mL) and water (20 mL) prior to the addition of Et$_3$N (5.6 mL). This was cooled to 0° C. and Boc$_2$O (4.4 g) was added. The reaction was warmed to rt and stirred overnight. The reaction was quenched with water and EtOAc. The EtOAc layer was washed with 1 N HCl solution, NaHCO$_3$ solution, and brine. The organic layer was dried, filtered, and concentrated. A portion of this material (500 mg) was dissolved in CH$_2$Cl$_2$ (7 mL) prior to the addition of phenyl disulfide (844.8 mg). At rt, Bu$_3$P (0.98 mL) was added dropwise and the solution was stirred overnight. The solution was placed directly on a flash column. This chromatography gave (±)(1S*,2R*) (2-phenyl-sulfanylmethyl-cyclohexyl)-carbamic acid tert-butyl ester (434 mg). MS found: (M+Na+CH$_3$CN)$^+$=466.3.

(1b) The above derivative (1a)(425 mg) was dissolved in CH$_2$Cl$_2$ (4 mL) and was cooled to 0° C. Trifluoroacetic acid (4 mL) was added and the reaction was warmed to rt. After the reaction was stirred for 1 h, it was concentrated. A portion of this (364 mg) was dissolved in DMF prior to the addition of Hunig's base (0.5 mL) and N-Boc-Gly-OH (209 mg). After cooling to 0° C., BOP Reagent (526 mg) was added. The resulting mixture was warmed to rt and was stirred overnight. EtOAc was added along with 1 N HCl solution. The EtOAc layer was washed with 1 N HCl, NaHCO$_3$ solution, and brine. The EtOAc was dried (MgSO$_4$), filtered, and concentrated (336 mg). A portion of this material (325 mg) was dissolved in CH$_2$Cl$_2$ (4 mL) and was cooled to 0° C. Trifluoroacetic acid (4 mL) was added and the reaction was warmed to rt. After the reaction was stirred for 1 h, it was concentrated. This was dissolved in DMF prior to the addition of Hunig's base (0.5 mL) and 2-(tert-butoxycarbonyl)amino-5-trifluoromethyl-benzoic acid (342 mg) (Takagishi et al., *Synlett* 1992, 360). After cooling to 0° C., BOP Reagent (486 mg) was added. The resulting mixture was warmed to rt and was stirred overnight. EtOAc was added along with 1 N HCl solution. The EtOAc layer was washed with 1 N HCl, NaHCO$_3$ solution, and brine. The EtOAc was dried (MgSO$_4$), filtered, and concentrated. Flash chromatography of the resulting residue gave the title compound (277 mg). MS found: (M+Na)$^+$=588.3.

Example 2

(±)tert-Butyl 2-({[2-({(1S*,2R*)-2-[(phenylsulfonyl) methyl]cyclohexyl}amino)-2-oxoethyl] amino}carbonyl)-4-(trifluoromethyl)phenylcarbamate (2a) A portion (158 mg) of the above material, Example 1, was dissolved in CH$_2$Cl$_2$ (3 mL) and cooled to 0° C. prior to the addition of 65% MCPBA (183 mg). After 1.5 hr, additional 65% MCPBA (100 mg) was added. The solution was stirred for 45 min before saturated NaHCO$_3$ solution (aq) was added. The organic layer was dried, filtered, and concentrated. Flash chromatography of the resulting residue gave the title compound (133 mg). MS found: (M+Na)$^+$=620.2.

Example 3

(±)tert-Butyl 2-({[2-({(1S*,2R*)-2-[(1,3-benzothiazol-2-ylthio)methyl]cyclohexyl}amino)-2-oxoethyl] amino}carbonyl)-4-(trifluoromethyl)phenylcarbamate (3a) 2,2'-Dithiobis(benzothiazole) (1.5 g) was incorporated into Example 1, step (1a), to give the title compound (28 mg). MS found: (M+H)$^+$=623.2.

Example 4

(±)tert-Butyl 2-({[2-({(1S*,2R*)-2-[(4-methylphenylthio)methyl]cyclohexyl}amino)-2-oxoethyl] amino}carbonyl)-4-(trifluoromethyl)phenylcarbamate (4a) p-Tolyl disulfide (2.4 g) was incorporated into Example 1, step (1a), to give the title compound (341 mg). MS found: (M+H)$^+$=580.5.

Example 5

(±)2-Amino-N-{2-[((1S*,2R*)-2-{[(4-methylphenyl)thio]methyl}cyclohexyl)amino]-2-oxoethyl}-5-(trifluoromethyl)benzamide (5a) A portion of the above material (14 mg), (4a), was dissolved in $CH_2Cl_2$ (3 mL) prior to the addition of TFA (1 mL). After 45 min, the solution was concentrated to give the title benzamide (11 mg). MS found: $(M+H)^+=480.2$.

Example 6

(±)tert-Butyl 2-({[2-({(1S*,2R*)-2-[(4-methylphenylsulfonyl)methyl]cyclohexyl}amino)-2-oxoethyl]amino}carbonyl)-4-(trifluoromethyl)phenylcarbamate (6a) A portion of Example 4 (290 mg) was incorporated into Example 2 to give the title compound (280 mg). MS found: $(M+Na)^+=635.2$.

Example 7

(±)2-Amino-N-{2-[((1S*,2R*)-2-{[(4-methylphenyl)sulfonyl]methyl}cyclohexyl)amino]-2-oxoethyl}-5-(trifluoromethyl)benzamide (7a) A portion of the above material (21 mg), (6a), was dissolved in $CH_2Cl_2$ (5 mL) prior to the addition of TFA (1.5 mL). After 45 min, the solution was concentrated to give the title benzamide (15 mg). MS found: $(M+H)^+=512.2$.

Example 8

(±)2-Amino-N-{2-[((1S*,2R*)2-{[1,3-benzothiazol-2-ylthio]methyl}cyclohexyl)amino]-2-oxoethyl}-5-(trifluoromethyl)benzamide (8a) A portion of Example 3 (5 mg) was dissolved in $CH_2Cl_2$ (1.5 mL) prior to the addition of TFA (1.5 mL). After 45 min, the solution was concentrated to give the title benzamide (3 mg). MS found: $(M+H)^+=523.1$.

Example 9

(±)N-{2-[((1S*,2R*)-2-{[(4-methylphenyl)thio]methyl}cyclohexyl)amino]-2-oxoethyl}-2-[(trifluoroacetyl)amino]-5-(trifluoromethyl)benzamide (9a) p-Tolyl disulfide was incorporated into Example 1, step (1a), and 2-(trifluoromethylcarbonyl)amino-5-trifluoromethylbenzoic acid (350 mg) was incorporated into the Example 1, step (1b), to give the title benzamide (148 mg). MS found: $(M-H)^-=574.3$.

Example 10

(±)N-{2-[((1S*,2R*)-2-{[(4-methylphenyl)sulfonyl]methyl}cyclohexyl)amino]-2-oxoethyl}-2-[(trifluoroacetyl)amino]-5-(trifluoromethyl)benzamide (10a) A portion of Example 9 (148 mg) was incorporated into Example 2 to give the title benzamide (146 mg). MS found: $(M-H)^-=606.2$.

Example 11

(2-tert-Butoxycarbonylamino-5-trifluoromethyl-benzoylamino)-acetic acid (11a) Glycine benzyl ester p-toluenesulfonate salt (6.03 g) was dissolved in DMF prior to the addition of Hunig's base (12.4 mL) and 2-(tert-butoxycarbonyl)amino-5-trifluoromethylbenzoic acid (6 g) (Takagishi et al., *Synlett* 1992, 360). After cooling to 0° C., BOP Reagent (8.69 g) was added. The resulting mixture was warmed to rt and was stirred 96 h. EtOAc was added along with 1 N HCl solution. The EtOAc layer was washed with 1 N HCl (aq), $NaHCO_3$ solution (aq), and brine. The EtOAc was dried ($MgSO_4$), filtered, and concentrated. Flash chromatography of the resulting residue gave 2-tert-butoxycarbonylamino-5-trifluoromethyl-benzoylamino)-acetic acid benzyl ester (5.78 g). MS found: $(M+Na)^+=475.3$.

(11b) The above material (5.7 g) was dissolved in MeOH prior to the addition of 10% Pd/C (1 g). A hydrogen balloon was added and the mixture was stirred for 3 h. The Pd/C was filtered off and the solvent was concentrated to the title compound as a white solid (4.56 g). MS found: $(M-H)^-=361.3$.

Example 12

(±)tert-Butyl 2-({[2-({(1S*,2R*)-2-[(4-ethylphenylsulfonyl)methyl]cyclohexyl}amino)-2-oxoethyl]amino}carbonyl)-4-(trifluoromethyl)phenylcarbamate (12a) (±)cis-2-Hydroxymethyl-1-cyclohexylamine hydrochloride (3.3 g) was dissolved in THF (60 mL) and water (20 mL) prior to the addition of $Et_3N$ (5.6 mL). This was cooled to 0° C. and $Boc_2O$ (4.4 g) was added. The reaction was warmed to rt and stirred overnight. The reaction was quenched with water and EtOAc. The EtOAc layer was washed with 1 N HCl solution, $NaHCO_3$ solution, and brine. The organic layer was dried, filtered, and concentrated. A portion of this material (1 g) was dissolved in $CH_2Cl_2$ (20 mL) and cooled to 0° C. prior to the addition of $Et_3N$ (0.91 mL). Next, methanesulfonyl chloride (0.51 mL) in $CH_2Cl_2$ (5 mL) was added dropwise. After 2 hr, water was added along with some 10% citric acid solution (aq). The organic layer was separated and was washed with brine. The organic layer was then dried, filtered, and concentrated to the mesylate. A portion of this mesylate (185 mg) was dissolved in THF. In a separate flask 60% NaH was added to THF (3 mL) and cooled to 0° C. prior to the addition of 4-ethylthiophenol (108 mg). After 10 min, the mesylate solution was added. This was warmed to rt and was stirred overnight. EtOAc was added and the resulting solution was washed with saturated $NaHCO_3$ solution (aq) and brine. The organic layer was dried, filtered, and concentrated. Flash chromatography of the resulting residue gave (±)[(1S*,2R*)-2-(4-ethyl-phenylsulfanylmethyl)-cyclohexyl]-carbamic acid tert-butyl ester (100 mg). MS found: $(M+H)^+=372.3$.

(12b) Some of the above material (175 mg), 11(a), was dissolved in $CH_2Cl_2$ (5 mL) prior to the addition of TFA (10 mL). After 1 h, the solution was concentrated. This was dissolved in DMF prior to the addition of Hunig's base (0.35 mL) and 2-tert-butoxycarbonylamino-5-trifluoromethyl-benzoylamino)-acetic acid (200 mg), Example 11. After cooling to 0° C., BOP Reagent (244 mg) was added. The resulting mixture was warmed to rt and was stirred overnight. EtOAc was added along with 1 N HCl solution (aq). The EtOAc layer was washed with 1 N HCl, $NaHCO_3$ solution (aq), and brine.

The EtOAc was dried (MgSO$_4$), filtered, and concentrated. A portion (250 mg) of the resulting material was dissolved in CH$_2$Cl$_2$ (10 mL) and cooled to 0° C. prior to the addition of 65% mCPBA (257 mg). The solution was stirred for 1 h before saturated NaHCO$_3$ solution (aq) was added. The organic layer was dried, filtered, and concentrated to give the title compound (285 mg). MS found: (M−H)$^-$=624.

Example 13

(±)tert-Butyl 2-({[2-({(1S*,2R*)-2-[(4-bromophenylsulfonyl)methyl]cyclohexyl}amino)-2-oxoethyl]amino}carbonyl)-4-(trifluoromethyl)phenylcarbamate (13a) 4-Bromothiophenol (246 mg) was incorporated into the above procedure, Example 12, to give the title compound (1.46 g). MS found: (M+Na)$^+$=700.2.

Example 14

(±)2-Amino-N-{2-[((1S*,2R*)-2-{[(4-ethylphenyl)sulfonyl]methyl}cyclohexyl)amino]-2-oxoethyl}-5-(trifluoromethyl)benzamide (14a) A portion of Example 12 (58 mg) was dissolved in TFA (4 mL). After 30 min, the solution was concentrated to give the title benzamide. MS found: (M+H)$^+$=526.3.

Example 15

(±)2-Amino-N-{2-[((1S*,2R*)-2-{[(4-bromophenyl)sulfonyl]methyl}cyclohexyl)amino]-2-oxoethyl}-5-(trifluoromethyl)benzamide (15a) A portion of Example 13 (53 mg) was dissolved in TFA (4 mL). After 30 min, the solution was concentrated to give the title benzamide. MS found: (M+H)$^+$=578.2.

Example 16

(±)tert-Butyl 2-({[2-({(1S*,2R*)-2-[(4-vinylphenylsulfonyl)methyl]cyclohexyl}amino)-2-oxoethyl]amino}carbonyl)-4-(trifluoromethyl)phenylcarbamate (16a) Example 13 (350 mg) was dissolved in toluene (3 mL) prior to the addition of Pd(PPh)$_4$ (18 mg), BHT (few crystals), and tributyl(vinyl)tin (0.17 mL). This solution was stirred at reflux for 3.5 h. After cooling to rt, the solution was treated with saturated KF solution (aq). This was stirred for 96 h before EtOAc was added. The solution was filtered and the organic layer was concentrated. Flash chromatography of the resulting residue gave the title compound (222 mg). MS found: (M+H)$^+$=624.2.

Example 17

(±)tert-butyl 2-{[(2-{[(1S*,2R*)-2-({[4-(1,2-dihydroxyethyl)phenyl]sulfonyl}methyl)cyclohexyl]amino}-2-oxoethyl)amino]carbonyl}-4-(trifluoromethyl)phenylcarbamate (17a) Example 16 (87 mg) was dissolved in THF prior to the addition of water (0.06 mL), 4-methylmorpholine N-oxide (20 mg), and finally 0.05M OSO$_4$ (0.06 mL) in THF. The solution was stirred overnight at rt before 10% HCl solution (aq) and 15% NaHSO$_3$ solution (aq) were added. This was extracted with CH$_2$Cl$_2$. The organic layer was dried, filtered, and concentrated to the title compound (73 mg). MS found: (M+Na)$^+$=680.3.

Example 18

(±)tert-butyl 2-{[(2-{[(1S*,2R*)-2-({[4-formylphenyl]sulfonyl}methyl)cyclohexyl]amino}-2-oxoethyl)amino]carbonyl}-4-(trifluoromethyl)phenylcarbamate (18a) Example 17 (60 mg) was dissolved in CH$_2$Cl$_2$ with water (1 drop) prior to the addition of NaIO$_4$ (39 mg). After stirring for 3 h, MgSO$_4$ was added and this was stirred for 1 h. This was added to a flash column for purification and yielded the title compound (43 mg). MS found: (M+H)$^+$=626.3.

Example 19

(±)tert-butyl 2-{[(2-{[(1S*,2R*)-2-({[4-(methylthio)phenyl]sulfonyl}methyl)cyclohexyl]amino}-2-oxoethyl)amino]carbonyl}-4-(trifluoromethyl)phenylcarbamate (19a) (±)(1S*,2R*)-[2-(4-Bromo-phenylsulfanylmethyl)-cyclohexyl]-carbamic acid tert-butyl ester (4.93 g) (from 13a and made as in 12a but with 4-bromothiophenol) was dissolved in CH$_2$Cl$_2$ (216 mL) and cooled to 0° C. prior to the addition of 65% m-CPBA (6.6 g). The solution was stirred for 2.5 h before saturated NaHCO$_3$ solution (aq) and brine were added. The organic layer was dried, filtered, and concentrated. A quick flash column of the resulting residue gave the sulfone (4.1 g). A portion (300 mg) of this was dissolved in DMF prior to the addition of NaSMe (51 mg). After stirring for 3 h at 60° C., ice water was added and the solution was acidified with 1N HCl solution (aq). This was exacted with CH$_2$Cl$_2$. The organic layer was dried, filtered, and concentrated to (±)(1S*,2R*)[2-(4-methylsulfanyl-benzenesulfonylmethyl)-cyclohexyl]-carbamic acid tert-butyl ester (MS found: (M+H)$^+$=400.3).

(19b) All of this material, 19a, was dissolved in TFA (10 mL). After 15 min, the solution was concentrated. This was dissolved in DMF prior to the addition of Hunig's base (0.48 mL) and 2-tert-butoxycarbonylamino-5-trifluoromethyl-benzoylamino)-acetic acid (277 mg), Example 11. After cooling to 0° C., BOP Reagent (338 mg) was added. The resulting mixture was warmed to rt and was stirred overnight. EtOAc was added along with 1 N HCl solution (aq). The EtOAc layer was washed with 1 N HCl, NaHCO$_3$ solution (aq), and brine. The EtOAc was dried (MgSO$_4$), filtered, and concentrated. Flash chromatography of the resulting residue gave the title compound (236 mg). MS found: (M+Na)$^+$=666.4.

Example 20

(±)2-Amino-N-{2-[((1S*,2R*)-2-{[(4-(methylthio)phenyl)sulfonyl]methyl}cyclohexyl)amino]-2-oxoethyl}-5-(trifluoromethyl)benzamide (20a) A portion of Example 19 (210 mg) was dissolved in CH$_2$Cl$_2$ (10 mL) and TFA (3 mL). After 3 h, the solution was concentrated to give the title compound (167 mg). MS found: (M+Na)$^+$=566.2.

Example 21

(±)2-Amino-N-{2-[((1S*,2R*)-2-{[(4-vinylphenyl)sulfonyl]methyl}cyclohexyl)amino]-2-oxoethyl}-5-(trifluoromethyl)benzamide (21a) A portion of Example 16 (26 mg) was dissolved in $CH_2Cl_2$ (2 mL) and TFA (2 mL). After 15 min, the solution was concentrated to give the title compound (20 mg). MS found: $(M+H)^+=524.3$.

Example 22

(±)tert-butyl 2-{[(2-{[(1S*,2R*)-2-({[4-(hydroxymethyl)phenyl]sulfonyl}methyl)cyclohexyl]amino}-2-oxoethyl)amino]carbonyl}-4-(trifluoromethyl)phenylcarbamate (22a) Example 18 (30 mg) was dissolved in THF (1 mL) and MeOH (1 mL) prior to the addition of $NaBH_4$ (10 mg). After 5 min, the reaction was quenched with water and extracted with $CH_2Cl_2$. The organic layer was washed with brine, dried, and concentrated to give the title compound (11 mg). MS found: $(M+Na)^+=650.3$.

Example 23

2-Isopropoxycarbonylamino-5-trifluoromethyl-benzoic acid (23a) 2-(tert-Butoxycarbonyl)amino-5-trifluoromethyl-benzoic acid (6.0 g) was dissolved in 4M HCl (4 mL) in dioxane. After 3 h, the solution was concentrated to a white solid. A portion of this material (900 mg) was dissolved in THF (10 mL), water (2 mL), and $Et_3N$ (1.8 mL) prior to the addition of 1M i-propyl chloroformate (4.5 mL) in toluene. The reaction was stirred for 4 h before EtOAc was added. The EtOAc layer was washed with 1N HCl and brine before it was dried, filtered, and concentrated to a crude material. This material was crystallized with $CH_2Cl_2$ to give the title compound (800 mg). MS found: $(2M-1)^-=581.2$.

Example 24

(±)[iso-propyl 2-{[(2-{[(1S*,2R*)-2-({[4-(methylthio)phenyl]sulfonyl}methyl)cyclohexyl]amino}-2-oxoethyl)amino]carbonyl}-4-(trifluoromethyl)phenylcarbamate (24a) (±)(1S*,2R*)[2-(4-Methylsulfanyl-benzenesulfonylmethyl)-cyclohexyl]-carbamic acid tert-butyl ester (see Example 19a) (1.39 g) was dissolved in $CH_2Cl_2$ (10 mL) and TFA (10 mL). After 1.5 h, the solution was concentrated. This was dissolved in DMF (10 mL) prior to the addition of Hunig's base (2.4 mL) and N-Boc-Gly-OH (669 mg). After cooling to 0° C., BOP Reagent (1.69 g) was added. The resulting mixture was warmed to rt and was stirred overnight. EtOAc was added along with 1 N HCl solution (aq). The EtOAc layer was washed with 1 N HCl, $NaHCO_3$ solution (aq), and brine. The EtOAc was dried ($MgSO_4$), filtered, and concentrated to give (±)(1S*,2R*){[2-(4-methylsulfanyl-benzenesulfonylmethyl)-cyclohexylcarbamoyl]-methyl}-carbamic acid tert-butyl ester as a tan powder [MS found: $(M+Na)^+=666.4$]. A portion of this material (668 mg) was dissolved in $CH_2Cl_2$ (2 mL) and TFA (5 mL). After 15 min, the solution was concentrated. A portion of this material (100 mg) was dissolved in DMF prior to the addition of Hunig's base (0.15 mL) and Example 23 (68 mg). After cooling to 0° C., BOP Reagent (103 mg) was added. The resulting mixture was warmed to rt and was stirred overnight. EtOAc was added along with 1 N HCl solution (aq). The EtOAc layer was washed with 1 N HCl, $NaHCO_3$ solution (aq), and brine. The EtOAc was dried ($MgSO_4$), filtered, and concentrated. Flash chromatography of the resulting residue gave the title compound (12 mg). MS found: $(M+H)^+=630.3$.

Example 25

2-(3-Isopropyl-ureido)-5-trifluoromethyl-benzoic acid (25a) 2-(tert-Butoxycarbonyl)amino-5-trifluoromethyl-benzoic acid (2 g) was dissolved in DMF prior to the addition of $K_2CO_3$ (1.08 g) and allyl bromide (0.68 mL). The mixture was stirred for 18 h before EtOAc and water were added. The organic layer was washed with brine, dried, filtered, and concentrated (2.05 g). The resulting material was dissolved in $CH_2Cl_2$ (4 mL) and TFA (4 mL). After 1 h, the solution was concentrated. This material was dissolved in THF and added dropwise to a THF (50 mL) solution of trichloromethyl chloroformate (1.9 mL). After stirring for 18 h, the solution was concentrated and a THF (30 mL) solution of iso-propylamine (4.3 mL) was added. After 18 h, the solution was diluted with EtOAc and was washed with brine solution and 1N HCl. The organic layer was dried ($MgSO_4$), filtered, and concentrated to a white solid. This solid was dissolved in $CH_3CN$ (22 mL) prior to the addition of pyrrolidine (0.41 mL) and $Pd(PPh)_4$ (105 mg). After 18 h, the solution was diluted with EtOAc and was washed 1N HCl. The organic layer was dried ($MgSO_4$), filtered, and concentrated to give the title compound (1.1 g) as a white solid: $^1$H NMR (DMSO, δppm, 300 mHz) 1.11 (d, 6H), 3.78 (m, 1H), 7.63 (br d, 1H), 7.81 (dd, 1H), 8.14 (d, 1H), 8.64 (d, 1H), 10.27 (s, 1H), 13.83 (br s, 1H).

Example 26

(±)2-{[(Isopropylamino)carbonyl]amino}-N-(2-{[(1S*,2R*)-2-({[4-(methylthio)phenyl]sulfonyl}methyl)cyclohexyl]amino}-2-oxoethyl)-5-(trifluoromethyl)benzamide (26a) Example 25 (68 mg) was incorporated into Example 24 to give the title benzamide (57 mg). MS found: $(M+H)^+=629.2$.

Example 27

2-Isopropoxycarbonylamino-5-trifluoromethyl-benzoic acid (27a) 2-(tert-Butoxycarbonyl)amino-5-trifluoromethyl-benzoic acid (6.0 g) was dissolved in 4M HCl (4 mL) in dioxane. After 3 h, the solution was concentrated to a white solid. A portion of this material (200 mg) was dissolved in THF (2.5 mL) and 2M $K_2CO_3$ (1.46 mL) was added followed by cyclohexanecarbonyl chloride (0.2 mL). The reaction was stirred for 10 min before EtOAc was added. The EtOAc layer was washed with 1N HCl and brine before it was dried, filtered, and concentrated to a crude material. This was crystallized with $CH_3CN$ to give the title compound (302 mg). MS found: $(2M-1)^-=629.2$.

Example 28

(±)2-[(cyclohexylcarbonyl)amino]-N-(2-{[(1S*,2R*)-2-({[4-(methylthio)phenyl]sulfonyl}methyl)cyclohexyl]amino}-2-oxoethyl)-5-(trifluoromethyl)benzamide (28a) Example 27 (74 mg) was incorporated into Example 24 to give the title benzamide (55 mg). MS found: $(M+H)^+=654.1$.

Example 29

(±)2-{[(cyclopentylamino)carbonyl]amino}-N-(2-{[(1S*,2R*)-2-({[4-(methylthio)phenyl]sulfonyl}methyl)cyclohexyl]amino}-2-oxoethyl)-5-(trifluoromethyl)benzamide (29a) Cyclopentyl amine (0.94 mL) was incorporated into Example 25 and a portion of this material was incorporated into Example 24 to give the title benzamide (65 mg). MS found: $(M+Na)^+=677.3$.

Example 30

(±)2-{[(Isobutylamino)carbonyl]amino}-N-(2-{[(1S*,2R*)-2-({[4-(methylthio)phenyl]sulfonyl}methyl)cyclohexyl]amino}-2-oxoethyl)-5-(trifluoromethyl)benzamide (30a) Isobutylamine (0.95 mL) was incorporated into Example 25 and a portion of this material was incorporated into Example 24 to give the title benzamide (120 mg). MS found: $(M+Na)^+=665.4$.

Example 31

(±)2-{[(Ethylamino)carbonyl]amino}-N-(2-{[(1S*,2R*)-2-({[4-(methylthio)phenyl]sulfonyl}methyl)cyclohexyl]amino}-2-oxoethyl)-5-(trifluoromethyl)benzamide (31a) 2M Ethylamine (4.8 mL) in THF was incorporated into Example 25 and a portion of this material was incorporated into Example 24 to give the title benzamide (115 mg). MS found: $(M+Na)^+=637.3$.

Example 32

(±)2-{[(Dimethylamino)carbonyl]amino}-N-(2-{[(1S*,2R*)-2-({[4-(methylthio)phenyl]sulfonyl}methyl)cyclohexyl]amino}-2-oxoethyl)-5-(trifluoromethyl)benzamide (32a) Dimethylamine (329 mg) was incorporated into Example 25 and a portion of this material was incorporated into Example 24 to give the title benzamide (11 mg). MS found: $(M+Na)^+=637.2$.

Example 33

(±)2-{[(Diethylamino)carbonyl]amino}-N-(2-{[(1S*,2R*)-2-({[4-(methylthio)phenyl]sulfonyl}methyl)cyclohexyl]amino}-2-oxoethyl)-5-(trifluoromethyl)benzamide (33a) Diethylamine (0.42 mL) was incorporated into Example 25 and a portion of this material was incorporated into Example 24 to give the title benzamide (5 mg). MS found: $(M+Na)^+=665.4$.

Example 34

(±)N-[2-{[(2-{[(1S*,2R*)-2-({[4-(methylthio)phenyl]sulfonyl}methyl)cyclohexyl]amino}-2-oxoethyl)amino]carbonyl}-4-(trifluoromethyl)phenyl]-1-pyrrolidinecarboxamide (34a) Pyrrolidine (0.34 mL) was incorporated into Example 25 and a portion of this material was incorporated into Example 24 to give the title benzamide (19 mg). MS found: $(M+Na)^+=663.4$.

Example 35

(±)tert-Butyl 2-{[(2-{[(1S*,2R*,5S*)-5-hydroxy-2-({[4-(methylthio)phenyl]sulfonyl}methyl)cyclohexyl]amino}-2-oxoethyl)amino]carbonyl}-4-(trifluoromethyl)phenylcarbamate (35a) 1-Methanesulfonyl-4-methylsulfanyl-benzene (3.25 g) was dissolved in THF (50 mL) and cooled to −78° C. prior to the addition of 1.6 M nBuLi (10 mL). After 0.5 h, $BF_3$-$Et_2O$ (2.04 mL) was added followed by (±)(1S*,2R*,4S*)-4-(benzyloxy)-1,2-epoxycyclohexane (2.19 g) (Chini et al. *J. Org. Chem.* 1990, 55, 4265) in THF (20 mL). After an addition 1 h at −78° C., the solution was warmed to 0° C. After 2 h, the solution was cooled to −78° C. and saturated $NH_4Cl$ solution (aq) was added. The solution was warmed to rt and EtOAc was added. The organic layer was washed with brine, dried, filtered, and concentrated. Flash chromatography of the resulting residue gave (±)(1R*,2R*,5S*)-5-benzyloxy-2-(4-methylsulfanyl-benzenesulfonylmethyl)-cyclohexanol (3.5 g) as the major product: $^1$H NMR ($CDCl_3$, δppm, 300 mHz) 1.41 (m, 2H), 1.59 (m, 1H), 1.95 (m, 1H), 2.05-2.35 (m, 2H), 2.54 (s, 3H), 2.96 (dd, 1H), 3.64 (m, 2H), 3.81 (s, 1H), 4.48 (m, 2H), 7.3 (m, 7H), 7.82 (d, 2H).

(35b) A portion of the above material (2.95 g) was dissolved in $CH_2Cl_2$ (30 mL) and cooled to 0° C. prior to the addition of $Et_3N$ (3 mL) and methanesulfonyl chloride (0.84 mL). After 1 h, the $CH_2Cl_2$ was removed and EtOAc was added. This was washed with 1N HCl, saturated $NaHCO_3$, and brine. The organic layer was dried, filtered, and concentrated to a light yellow solid. This solid was dissolved in DMSO (20 mL) prior to the addition of $NaN_3$ (2.35 g). This was heated at 80° C. for 18 h. After cooling to 0° C., water was added and it was extracted with EtOAc. The organic layer was washed with brine, dried, filtered, and concentrated. Flash chromatography of the resulting residue gave (±)(1S*,2R*,5S*)-5-benzyloxy-2-(4-methylsulfanyl-benzenesulfonylmethyl)-azidocyclohexane (2.8 g): $^1$H NMR ($CDCl_3$, δppm, 300 mHz) 1.45 (m, 1H), 1.68-2.09 (m, 5H), 2.4 (m, 1H), 2.56 (s, 3H), 3.04 (dd, 1H), 3.27 (dd, 1H), 3.55 (m, 1H), 3.84 (m, 1H), 4.56 (m, 1H), 7.35 (m, 7H), 7.82 (d, 2H).

(35c) A portion of the above material (80 mg) was dissolved in $CH_2Cl_2$ (1 mL) and cooled to −78° C. prior to the addition of 1.0M $BCl_3$ (0.29 mL) in $CH_2Cl_2$. The reaction was stirred at 0° C. for 2 h. After cooling to −78° C., MeOH (2 mL) was added. The reaction was warmed to 0° C. and then rt. The resulting solution was extracted with $CH_2Cl_2$. The organic layer was washed with saturated $NaHCO_3$ solution (aq), brine, dried, filtered, and concentrated. Flash chromatography of the resulting residue gave (±)(1S*,2R*,5S*)-5-hydroxy-2-(4-methylsulfanyl-benzenesulfonylmethyl)-azidocyclohexane (43 mg): $^1$H NMR ($CDCl_3$, δppm, 300 mHz) 1.43 (m, 1H), 1.6-1.98 (m, 5H), 2.34 (m, 1H), 2.47 (m, 1H), 2.54 (s, 3H), 2.95 (dd, 1H), 3.27 (dd, 1H), 3.89 (m, 1H), 4.03 (m, 1H), 7.34 (d, 2H), 7.78 (d, 2H).

(35d) The above material (185 mg) was dissolved in MeOH (5 mL) prior to the addition of 5% Pd/BaSO$_4$ (150 mg). A hydrogen balloon was added and the solution was stirred for 1.5 h. The palladium was filtered and the solution was concentrated. A portion (50 mg) of this was dissolved in DMF prior to the addition of 4-methylmorpholine (0.08 mL) and Example 11 (64 mg). After cooling to 0° C., BOP Reagent (92 mg) was added. The resulting mixture was warmed to rt and was stirred overnight. The solution was partially concentrated and reverse phase HPLC purification (gradient elution, water/acetonitrile/TFA) provided the title benzamide (70 mg). MS found: (M+H)$^+$=660.5.

Example 36

(±)N-[2-{[(2-{[(1S*,2R*,5S*)-5-hydroxy-2-({[4-(methylthio)phenyl]sulfonyl}methyl)cyclohexyl]amino}-2-oxoethyl)amino]carbonyl}-4-(trifluoromethyl)phenyl]-1-pyrrolidinecarboxamide (36a) Pyrrolidine (0.34 mL) was incorporated into Example 25 and a portion of this material was incorporated into Example 11 and a portion of this material was incorporated into Example 35 (step 35d) to give the title compound (20 mg). MS found: (M+H)$^+$=657.3.

Example 37

(±)2-{[(ethylamino)carbonyl]amino}-N-(2-{[(1S*,2R*,5S*)-5-hydroxy-2-({[4-(methylthio)phenyl]sulfonyl}methyl)cyclohexyl]amino}-2-oxoethyl)-5-(trifluoromethyl)benzamide (37a) 2M Ethylamine(4.8 mL) in THF was incorporated into Example 25 and a portion of this material was incorporated into Example 11 and a portion of this material was incorporated into Example 35 (step 35d) to give the title compound (30 mg). MS found: (M+H)$^+$=631.3.

Example 38

(±)2-Amino-N-(2-{[(1S*,2R*,5S*)-5-hydroxy-2-({[4-(methylthio)phenyl]sulfonyl}methyl)cyclohexyl]amino}-2-oxoethyl)-5-(trifluoromethyl)benzamide (38a) A portion of Example 35 (42 mg) was dissolved in CH$_2$Cl$_2$ (2.5 mL) and TFA (2.5 mL). After 1.5 h, the solution was concentrated to give the title compound (30 mg). MS found: (M+H)$^+$=560.4.

Example 39

[2-Isopropylamino-5-(trifluoromethyl)]benzoic acid (39a) Isopropylamine (4.0 mL) was dissolved in THF (20 mL). This solution was cooled to 0° C. and n-butyllithium (2.5 M, 20 mL) was added. The reaction was stirred for 90 min, then transferred to a solution of [2-fluoro-5-(trifluoromethyl)]benzoic acid (4.2 g) in THF (40 mL) at −78° C. This mixture was stirred for 15 min and the reaction was quenched with aqueous NH$_4$Cl. The mixture was extracted with EtOAc (3×). The organic layer was dried, filtered, and concentrated. Flash chromatography of the resulting residue provided the title compound (2.4 g). MS found: (M+H)$^+$=248.2.

Example 40

(±)2-Isopropylamino-N-(2-{[(1S*,2R*,5S*)-5-hydroxy-2-({[4-(methylthio)phenyl]sulfonyl}methyl)cyclohexyl]amino}-2-oxoethyl)-5-(trifluoromethyl)benzamide (40a) Example 39 was incorporated into Example 11 and a portion of this material was incorporated into Example 35 (step 35d) to give the title compound (40 mg). MS found: (M+H)$^+$=602.4.

Example 41

N-[2-{[(2-{[(1S,2R)-2-({[4-(methylthio)phenyl]sulfonyl}methyl)cyclohexyl]amino}-2-oxoethyl)amino]carbonyl}-4-(trifluoromethyl)phenyl]-1-pyrrolidinecarboxamide (41a) Example 34 (racemic) was placed on a chiral OD column eluting with 20% EtOH/Hexane to give the title compound first off the column (33.1 min). MS found: (M+H)$^+$=663.4.

Example 42

N-[2-{[(2-{[(1R,2S)-2-({[4-(methylthio)phenyl]sulfonyl}methyl)cyclohexyl]amino}-2-oxoethyl)amino]carbonyl}-4-(trifluoromethyl)phenyl]-1-pyrrolidinecarboxamide (42a) Example 34 (racemic) was placed on a chiral OD column eluting with 20% EtOH/Hexane to give the title compound second off the column (48.1 min). MS found: (M+H)$^+$=663.4.

Example 43

(±)N-[2-{[(2-{[(1S*,2R*,5S*)-5-methoxy-2-({[4-(methylthio)phenyl]sulfonyl}methyl)cyclohexyl]amino}-2-oxoethyl)amino]carbonyl}-4-(trifluoromethyl)phenyl]-1-pyrrolidinecarboxamide (43a) 5-Hydroxy-2-(4-methylsulfanyl-benzenesulfonylmethyl)-azidocyclohexane (100 mg), Example 35c, was dissolved in THF (5 mL) and cooled to 0° C. prior to the addition of 60% NaH (13 mg). After 10 min, MeI (0.024 mL) was added and the reaction was stirred at 0° C. for 2 h and 30 min at rt. The reaction was re-cooled to 0° C., and water was added. The resulting solution was extracted with EtOAc. The organic layer was washed with saturated brine, dried, filtered, and concentrated. This material was dissolved in MeOH (2.5 mL) prior to the addition of 5% Pd/BaSO$_4$ (cat.). A hydrogen balloon was added and the solution was stirred for 2 h. The palladium was filtered and the solution was concentrated. A portion (50 mg) of this was dissolved in DMF prior to the addition of 4-methylmorpholine (0.08 mL) and {2-[(pyrrolidine-1-carbonyl)-amino]-5-trifluoromethyl-benzoylamino}-acetic acid (10 mg) (as described with Example 11 and Example 25 with pyrrolidine). After cooling to 0° C., BOP Reagent (86 mg) was added. The resulting mixture was warmed to rt and was stirred overnight. The solution was partially concentrated and reverse phase HPLC purification

Example 44

(±)2-{[(Ethylamino)carbonyl]amino}-N-(2-{[(1S*,2R*,5S*)-5-methoxy-2-({[4-(methylthio)phenyl]sulfonyl}methyl)cyclohexyl]amino}-2-oxoethyl)-5-(trifluoromethyl)benzamide (44a) 2M Ethylamine(4.8 mL) in THF was incorporated into Example 25 and a portion of this material was incorporated into Example 11 and a portion of this material was incorporated into Example 43 to give the title compound (40 mg). MS found: $(M+H)^+$=645.4.

Example 45

(±) N-[2-{[(2-{[(1S*,2R*)-2-({[4-(methylthio)phenyl]sulfonyl}methyl)cyclohexyl]amino}-2-oxoethyl)amino]carbonyl}-4-(trifluoromethyl)phenyl]-1-azetidinecarboxamide (45a) Azetidine (2.75 g) was incorporated into Example 25 and a portion of this material was incorporated into Example 11 and a portion of this material was incorporated into Example 19 to give the title compound (40 mg). MS found: $(M+H)^+$=627.4.

Example 46

(±)N-[2-{[(2-{[(1S*,2R*)-2-({[4-(methylthio)phenyl]sulfonyl}methyl)cyclohexyl]amino}-2-oxoethyl)amino]carbonyl}-4-(trifluoromethyl)phenyl]-4-morpholinecarboxamide (46a) Morpholine (3.1 mL) was incorporated into Example 25 and a portion of this material was incorporated into Example 11 and a portion of this material was incorporated into Example 19 to give the title compound (30 mg). MS found: $(M+H)^+$=657.4.

Example 47

(±)N-[2-{[(2-{[(1S*,2R*,5S*)-5-hydroxy-2-({[4-(methylthio)phenyl]sulfonyl}methyl)cyclohexyl]amino}-2-oxoethyl)amino]carbonyl}-4-(trifluoromethyl)phenyl]-1-azetidinecarboxamide (47a) Azetidine (2.75 g) was incorporated into Example 25 and a portion of this material was incorporated into Example 11 and a portion of this material was incorporated into Example 35 (step 35d) to give the title compound (20 mg). MS found: $(M+H)^+$=643.3.

Example 48

(±)N-[2-{[(2-{[(1S,2R,5S)-5-hydroxy-2-({[4-(methylthio)phenyl]sulfonyl}methyl)cyclohexyl]amino}-2-oxoethyl)amino]carbonyl}-4-(trifluoromethyl)phenyl]-4-morpholinecarboxamide (48a) Morpholine (3.1 mL) was incorporated into Example 25 and a portion of this material was incorporated into Example 11 and a portion of this material was incorporated into Example 35 (step 35d) to give the title compound (30 mg). MS found: $(M+H)^+$=673.5.

Example 49

(±)tert-Butyl 4-({[2-{[(2-{[(1S*,2R*,5S*)-5-hydroxy-2-({[4-(methylthio)phenyl]sulfonyl}methyl)cyclohexyl]amino}-2-oxoethyl)amino]carbonyl}-4-(trifluoromethyl)phenyl]amino}carbonyl)-1-piperazinecarboxylate (49a) piperazine-1-carboxylic acid tert-butyl ester (744 mg) was incorporated into Example 25 and a portion of this material was incorporated into Example 11 and a portion of this material was incorporated into Example 35 (step 35d) to give the title compound (25 mg). MS found: $(M+H)^+$=772.6.

Example 50

(±)N-[2-{[(2-{[(1S*,2R*,5S*)-5-hydroxy-2-({[4-(methylthio)phenyl]sulfonyl}methyl)cyclohexyl]amino}-2-oxoethyl)amino]carbonyl}-4-(trifluoromethyl)phenyl]-1-piperazinecarboxamide (50a) A portion of Example 49 (30 mg) was dissolved in $CH_2Cl_2$ (10 mL) and TFA (5 mL). After 1.5 h, the solution was concentrated and reverse phase HPLC purification (gradient elution, water/acetonitrile/TFA) provided the title benzamide (15 mg). MS found: $(M+H)^+$=672.5.

Example 51

(±)tert-Butyl 4-({[2-{[(2-{[(1S*,2R*)-2-({[4-(methylthio)phenyl]sulfonyl}methyl)cyclohexyl]amino}-2-oxoethyl)amino]carbonyl}-4-(trifluoromethyl)phenyl]amino}carbonyl)-1-piperazinecarboxylate (51a) piperazine-1-carboxylic acid tert-butyl ester (744 mg) was incorporated into Example 25 and a portion of this material was incorporated into Example 11 and a portion of this material was incorporated into Example 19 to give the title compound (30 mg). MS found: $(M+Na)^+$=778.5.

Example 52

(±)N-[2-{[(2-{[(1S*,2R*)-2-({[4-(methylthio)phenyl]sulfonyl}methyl)cyclohexyl]amino}-2-oxoethyl)amino]carbonyl}-4-(trifluoromethyl)phenyl]-1-piperazinecarboxamide (52a) A portion of Example 51 (21 mg) was dissolved in $CH_2Cl_2$ (3 mL) and TFA (1 mL). After 30 min, the solution was concentrated and reverse phase HPLC purification (gradient elution, water/acetonitrile/TFA) provided the title benzamide (8 mg). MS found: $(M+H)^+$=656.5.

Example 53

(±)2-Isobutylamino-N-(2-{[(1S*,2R*)-2-({[4-(methylthio)phenyl]sulfonyl}methyl)cyclohexyl]amino}-2-oxoethyl)-5-(trifluoromethyl)benzamide (53a) Isobutylamine was incorporated into Example 39 and a portion of this material was incorporated into Example 11 and a portion of this material was incorporated into Example 19 to give the title compound (15 mg). MS found: $(M+H)^+$=600.5.

Example 54

(±)2-Neopentylamino-N-(2-{[(1S*,2R*)-2-({[4-(methylthio)phenyl]sulfonyl}methyl)cyclohexyl]amino}-2-oxoethyl)-5-(trifluoromethyl)benzamide (54a) Neopentylamine was incorporated into Example 39 and a portion of this material was incorporated into Example 11 and a portion of this material was incorporated into Example 19 to give the title compound (10 mg). MS found: $(M+H)^+=614.5$.

Example 55

(±)N-(2-{[(1S*,2R*,4R*)-4-Amino-2-({[4-(methylthio)phenyl]sulfonyl}methyl)cyclohexyl]amino}-2-oxoethyl)-3-(trifluoromethyl)benzamide trifluoroacetate (55a) 1-Methanesulfonyl-4-methylsulfanyl-benzene (3.4 g) was dissolved in THF (40 mL) and cooled to −78° C. prior to the addition of 1.6 M nBuLi (10.4 mL). After 0.5 h, $BF_3 \cdot Et_2O$ (2.1 mL) was added followed by (±)cis-4-(benzyloxy)-1,2-epoxycyclohexane (2.3 g) (Chini et al. *J. Org. Chem.* 1990, 55, 4265) in THF (20 mL). After an addition 1 h at −78° C., the solution was warmed to 0° C. After 2 h, the solution was cooled to −78° C. and 1N HCl solution (aq) was added. The solution was warmed to rt and EtOAc was added. The organic layer was washed with brine, dried, filtered, and concentrated. Flash chromatography of the resulting residue gave (±)(1R*,2R*,4S*)-4-benzyloxy-2-(4-methylsulfanyl-benzenesulfonylmethyl)-cyclohexanol (2.9 g) as the major product. MS found: $(M+H)^+=407.1$.

(55b) A portion of the above material (1.9 g) was dissolved in $CH_2Cl_2$ (15 mL) and cooled to 0° C. prior to the addition of $Et_3N$ (2 mL) and methanesulfonyl chloride (0.55 mL). After 1 h, the $CH_2Cl_2$ was removed and EtOAc was added. This was washed with 1N HCl, saturated $NaHCO_3$, and brine. The organic layer was dried, filtered, and concentrated. This solid was dissolved in DMSO (20 mL) prior to the addition of $NaN_3$ (2.35 g). This was heated at 80° C. for 18 h. After cooling to 0° C., water was added and it was extracted with EtOAc. The organic layer was washed with brine, dried, filtered, and concentrated. Flash chromatography of the resulting residue gave (±)(1S*,2R*,4S*)-4-benzyloxy-2-(4-methylsulfanyl-benzenesulfonylmethyl)-azidocyclohexane (1.4 g). MS found: $(M-N_3)^+=388.5$.

(55c) A portion of the above material (1.3 g) was dissolved in $CH_2Cl_2$ (15 mL) and cooled to −78° C. prior to the addition of 1.0M $BCl_3$ (3.9 mL) in $CH_2Cl_2$. The reaction was stirred at 0° C. for 2 h. After cooling to −78° C., MeOH (8 mL) was added. The reaction was warmed to 0° C. and then rt. The resulting solution was extracted with $CH_2Cl_2$. The organic layer was washed with saturated $NaHCO_3$ solution (aq), brine, dried, filtered, and concentrated. Flash chromatography of the resulting residue gave (±)(1S*,2R*,4S*)-4-hydroxy-2-(4-methylsulfanyl-benzenesulfonylmethyl)-azidocyclohexane (1.1 g). MS found: $(M-HN_3)^+=298.1$.

(55d) The above material (1.1 g) was dissolved in MeOH (10 mL) prior to the addition of 5% $Pd/BaSO_4$ (800 mg). A hydrogen balloon was added and the solution was stirred for 4.0 h. The palladium was filtered and the solution was concentrated to (±)(1S*,2R*,4S*)-4-hydroxy-2-(4-methylsulfanyl-benzenesulfonylmethyl)-cyclohexylamine: MS found: $(M+H)^+=316.2$. The resulting residue was dissolved in THF (10 mL) and water (2 mL) prior to the addition of $Et_3N$ (0.88 mL). This was cooled to 0° C. and $Boc_2O$ (761 mg) was added. The reaction was warmed to rt and stirred overnight. The reaction was quenched with water and EtOAc. The EtOAc layer was washed with 1 N HCl solution, $NaHCO_3$ solution, and brine. The organic layer was dried, filtered, and concentrated (1.44 g). This material (1.44 g) was dissolved in $CH_2Cl_2$ (15 mL) and cooled to 0° C. prior to the addition of $Et_3N$ (1.3 mL) and methanesulfonyl chloride (0.37 mL). After 1 h, the $CH_2Cl_2$ was removed and EtOAc was added. This was washed with 1N HCl, saturated $NaHCO_3$, and brine. The organic layer was dried, filtered, and concentrated. This solid was dissolved in DMSO (10 mL) prior to the addition of $NaN_3$ (1.03 g). This was heated at 80° C. for 18 h. After cooling to 0° C., water was added and it was extracted with EtOAc. The organic layer was washed with brine, dried, filtered, and concentrated. (±)(1S*,2R*,4R*)-[4-azido-2-(4-methylsulfanyl-benzenesulfonylmethyl)-cyclohexyl]-carbamic acid tert-butyl ester (1.2 g). MS found: $(M+Na^+ CH_3CN)^+=504.3$. This material was dissolved in 4M HCl in dioxane (10 mL). After 2 h, the reaction was concentrated. A portion of this material (500 mg) was dissolved in DMF prior to the addition of 4-methylmorpholine (0.75 mL) and 3-trifluoromethyl-benzoylamino)-acetic acid (465 mg). After cooling to 0° C., BOP Reagent (762 mg) was added. The resulting mixture was warmed to rt and was stirred overnight. EtOAc was added along with 1 N HCl solution (aq). The EtOAc layer was washed with 1 N HCl, $NaHCO_3$ solution (aq), and brine. The EtOAc was dried ($MgSO_4$), filtered, and concentrated. Flash chromatography of the resulting residue (±)N-(2-{[(1S*,2R*,4R*)-4-azido-2-({[4-(methylthio)phenyl]sulfonyl}methyl)cyclohexyl]amino}-2-oxoethyl)-3-(trifluoromethyl)benzamide trifluoroacetate (729 mg). MS found: $(M+Na)^+=592.4$.

(55c) A portion of the above material (700 mg) was dissolved in MeOH (10 mL) prior to the addition of 10% $Pd/BaSO_4$ (500 mg). A hydrogen balloon was added and the solution was stirred for 60 min. The palladium was filtered and the solution was concentrated. A portion (50 mg) of this was purified by reverse phase HPLC purification (gradient elution, water/acetonitrile/TFA) to provide the title compound (20 mg). MS found: $(M+H)^+=544.3$.

Example 56

(±)N-(2-{[(1S*,2R*,4R*)-4-Amino-2-({phenylsulfonyl}methyl)cyclohexyl]amino}-2-oxoethyl)-3-(trifluoromethyl)benzamide trifluoroacetate (56a) The title compound was also isolated (6 mg) from the above final HPLC purification (55d). MS found: $(M+H)^+=498.4$.

Example 57

(±)N-(2-{[(1S*,2R*,4R*)-4-(dimethylamino)-2-({[4-(methylthio)phenyl]sulfonyl}methyl)cyclohexyl]amino}-2-oxoethyl)-3-(trifluoromethyl)benzamide trifluoroacetate (57a) A portion of Example 55 (50 mg) was dissolved in MeOH (2 mL) prior to the addition of 37% formaldehyde (0.014 mL) solution (aq). After 10 min, $NaBH_3CN$ (17.3 mg) was added. The reaction was stirred for 1 h before the solution was concentrated. EtOAc was added along with some water. The organic layer was dried, filtered, and concentrated. Reverse phase HPLC purification (gradient elution, water/acetonitrile/TFA) of the resulting residue gave the title compound (28 mg). MS found: $(M+H)^+=572.4$.

Example 58

(±)N-(2-{[(1S*,2R*,4R*)-4-(isopropylamino)-2-({[4-(methylthio)phenyl]sulfonyl}methyl)cyclohexyl]amino}-2-oxoethyl)-3-(trifluoromethyl)benzamide trifluoroacetate (58a) A portion of Example 55 (50 mg) was dissolved in dichloroethane (2.5 mL) prior to the addition of acetone (0.034 mL), acetic acid (0.026 mL), and NaHB(OAc)$_3$ (97 mg). The reaction was stirred for 1 h before the solution was filtered and concentrated. Reverse phase HPLC purification (gradient elution, water/acetonitrile/TFA) of the resulting residue gave the title compound (15 mg). MS found: (M+H)$^+$=586.5.

Example 59

(±) N-(2-{[(1S*,2R*,4R*)-4-(cyclobutylamino)-2-({[4-(methylthio)phenyl]sulfonyl}methyl)cyclohexyl]amino}-2-oxoethyl)-3-(trifluoromethyl)benzamide trifluoroacetate (59a) Cyclobutanone (0.01 mL) was incorporated into Example 58 to give the title compound (18 mg). MS found: (M+H)$^+$=598.4.

Example 60

(±) N(2-{[(1S*,2R*,4R*)-4-(diethylamino)-2-({[4-(methylthio)phenyl]sulfonyl}methyl)cyclohexyl]amino}-2-oxoethyl)-3-(trifluoromethyl)benzamide trifluoroacetate (60a) Acetaldehyde (0.015 mL) was incorporated into Example 58 to give the title compound (20 mg). MS found: (M+H)$^+$=600.4.

Example 61

(±)N-(2-{[(1S*,2R*,4R*)-4-(dipropylamino)-2-({[4-(methylthio)phenyl]sulfonyl}methyl)cyclohexyl]amino}-2-oxoethyl)-3-(trifluoromethyl)benzamide trifluoroacetate (61a) Propionaldehyde (0.02 mL) was incorporated into Example 58 to give the title compound (10 mg). MS found: (M+H)$^+$=628.4.

Example 62

(±)N-(2-{[(1S*,2R*,4R*)-4-(benzylamino)-2-({[4-(methylthio)phenyl]sulfonyl}methyl)cyclohexyl]amino}-2-oxoethyl)-3-(trifluoromethyl)benzamide trifluoroacetate (62a) Benzaldehyde (0.006 mL) was incorporated into Example 58 to give the title compound (10 mg). MS found: (M+H)$^+$=634.4.

Example 63

(±)N-(2-{[(1S*,2R*,4R*)-4-(Bis-cyclopropylmethylamino)-2-({[4-(methylthio)phenyl]sulfonyl}methyl)cyclohexyl]amino}-2-oxoethyl)-3-(trifluoromethyl)benzamide trifluoroacetate (63a) Cyclopropanecarboxaldehyde (0.007 mL) was incorporated into Example 58 (without acetic acid) to give the title compound (8 mg). MS found: (M+H)$^+$=652.3.

Example 64

(±)N-(2-{[(1S*,2R*,4R*)-4-(dibutylamino)-2-({[4-(methylthio)phenyl]sulfonyl}methyl)cyclohexyl]amino}-2-oxoethyl)-3-(trifluoromethyl)benzamide trifluoroacetate (64a) Butyraldehyde (0.03 mL) was incorporated into Example 58 to give the title compound (20 mg). MS found: (M+H)$^+$=656.5.

Example 65

(±)N-(2-{[(1S*,2R*,4R*)-4-(N-isopropyl-N-methylamino)-2-({[4-(methylthio)phenyl]sulfonyl}methyl)cyclohexyl]amino}-2-oxoethyl)-3-(trifluoromethyl)benzamide trifluoroacetate (65a) Example 58 (25 mg) was incorporated into Example 57 to give the title compound (10 mg). MS found: (M+H)$^+$=606.5.

Example 66

(±)N-(2-{[(1S*,2R*,4R*)-4-(acetylamino)-2-({[4-(methylthio)phenyl]sulfonyl}methyl)cyclohexyl]amino}-2-oxoethyl)-3-(trifluoromethyl)benzamide (66b) Example 55 (50 mg) was dissolved in CHCl$_3$ (2 mL) and cooled to 0° C. prior to the addition of Et$_3$N (0.04 mL) and acetyl chloride (0.01 mL). After 1 h at rt, more CHCl$_3$ was added and this was washed with 1N HCl solution (aq). The organic layer was dried, filtered, and concentrated. Reverse phase HPLC purification (gradient elution, water/acetonitrile/TFA) of the resulting residue gave the title compound (20 mg). MS found: (M+H)$^+$=586.4.

Example 67

(±)N-(2-{[(1S*,2R*,4R*)-4-[(methylsulfonyl)amino]-2-({[4-(methylthio)phenyl]sulfonyl}methyl)cyclohexyl]amino}-2-oxoethyl)-3-(trifluoromethyl)benzamide (67a) Methanesulfonyl chloride (0.01 mL) was incorporated (for acetyl chloride) into Example 66 to give the title compound (10 mg). MS found: (M+H)$^+$=622.3.

Example 68

(±)N-[2-({(1S*,2R*,4R*)-2-({[4-(methylthio)phenyl]sulfonyl}methyl)-4-[(trifluoroacetyl)amino]cyclohexyl}amino)-2-oxoethyl]-3-(trifluoromethyl)benzamide (68a) Ethyl trifluoroacetate was incorporated (for acetyl chloride) into Example 66 to give the title compound (80 mg). MS found: (M+H)$^+$=640.2.

Example 69

(±)N-(2-{[(1S*,2R*,4R*)-4-(methylamino)-2-({[4-(methylthio)phenyl]sulfonyl}methyl)cyclohexyl]amino}-2-oxoethyl)-3-(trifluoromethyl)benzamide trifluoroacetate (69a) Example 68 (80 mg) was dissolved in DMF (1.5 mL) prior to the addition of K$_2$CO$_3$ (35 mg) and MeI (0.12 mL). The reaction was stirred at rt for 18 h and then 80° C. for 3 h. After cooling EtOAc was added along with water. The organic layer was dried, filtered, and concentrated. The resulting residue was dissolved in MeOH (2 mL) and 2M $K_2CO_3$ (0.1 mL) (aq) was added. After 2 h, the solution was filtered and reverse phase HPLC purification (gradient elution, water/acetonitrile/TFA) gave the title compound (20 mg). MS found: $(M+H)^+=558.3$.

Example 70

(±)N-(2-{[(1S*,2R*,4R*)-4-{[amino(imino)methyl]amino}-2-({[4-(methylthio)phenyl]sulfonyl}methyl)cyclohexyl]amino}-2-oxoethyl)-3-(trifluoromethyl)benzamide bistrifluoroacetate (70a) Example 55 (80 mg) was dissolved in DMF (1.5 mL) prior to the addition of Hunig's base (0.026 mL) and 1H-pyrazole-1-carboxamiaine hydrogen chloride (22 mg). The reaction was stirred at rt for 24 h before 1N HCl (aq) (1 mL) and MeOH were added. Reverse phase HPLC purification (gradient elution, water/acetonitrile/TFA) gave the title compound (6 mg). MS found: $(M+H)^+=586.3$.

Example 71

(±)N-(2-{[(1S*,2R*,5R*)-5-amino-2-({[4-(methylthio)phenyl]sulfonyl}methyl)cyclohexyl]amino}-2-oxoethyl)-3-(trifluoromethyl)benzamide trifluoroacetate (71a) (±)(1S*,2R*,5S*)-5-hydroxy-2-(4-methylsulfanyl-benzenesulfonylmethyl)-azidocyclohexane (35c) (1.9 g) was dissolved in MeOH (30 mL) prior to the addition of 10% Pd/BaSO$_4$ (1.9 g). A hydrogen balloon was added and the solution was stirred for 2 h. The palladium was filtered and the solution was concentrated. The resulting residue was dissolved in THF (20 mL) and water (6 mL) prior to the addition of Et$_3$N (1.7 mL). This was cooled to 0° C. and Boc$_2$O (1.4 g) was added. The reaction was warmed to rt and stirred 105 min. The reaction was quenched with water and EtOAc. The EtOAc layer was washed with 1 N HCl solution, NaHCO$_3$ solution, and brine. The organic layer was dried, filtered, and concentrated to give (±)(1S*,2R*,5S*)-[5-hydroxy-2-(4-methylsulfanyl-benzenesulfonylmethyl)-cyclohexyl]-carbamic acid tert-butyl ester. MS found: $(M+H)^+=416.3$.

(71b) A portion of the above material (71a) (340 mg) was dissolved in CH$_2$Cl$_2$ (20 mL) and cooled to 0° C. prior to the addition of Et$_3$N (0.17 mL) and methanesulfonyl chloride (0.09 mL). After 1 h, water was added and the layers were separated. The organic layer was washed with water and brine. The organic layer was dried, filtered, and concentrated. This solid was dissolved in DMSO (5 mL) prior to the addition of NaN$_3$ (532 mg). This was heated at 80° C. for 40 h. After cooling to 0° C., water was added and it was extracted with EtOAc. The organic layer was washed with brine, dried, filtered, and concentrated. Flash chromatography of the resulting residue gave (±)(1S*,2R*,5R*)-[5-azido-2-(4-methylsulfanyl-benzenesulfonylmethyl)-cyclohexyl]-carbamic acid tert-butyl ester. MS found: $(M+H)^+=441.3$.

(71c) This material (71b) was dissolved in 4M HCl in dioxane (10 mL). After 1 h, the reaction was concentrated. The resulting residue was dissolved in DMF prior to the addition of Hunig's base (0.1 mL) and 3-trifluoromethyl-benzoylamino)-acetic acid (40 mg). After cooling to 0° C., BOP Reagent (72 mg) was added. The resulting mixture was warmed to rt and was stirred overnight. EtOAc was added along with 1 N HCl solution (aq). The EtOAc layer was washed with 1 N HCl, NaHCO$_3$ solution (aq), and brine. The EtOAc was dried (MgSO$_4$), filtered, and concentrated. Flash chromatography of the resulting residue gave (±)(1S*,2R*,5R*)-N-{[5-azido-2-(4-methylsulfanyl-benzenesulfonylmethyl)-ethyl]-cyclohexylcarbamoyl]-methyl}-3-trifluoromethyl-benzamide (120 mg). MS found: $(M+Na)^+=592.3$.

(71d) A portion of the above material (120 mg) was dissolved in MeOH (5 mL) prior to the addition of 10% Pd/BaSO$_4$ (60 mg). A hydrogen balloon was added and the solution was stirred for 60 min. The palladium was filtered and the solution was concentrated. A portion of this was purified by reverse phase HPLC purification (gradient elution, water/acetonitrile/TFA) to provide the title compound. MS found: $(M+H)^+=544.3$.

Example 72

(±)N-(2-{[(1S*,2R*,5R*)-5-(isopropylamino)-2-({[4-(methylthio)phenyl]sulfonyl}methyl)cyclohexyl]amino}-2-oxoethyl)-3-(trifluoromethyl)benzamide trifluoroacetate (72a) A portion of Example 71 (50 mg) was dissolved in dichloroethane (0.5 mL) prior to the addition of acetone (0.01 mL) and NaHB(OAc)$_3$ (29 mg). After 5 min., acetic acid (0.01 mL) was added to the solution. The reaction was stirred for 2 h before the solution was quenched with saturated NaHCO$_3$ solution (aq) and EtOAc. The organic layer was washed with brine, dried, filtered, and concentrated. Reverse phase HPLC purification (gradient elution, water/acetonitrile/TFA) of the resulting residue gave the title compound (15 mg). MS found: $(M+H)^+=586.4$.

Example 73

(±)N-(2-{[(1S*,2R*,5R*)-5-((bis-isobutyl)amino)-2-({[4-(methylthio)phenyl]sulfonyl}methyl)cyclohexyl]amino}-2-oxoethyl)-3-(trifluoromethyl)benzamide trifluoroacetate (73a) Isobutyraldehyde (0.01 mL) was incorporated into Example 72 to give the title compound (5 mg). MS found: $(M+H)^+=656.5$.

Example 74

(±)N-(2-{[(1S*,2R*,5R*)-5-(acetylamino)-2-({[4-(methylthio)phenyl]sulfonyl}methyl)cyclohexyl]amino}-2-oxoethyl)-3-(trifluoromethyl) benzamide (74b) A portion of the above material (71a) (340 mg) was dissolved in CH$_2$Cl$_2$ (20 mL) and cooled to 0° C. prior to the addition of acetic anhydride (0.09 mL) and Et$_3$N (0.17 mL). After 1 h, a drop of 1N HCl (aq) was added and the solution was concentrated. Reverse phase HPLC purification (gradient elution, water/acetonitrile/TFA) of the resulting residue gave the title compound (26 mg). MS found: $(M+H)^+=586.3$.

Example 75

(±)N-(2-{[(1S*,2R*,5R*)-5-[(methylsulfonyl)amino]-2-({[4-(methylthio)phenyl]sulfonyl}methyl)cyclohexyl]amino}-2-oxoethyl)-3-(trifluoromethyl)benzamide (75b) Methanesulfonyl chloride was incorporated into Example 74 to give the title compound (15 mg). MS found: $(M+H)^+=622.2$.

Example 76

(±)tert-Butyl 2-{[(2-{[(1S*,2R*,5R*)-5-amino-2-({[4-(methylthio)phenyl]sulfonyl}methyl)cyclohexyl]amino}-2-oxoethyl)amino]carbonyl}-4-(trifluoromethyl)phenylcarbamate trifluoroacetate (76a) Example 11 was incorporated into Example 71 (step 71c) to give the title compound. MS found: (M+H)$^+$=659.3.

Example 77

(±)2-Amino-N-(2-{[(1S*,2R*,5R*)-5-amino-2-({[4-(methylthio)phenyl]sulfonyl}methyl)cyclohexyl]amino}-2-oxoethyl)-5-(trifluoromethyl)benzamide hydrogen chloride (77a) Example 76 (210 mg) was dissolved in 4M HCl/dioxane (3 mL). The solution was stirred overnight before it was concentrated. A portion of this was purified by reverse phase HPLC purification (gradient elution, water/acetonitrile/TFA) and gave the title compound (9 mg). MS found: (M+H)$^+$=559.3.

Example 78

(±)2-Amino-N-(2-{[(1S*,2R*,5R*)-5-isopropylamino-2-({[4-(methylthio)phenyl]sulfonyl}methyl)cyclohexyl]amino}-2-oxoethyl)-5-(trifluoromethyl)benzamide trifluoroacetate (78a) Example 77 was incorporated into Example 72 to give the title compound. MS found: (M+H)$^+$=601.3.

Example 79

(±)tert-Butyl 2-{[(2-{[(1S*,2R*,5R*)-5-amino-2-({[4-(methylthio)phenyl]sulfonyl}methyl)cyclohexyl]amino}-2-oxoethyl)amino]carbonyl}-4-(trifluoromethoxy)phenylcarbamate trifluoroacetate (79a) (2-tert-Butoxycarbonylamino-5-trifluoromethoxy-benzoylamino)-acetic acid (made in analogy to Example 11 with 2-(tert-butoxycarbonyl)amino-5-trifluoromethoxybenzoic acid; Takagishi et al. *Synlett* 1992, 360) was incorporated into Example 71 (step 71c) to give the title compound. MS found: (M+H)$^+$=675.3.

Example 80

(±)2-Amino-N-(2-{[(1S*,2R*,5R*)-5-amino-2-({[4-(methylthio)phenyl]sulfonyl}methyl)cyclohexyl]amino}-2-oxoethyl)-5-(trifluoromethoxy)benzamide trifluoroacetate (80a) Example 79 (300 mg) was dissolved in 4M HCl/dioxane (20 mL). The solution was stirred 45 min before it was concentrated. A portion of this was purified by reverse phase HPLC purification (gradient elution, water/acetonitrile/TFA) and gave the title compound (11 mg). MS found: (M+H)$^+$=575.3.

Example 81

(±)N-[2-{[(2-{[(3R*,4R*)-4-({[4-(methylthio)phenyl]sulfonyl}methyl)tetrahydro-2H-pyran-3-yl]amino}-2-oxoethyl)amino]carbonyl}-4-(trifluoromethyl)phenyl]-1-pyrrolidinecarboxamide (81a) 1-Methanesulfonyl-4-methylsulfanyl-benzene (4.33 g) was dissolved in THF (50 mL) and cooled to −78° C. prior to the addition of 1.6 M nBuLi (13.4 mL). After 0.5 h, BF$_3$.Et$_2$O (2.7 mL) was added followed (±)3,4-epoxytetrahydropyran (1.2 g) (*Tetrahedron* 1974, 4013). After an addition 1 h at −78° C., the solution was warmed to 0° C. After 2 h, the solution was cooled to −78° C. and saturated NH$_4$Cl solution (aq) was added. The solution was warmed to rt and EtOAc was added. The organic layer was washed with brine, dried, filtered, and concentrated. Flash chromatography of the resulting residue gave (±) (3S*,4R*)-4-(4-methylsulfanyl-benzenesulfonylmethyl)-tetrahydro-pyran-3-ol (1.3 g) as the major product. MS found: (M+H)$^+$=303.0.

(81b) The above material (1.3 g) was dissolved in CH$_2$Cl$_2$ (15 mL) and cooled to 0° C. prior to the addition of Et$_3$N (1.7 mL) and methanesulfonyl chloride (0.5 mL). After 1.5 h, water was added and the layers were separated. The organic layer was washed with water and brine. The organic layer was dried, filtered, and concentrated. This solid was dissolved in DMSO (10 mL) prior to the addition of NaN$_3$ (1.3 g). This was heated at 80° C. for 18 h. After cooling to 0° C., water was added and it was extracted with EtOAc. The organic layer was washed with brine, dried, filtered, and concentrated. Flash chromatography of the resulting residue gave (±) (3R*,4R*)-3-azido-4-(4-methylsulfanyl-benzenesulfonylmethyl)-tetrahydro-pyran (930 mg). MS found: (M+H)$^+$=328.0.

(81c) The above material (920 mg) was dissolved in MeOH (10 mL) prior to the addition of 5% Pd/BaSO$_4$ (800 mg). A hydrogen balloon was added and the solution was stirred for 1.5 h. The palladium was filtered and the solution was concentrated. A portion (70 mg) of this material was dissolved in DMF (2.5 mL) prior to the addition of 4-methylmorpholine (0.13 mL) and {2-[(pyrrolidine-1-carbonyl)-amino]-5-trifluoromethyl-benzoylamino}-acetic acid (91 mg) (pyrrolidine was incorporated into Example 25 and a portion of this material was incorporated into Example 11). After cooling to 0° C., BOP Reagent (132 mg) was added. The resulting mixture was warmed to rt and was stirred overnight. The solution was partially concentrated and reverse phase HPLC purification (gradient elution, water/acetonitrile/TFA) provided the title benzamide (25 mg). MS found: (M+H)$^+$=643.4.

Example 82

N-[2-{[(2-{[(3R,4R)-4-({[4-(methylthio)phenyl]sulfonyl}methyl)tetrahydro-2H-pyran-3-yl]amino}-2-oxoethyl)amino]carbonyl}-4-(trifluoromethyl)phenyl]-1-pyrrolidinecarboxamide (82a) Chiral HPLC (chiral AD column, 90% EtOH/Hexane elution) with Example 81 gave the title compound as the first peak with a 13.0 min retention time. MS found: (M+H)$^+$=643.4.

Example 83

N-[2-{[(2-{[(3S,4S)-4-({[4-(methylthio)phenyl]sulfonyl}methyl)tetrahydro-2H-pyran-3-yl]amino}-2-oxoethyl)amino]carbonyl}-4-(trifluoromethyl)phenyl]-1-pyrrolidinecarboxamide (83a) Chiral HPLC (chiral AD column, 90% EtOH/Hexane elution) with Example 81 gave the title compound as the second peak with a 17.28 min retention time. MS found: (M+H)$^+$=643.4.

Example 84

(±)2-{[(Ethylamino)carbonyl]amino}-N-(2-{[(3R*,4R*)-4-({[4-(methylthio)phenyl]sulfonyl}methyl)tetrahydro-2H-pyran-3-yl]amino}-2-oxoethyl)-5-(trifluoromethyl)benzamide (84a) [2-(3-Ethyl-ureido)-5-trifluoromethyl-benzoylamino]-acetic acid (ethylamine was incorporated into

Example 85

(±)2-{[(ethylamino)carbonyl]amino}-N-(2-{[(3R*,4R*)-4-({phenylsulfonyl}methyl)tetrahydro-2H-pyran-3-yl]amino}-2-oxoethyl)-5-(trifluoromethyl)benzamide (85a) A minor amount of the title compound was also isolated from the above preparation. MS found: $(M+H)^+$= 571.4.

Example 86

(±)N-[2-{[(2-{[(3R*,4R*)-4-({[4-(methylthio)phenyl]sulfonyl}methyl)tetrahydro-2H-pyran-3-yl]amino}-2-oxoethyl)amino]carbonyl}-4-(trifluoromethyl)phenyl]-4-morpholinecarboxamide (86a) {2-[(Morpholine-4-carbonyl)-amino]-5-trifluoromethyl-benzoylamino}-acetic acid (morpholine was incorporated into Example 25 and a portion of this material was incorporated into Example 11) was incorporated into Example 81 (step 81c) to give the title compound. MS found: $(M+H)^+$=659.4.

Example 87

(±)2-{[(Methylamino)carbonyl]amino}-N-(2-{[(3R*,4R*)-4-({[4-(methylthio)phenyl]sulfonyl}methyl)tetrahydro-2H-pyran-3-yl]amino}-2-oxoethyl)-5-(trifluoromethyl)benzamide (87a) [2-(3-Methyl-ureido)-5-trifluoromethyl-benzoylamino]-acetic acid (methylamine was incorporated into Example 25 and a portion of this material was incorporated into Example 11) was incorporated into Example 81 (step 81c) to give the title compound. MS found: $(M+H)^+$=603.4.

Example 88

(±)N-[2-{[(2-{[(3R*,4R*)-4-({[4-(methylthio)phenyl]sulfonyl}methyl)tetrahydro-2H-pyran-3-yl]amino}-2-oxoethyl)amino]carbonyl}-4-(trifluoromethyl)phenyl]-1-azetidinecarboxamide (88a) {2-[(Azetidine-1-carbonyl)-amino]-5-trifluoromethyl-benzoylamino}-acetic acid (azetidine was incorporated into Example 25 and a portion of this material was incorporated into Example 11) was incorporated into Example 81 (step 81c) to give the title compound. MS found: $(M+H)^+$= 629.3.

Example 89

(±)2-{[(Isopropylamino)carbonyl]amino}-N-(2-{[(3R*,4R*)-4-({[4-(methylthio)phenyl]sulfonyl}methyl)tetrahydro-2H-pyran-3-yl]amino}-2-oxoethyl)-5-(trifluoromethyl)benzamide (89a) [2-(3-Isopropyl-ureido)-5-trifluoromethyl-benzoylamino]-acetic acid (Example 25 was incorporated into Example 11) was incorporated into Example 81 (step 81c) to give the title compound. MS found: $(M+H)^+$=631.4.

Example 90

(±)Isopropyl 2-{[(2-{[(3R*,4R*)-4-({[4-(methylthio)phenyl]sulfonyl}methyl)tetrahydro-2H-pyran-3-yl]amino}-2-oxoethyl)amino]carbonyl}-4-(trifluoromethyl)phenylcarbamate (90a) (2-Isopropoxycarbonylamino-5-trifluoromethyl-benzoylamino)-acetic acid (Example 23 was incorporated into Example 11) was incorporated into Example 81 (step 81c) to give the title compound. MS found: $(M+H)^+$=632.3.

Example 91

(±)Ethyl 2-{[(2-{[(3R*,4R*)-4-({[4-(methylthio)phenyl]sulfonyl}methyl)tetrahydro-2H-pyran-3-yl]amino}-2-oxoethyl)amino]carbonyl}-4-(trifluoromethyl)phenylcarbamate (91a) (2-Ethoxycarbonylamino-5-trifluoromethyl-benzoylamino)-acetic acid (ethyl chloroformate into Example 23 then incorporated into Example 11) was incorporated into Example 81 (step 81c) to give the title compound. MS found: $(M+H)^+$=618.4.

Example 92

(±)tert-Butyl (3R*,4R*)-3-{[1-({[2-[(tert-butoxycarbonyl)amino]-5-(trifluoromethyl)benzoyl]amino}methyl)carbonyl]amino}-4-({[4-(methylthio)phenyl]sulfonyl}methyl)-1-piperidinecarboxylate (92a) 1,2,3,6-Tetrahydropyridine (10.4 g) was dissolved in THF (400 mL) and water (120 mL) prior to the addition of $Et_3N$ (35 mL). This was cooled to 0° C. and $Boc_2O$ (27.3 g) was added. The reaction was warmed to rt and stirred overnight. The reaction was quenched with water and EtOAc. The EtOAc layer was washed with 1 N HCl solution, $NaHCO_3$ solution, and brine. The organic layer was dried, filtered, and concentrated. This material was dissolved in $CH_2Cl_2$ and was added dropwise to a cooled (0° C.) solution of 77% mCPBA (20.4 g) in $CH_2Cl_2$ (240 mL). The reaction was warmed to rt and was stirred overnight. The solids were filtered off and discarded. The filtrate was washed with saturated $NaHCO_3$ solution (aq) and 10% $Na_2S_2O_3$ solution (aq) and brine. The organic layer was dried, filtered, and concentrated. Flash chromatography of the resulting residue gave (±)1-(tert-butoxycarbonyl)-3,4-epoxypiperidine (7.6 g). MS found: $(M+H)^+$=199.9.

(92b) 1-Methanesulfonyl-4-methylsulfanyl-benzene (1.0 g) was dissolved in THF (20 mL) and cooled to -78° C. prior to the addition of 1.6 M nBuLi (3.1 mL). After 0.5 h, $BF_3$-$Et_2O$ (0.63 mL) was added followed by Example 93a, from above, (657 mg) in THF (2 mL). After an addition 1 h at -78° C., the solution was warmed to rt over 1.5 h. This was quenched with saturated $NH_4Cl$ solution (aq). The organic layer was washed with brine, dried, filtered, and concentrated. Flash chromatography of the resulting residue (±) (3S*,4R*)-3-hydroxy-4-(4-methylsulfanyl-benzenesulfonylmethyl)-piperidine-1-carboxylic acid tert-butyl ester (580 mg) as the major product. MS found: $(M+H)^+$=402.3.

(92c) A portion of the above material (2.4 g) was dissolved in $CH_2Cl_2$ (20 mL) and cooled to 0° C. prior to the addition of $Et_3N$ (1.2 mL) and methanesulfonyl chloride (0.7 mL). After 1 h, the $CH_2Cl_2$ was removed and EtOAc was added. This was washed with 1N HCl, saturated $NaHCO_3$, and brine. The organic layer was dried, filtered, and concentrated (2.0 g). A portion of this solid was dissolved in DMSO (20 mL) prior to the addition of NaN$_3$ (1.0 g). This was heated at 80° C. for 8 h and two days at rt. Brine was added and it was extracted with EtOAc. The organic layer was washed with 1N HCl (aq), brine, dried, filtered, and concentrated. Flash chromatography of the resulting residue gave (±)(3R*,4R*)-3-azido-4-(4-methylsulfanyl-benzenesulfonylmethyl)-piperidine-1-carboxylic acid tert-butyl ester (0.8 g) as the major product. MS found: (M+Na)$^+$=449.4.

(92d) A portion of the above material (1.0 g) was dissolved in MeOH (10 mL) prior to the addition of 5% Pd/BaSO$_4$ (1.0 g). A hydrogen balloon was added and the solution was stirred for 3 h. The palladium was filtered and the solution was concentrated. A portion (60 mg) of this was dissolved in DMF prior to the addition of Hunig's base (0.1 mL) and Example 11 (60 mg). After cooling to 0° C., BOP Reagent (73 mg) was added. The resulting mixture was warmed to rt and was stirred overnight. The solution was partially concentrated and reverse phase HPLC purification (gradient elution, water/acetonitrile/TFA) provided the title compound (50 mg). MS found: (M+Na)$^+$=767.5.

Example 93

(±)2-Amino-N-(2-{[(3R*,4R*)-4-({[4-(methylthio) phenyl]sulfonyl}methyl)-3-piperidinyl]amino}-2-oxoethyl)-5-(trifluoromethyl)benzamide trifluoroacetate (93a) A portion of Example 92 (27 mg) was dissolved in CH$_2$Cl$_2$ (1.4 mL) and TFA (0.8 mL). After 30 min, the solution was concentrated to give the title compound (20 mg). MS found: (M+H)$^+$=545.4.

Example 94

(±)N-(2-{[(3R*,4R*)-1-allyl-4-({[4-(methylthio) phenyl]sulfonyl}methyl)-3-piperidinyl]amino}-2-oxoethyl)-2-amino-5-(trifluoromethyl)benzamide trifluoroacetate (94a) Example 93 (13 mg) was dissolved in CH$_3$CN prior to the addition of K$_2$CO$_3$ (8.2 mg) and allyl bromide (0.002 mL). This was stirred overnight at rt. EtOAc and brine were added. The organic layer was dried, filtered, and concentrated. Reverse phase HPLC purification (gradient elution, water/acetonitrile/TFA) provided the title compound (4 mg). MS found: (M+H)$^+$=585.5.

Example 95

(±)tert-Butyl (3R*,4R*)-4-({[4-(methylthio)phenyl] sulfonyl}methyl)-3-{[1-({[2-[(1-pyrrolidinylcarbonyl)amino]-5-(trifluoromethyl)benzoyl] amino}methyl)carbonyl]amino}-1-piperidinecarboxylate (95a) {2-[(Pyrrolidine-1-carbonyl)-amino]-5-trifluoromethyl-benzoylamino}-acetic acid (pyrrolidine was incorporated into Example 25 and a portion of this material was incorporated into Example 11) was incorporated into Example 92 (step 92d) to give the title compound. MS found: (M+H)$^+$=764.5.

Example 96

(±)tert-Butyl (3R*,4R*)-3-{[1-({[2-{[(methylamino) carbonyl]amino}-5-(trifluoromethyl)benzoyl] amino}methyl)carbonyl]amino}-4-({[4-(methylthio) phenyl]sulfonyl}methyl)-1-piperidinecarboxylate (96a) [2-(3-Methyl-ureido)-5-trifluoromethyl-benzoylamino]-acetic acid (methylamine was incorporated into Example 25 and a portion of this material was incorporated into Example 11) was incorporated into Example 92 (step 92d) to give the title compound. MS found: (M+H)$^+$=724.5.

Example 97

(±)N-[2-{[(2-{[(3R*,4R*)-4-({[4-(methylthio)phenyl]sulfonyl}methyl)-3-piperidinyl]amino}-2-oxoethyl)amino]carbonyl}-4-(trifluoromethyl)phenyl]-1-pyrrolidinecarboxamide trifluoroacetate (97a) A portion of Example 95 (30 mg) was dissolved in CH$_2$Cl$_2$ (1 mL) and TFA (1 mL) at 0° C. After 45 min, the solution was concentrated. Reverse phase HPLC purification (gradient elution, water/acetonitrile/TFA) provided the title compound (8 mg). MS found: (M+H)$^+$=642.5.

Example 98

(±)2-{[(Methylamino)carbonyl]amino}-N-(2-{[(3R*, 4R*)-4-({[4-(methylthio)phenyl]sulfonyl}methyl)-3-piperidinyl]amino}-2-oxoethyl)-5-(trifluoromethyl) benzamide trifluoroacetate (98a) A portion of Example 96 (12 mg) was dissolved in CH$_2$Cl$_2$ (1 mL) and TFA (1 mL) at 0° C. After 45 min, the solution was concentrated to provided the title compound (12 mg). MS found: (M+H)$^+$=602.5.

Example 99

(±)tert-Butyl (3R*,4R*)-4-({[4-(methylthio)phenyl] sulfonyl}methyl)-3-{[1-({[2-[(1-azetidinecarbonyl) amino]-5-(trifluoromethyl)benzoyl]amino}methyl) carbonyl]amino}-1-piperidinecarboxylate (99a) {2-[(Azetidine-1-carbonyl)-amino]-5-trifluoromethyl-benzoylamino}-acetic acid (azetidine was incorporated into Example 25 and a portion of this material was incorporated into Example 11) was incorporated into Example 92 (step 92d) to give the title compound. MS found: (M+Na)$^+$=750.7.

Example 100

(±)N-[2-{[(2-{[(3R*,4R*)-4-({[4-(methylthio)phenyl]sulfonyl}methyl)-3-piperidinyl]amino}-2-oxoethyl)amino]carbonyl}-4-(trifluoromethyl)phenyl]-1-azetidinecarboxamide trifluoroacetate (100a) A portion of Example 99 (100 mg) was dissolved in CH$_2$Cl$_2$ (10 mL) and TFA (3.3 mL). After 45 min, the solution was concentrated to provided the title compound (12 mg). MS found: (M+H)$^+$=628.6.

Example 101

(±)N-[2-{[(2-{[(3R*,4R*)-4-({[4-(methylthio)phenyl]sulfonyl}methyl)-1-propyl-3-piperidinyl]amino}-2-oxoethyl)amino]carbonyl}-4-(trifluoromethyl)phenyl]-1-azetidinecarboxamide trifluoroacetate (101a) A portion of Example 101 (85 mg) was dissolved in THF (2 mL) prior to the addition of propionaldehyde (0.01 mL) and acetic acid (0.07 mL). After 45 min, the NaHB(OAc)$_3$ (276 mg) was added. The reaction was stirred overnight before the solution was quenched with saturated NaHCO$_3$ solution (aq) and EtOAc. The organic layer was washed with brine, dried, filtered, and concentrated. Reverse phase HPLC purification (gradient elution, water/acetonitrile/TFA) of the resulting residue gave the title compound (8 mg). MS found: (M+H)$^+$=670.7.

Example 102

(±)tert-Butyl (3R*,4R*)-4-({[4-(methylthio)phenyl]sulfonyl}methyl)-3-{[1-({2-[(4-morpholinecarbonyl)amino]-5-(trifluoromethyl)benzoyl]amino}methyl)carbonyl]amino}-1-piperidinecarboxylate (102a) Morpholine was incorporated into Example 99 (for azetidine) to give the title compound. MS found: (M+Na)$^+$=780.7.

Example 103

(±)N-[2-{[(2-{[(3R*,4R*)-4-({[4-(methylthio)phenyl]sulfonyl}methyl)-3-piperidinyl]amino}-2-oxoethyl)amino]carbonyl}-4-(trifluoromethyl)phenyl]-4-morpholinecarboxamide trifluoroacetate (103a) A portion of Example 102 (90 mg) was dissolved in CH$_2$Cl$_2$ (10 mL) and TFA (3.3 mL). After 45 min, the solution was concentrated to provided the title compound. MS found: (M+H)$^+$=658.6.

Example 104

(±)N-[2-{[(2-{[(3R*,4R*)-4-({[4-(methylthio)phenyl]sulfonyl}methyl)-1-propyl-3-piperidinyl]amino}-2-oxoethyl)amino]carbonyl}-4-(trifluoromethyl)phenyl]-4-morpholinecarboxamide trifluoroacetate (104a) Example 103 was incorporated into Example 101 to give the title compound. MS found: (M+H)$^+$=700.6.

Example 105

(±)-N-[2-{(2-{[(3R*,4*)-4-[({[4-(methylthio)phenyl]sulfonyl}methyl)-1-propyl-3-piperidinyl]amino}-2-oxoethyl)amino]carbonyl}-4-(trifluoromethyl)phenyl]-1-pyrrolidinecarboxamide trifluoroacetate (105a) Example 97 was incorporated into Example 101 to give the title compound. MS found: (M+H)$^+$=684.6.

Example 106

(±)2-amino-N-(2-{[(1S*,2R*)-2-({[4-bromophenyl]thio}methyl)cyclohexyl]amino}-2-oxoethyl)-5-(trifluoromethyl)benzamide (106a) (±)cis-2-Hydroxymethyl-1-cyclohexylamine hydrochloride (3.3 g) was dissolved in THF (60 mL) and water (20 mL) prior to the addition of Et$_3$N (5.6 mL). This was cooled to 0° C. and Boc$_2$O (4.4 g) was added. The reaction was warmed to rt and stirred overnight. The reaction was quenched with water and EtOAc. The EtOAc layer was washed with 1 N HCl solution, NaHCO$_3$ solution, and brine. The organic layer was dried, filtered, and concentrated. A portion of this material (300 mg) was dissolved in THF and placed in a high-pressure reaction vessel prior to the addition of bis(4-bromophenyl)disulfide (1.25 g) and Bu$_3$P (1.3 mL). The reaction was heated at 75° C. for 72 h. After cooling, Et$_2$O was added along with 2N NaOH (aq). The ether layer was dried, filtered, and concentrated. The resulting residue was placed directly on a flash column. This chromatography gave (±)(1R*,2S*)-2-tert-butyloxycarbonylamino-1-[(4-bromophenyl)sulfanylmethyl]cyclohexane (324 mg). MS found: (M+H)$^+$=402.1.

(106b) The above derivative (106a) (218 mg) was incorporated into step 19b to provide (±)tert-butyl 2-[({2-[((1S*,2R*)-2-{[(4-bromophenyl)thio]methyl}cyclohexyl)amino]-2-oxoethyl}amino)carbonyl]-4-(trifluoromethyl)phenylcarbamate (273 mg). MS found: (M+H)$^+$=643.4.

(106c) The above derivative (4b) (103 mg) was dissolved in CH$_2$Cl$_2$ (10 mL) and TFA (5 mL). After 45 min, the solution was concentrated to provided the title compound (87 mg). MS found: (M+H)$^+$=545.9.

Example 107

(±)2-amino-N-(2-{[(1S*,2R*)-2-({[4-chlorophenyl]thio}methyl)cyclohexyl]amino}-2-oxoethyl)-5-(trifluoromethyl)benzamide (107a) Bis(4-chlorophenyl)disulfide (0.89 g) was incorporated into Example 106 to give the title compound. MS found: (M+H)$^+$=500.0.

Example 108

(±)2-amino-N-(2-{[(1S*,2R*)-2-({[4-(methylthio)phenyl]thio}methyl)cyclohexyl]amino}-2-oxoethyl)-5-(trifluoromethyl)benzamide (108a) Bis[(4-methylthio)phenyl]disulfide (0.36 g) was incorporated into Example 106 to give the title compound. MS found: (M+H)$^+$=512.0.

Example 109

(±)N-{2-[((1S*,2R*)-2-{[(4-bromophenyl)thio]methyl}cyclohexyl)amino]-2-oxoethyl}-2-{[(isopropylamino)carbonyl]amino}-5-(trifluoromethyl)benzamide (109a) Derivative (106a) (51 mg) was dissolved in CH$_2$Cl$_2$ and cooled to 0° C. Trifluoroacetic acid (2 mL) was added and the reaction was warmed to rt. The reaction was stirred for 90 min and concentrated. The residue was dissolved in CH$_2$Cl$_2$ and [[2-(3-isopropylureido)-5-(trifluoromethyl)benzoyl]amino]acetic acid (Example 39 incorporated into Example 11) (91 mg) and HATU (186 mg) were added. Hunig's base (0.2 mL) was added and the reaction was stirred for 8 h. The reaction was quenched with aqueous NH₄Cl, and extracted with EtOAc (3×). The combined organic extracts were dried, filtered, and concentrated. Flash chromatography of the residue provided the title compound (67 mg). MS found: $(M+H)^+=628.9$.

Example 110

(±)2-amino-N-[2-({(1S*,2R*)-2-[({[4-(methylthio)phenyl]amino}carbonyl)amino]cyclohexyl}amino)-2-oxoethyl]-5-(trifluoromethyl)benzamide (110a) (±)N-tert-Butyloxycarbonyl-cis-cyclohexane-1,2-diamine (1.68 g) was dissolved in THF (35 mL) prior to the addition of 4-(methylthio)-phenylisocyanate (1.3 g). The reaction was stirred at rt for 8 h then concentrated. Flash chromatography of the resulting residue gave (±)(1S*,2R*)-{2-[3-(4-methylsulfanylphenyl)ureido]cyclohexyl}carbamic acid tert-butyl ester (1.15 g). MS found: $(M+H)^+=380.0$.

(110b) The above derivative (110a) (200 mg) was incorporated into step 106b. Reverse phase HPLC purification (gradient elution, water/acetonitrile/TFA) of the resulting residue provided (±){2-[({(1S*,2R*)-2-[3-(4-methylsulfanylphenyl)ureido]cyclohexylcarbamoyl}methyl)carbamoyl]-4-trifluoromethylphenyl}carbamic acid tert-butyl ester (60 mg). MS found: $(M+H)^+=624.0$.

(110c) The above derivative (110b) (103 mg) was incorporated into step 106c. Reverse phase HPLC purification (gradient elution, water/acetonitrile/TFA) of the resulting residue gave the title compound (24 mg). MS found: $(M+H)^+=524.1$.

Example 111

(±)tert-Butyl 2-({[2-({(1S*,2R*)-2-[({[4-(methylsulfonyl)phenyl]amino}carbonyl)amino]cyclohexyl}amino)-2-oxoethyl]amino}carbonyl)-4-(trifluoromethyl)phenylcarbamate (111a) Example 110b (280 mg) was dissolved in CH₂Cl₂ (20 mL) prior to the addition of M-CPBA (120 mg). The reaction mixture was stirred at rt for 18 h. The mixture was washed with aqueous NaHCO₃, dried, filtered, and concentrated. Flash chromatography of the residue provided the title compound (231 mg). MS found: $(M-Boc+H)^+=555.9$.

Example 112

(±)N-(2-{[(1S*,2R*,5S*)-5-amino-2-({[4-(methylthio)phenyl]sulfonyl}methyl)cyclohexyl]amino}-2-oxoethyl)-3-(trifluoromethyl)benzamide trifuoroacetate (112a) 1-Methanesulfonyl-4-methylsulfanyl-benzene (750 mg) and cis-4-(benzyloxy)-1,2-epoxycyclohexane (0.63 mg) (Marczak and Wicha *Syn. Comm.* 1990, 20, 1511) were dissolved in toluene (20 mL) and heated at 60-65° C. While at this temperature, 1.6 M BuLi in hexane (2.3 mL) was added dropwise. This was stirred at 60-65° C. for 40 min before the temperature was increased to reflux. After stirring overnight, the solution was cooled and quenched with ice water. This was extracted with EtOAc. The organic layer was washed with water, brine, dried, filtered, and concentrated. Flash chromatography of the resulting residue gave (1,5-cis-2-trans)-5-(benzyloxy)-2-({[4-(methylthio)phenyl]sulfonyl}methyl)cyclohexanol as the major product in a mixture with (1,4-cis-2-trans)-4-(benzyloxy)-2-({[4-(methylthio)phenyl]sulfonyl}methyl)cyclohexanol [1.14 g total mixture, MS found: $(M+Na)^+=429.2$]. This material was dissolved in CH₂Cl₂ (15 mL) and cooled to 0° C. prior to the addition of Et₃N (1.1 mL) and methanesulfonyl chloride (0.29 mL). After 1 h, the CH₂Cl₂ was removed and EtOAc was added. This was washed with 1N HCl, saturated NaHCO₃, and brine. The organic layer was dried, filtered, and concentrated to a light yellow solid. This solid was dissolved in DMSO (10 mL) prior to the addition of NaN₃ (800 mg). This was heated at 80° C. for 18 h. After cooling to 0° C., water was added and it was extracted with EtOAc. The organic layer was washed with brine, dried, filtered, and concentrated. Flash chromatography of the resulting residue gave 1-({[(1,2-cis, 4-trans)-2-azido-4-(benzyloxy)cyclohexyl]methyl}sulfonyl)-4-(methylthio)benzene (650 mg) as the major product. MS found: $(M+H)^+=432.0$.

(112b) A portion of the above material (530 mg) was dissolved in CH₂Cl₂ (5 mL) and cooled to −78° C. prior to the addition of 1.0 M BCl₃ (1.6 mL) in CH₂Cl₂. The reaction was stirred at 0° C. for 2 h. After cooling to −78° C., MeOH (3.2 mL) was added. The reaction was warmed to 0° C. and then rt. The resulting solution was extracted with CH₂Cl₂. The organic layer was washed with saturated NaHCO₃ solution (aq), brine, dried, filtered, and concentrated. Flash chromatography of the resulting residue gave (1-trans, 3,4-cis)-3-azido-4-({[4-(methylthio)phenyl]sulfonyl}methyl)cyclohexanol (170 mg). MS found: $(2M-H)^-=681.2$.

(112c) The above material (190 mg) was dissolved in MeOH (5 mL) prior to the addition of 5% Pd/BaSO₄ (110 mg). A hydrogen balloon was added and the solution was stirred for 1.0 h. The palladium was filtered and the solution was concentrated. The resulting residue was dissolved in THF (5 mL) and water (1 mL) prior to the addition of Et₃N (0.12 mL). This was cooled to 0° C. and Boc₂O (107 mg) was added. The reaction was warmed to rt and stirred overnight. The reaction was quenched with water and EtOAc. The EtOAc layer was washed with 1 N HCl solution, NaHCO₃ solution, and brine. The organic layer was dried, filtered, and concentrated. This material was dissolved in CH₂Cl₂ (2.5 mL) and cooled to 0° C. prior to the addition of Et₃N (0.18 mL) and methanesulfonyl chloride (0.05 mL). After 1 h, the CH₂Cl₂ was removed and EtOAc was added. This was washed with 1N HCl, saturated NaHCO₃, and brine. The organic layer was dried, filtered, and concentrated. This solid was dissolved in DMSO (5 mL) prior to the addition of NaN₃ (143 mg). This was heated at 80° C. for 18 h. After cooling to 0° C., water was added and it was extracted with EtOAc. The organic layer was washed with brine, dried, filtered, and concentrated. This material was dissolved in 4M HCl in dioxane (5 mL). After 2 h, the reaction was concentrated and was dissolved in DMF prior to the addition of 4-methylmorpholine (0.24 mL) and 3-trifluoromethyl-benzoylamino)-acetic acid (151 mg). After cooling to 0° C., BOP Reagent (241 mg) was added. The resulting mixture was warmed to rt and was stirred overnight. EtOAc was added along with 1 N HCl solution (aq). The EtOAc layer was washed with 1 N HCl, NaHCO₃ solution (aq), and brine. The EtOAc was dried (MgSO₄), filtered, and concentrated. Flash chromatography of the resulting residue gave N-(2-{[(1,2,5-cis)-5-azido-2-({[4-(methylthio)phenyl]sulfonyl}methyl)cyclohexyl]amino}-2-oxoethyl)-3-(trifluoromethyl)benzamide (210 mg). MS found: $(M+Na)^+=592.3$.

(112d) The above material (210 mg) was dissolved in MeOH (5 mL) prior to the addition of 10% Pd/BaSO₄ (170 mg). A hydrogen balloon was added and the solution was stirred for 60 min. The palladium was filtered and the solution was concentrated. Reverse phase HPLC purification (gradient elution, water/acetonitrile/TFA) of the resulting residue gave the title compound (106 mg). MS found: $(M+H)^+=$ 544.4.

Example 113

(1S,2R,4S/4R)-N-{[4-Dimethylamino-2-(4-methylsulfanyl-benzenesulfonylmethyl)-cyclohexylcarbamoyl]-methyl}-3-trifluoromethyl-benzamide (113a) 1,4-Cyclohexanedione mono-ethylene ketal (25 g) was dissolved in THF and cooled to −78° C. 1.0 M Lithium bis(trimethylsily)amide (160 mL) in THF was added dropwise. After 30 min, ethyl cyanoformate (15.9 mL) was added dropwise. After 60 min, the solution was poured into EtOAc and water containing ice. The organic layer was washed with water and brine before it was dried and concentrated. This crude was filtered through a plug of silica to give the 8-oxo-1,4-dioxa-spiro[4.5]decane-7-carboxylic acid ethyl ester (32.4 g). MS found: $(M+H)^+=228.9$.

(113b) The above derivative (113a)(36.5 g) was dissolved in toluene (500 ml) prior to the addition of (S)-methylbenzyl amine (23 ml) and ytterbium (III) triflate (0.37 g). This miture was stirred at reflux for 3 h. After cooling to rt overnight, the solvent was removed to a golden oil. This oil was dissolved in acetonitrile (420 ml) prior to the addition of acetic acid (100 ml) and NaBH(OAc)$_3$ (67.8 g). The mixture was stirred for 5 days at rt. The solvent was removed before being redissolved in CH$_2$Cl$_2$. After cooling in an ice bath, 1N NaOH was added (pH=8). The organic layer was washed with brine, dried, filtered, and concentrated. Flash chromatography of the resulting residue gave 8(S)-(1(S)-phenyl-ethylamino)-1,4-dioxa-spiro[4.5]decane-7(R)-carboxylic acid ethyl ester (26.2 g): $^1$H NMR (CDCl$_3$, δppm, 300 mHz) 1.31 (m, 6H), 1.46 (m, 1H), 1.6-1.84 (m, 4H), 2.1 (t, 1H), 2.85 (m, 1H), 3.16 (m, 1H), 3.76 (m, 1H), 3.93 (m, 4H), 4.19 (q, 2H), 7.2-7.4 (m, 5H).

(113c) The above derivative (113b) (16.3 g) was dissolved in Et$_2$O (160 ml) and cooled to 0° C. 1.0 M lithium aluminum hydride in THF (117.3 mL) was added dropwise. After the addition, the solution was stirred for 2 h at 0° C. The reaction was quenched with water (4.4 ml) and then 1N NaOH (17.6 ml). The solids were filtered off through a pad of celite. The filtrate was concentrated to an oil. This material was dissolved in MeOH (20 ml) prior to the addition of 20% Pd(OH)$_2$ (3 g). This solution was placed on a Parr aparatus at 50 psi. The solution was mixed overnight. The palladium was filtered off and the solution was concentrated. The resulting oil was dissolved in THF (160 ml) and water (20 ml) prior to the addition of triethylamine (8.8 ml). After cooling to 0° C., dibenzyl dicarbonate (18.2 g) was added. The solution was warmed to rt and was stirred overnight. Ethyl acetate was added along with brine. The organic layer was washed with brine, dried, filtered, and concentrated. Flash chromatography of the resulting residue gave (7R,8S)-(7-hydroxymethyl-1,4-dioxa-spiro[4.5]dec-8-yl)-carbamic acid benzyl ester (9.8 g). MS found: $(M+H)^+=322.2$.

(113d) A portion (100 mg) of the above derivative (113c) was dissolved in THF (10 ml) prior to the addition of tri-n-butylphosphine (0.86 ml). 4-Bromophenyl disulfide (233 mg) was added and the solution was stirred in a 75° C. oil bath. After 5 h, the reaction was cooled to rt and flash chromatography gave (7R,8S)-[7-(4-bromo-phenylsulfanylmethyl)-1,4-dioxa-spiro[4.5]dec-8-yl]-carbamic acid benzyl ester (137 mg). $^1$H NMR (CDCl$_3$, δppm, 300 mHz) 1.39 (t, 1H), 1.5-1.9 (m, 9H), 2.05 (m, 1H), 2.73 (m, 1H), 3.0 (dd, 1H), 3.93 (m, 4H), 4.08 (m, 1H), 4.9 (br d, 1H), 5.1 (s, 2H), 7.17 (d, 2H), 7.36 (m, 7H).

(113e) A portion (2.5 g) of the above derivative (113d) was dissolved in CH$_2$Cl$_2$ (100 ml) and cooled to 0° C. prior to the addition 65% m-CPBA (3.1 g). After 2 h, the solution was washed with saturated NaHCO$_3$ solution, brine solution, dried, filtered, and concentrated. Flash chromatography of the resulting residue gave (7R,8S)-[7-(4-bromo-benzenesulfonylmethyl)-1,4-dioxa-spiro[4.5]dec-8-yl]-carbamic acid benzyl ester (2.59 g). MS found: $(M+H)^+=525.9$.

(113f) The above derivative (113e) (2.6 g) was dissolved in DMF (20 ml) prior to the addition of NaSMe (619 mg). The resulting solution was heated in an oil bath at 100° C. for 6 h. After cooling, the solution was concentrated. EtOAc and water were added. The organic layer was washed with brine, dried, filtered, and concentrated to give crude (7R,8S) [7-(4-Methylsulfanyl-benzenesulfonylmethyl)-1,4-dioxa-spiro [4.5]dec-8-yl]-carbamic acid-benzyl-ester-(2.28 g), MS found: $(M+Na)^+=514.2$.

(113g) A portion (500 mg) of the above derivative (113f) was dissolved in acetone (10 ml) prior to the addition of 1N HCl (40 ml). The mixture was heated to reflux for 5 h. After cooling, the solution was concentrated. EtOAc and 5% NaHCO$_3$ (aq) were added. The organic layer was washed with brine, dried, filtered, and concentrated to give crude (1S,2R)-[2-(4-Methylsulfanyl-benzenesulfonylmethyl)-4-oxo-cyclohexyl]-carbamic acid benzyl ester (381 mg), MS found: $(M+H)^+=448.2$.

(113h) A portion (300 mg) of the above derivative (113g) was dissolved in THF (2 ml) and cooled to −78° C. prior to the addition of NaBH$_4$ (36 mg). After 1.5 h, the resulting solution was warmed to rt and stirred at rt for 3 h. This was quenched with NH$_4$Cl and exacted with EtOAc twice. The combined organic layer was washed with brine, dried, filtered, and concentrated to give a mixture of diastereomers (1S,2R,4R/4S)-[4-hydroxy-2-(4-methylsulfanyl-benzenesulfonylmethyl)-cyclohexyl]-carbamic acid benzyl ester (300 mg), MS found: $(M+Na)^+=472.2$.

(113i) The above derivative (300 mg)(113h) was dissolved in CH$_2$Cl$_2$ (5 ml) and cooled to 0° C. prior to the addition of Et$_3$N (0.14 ml) and methanesulfonyl chloride (0.08 ml). After 1 h, the CH$_2$Cl$_2$ was removed and EtOAc was added. This was washed with 1N HCl, saturated NaHCO$_3$, and brine. The organic layer was dried, filtered, and concentrated. This solid was dissolved in DMSO (5 ml) prior to the addition of NaN$_3$ (435 mg). This was heated at 80° C. for 18 h. Ice water was added and the reaction was extracted with EtOAc. The organic layer was washed with brine, dried, filtered, and concentrated. Flash chromatography of the resulting residue gave a mixture of diastereomers(1S,2R,4R/4S)-[4-azido-2-(4-methylsulfanyl-benzenesulfonylmethyl)-cyclohexyl]-carbamic acid benzyl ester (120 mg). MS found: $(M+H)^+=475.3$.

(113j) A portion (100 mg) of the above derivative (113i) was dissolved in THF (4 ml) prior to the addition of Ph$_3$P (83 mg). After overnight, The reaction was concentrated. The residue was dissoved in 1N HCl and the solution was extracted with ether. The acid layer was basified with Na$_2$CO$_3$ and extracted with EtOAc. The organic layer was washed with brine, dried, filtered, and concentrated to give a mixture of diastereomers (1S,2R,4R/4S)-[4-amino-2-(4-methylsulfanyl-benzenesulfonylmethyl)-cyclohexyl]-carbamic acid benzyl ester (72 mg). MS found: $(M+H)^+=449.3$.

(113k) The above derivative (72 mg) (113j) was dissolved in MeOH (1 ml) prior to the addition of 37% formaldehyde (aq) (0.04 ml) solution (aq). After 10 min, NaBH$_3$CN (40 mg) was added. The reaction was stirred for 1.5 h before being concentrated. EtOAc was added along with some water. The organic layer was dried, filtered, and concentrated to give crude (1S,2R,4R/4S)-[4-dimethylamino-2-(4-methylsulfanyl-benzenesulfonylmethyl)-cyclohexyl]-carbamic acid benzyl ester (40 mg). MS found: (M+H)$^+$=477.4.

(113l) The above derivative (40 mg) (113k) was dissolved in 30 wt. % hydrogen bromide solution in acetic acid (4 ml). The resulting solution was stirred for 35 min and then cooled to 0° C. Ether was added and solid was formed. The top liquid was decanted off. This process was repeated for several times to give HBr salt (1S,2R,4R/4S)-N-4-dimethyl-2-(4-methylsulfanyl-benzenesulfonylmethyl)-cyclohexane-1,4-diamine (24 mg), MS found: (M+H)$^+$=343.1.

(113m) The above material (24 mg)(113l) was dissolved in DMF (10 mL) prior to the addition of DIEA (0.05 ml) and 3-trifluoromethyl-benzoylamino)-acetic acid (11 mg). After cooling to 0° C., BOP Reagent (21 mg) was added. The resulting mixture was warmed to rt and was stirred overnight. EtOAc was added along with 1 N HCl solution (aq). The EtOAc layer was washed with 1 N HCl, NaHCO$_3$ solution (aq), brine, dried (MgSO$_4$), filtered, and concentrated. Reverse phase HPLC purification (gradient elution, water/acetonitrile/TFA) of the resulting residue provided the title compound (8 mg). MS found: (M+H)$^+$=572.3.

Example 114

(1S,2S,4S)-N-{[4-Dimethylamino-2-(4-methylsulfanyl-benzenesulfonylmethyl)-cyclohexylcarbamoyl]-methyl}-3-trifluoromethyl-benzamide (114a) Chiral HPLC (chiral OD column, 85% Hexane/EtOH elution) with Example 57 gave the title compound. MS found: (M+H)$^+$=572.2

Example 115

(1S,2R,4R)-N-{[4-Dimethylamino-2-(4-methylsulfanyl-benzenesulfonylmethyl)-cyclohexylcarbamoyl]-methyl}-3-trifluoromethyl-benzamide (115a) Chiral HPLC (chiral OD column, 85% Hexane/EtOH elution) with Example 57 gave the title compound. MS found: (M+H)$^+$=572.3.

Example 116

±(1S*,2R*,4S*)-N-{[4-Hydroxy-2-(4-methylsulfanyl-benzenesulfonylmethyl)-cyclohexylcarbamoyl]-methyl}-3-trifluoromethyl-benzamide (116a) The example (55c) (1.1 g) was dissolved in MeOH (10 mL) prior to the addition of 5% Pd/BaSO$_4$ (800 mg). A hydrogen balloon was added and the solution was stirred for 4.0 h. The palladium was filtered off and the solution was concentrated to ±(1S*,2R*,4S*)-4-amino-3-(4-methylsulfanyl-benzenesulfonylmethyl)-cyclohexanol (MS found: (M+H)$^+$=316.2). A portion of this material (29 mg) was dissolved in DMF prior to the addition of DIEA (0.04 ml) and 3-trifluoromethyl-benzoylamino)-acetic acid (16 mg). After cooling to 0° C., BOP Reagent (31 mg) was added. The resulting mixture was warmed to rt and was stirred overnight. EtOAc was added along with 1 N HCl solution (aq). The EtOAc layer was washed with 1 N HCl, NaHCO$_3$ solution (aq), and brine. The EtOAc was dried (MgSO$_4$), filtered, and concentrated. Reverse phase HPLC purification (gradient elution, water/acetonitrile/TFA) of the resulting residue provided the title compound (15 mg). MS found: (M+H)$^+$=545.1.

Example 11

±(1S*,2R*,4S*)-[2-({[4-Hydroxy-2-(4-methylsulfanyl-benzenesulfonylmethyl)-cyclohexylcarbamoyl]-methyl}-carbamoyl)-4-trifluoromethyl-phenyl]-carbamic acid tert-butyl ester 117(a)(2-tert-Butoxycarbonylamino-5-trifluoromethoxy-benzoylamino)-acetic acid (made in analogy to Example 11 with 2-(tert-butoxycarbonyl)amino-5-trifluoromethoxybenzoic acid; Takagishi et al. *Synlett* 1992, 360) was incorporated into Example 116 to give the title compound. MS found: (M+H)$^+$=660.2.

Example 118

(1S,2R,4R)-N-{[2-(4-Bromo-benzenesulfonylmethyl)-4-(isopropyl-methyl-amino)-cyclohexylcarbamoyl]-methyl}-3-trifluoromethyl-benzamide 118(a) The example (113e) (2.6 g) was dissolved in CH$_3$CN (25 ml) prior to the addition of 1N HCl (25 ml). The resulting solution was heated in an oil bath at 60° C. for over night. After cooling, the solution was concentrated. EtOAc and 10% NaHCO$_3$ were added. The organic layer was washed with brine, dried, filtered, and concentrated to give crude (1S,2R)-[2-(4-bromo-benzenesulfonylmethyl)-4-oxo-cyclohexyl]-carbamic acid benzyl ester (2.4 g). $^1$H NMR (CDCl$_3$, δppm, 300 mHz) 1.96 (m, 2H), 2.40 (m, 2H), 2.75-2.96 (m, 4H), 3.30 (m, 1H), 4.20 (m, 1H), 5.11 (m, 3H), 7.40 (m, 5H) 7.75 (m, 4H).

(118b) The above derivative (118a) (2.4 g) was dissolved in Ti(OiPr)$_4$ (15 ml) prior to the addition of isopropylamine (2.1 ml). After 1.0 h, the reaction was cooled to 0° C. and MeOH (100 ml) was slowly added followed by NaBH$_4$ (567 mg). After 1 h at 0° C., the reaction was quenched by the addition of 1N NaOH and filtered through celite. The filtrate was concentrated to a mixture of two diastereomers. Flash chromatography of the resulting mixture gave two diastereomers [(1S,2R,4R)-2-(4-bromo-benzenesulfonylmethyl)-4-isopropylamino-cyclohexyl]-carbamic acid benzyl ester (118ba) (1.96 g), MS found: (M+H)$^+$=523.3; and [(1S,2R,4S)-2-(4-bromo-benzenesulfonylmethyl)-4-isopropylamino-cyclohexyl]-carbamic acid benzyl ester (118bb) (300 mg), MS found: (M+H)$^+$=523.3.

(118c) The above derivative (118ba) (1.96 g) was dissolved in MeOH (15 ml) prior to the addition of 37% formaldehyde in water (1.41 ml). After 10 min, NaBH$_3$CN (708 mg) was added. After 2 h, the reaction was concentrated. EtOAc was added and the organic layer was washed with H$_2$O, brine, dried, filtered, and concentrated to give [(1S,2R,4R)-2-(4-Bromo-benzenesulfonylmethyl)-4-(isopropyl-methyl-amino)-cyclohexyl]-carbamic acid benzyl ester (1.9 g), MS found: (M+H)$^+$=539.3

(118d) A portion (940 mg) of the above derivative (118c) was dissolved in 30 wt. % hydrogen bromide solution in acetic acid (6.9 ml). The resulting solution was stirred for 1 hr and then cooled to 0° C. Ether was added and solid was formed. The top liquid was decanted off. This process was repeated for several times to give HBr salt (1S,2R,4R)-2-(4-bromo-benzenesulfonylmethyl)-N4-isopropyl-N4-methyl-cyclohexane-1,4-diamine (1.0 g). MS found: (M+2H)$^+$=405.2

(118e) A portion (45 mg) of the above derivative (118d) was dissolved in DMF (1.5 ml) prior to the addition of 4-methylmorpholine (40 µl) and 3-trifluoromethyl-benzoylamino)-acetic acid (39.3 mg). After cooling to 0° C., BOP (71 mg) was added. The resulting mixture was warmed to rt and stirred overnight before being concentrated. Water was added and the solution was extracted with EtOAc. The organic layer was washed with NaHCO$_3$ solution (aq), dried (MgSO$_4$), filtered, and concentrated. Reverse phase HPLC purification (gradient elution, water/acetonitrile/TFA) of the resulting residue provided the title compound (12.3 mg). MS found: $(M+2H)^+=634.1$.

Example 119

(1S,2R,4R)-N-{[2-(4-Bromo-benzenesulfonylmethyl)-4-(isopropyl-methyl-amino)-cyclohexylcarbamoyl]-methyl}-3-trifluoromethyl-benzamide (119a) The example (118c) (100 mg) was dissolved in MeOH (2 ml) prior to the addition of 10% Pd/C (100 mg). A hydrogen balloon was added and the solution was stirred for 5 h. The palladium was filtered off and the solution was concentrated to (1S,2R,4R)-2-benzenesulfonylmethyl-N4-isopropyl-N4-methyl-cyclohexane-1,4-diamine: MS found: $(M+H)^+=325.2$. A portion (20 mg) of this material was dissolved in DMF prior to the addition of DIEA (0.05 ml) and 3-trifluoromethyl-benzoylamino)-acetic acid (18 mg). After cooling to 0° C., HATU Reagent (34 mg) was added. The resulting mixture was warmed to rt and was stirred overnight before being concentrated. Reverse phase HPLC purification (gradient elution, water/acetonitrile/TFA) of the resulting residue provided the title compound (8 mg). MS found: $(M+H)^+=554.4$.

Example 120

(1S,2R,4R)-N-{[4-(Isopropyl-methyl-amino)-2-(toluene-4-sulfonylmethyl)-cyclohexylcarbamoyl]-methyl}-3-trifluoromethyl-benzamide (120a) (1S,2R)-[7-(4-Bromo-benzenesulfonylmethyl)-1,4-dioxa-spiro[4.5]dec-8-yl]-carbamic acid benzyl ester from example (113e) (1.0 g), was dissolved in DMF (10 ml) prior to the addition of PdCl$_2$(PPh$_3$)$_2$ (54 mg) and Sn(Me)$_4$ (0.32 ml), and a few crystals of 2,6-tert-butyl-4-methylphenol. The resulting solution was heated in an oil bath at 75° C. for 32 h. After cooling to rt, 10% ammonium hydroxide(aq) was added. The reaction was extracted twice with EtOAc. The combined organic layer was washed with brine, dried, filtered, and concentrated. Flash chromatography of the resulting residue gave (1S,2R)-(7-(toluene-4-sulfonylmethyl)-1,4-dioxa-spiro[4.5]dec-8-yl]-carbamic acid benzyl ester (668 mg). MS found: $(M+H)^+=460.3$.

(120b) A portion (500 mg) of the above derivative (120a) was dissolved in acetone (33 ml) prior to the addition of 1N HCl (11 ml). The resulting solution was heated in an oil bath at 80° C. for 5 h. After cooling, the solution was concentrated. EtOAc were added along with 10% NaHCO$_3$ solution(aq). The organic layer was washed with brine, dried, filtered, and concentrated. The resulting residue was dissolved in Ti(O-iPr)$_4$ (2.6 ml) prior to the addition of isopropylamine (2.6 ml). After 1.0 h, the reaction was cooled to 0° C. and MeOH (100 ml) was slowly added followed by NaBH$_4$ (567 mg). After 1 h at 0° C., the reaction was quenched by the addition of 1N NaOH and was filtered through celite. The filtrate was concentrated to a mixture of diastereomers. Flash chromatography of the resulting mixture gave desired isomer (1S,2R,4R)-[4-isopropylamino-2-(toluene-4-sulfonylmethyl)-cyclohexyl]-carbamic acid benzyl ester (100 mg). MS found: $(2M+H)^+=917.3$ (120c) The above derivative (120b) (100 mg) was dissolved in MeOH (2 ml) prior to the addition of a solution of 37% formaldehyde in water (82 µl). After 10 min, NaBH$_3$CN (41 mg) was added. After 2 h, the reaction was concentrated and EtOAc was added. The organic layer was washed with H$_2$O, brine, dried, filtered, and concentrated to give [(1S,2R,4R)-[4-(isopropyl-methyl-amino)-2-(toluene-4-sulfonylmethyl)-cyclohexyl]-carbamic acid benzyl ester (80 mg). MS found: $(M+H)^+=473.4$ (120d) The above derivative (120c) (80 mg) was dissolved in MeOH (2 ml) prior to the addition of 10% Pd/C (60 mg). A hydrogen balloon was added and the mixture was stirred for 1.5 h. The Pd/C was filtered off and the solvent was concentrated to give (1S,2R, 4R)-N4-isopropyl-N4-methyl-2-(toluene-4-sulfonylmethyl)-cyclohexane-1,4-diamine (50 mg).

(120e) A portion of the above derivative (120d) (12.5 mg) was dissolved in DMF (2 ml) prior to the addition of 4-methylmorpholine (25 µl) and 3-trifluoromethyl-benzoylamino)-acetic acid (11 mg). After cooling to 0° C., BOP (25 mg) was added. The resulting mixture was warmed to rt and stirred overnight before being concentrated. Reverse phase HPLC purification (gradient elution, water/acetonitrile/TFA) of the resulting residue provided the title compound (5 mg). MS found: $(M+H)^+=568.5$.

Example 121

(1S,2R,4R)-N-{[2-(4-Ethyl-benzenesulfonylmethyl)-4-(isopropyl-methyl-amino)-cyclohexylcarbamoyl]-methyl}-3-trifluoromethyl-benzamide (121a) (1S,2R)-[7-(4-Bromo-benzenesulfonylmethyl)-1,4-dioxa-spiro[4.5]dec-8-yl]-carbamic acid benzyl ester from example (113e) (1.0 g), was dissolved in toluene (15 ml) prior to the addition of PdCl$_2$(PPh$_3$)$_2$ (66 mg) and Sn(vinyl)Bu$_3$ (0.61 ml), and a few crystals of 2,6-di-tert-butyl-4-methylphenol. The resulting solution was heated to reflux for 4 h. After cooling, the solution was concentrated. Flash chromatography of the resulting residue gave (7R, 8S)[7-(4-vinyl-benzenesulfonylmethyl)-1,4-dioxa-spiro[4.5]dec-8-yl]-carbamic acid benzyl ester (668 mg). MS found: $(M+H)^+=460.3$.

(121b) A portion of the above derivative (121a) (360 mg) was dissolved in acetone (30 mL) prior to the addition of 1N HCl (10 ml). The resulting solution was heated to reflux for 5 h. After cooling, the solution was concentrated. EtOAc and 10% NaHCO$_3$ (aq) were added. The organic layer was washed with brine, dried, filtered, and concentrated. The resulting residue was dissolved in Ti(OiPr)$_4$ (2.0 ml) prior to the addition of isopropylamine (0.3 ml). After 1.0 h, the reaction was cooled to 0° C. and MeOH (100 ml) was added slowly followed by NaBH$_4$ (79 mg). After 1 h at 0° C., the reaction was quenched by the addition of 1N NaOH and filtered through celite. The filtrate was concentrated to a mixture of diastereomers. Flash chromatography of the resulting mixture gave the desired isomer (1S, 2R,4R)-[4-isopropylamino-2-(4-vinyl-benzenesulfonylmethyl)-cyclohexyl]-carbamic acid benzyl ester (100 mg). MS found: $(M+H)^+=471.4$ (121c) A portion of the above derivative (121b) (80 mg) was dissolved in dichloroethane (2 ml) prior to the addition of 37% formaldehyde in water (64 µl). After 10 min, NaBH(OAc)$_3$ (108 mg) was added. After 2 h, the reaction was concentrated and EtOAc was added. The organic layer was washed with H₂O, brine, dried, filtered, and concentrated to give [(1S, 2R,4R)-[4-(isopropyl-methyl-amino)-2-(4-vinyl-benzenesulfonylmethyl)-cyclohexyl]-carbamic acid benzyl ester(54 mg). MS found: (M+H)⁺=485.4

(121d) The above derivative (121c) (50 mg) was dissolved in MeOH (2 ml) prior to the addition of 5% Pd/BaSO₄ (50 mg). A hydrogen balloon was added and the mixture was stirred for 2 h. The palladium was filtered off and the solvent was concentrated to give (1S,2R,4R)-2-(4-ethyl-benzenesulfonylmethyl)-N4-isopropyl-N4-methyl-cyclohexane-1,4-diamine (37 mg). MS found: (M+H)⁺=353.4

(121e) A portion (17 mg) of the above derivative (121d) was dissolved in DMF (1.5 ml) prior to the addition of 4-methylmorpholine (50 μl) and 3-trifluoromethyl-benzoylamino)-acetic acid (14 mg). After cooling to 0° C., BOP (32 mg) was added. The resulting mixture was warmed to rt and stirred overnight before being concentrated. Reverse phase HPLC purification (gradient elution, water/acetonitrile/TFA) of the resulting residue provided the title compound (7 mg). MS found: (M+H)⁺=582.5.

Example 122

±(1S*,2R*,4R*)-N-[4-Dimethylamino-2-(4-methylsulfanyl-benzenesulfonylmethyl)-cyclohexyl]-2-(5-trifluoromethyl-1H-indazol-3-ylamino)-acetamide (122a) 2-Fluoro-5-trifluoromethyl-benzonitrile (2.66 g) was dissolved in n-BuOH (51 ml) prior to the addition of NH₂NH₂.H₂O (1.02 ml). The solution was heated to reflux for 30 min. After cooling to rt, the solution was concentrated and CH₂Cl₂ was added. The organic layer was washed with H₂O, brine, dried, filtered, and concentrated in high vacuum to give 5-trifluoromethyl-1H-indazol-3-ylamine (2.25 g): ¹H NMR (DMSO, δppm, 300 mHz) 5.70 (s, br, 2H), 7.40 (dd, 2H), 8.20 (s, 1H), 11.90 (s, br, 1H).

(122b) A solution of 50% oxo-acetic acid ethyl ester in toluene (118 μl) was heated at 100° C. for 1.5 h and was cooled to 60° C. prior to the addition of 122 (a) (120 mg) in MeOH (6 ml), NaBH₃CN and HOAc (0.1 ml). After 2.5 h, the reaction was concentrated and EtOAc was added. The organic layer was washed with H₂O, brine, dried, filtered, and concentrated to give (5-trifluoromethyl-1H-indazol-3-ylamino)-acetic acid ethyl ester (112 mg). MS found: (M+H)⁺=288.2.

(122c) A portion (50 mg) of the above derivative (122b) was dissolved in THF (4.4 ml) prior to the addition of a solution of LiOH.H₂O (15 mg) in water (1.5 ml) and MeOH (1.5 ml). After 2 h at rt, the reaction was concentrated. EtOAc was added along with some water. The organic layer was dried, filtered, and concentrated to give (5-trifluoromethyl-1H-indazol-3-ylamino)-acetic acid(33 mg). MS found: (M+H)⁺=260.0

(122d) ±(1S*,2R*,4R*)-[4-Azido-2-(4-methylsulfanyl-benzenesulfonylmethyl)-cyclohexyl]-carbamic acid tert-butyl ester (from example 55d), (100 mg) was dissolved in MeOH (1 ml) prior to the addition of 5% Pd/BaSO₄ (120 mg). A hydrogen balloon was added and the solution was stirred for 1.5 h. The palladium was filtered off and the solution was concentrated to give ±(1S*,2R*,4R*)-[4-amino-2-(4-methylsulfanyl-benzenesulfonylmethyl)-cyclohexyl]-carbamic acid tert-butyl ester (94 mg). MS found: (M+H)⁺=415.2

(122e) A portion (72 mg) of the above derivative (122d) was incorporated into example 57 to give ±(1S*,2R*,4R*)-[4-dimethylamino-2-(4-methylsulfanyl-benzenesulfonylmethyl)-cyclohexyl]-carbamic acid tert-butyl ester (72 mg). MS found: (M+H)⁺=443.3

(122f) The above derivative (122e) (72 mg) was dissolved in CH₂Cl₂ (10 ml) prior to the addition of TFA (4 ml). After 1 h, the reaction was concentrated. The resulting residue (93 mg) was dissolved in DMF prior to the addition of DIEA (0.16 ml) and Example (122c) (33 mg). After cooling to 0° C., HATU (62 mg) was added. The resulting mixture was warmed to rt and was stirred overnight. EtOAc was added along with 1 N HCl solution (aq). The organic layer was washed with 10% NaHCO₃ solution (aq), dried (MgSO₄), filtered, and concentrated. Reverse phase HPLC purification (gradient elution, water/acetonitrile/TFA) of the resulting residue provided the title compound (42 mg). MS found: (M+H)⁺=584.3.

Example 123

±(1S*,2R*,4R*)-N-[4-(Isopropyl-methyl-amino)-2-(4-methylsulfanyl-benzenesulfonylmethyl)-cyclohexyl]-2-(5-trifluoromethyl-1H-indazol-3-ylamino)-acetamide (123a) A portion (65 mg) of Example (122d) was dissolved in dichloroethane (3 ml) prior to the addition of acetone (0.04 ml), acetic acid (0.05 ml), and NaBH(OAc)₃ (100 mg). The reaction was stirred for 2.5 h before the solution was concentrated. EtOAc was added along with 10% NaHCO₃. The organic layer was dried, filtered, and concentrated to give ±(1S*,2R*,4R*)-[4-isopropylamino-2-(4-methylsulfanyl-benzenesulfonylmethyl)-cyclohexyl]-carbamic acid tert-butyl ester (MS found: (M+H)⁺=457.4). The resulting residue was dissolved in MeOH (3 ml) prior to the addition of 37% formaldehyde (0.06 ml) solution (aq). After 10 min, NaBH₃CN (15 mg) was added. The reaction was stirred for 45 min before the solution was concentrated. EtOAc was added along with some water. The organic layer was dried, filtered, and concentrated to give ±(1S*,2R*,4R*)-[4-(isopropyl-methyl-amino)-2-(4-methylsulfanyl-benzenesulfonylmethyl)-cyclohexyl]-carbamic acid tert-butyl ester (74 mg). MS found: (M+H)⁺=471.4.

(123b) The above derivative (123a) (74 mg) was incorporated into Example (122f) to give the title compound (30 mg). MS found: (M+H)⁺=612.2.

Example 124

±(1S*,2R*,4R*)-N-[4-(Isopropyl-methyl-amino)-2-(4-methylsulfanyl-benzenesulfonylmethyl)-cyclohexyl]-2-(1-methyl-5-trifluoromethyl-1H-indazol-3-ylamino)-acetamide (124a) A portion (300 mg) of Example (122a) was dissolved in NaOH (3 ml) and cooled to 0° C. prior to the addition of MeI (93 μl) in 1,4-dioxane (9 ml). The reaction was warmed to rt and stirred overnight. After cooling to 0° C., the reaction was neutralized with 1N KHSO₄ and exacted with EtOAc. The organic layer was dried, filtered, and concentrated. Flash chromatography of the resulting residue gave 1-methyl-5-trifluoromethyl-1H-indazol-3-ylamine (176 mg). MS found: (M+H)⁺=216.3.

(124b) The above derivative (124a) (176 mg) was incorporated into Example (122b) and (122c) to give (1-methyl-5-trifluoromethyl-1H-indazol-3-ylamino)-acetic acid-lithium salt (98.6 mg): ¹H NMR (DMSO, δppm, 300 mHz) 3.47 (d, 2H), 3.78 (s, 3H), 5.84 (t, 1H), 7.5 (m, 2H), 8.2 (s, 1H).

(124c) The above derivative (124b) (32 mg) was incorporated into Example (122f)(50 mg) to give the title compound (20 mg). MS found: (M+H)⁺=626.2.

Example 125

±(1S*,2R*,4R*)-[2-({[4-Isopropylamino-2-(4-methylsulfanyl-benzenesulfonylmethyl)-cyclohexylcarbamoyl]-methyl}-carbamoyl)-4-trifluoromethyl-phenyl]-carbamic acid tertbutylester (125a) (2-tert-Butoxycarbonylamino-5-trifluoromethyl-benzoylamino)-acetic acid, from Example (11b)(780 mg) was incorporated into Example (55d) to give the ±(1S*,2R*,4R*)-[2-({[4-azido-2-(4-methylsulfanyl-benzenesulfonylmethyl)-cyclohexylcarbamoyl]-methyl}-carbamoyl)-4-trifluoromethyl-phenyl]-carbamic acid tert-butyl ester (606 mg). MS found: (M+H)$^+$=685.3

(125b) A portion of the above derivative (519 mg) was dissolved in MeOH (5 ml) prior to the addition of 5% Pd/BaSO$_4$ (360 mg). A hydrogen balloon was added and the solution was stirred for 1 h. The palladium was filtered off and the solution was concentrated to give ±(1S*,2R*,4R*)-[2-({[4-amino-2-(4-methylsulfanyl-benzenesulfonylmethyl)-cyclohexylcarbamoyl]-methyl)-carbamoyl)-4-trifluoromethyl-phenyl]-carbamic acid tert-butyl ester (400 mg). This residue was dissolved in dichloroethane (4 ml) prior to the addition of acetone (0.14 ml). After 15 min, NaBH(OAc)$_3$ (390 mg) and HOAc (0.1 ml) was added. The reaction was stirred for 4 h before the solution was quenched with sat. NaHCO$_3$. This was extracted twice with EtOAc. The combined organic layer was dried, filtered, and concentrated. A portion of the crude residue was purified by reverse-phase HPLC (gradient elution, water/acetonitrile/TFA) to provide the title compound (8 mg). MS found: (M+H)$^+$=701.6

Example 126

±(1S*,2R*,4R*)-2-Amino-N-{[4-isopropylamino-2-(4-methylsulfanyl-benzenesulfonylmethyl)-cyclohexylcarbamoyl]-methyl}-5-trifluoromethyl-benzamide (126a) A portion (18 mg) of Example 125 was dissolved in CH$_2$Cl$_2$ (1 ml) prior to the addition of TFA (1 ml). After 1 h, the reaction was concentrated. Reverse phase HPLC purification (gradient elution, water/acetonitrile/TFA) of the resulting residue provided the title compound (12 mg). MS found: (M+H)$^+$=601.2.

Example 127

±(1S*,2R*,4R*)-[2-({[4-(Isopropyl-methyl-amino)-2-(4-methylsulfanyl-benzenesulfonylmethyl)-cyclohexylcarbamoyl]-methyl}-carbamoyl)-4-trifluoromethyl-phenyl]-carbamic acid tert-butyl ester (127a) Example 125 (100 mg) was incorporated into Example 57 to give the title compound (27 mg). MS found: (M+H)$^+$=715.3.

Example 128

±(1S*,2R*,4R*)-2-Amino-N-{[4-(isopropyl-methyl-amino)-2-(4-methylsulfanyl-benzenesulfonylmethyl)-cyclohexylcarbamoyl]-methyl}-5-trifluoromethyl-benzamide (128a) Example 127 (29 mg) was incorporated into Example 126 to give the title compound (23 mg). MS found: (M+H)$^+$=615.2.

Example 129

±(1S*,2R*,4R*)-N-{[4-(Isopropyl-propyl-amino)-2-(4-methylsulfanyl-benzenesulfonylmethyl)-cyclohexylcarbamoyl]-methyl}-3-trifluoromethyl-benzamide (129a) Example 58 (107 mg) was dissolved in MeOH (1 ml) prior to the addition of propionaldehyde (0.02 ml). After 15 min, NaBH$_3$CN (23 mg) was added. The reaction was stirred for 3 h before the solution was quenched with sat. NaHCO$_3$. This was extracted twice with EtOAc. The combined organic layer was dried, filtered, and concentrated. Reverse-phase HPLC (gradient elution, water/acetonitrile/TFA) of the resulting residue provided the title compound (42 mg). MS found: (M+H)$^+$=628.3.

Example 130

±(1S*,2R*,4R*)-N-{[4-(Cyclopropylmethyl-isopropyl-amino)-2-(4-methylsulfanyl-benzenesulfonylmethyl)-cyclohexylcarbamoyl]-methyl}-3-trifluoromethyl-benzamide (130a) Cyclopropanecarbaldehyde (18 mg) was incorporated into Example 129 to provide the title compound (52 mg). MS found: (M+H)$^+$=640.2

Example 131

±(1S*,2R*,4R*)-N-{[4-(Ethyl-isopropyl-amino)-2-(4-methylsulfanyl-benzenesulfonylmethyl)-cyclohexylcarbamoyl]-methyl}-3-trifluoromethyl-benzamide (131a) Acetaldehyde (0.02 ml) was incorporated into Example 129 to provide the title compound (37 mg). MS found: (M+H)$^+$=614.2

Example 132

±(1S*,2R*,4R*)-N-{[4-(Isobutyl-isopropyl-amino)-2-(4-methylsulfanyl-benzenesulfonylmethyl)-cyclohexylcarbamoyl]-methyl}-3-trifluoromethyl-benzamide (132a) 2-Methyl-propionaldehyde (0.02 ml) was incorporated into Example 129 to provide the title compound (26 mg). MS found: (M+H)$^+$=642.6

Example 133

±(1S*,2R*,4R*)-N-{[4-(Isopropyl-prop-2-ynyl-amino)-2-(4-methylsulfanyl-benzenesulfonylmethyl)-cyclohexylcarbamoyl]-methyl}-3-trifluoromethyl-benzamide (133a) Example 58 (97 mg) was dissolved in acetonitrile (1 ml) prior to the addition of K$_2$CO$_3$ (114 mg). After 5 min, 3-bromo-propyne (0.03 ml) was added. The reaction was heated at 60° C. for 5 h before the solution was quenched with sat. NaHCO$_3$. This was extracted twice with EtOAc. The combined organic layer was dried, filtered, and concentrated. Reverse-phase HPLC (gradient elution, water/acetonitrile/TFA) of the resulting residue provided the title compound (30 mg). MS found: (M+H)$^+$=624.2.

Example 134

±(1S*,2R*,4R*)-N-({[4-Azido-2-(4-methylsulfanyl-benzenesulfonylmethyl)-cyclohexyl]-methyl-carbamoyl}-methyl)-3-trifluoromethyl-benzamide (134a) ±(1S*,2R*,4R*)-[4-Azido-2-(4-methylsulfanyl-benzenesulfonylmethyl)-cyclohexyl]-carbamic acid tert-butyl ester, from Example (55d) (389 mg) was dissolved in THF (3 ml) and cooled to −78° C. prior to the slow addition of a solution of 0.5M KHMDS in THF (2.65 ml). After 20 min, $Me_2SO_4$ (0.15 ml) was added. The reaction was warmed to rt and stirred for 2 h before the solution was quenched with sat. $NH_4Cl$. This was extracted twice with EtOAc. The combined organic layer was dried, filtered, and concentrated. Flash chromatography of the resulting residue gave ±(1S*,2R*,4R*)-[4-azido-2-(4-methylsulfanyl-benzenesulfonylmethyl)-cyclohexyl]-methyl-carbamic acid tert-butyl ester (207 mg): $^1$H NMR ($CDCl_3$, δppm, 300 mHz) 1.39 (s, 9H), 1.55-1.93 (m, 4H), 2.00 (m, 1H), 2.52 (s, 3H), 2.65 (m, 1H), 2.80 (s, 3H), 3.00 (m, 2H), 3.81 (m, 3H), 7.34 (d, 2H) 7.80 (d, 2H).

(134b) The above derivative (134a)(64 mg) was dissolved in $CH_2Cl_2$ (2 ml) prior to the addition of TFA (2 ml). After 2 h, the reaction was concentrated. A portion (16 mg) of this residue was dissolved in DMF prior to the addition of DIEA (79 μl) and N-Boc-L-Gly-OH (26 mg). After cooling to 0° C., HATU (51 mg) was added. The resulting mixture was warmed to rt and was stirred overnight. EtOAc was added along with 1 N HCl solution (aq). The organic layer was washed with $NaHCO_3$ solution (aq), dried, filtered, and concentrated. Flash chromatography of the resulting residue gave ±(1S*,2R*,4R*)-[4-azido-2-(4-methylsulfanyl-benzene-sulfony-methyl)-cyclohexyl]-methyl-carbamoyl}-methyl)-carbamic acid tert-butyl ester (21 mg). MS found: $(M+H)^+=512.0$.

(134c) The above derivative (134b)(21 mg) was dissolved in $CH_2Cl_2$ (2 ml) prior to the addition of TFA (2 ml). After 0.5 h, the reaction was concentrated. The resulting residue was dissolved in $CH_2Cl_2$ (2 ml) and cooled to 0° C. prior to the addition of DIEA (71 μl) and 3-trifluoromethyl-benzoyl chloride (12 μl). The resulting mixture was warmed to rt and was stirred overnight. $CH_2Cl_2$ was added along with $NaHCO_3$ solution (aq). The organic layer was dried, filtered, and concentrated. Flash chromatography of the resulting residue provided the title compound (19 mg). MS found: $(M+H)^+=584.0$.

Example 135

±(1S*,2R*,4R*)-N-({[4-Amino-2-(4-methylsulfanyl-benzenesulfonylmethyl)-cyclohexyl]-methyl-carbamoyl}-methyl)-3-trifluoromethyl-benzamide (135a) Example 134 (18 mg) was incorporated into Example (55e) to give the title compound (15 mg). MS found: (M+H)=558.0.

Example 136

±(1S*,2R*,4R*)-N-({[4-Isopropylamino-2-(4-methylsulfanyl-benzenesulfonylmethyl)-cyclohexyl]-methyl-carbamoyl}-methyl)-3-trifluoromethyl-benzamide (136a) Example 135 (14 mg) was incorporated into Example 58 to give the title compound (7 mg). MS found: $(M+H)^+=600.0$.

Example 137

N-{1(R)-[(1S*,2R*,4R*)-4-Azido-2-(4-methylsulfanyl-benzenesulfonylmethyl)-cyclohexylcarbamoyl]-ethyl}-3-trifluoromethyl-benzamide (137a) ±(1S*,2R*,4R*)-[4-Azido-2-(4-methylsulfanyl-benzenesulfonylmethyl)-cyclohexyl]-carbamic acid tert-butyl ester, from Example (55d) (253 mg) was dissolved in $CH_2Cl_2$ (5 ml) prior to the addition of TFA (5 ml) After 2 h, the reaction was concentrated. A portion (100 mg) of this residue was dissolved in DMF prior to the addition of DIEA (0.25 ml) and N-Boc-D-Ala-OH (110 mg). After cooling to 0° C., HATU (219 mg) was added. The resulting mixture was warmed to rt and was stirred overnight. EtOAc was added along with 1 N HCl solution (aq). The organic layer was washed with $NaHCO_3$ solution (aq), dried, filtered, and concentrated. Flash chromatography of the resulting residue gave {1(R)-[(1S*,2R*,4R*)-4-azido-2-(4-methylsulfanyl-benzenesulfonylmethyl)-cyclohexylcarbamoyl]-ethyl}-carbamic acid tert-butyl ester (101 mg). MS found: $(M+Na)^+=534.4$.

(137b) The Example 137a (101 mg) was dissolved in $CH_2Cl_2$ (2 ml) prior to the addition of TFA (2 ml). After 0.5 h, the reaction was concentrated. The resulting residue was dissolved in $CH_2Cl_2$ (2 ml) and cooled to 0° C. prior to the addition of DIEA (0.14 ml) and 3-trifluoromethyl-benzoyl chloride (49 mg). The resulting mixture was warmed to rt and was stirred overnight. $CH_2Cl_2$ was added along with $NaHCO_3$ solution (aq). The organic layer was dried, filtered, and concentrated. Flash chromatography of the resulting residue provided the title compound (87 mg) as a mixture of diastereomers. MS found: $(M+H)^+=584.4$

Example 138

N-{1(R)-[(1S*,2R*,4R*)-4-Amino-2-(4-methylsulfanyl-benzenesulfonylmethyl)-cyclohexylcarbamoyl]-ethyl}-3-trifluoromethyl-benzamide (138a) Example 137 (73 mg) was dissolved in MeOH (3 ml) prior to the addition of 5% $Pd/BaSO_4$ (100 mg). A hydrogen balloon was added and the solution was stirred for 1 h. The palladium was filtered off and the solution was concentrated. Reverse phase HPLC purification (gradient elution, water/acetonitrile/TFA) of the resulting residue gave the title compound (67 mg) as a mixture of diastereomers. MS found: $(M+H)^+=558.4$

Example 139

N-{1(R)-[(1S*,2R*,4R*)-4-Isopropylamino-2-(4-methylsulfanyl-benzenesulfonylmethyl)-cyclohexylcarbamoyl]-ethyl}-3-trifluoromethyl-benzamide (139a) Example 138 (67 mg) was incorporated into Example 58 to give the title compound (48 mg) as a mixture of diastereomers. MS found: $(M+H)^+=600.5$

Example 140

N-{1(R)-[(1S*,2R*,4R*)-4-(Isopropyl-methyl-amino)-2-(4-methylsulfanyl-benzenesulfonylmethyl)-cyclohexylcarbamoyl]-ethyl}-3-trifluoromethyl-benzamide (140a) Example 139 (46 mg) was incorporated into Example (118c) to give the title compound (19 mg) as a mixture of diastereomers. MS found: $(M+H)^+=614.6$

Example 141

N-{1(S)-[(1S*,2R*,4R*)-4-(Isopropyl-methyl-amino)-2-(4-methylsulfanyl-benzenesulfonylmethyl)-cyclohexylcarbamoyl]-ethyl}-3-trifluoromethyl-benzamide (141a) N-Boc-L-Ala-OH (110 mg) was incorporated into Example 140 to give the title compound (24 mg) as a mixture of diastereomers. MS found: (M+H)$^+$=614.6

Example 142

±(1S*,2R*,5R*)-2-Amino-N-{[5-dimethylamino-2-(4-methylsulfanyl-benzenesulfonylmethyl)-cyclohexylcarbamoyl]-methyl}-5-trifluoromethyl-benzamide (142a) Example 77 was incorporated into Example 57 to give the title compound as a major product. MS found: (M+H)$^+$=587.4

Example 143

±(1S*,2R*,5R*)-N-{[5-Dimethylamino-2-(4-methylsulfanyl-benzenesulfonylmethyl)-cyclohexylcarbamoyl]-methyl}-2-methylamino-5-trifluoromethoxy-benzamide (143a) Example 80 was incorporated into Example 57 to give the title compound. MS found: (M+H)$^+$=617.4

Example 144

±(1S*,2R*,5R*)-2-Amino-N-{[5-isopropylamino-2-(4-methylsulfanyl-benzenesulfonylmethyl)-cyclohexylcarbamoyl]-methyl}-5-trifluoromethoxy-benzamide (144a) Example 80 was incorporated into Example 58 to give the title compound. MS found: (M+H)$^+$=617.3.

Example 145

±(1R*,3R*,4S*)-N-[(3-Benzenesulfonylmethyl-4-amino-cyclohexylcarbamoyl)-methyl]-3-trifluoromethyl-benzamide (145a) Methyl phenyl sulfone was incorporated into Example 55 steps (55a) to (55d) to afford ±(1S*,2R*,4R*)-(4-azido-2-benzenesulfonylmethyl-cyclohexyl)-carbamic acid tert-butyl ester. MS found: (M−C$_5$H$_8$O$_2$+H)$^+$=295.2

(145b) Example (145a) (200 mg) was dissolved in MeOH (10 mL) prior to the addition of 10% Pd/C (40 mg). A hydrogen balloon was added and the solution was stirred for 4.0 h. The palladium was filtered and the solution was concentrated to ±(1S*,2R*,4R*)-(4-amino-2-benzenesulfonylmethyl-cyclohexyl)-carbamic acid tert-butyl ester (5dd-1): MS found: (M+H)$^+$=369.

(145c) The above material was dissolved in DMF prior to the addition of Hunig's base (0.05 mL) and 3-trifluoromethyl-benzoylamino)-acetic acid (67 mg). After cooling to 0° C., HATU Reagent (112 mg) was added. The resulting mixture was warmed to rt and was stirred overnight. EtOAc was added along with 1 N HCl solution (aq). The EtOAc layer was washed with 1 N HCl, NaHCO$_3$ solution (aq), and brine. The EtOAc was dried (MgSO$_4$), filtered, and concentrated. Flash chromatography of the resulting residue gave ±(1S*,2R*,4R*)-({2-benzenesulfonylmethyl-4-[2-(3-trifluoromethyl-benzoylamino)-acetylamino]-cyclohexyl}-carbamic acid tert-butyl ester (130 mg). MS found: (M+H)$^+$=598.

(145d) the resulting residue (130 mg) was dissolved in CH$_2$Cl$_2$ (10 mL) and TFA (3.3 mL). After 45 min, the solution was concentrated to provide the title compound. MS found: (M+H)$^+$=498.

Example 146

±(1R*,3R*,4S*)-N-[(3-Benzenesulfonylmethyl-4-isopropylamino-cyclohexylcarbamoyl)-methyl]-3-trifluoromethyl-benzamide (146a) Example 145 (20 mg) was dissolved in dichloroethane (1 mL) prior to the adddition of glacial acetic acid (8 mg), acetone (0.1 mL), and NaBH(OAc)$_3$ (16 mg). After 20 h, the solution was concentrated. The resulting residue was dissolved in EtOAc and washed with saturated NaHCO$_3$, water, and brine. The organic layer was dried, filtered, and concentrated. Reverse phase HPLC purification (gradient elution, water/acetonitrile/TFA) of the resulting residue provided the title compound (10 mg). MS found: (M+H)$^+$=540.

Example 147

±(1R*,3R*,4S*)-N-[(3-Benzenesulfonylmethyl-4-piperidin-1-yl-cyclohexylcarbamoyl)-methyl]-3-trifluoromethyl-benzamide (147a) Example 145 (20 mg) was dissolved in dichloroethane (1 mL) prior to the adddition of glacial acetic acid (8 mg), pentanedial (0.1 mL), and NaBH(OAc)$_3$ (17 mg). After 20 h, the solution was concentrated. The resulting residue was dissolved in EtOAc and washed with saturated NaHCO$_3$, water, and brine. The organic layer was dried, filtered, and concentrated. Reverse phase HPLC purification (gradient elution, water/acetonitrile/TFA) of the resulting residue provided the title compound (10 mg). MS found: (M+H)$^+$=566.

Table 1 contains representative examples of the present invention. Each of the following structural formulas are to be used in the indicated example (Ex) range paired with the given R$^1$ and R$^2$ substituent.

TABLE 1

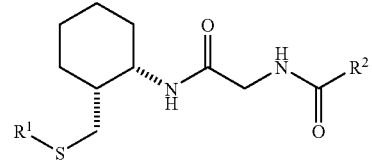

Ex 1, 3-5, 8, 106-109

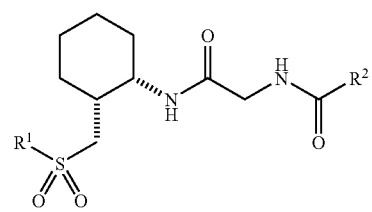

Ex 2, 6, 7, 10, 12-22, 24, 26, 28-34, 45, 46, 51-54

TABLE 1-continued

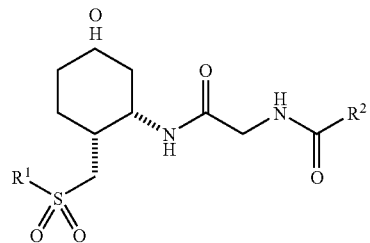

Ex 35-38, 40, 47-50

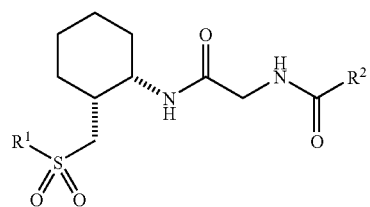

Ex 41

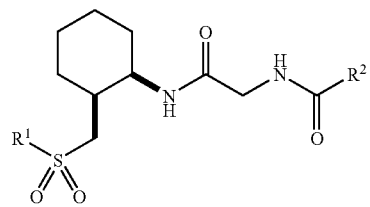

Ex 42

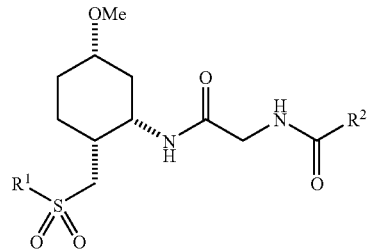

Ex 43, 44

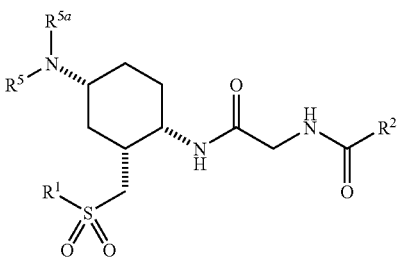

Ex 55 $R^5 = H, R^{5a} = H$
EX 56 $R^5 = H, R^{5a} = H$
EX 57 $R^5, R^{5a}$ = methyl
EX 58 $R^5$ = i-propyl, $R^{5a}$ = H
EX 59 $R^5$ = cyclobutyl, $R^{5a}$ = H
EX 60 $R^5, R^{5a}$ = ethyl
EX 61 $R^5, R^{5a}$ = propyl
EX 62 $R^5$ = benzyl, $R^4$ = H
EX 118 $R^5$ = i-propyl, $R^{5a}$ = Me
EX 119 $R^5$ = i-propyl, $R^{5a}$ = Me
EX 120 $R^5$ = i-propyl, $R^{5a}$ = Me
EX 121 $R^5$ = i-propyl, $R^{5a}$ = Me TABLE 1-continued

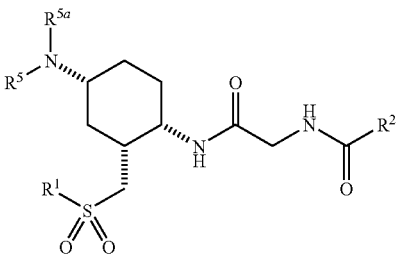

Ex 63 $R^5, R^{5a}$ = cyclopropylmethyl
EX 64 $R^5, R^{5a}$ = butyl
EX 65 $R^5$ = methyl, $R^{5a}$ = i-propyl
EX 66 $R^5$ = acetyl, $R^{5a}$ = H
EX 67 $R^5$ = methylsulfonyl, $R^{5a}$ = H
EX 68 $R^5$ = trifluoroacetyl, $R^{5a}$ = H
EX 69 $R^5$ = methyl, $R^{5a}$ = H
EX 70 $R^5$ = C(=NH)NH$_2$, $R^{5a}$ = H

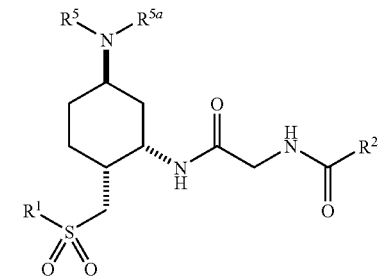

Ex 71 $R^5, R^{5a}$ = H
EX 72 $R^5$ = H, $R^{5a}$ = i-propyl
EX 73 $R^5, R^{5a}$ = i-butyl
EX 74 $R^5$ = acetyl, $R^{5a}$ = H
EX 75 $R^5$ = methylsulfonyl, $R^{5a}$ = H
EX 76 $R^5, R^{5a}$ = H
EX 77 $R^5, R^{5a}$ = H
EX 78 $R^5$ = H, $R^{5a}$ = i-propyl
EX 79 $R^5, R^{5a}$ = H
EX 80 $R^5, R^{5a}$ = H
EX 142 $R^5, R^{5a}$ = Me
EX 143 $R^5, R^{5a}$ = Me
EX 144 $R^5$ = H, $R^{5a}$ = iPr

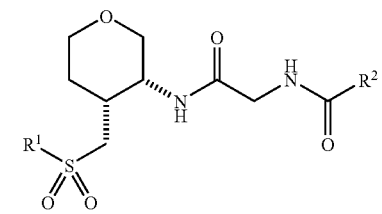

Ex 81, 84-91

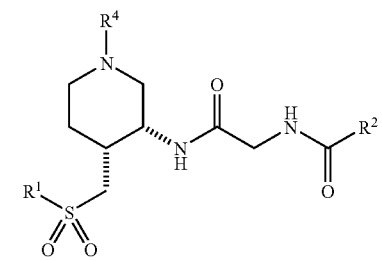

Ex 92 $R^4$ = tert-butoxycarbonyl
Ex 93 $R^4$ = H
Ex 94 $R^4$ = allyl

TABLE 1-continued

Ex 95 R⁴ = tert-butoxycarbonyl
Ex 96 R⁴ = tert-butoxycarbonyl
Ex 97 R⁴ = H

Ex 98 R⁴ = H
Ex 101 R⁴ = propyl
Ex 104 R⁴ = propyl
Ex 105 R⁴ = propyl

Ex 82

Ex 83

Ex 110-111

Ex 112

Ex 113 R⁵, R⁵ᵃ = Me

Ex 115 R⁵, R⁵ᵃ = Me
Ex 125 R⁵ = H, R⁵ᵃ = iPr
Ex 126 R⁵ = H, R⁵ᵃ = iPr
Ex 127 R⁵ = Me, R⁵ᵃ = iPr
Ex 128 R⁵ = Me, R⁵ᵃ = iPr

Ex 114 R⁵, R⁵ᵃ = Me

Ex 116, 117

Ex 122 R⁵, R⁵ᵃ = Me
Ex 123 R⁵ = iPr, R⁵ᵃ = Me
Ex 124 R⁵ = iPr, R⁵ᵃ = Me

TABLE 1-continued

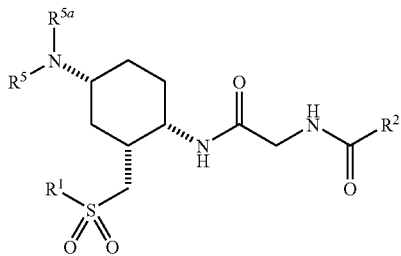

Ex 129 R⁵ = Me, R⁵ᵃ = nPr
Ex 130 R⁵ = CH₂cyclopropyl, R⁵ᵃ = iPr
Ex 131 R⁵ = Et, R⁵ᵃ = iPr
Ex 132 R⁵ = iBu, R⁵ᵃ = iPr
Ex 133 R⁵ = CH₂CCH, R⁵ᵃ = iPr

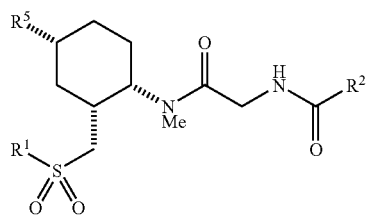

Ex 134 R⁵ = N₃
Ex 135 R⁵ = NH₂
Ex 136 R⁵ = NHiPr

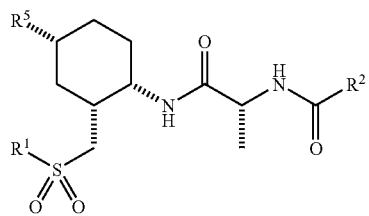

Ex 137 R⁵ = N₃
Ex 138 R⁵ = NH₂
Ex 139 R⁵ = NHiPr
Ex 140 R⁵ = N(Me)iPr

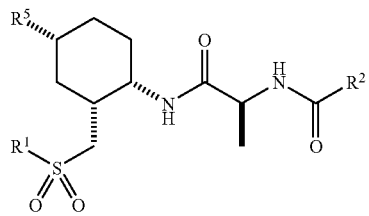

Ex 141 R⁵ = N(Me)iPr

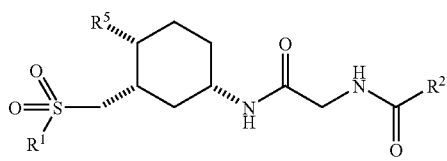

EX 145 R⁵ = NH₂
Ex 146 R⁵ = NHiPr
Ex 147 R⁵ = N-piperidinyl

| Ex | R¹ | R² | MS [M+H] |
|---|---|---|---|
| 1 | phenyl | 2-(t-butoxycarbonyl)amino-5-trifluoromethylphenyl | 588.3 M+Na |

TABLE 1-continued

| | | | |
|---|---|---|---|
| 2 | phenyl | 2-(t-butoxycarbonyl)amino-5-trifluoromethylphenyl | 620.2 M+Na |
| 3 | 1,3-benzothiazol-2-yl | 2-(t-butoxycarbonyl)amino-5-trifluoromethylphenyl | 623.2 |
| 5 | 4-methylphenyl | 2-amino-5-trifluoromethylphenyl | 480.2 |
| 6 | 4-methylphenyl | 2-(t-butoxycarbonyl)amino-5-trifluoromethylphenyl | 635.2 M+Na |
| 7 | 4-methylphenyl | 2-amino-5-trifluoromethylphenyl | 512.2 |
| 8 | 1,3-benzothiazol-2-yl | 2-amino-5-trifluoromethylphenyl | 523.1 |
| 10 | 4-methylphenyl | 2-trifluoroacetylamino-5-trifluoromethylphenyl | 606.2 M–H |
| 12 | 4-ethylphenyl | 2-(t-butoxycarbonyl)amino-5-trifluoromethylphenyl | 624 M–H |
| 13 | 4-bromophenyl | 2-(t-butoxycarbonyl)amino-5-trifluoromethylphenyl | 700.2 M+Na |
| 14 | 4-ethylphenyl | 2-amino-5-trifluoromethylphenyl | 526.3 |
| 15 | 4-bromophenyl | 2-amino-5-trifluoromethylphenyl | 578.2 |
| 16 | 4-vinylphenyl | 2-(t-butoxycarbonyl)amino-5-trifluoromethylphenyl | 624.2 |
| 17 | 4-(1,2-dihydroxyethyl)phenyl | 2-(t-butoxycarbonyl)amino-5-trifluoromethylphenyl | 680.3 M+Na |
| 18 | 4-formylphenyl | 2-(t-butoxycarbonyl)amino-5-trifluoromethylphenyl | 626.3 |
| 19 | 4-(methylthio)phenyl | 2-(t-butoxycarbonyl)amino-5-trifluoromethylphenyl | 666.4 M+Na |
| 20 | 4-(methylthio)phenyl | 2-amino-5-trifluoromethylphenyl | 566.2 M+Na |
| 21 | 4-vinylphenyl | 2-amino-5-trifluoromethylphenyl | 524.3 |
| 22 | 4-(hydroxymethyl)phenyl | 2-(t-butoxycarbonyl)amino-5-trifluoromethylphenyl | 650.3 M+Na |
| 24 | 4-(methylthio)phenyl | 2-(i-propoxycarbonyl)amino-5-trifluoromethylphenyl | 630.3 |
| 26 | 4-(methylthio)phenyl | 2-(i-propylaminocarbonyl)amino-5-trifluoromethylphenyl | 629.2 |
| 28 | 4-(methylthio)phenyl | 2-(cyclohexylcarbonyl)amino-5-trifluoromethylphenyl | 654.1 |
| 29 | 4-(methylthio)phenyl | 2-(cyclopentylaminocarbonyl)amino-5-trifluoromethylphenyl | 677.3 |
| 30 | 4-(methylthio)phenyl | 2-(i-butylaminocarbonyl)amino-5-trifluoromethylphenyl | 665.4 M+Na |
| 31 | 4-(methylthio)phenyl | 2-(ethylaminocarbonyl)amino-5-trifluoromethylphenyl | 637.3 M+Na |
| 32 | 4-(methylthio)phenyl | 2-((dimethyl)aminocarbonyl)amino-5-trifluoromethylphenyl | 627.2 M+Na |
| 33 | 4-(methylthio)phenyl | 2-((diethyl)aminocarbonyl)amino-5-trifluoromethylphenyl | 665.4 M+Na |
| 34 | 4-(methylthio)phenyl | 2-(pyrrolidinylcarbonyl)amino-5-trifluoromethylphenyl | 663.4 M+Na |

TABLE 1-continued

| | | | |
|---|---|---|---|
| 35 | 4-(methylthio)phenyl | 2-(t-butoxycarbonyl) amino-5-trifluoromethylphenyl | 660.5 |
| 36 | 4-(methylthio)phenyl | 2-(pyrrolidinylcarbonyl) amino-5-trifluoromethylphenyl | 657.3 |
| 37 | 4-(methylthio)phenyl | 2-(ethylaminocarbonyl) amino-5-trifluoromethylphenyl | 631.3 |
| 38 | 4-(methylthio)phenyl | 2-amino-5-trifluoromethylphenyl | 560.4 |
| 40 | 4-(methylthio)phenyl | 2-(iso-propyl)amino-5-trifluoromethylphenyl | 620.4 |
| 41 | 4-(methylthio)phenyl | 2-(pyrrolidinylcarbonyl) amino-5-trifluoromethylphenyl | 663.4 M+Na |
| 42 | 4-(methylthio)phenyl | 2-(pyrrolidinylcarbonyl) amino-5-trifluoromethylphenyl | 663.4 M+Na |
| 43 | 4-(methylthio)phenyl | 2-(pyrrolidinylcarbonyl) amino-5-trifluoromethylphenyl | 671.4 |
| 44 | 4-(methylthio)phenyl | 2-(ethylaminocarbonyl) amino-5-trifluoromethylphenyl | 645.4 |
| 45 | 4-(methylthio)phenyl | 2-(azetidinylcarbonyl) amino-5-trifluoromethylphenyl | 627.4 |
| 46 | 4-(methylthio)phenyl | 2-(morpholinylcarbonyl) amino-5-trifluoromethylphenyl | 657.4 |
| 47 | 4-(methylthio)phenyl | 2-(azetidinylcarbonyl) amino-5-trifluoromethylphenyl | 643.3 |
| 48 | 4-(methylthio)phenyl | 2-(morpholinylcarbonyl) amino-5-trifluoromethylphenyl | 673.5 |
| 49 | 4-(methylthio)phenyl | 2-((4-tert-butoxycarbonylpiperazinyl)carbonyl)amino-5-trifluoromethylphenyl | 772.6 |
| 50 | 4-(methylthio)phenyl | 2-(piperazinylcarbonyl) amino-5-trifluoromethylphenyl | 672.5 |
| 51 | 4-(methylthio)phenyl | 2-((4-tert-butoxycarbonyl piperazinyl)carbonyl) amino-5-trifluoromethylphenyl | 778.5 M+Na |
| 52 | 4-(methylthio)phenyl | 2-(piperazinylcarbonyl) amino-5-trifluoromethylphenyl | 656.5 |
| 53 | 4-(methylthio)phenyl | 2-(iso-butyl)amino-5-trifluoromethylphenyl | 600.5 |
| 54 | 4-(methylthio)phenyl | 2-(neo-pentyl)amino-5-trifluoromethylphenyl | 614.5 |
| 55 | 4-(methylthio)phenyl | 3-trifluoromethylphenyl | 544.3 |
| 56 | phenyl | 3-trifluoromethylphenyl | 498.4 |
| 57 | 4-(methylthio)phenyl | 3-trifluoromethylphenyl | 572.4 |
| 58 | 4-(methylthio)phenyl | 3-trifluoromethylphenyl | 586.5 |
| 59 | 4-(methylthio)phenyl | 3-trifluoromethylphenyl | 598.4 |
| 60 | 4-(methylthio)phenyl | 3-trifluoromethylphenyl | 600.4 |
| 61 | 4-(methylthio)phenyl | 3-trifluoromethylphenyl | 628.4 |
| 62 | 4-(methylthio)phenyl | 3-trifluoromethylphenyl | 634.4 |
| 63 | 4-(methylthio)phenyl | 3-trifluoromethylphenyl | 652.3 |
| 64 | 4-(methylthio)phenyl | 3-trifluoromethylphenyl | 656.5 |
| 65 | 4-(methylthio)phenyl | 3-trifluoromethylphenyl | 606.5 |
| 66 | 4-(methylthio)phenyl | 3-trifluoromethylphenyl | 586.4 |
| 67 | 4-(methylthio)phenyl | 3-trifluoromethylphenyl | 622.3 |
| 68 | 4-(methylthio)phenyl | 3-trifluoromethylphenyl | 640.2 |
| 69 | 4-(methylthio)phenyl | 3-trifluoromethylphenyl | 558.3 |
| 70 | 4-(methylthio)phenyl | 3-trifluoromethylphenyl | 586.3 |
| 71 | 4-(methylthio)phenyl | 3-trifluoromethylphenyl | 544.3 |
| 72 | 4-(methylthio)phenyl | 3-trifluoromethylphenyl | 586.4 |
| 73 | 4-(methylthio)phenyl | 3-trifluoromethylphenyl | 656.5 |
| 74 | 4-(methylthio)phenyl | 3-trifluoromethylphenyl | 586.3 |
| 75 | 4-(methylthio)phenyl | 3-trifluoromethylphenyl | 622.2 |
| 76 | 4-(methylthio)phenyl | 2-(t-butoxycarbonyl)amino-5-trifluoromethylphenyl | 659.3 |
| 77 | 4-(methylthio)phenyl | 2-amino-5-trifluoromethylphenyl | 559.3 |
| 78 | 4-(methylthio)phenyl | 2-amino-5-trifluoromethylphenyl | 601.3 |
| 79 | 4-(methylthio)phenyl | 2-(t-butoxycarbonyl)amino-5-trifluoromethoxyphenyl | 674.7 |
| 80 | 4-(methylthio)phenyl | 2-amino-5-trifluoromethoxyphenyl | 575.3 |
| 81 | 4-(methylthio)phenyl | 2-(pyrrolidinylcarbonyl) amino-5-trifluoromethylphenyl | 643.4 |
| 82 | 4-(methylthio)phenyl | 2-(pyrrolidinylcarbonyl) amino-5-trifluoromethylphenyl | 643.4 |
| 83 | 4-(methylthio)phenyl | 2-(pyrrolidinylcarbonyl) amino-5-trifluoromethylphenyl | 643.4 |
| 84 | 4-(methylthio)phenyl | 2-(ethylaminocarbonyl) amino-5-trifluoromethylphenyl | 617.3 |
| 85 | phenyl | 2-(ethylaminocarbonyl) amino-5-trifluoromethylphenyl | 571.4 |
| 86 | 4-(methylthio)phenyl | 2-(morpholinylcarbonyl) amino-5-trifluoromethylphenyl | 659.4 |
| 87 | 4-(methylthio)phenyl | 2-(methylaminocarbonyl) amino-5-trifluoromethylphenyl | 603.4 |
| 88 | 4-(methylthio)phenyl | 2-(azetidinylcarbonyl) amino-5-trifluoromethylphenyl | 629.3 |
| 89 | 4-(methylthio)phenyl | 2-(iso-propylaminocarbonyl) amino-5-trifluoromethylphenyl | 631.4 |
| 90 | 4-(methylthio)phenyl | 2-(1-propoxycarbonyl)amino-5-trifluoromethylphenyl | 632.3 |
| 91 | 4-(methylthio)phenyl | 2-(ethoxycarbonyl)amino-5-trifluoromethylphenyl | 618.4 |
| 92 | 4-(methylthio)phenyl | 2-(t-butoxycarbonyl)amino-5-trifluoromethylphenyl | 767.5 M+Na |
| 93 | 4-(methylthio)phenyl | 2-amino-5-trifluoromethylphenyl | 545.4 |
| 94 | 4-(methylthio)phenyl | 2-amino-5-trifluoromethylphenyl | 585.5 |
| 95 | 4-(methylthio)phenyl | 2-(pyrrolidinylcarbonyl) amino-5-trifluoromethylphenyl | 764.5 |
| 96 | 4-(methylthio)phenyl | 2-(methylaminocarbonyl) amino-5-trifluoromethylphenyl | 724.5 |
| 97 | 4-(methylthio)phenyl | 2-(pyrrolidinylcarbonyl) amino-5-trifluoromethylphenyl | 642.5 |
| 98 | 4-(methylthio)phenyl | 2-(methylaminocarbonyl) amino-5-trifluoromethylphenyl | 602.5 |
| 101 | 4-(methylthio)phenyl | 2-(azetidinylcarbonyl) amino-5-trifluoromethylphenyl | 670.7 |
| 104 | 4-(methylthio)phenyl | 2-(morpholinylcarbonyl) amino-5-trifluoromethylphenyl | 700.6 |

TABLE 1-continued

| | | | |
|---|---|---|---|
| 105 | 4-(methylthio)phenyl | 2-(pyrrolidinylcarbonyl)amino-5-trifluoromethylphenyl | 684.6 |
| 107 | 4-chlorophenyl | 2-amino-5-trifluoromethylphenyl | 500.0 |
| 108 | 4-(methylthio)phenyl | 2-amino-5-trifluoromethylphenyl | 512.0 |
| 109 | 4-bromophenyl | 2-(iso-propylaminocarbonyl)amino-5-trifluoromethylphenyl | 628.9 |
| 110 | 4-(methylthio)phenyl | 2-amino-5-trifluoromethylphenyl | 524.1 |
| 111 | 4-(methylsulfonyl)phenyl | 2-(t-butoxycarbonyl)amino-5-trifluoromethylphenyl | 555.9 |
| 112 | 4-(methylthio)phenyl | 3-trifluoromethylphenyl | 544.4 |
| 113 | 4-(methylthio)phenyl | 3-trifluoromethylphenyl | 572.3 |
| 114 | 4-(methylthio)phenyl | 3-trifluoromethylphenyl | 572.2 |
| 115 | 4-(methylthio)phenyl | 3-trifluoromethylphenyl | 572.3 |
| 116 | 4-(methylthio)phenyl | 3-trifluoromethylphenyl | 545.1 |
| 117 | 4-(methylthio)phenyl | 2-(t-butoxycarbonyl) amino-5-trifluoromethylphenyl | 660.2 |
| 118 | 4-(bromo)phenyl | 3-trifluoromethylphenyl | 634.1 |
| 119 | phenyl | 3-trifluoromethylphenyl | 554.4 |
| 120 | 4-(methyl)phenyl | 3-trifluoromethylphenyl | 568.5 |
| 121 | 4-(ethyl)phenyl | 3-trifluoromethylphenyl | 582.5 |
| 122 | 4-(methylthio)phenyl | 3-(5-trifluoromethyl)indazolyl | 584.3 |
| 123 | 4-(methylthio)phenyl | 3-(5-trifluoromethyl)indazolyl | 612.2 |
| 124 | 4-(methylthio)phenyl | 3-(1-methyl-5-trifluoromethyl)indazolyl | 626.2 |
| 125 | 4-(methylthio)phenyl | 2-(t-butoxycarbonyl)amino-5-trifluoromethylphenyl | 701.6 |
| 126 | 4-(methylthio)phenyl | 2-amino-5-trifluoromethylphenyl | 601.2 |
| 127 | 4-(methylthio)phenyl | 2-(t-butoxycarbonyl)amino-5-trifluoromethylphenyl | 715.3 |
| 128 | 4-(methylthio)phenyl | 2-amino-5-trifluoromethylphenyl | 615.2 |
| 129 | 4-(methylthio)phenyl | 3-trifluoromethylphenyl | 628.3 |
| 130 | 4-(methylthio)phenyl | 3-trifluoromethylphenyl | 640.2 |
| 131 | 4-(methylthio)phenyl | 3-trifluoromethylphenyl | 614.2 |
| 132 | 4-(methylthio)phenyl | 3-trifluoromethylphenyl | 642.6 |
| 133 | 4-(methylthio)phenyl | 3-trifluoromethylphenyl | 624.2 |
| 134 | 4-(methylthio)phenyl | 3-trifluoromethylphenyl | 584.0 |
| 135 | 4-(methylthio)phenyl | 3-trifluoromethylphenyl | 558.0 |
| 136 | 4-(methylthio)phenyl | 3-trifluoromethylphenyl | 600.0 |
| 137 | 4-(methylthio)phenyl | 3-trifluoromethylphenyl | 584.4 |
| 138 | 4-(methylthio)phenyl | 3-trifluoromethylphenyl | 558.4 |
| 139 | 4-(methylthio)phenyl | 3-trifluoromethylphenyl | 600.5 |
| 140 | 4-(methylthio)phenyl | 3-trifluoromethylphenyl | 614.6 |
| 141 | 4-(methylthio)phenyl | 3-trifluoromethylphenyl | 614.6 |
| 142 | 4-(methylthio)phenyl | 3-trifluoromethylphenyl | 587.4 |
| 143 | 4-(methylthio)phenyl | 2-(methyl)amino-5-trifluoromethoxyphenyl | 617.4 |
| 144 | 4-(methylthio)phenyl | 2-amino-5-trifluoromethoxyphenyl | 617.3 |
| 145 | phenyl | 3-trifluoromethylphenyl | 498 |
| 146 | phenyl | 3-trifluoromethylphenyl | 540 |
| 147 | phenyl | 3-trifluoromethylphenyl | 566 |

Table 2 contains additional examples of the present invention. Each of the following structural formulas (A to GG) are to be matched with each $R^1$ and each $R^2$ independently.

TABLE 2

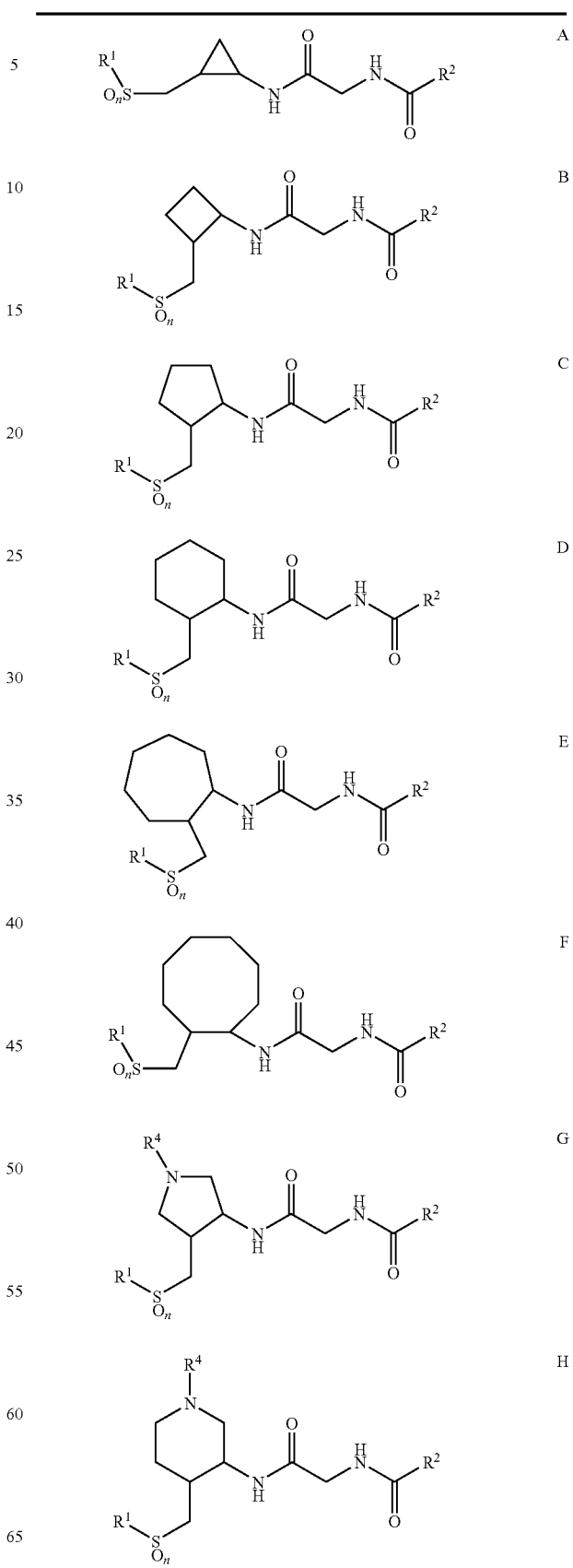

TABLE 2-continued
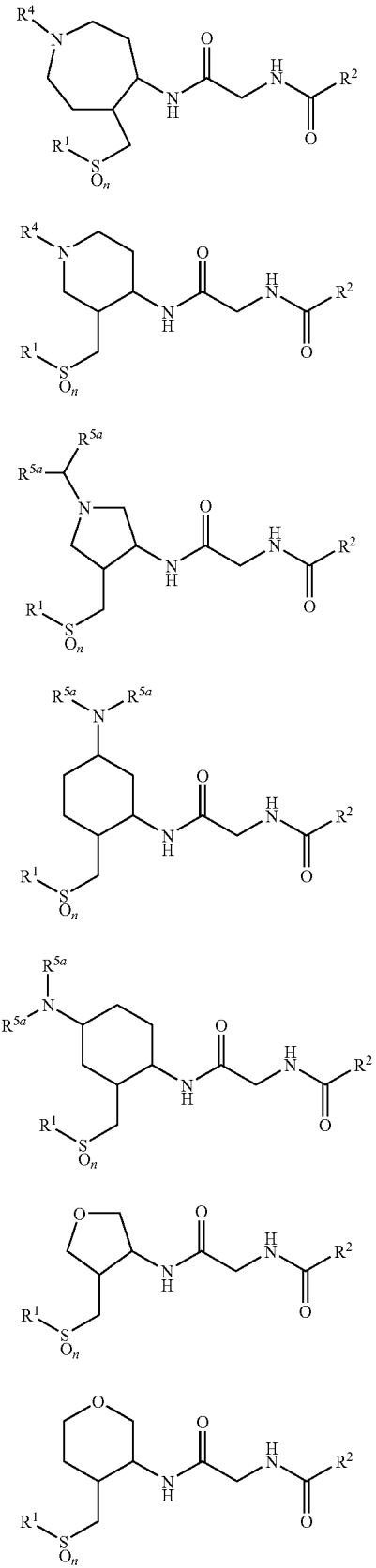
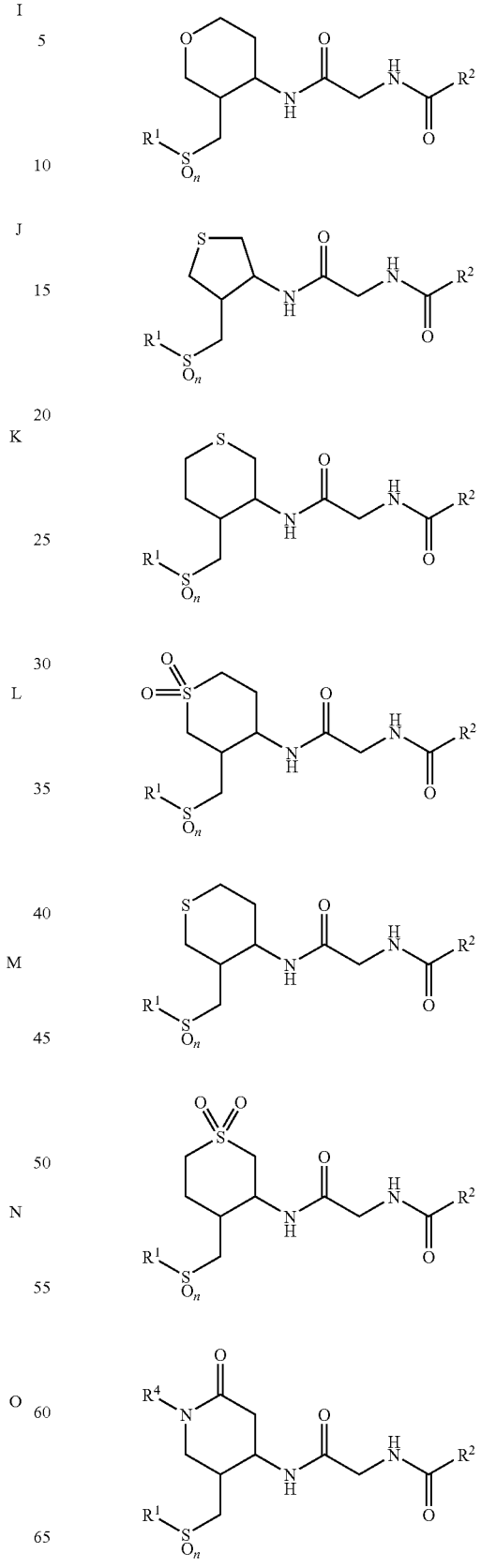

TABLE 2-continued
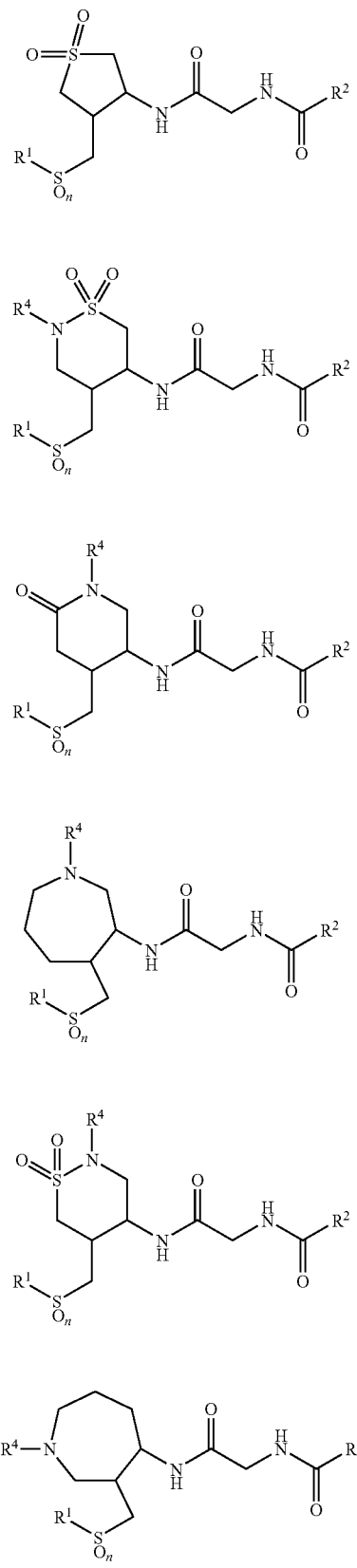
| | R¹ |
|---|---|
| 1 | 4-chlorophenyl |
| 2 | 4-bromophenyl |
| 3 | 4-iodophenyl |
| 4 | 4-ethenylphenyl |
| 5 | 4-ethylphenyl |
| 6 | 4-ethynylphenyl |
| 7 | 4-isopropylphenyl |
| 8 | 4-phenoxyphenyl |
| 9 | 4-trifluoromethylphenyl |
| 10 | 4-cyanophenyl |
| 11 | 4-nitrophenyl |
| 12 | 4-methylphenyl |
| 13 | 4-methylthiophenyl |
| 14 | 4-methylsulfonylphenyl |
| 15 | 4-methoxyphenyl |
| 16 | 3,4-dimethylphenyl |
| 17 | 4-fluorophenyl |
| 18 | 1-naphthyl |

TABLE 2-continued

| | |
|---|---|
| 19 | 2-naphthyl |
| 20 | 4-chloro-3-methylphenyl |
| 21 | 4-hydroxyphenyl |

| | $R^2$ |
|---|---|
| 1 | 3-trifluoromethylphenyl |
| 2 | 3-trifluoromethoxyphenyl |
| 3 | 3-trifluorothiophenyl |
| 4 | 2-amino-5-chlorophenyl |
| 5 | 2-amino-5-bromophenyl |
| 6 | 2-amino-5-iodophenyl |
| 7 | 2-amino-5-trifluoromethylphenyl |
| 8 | 2-amino-5-trifluoromethoxyphenyl |
| 9 | 2-(methylamino)-5-chlorophenyl |
| 10 | 2-(methylamino)-5-bromophenyl |
| 11 | 2-(methylamino)-5-iodophenyl |
| 12 | 2-(methylamino)-5-trifluoromethylphenyl |
| 13 | 2-(methylamino)-5-trifluoromethoxyphenyl |
| 14 | 2-(ethylamino)-5-chlorophenyl |
| 15 | 2-(ethylamino)-5-bromophenyl |
| 16 | 2-(ethylamino)-5-iodophenyl |
| 17 | 2-(ethylamino)-5-trifluoromethylphenyl |
| 18 | 2-(ethylamino)-5-trifluoromethoxyphenyl |
| 19 | 2-(aminocarbonyl)amino-5-chlorophenyl |
| 20 | 2-(aminocarbonyl)amino-5-bromophenyl |
| 21 | 2-(aminocarbonyl)amino-5-iodophenyl |
| 22 | 2-(aminocarbonyl)amino-5-trifluoromethylphenyl |
| 23 | 2-(aminocarbonyl)amino-5-trifluoromethyloxyphenyl |
| 24 | 2-[(methylamino)carbonyl)]amino-5-chlorophenyl |
| 25 | 2-[(methylamino)carbonyl)]amino-5-bromophenyl |
| 26 | 2-[(methylamino)carbonyl)]amino-5-iodophenyl |
| 27 | 2-[(methylamino)carbonyl)]amino-5-trifluoromethylphenyl |
| 28 | 2-[(methylamino)carbonyl)]amino-5-trifluoromethoxyphenyl |
| 29 | 2-[(ethylamino)carbonyl)]amino-5-trifluoromethylphenyl |
| 30 | 2-[(ethylamino)carbonyl)]amino-5-trifluoromethoxyphenyl |
| 31 | 2-[(iso-propylamino)carbonyl)]amino-5-trifluoromethylphenyl |
| 32 | 2-[(iso-propylamino)carbonyl)]amino-5-trifluoromethoxyphenyl |
| 33 | 2-[pyrrolidinylcarbonyl)]amino-5-trifluoromethylphenyl |
| 34 | 2-[pyrrolidinylcarbonyl)]amino-5-trifluoromethoxyphenyl |
| 35 | 2-[azetidinylcarbonyl)]amino-5-trifluoromethylphenyl |
| 36 | 2-[azetidinylcarbonyl)]amino-5-trifluoromethoxyphenyl |
| 37 | 2-[morpholinylcarbonyl)]amino-5-trifluoromethylphenyl |
| 38 | 2-[morpholinylcarbonyl)]amino-5-trifluoromethoxyphenyl | n = 2, 0

UTILITY

Compounds of formula I are shown to be modulators of chemokine receptor activity using assays know by those skilled in the art. In this section, we describe these assays and give their literature reference. By displaying activity in these assays of MCP-1 antagonism, compounds of formula I are expected to be useful in the treatment of human diseases associated with chemokines and their cognate receptors. The definition of activity in these assays is a compound demonstrating an $IC_{50}$ of 20 µM or lower in concentration when measured in a particular assay.

Antagonism of MCP-1 Binding to Human PBMC (Yoshimura et al., *J. Immunol.* 1990, 145, 292)

Compounds of the present invention have activity in the antagonism of MCP-1 binding to human PBMC (human peripheral blood mononuclear cells) described here.

Millipore filter plates (#MABVN1250) are treated with 100 µl of binding buffer (0.5% bovine serum albumin, 20 mM HEPES buffer and 5 mM magnesium chloride in RPMI 1640 media) for thirty minutes at room temperature. To measure binding, 50 µl of binding buffer, with or without a known concentration compound, is combined with 50 µl of $^{125}$-I labeled human MCP-1 (to give a final concentration of 150 pM radioligand) and 50 µl of binding buffer containing $5\times10^5$ cells. Cells used for such binding assays can include human peripheral blood mononuclear cells isolated by Ficoll-Hypaque gradient centrifugation, human monocytes (Weiner et al., *J. Immunol. Methods*. 1980, 36, 89), or the THP-1 cell line which expresses the endogenous receptor. The mixture of compound, cells and radioligand are incubated at room temperature for thirty minutes. Plates are placed onto a vacuum manifold, vacuum applied, and the plates washed three times with binding buffer containing 0.5M NaCl. The plastic skirt is removed from the plate, the plate allowed to air dry, the wells punched out and counted. The percent inhibition of binding is calculated using the total counts obtained in the absence of any competing compound and the background binding determined by addition of 100 nM MCP-1 in place of the test compound.

Antagonism of MCP-1-induced Calcium Influx (Sullivan, et al. *Methods Mol. Biol.*, 114, 125-133 (1999)

Compounds of the present invention have activity in the antagonism of MCP-1-induced calcium influx assay described here.

Calcium mobilization is measured using the fluorescent $Ca^{2+}$ indicator dye, Fluo-3. Cells are incubated at $8\times10^5$ cells/ml in phosphate-buffered saline containing 0.1% bovine serum albumin, 20 mM HEPES buffer, 5 mM glucose, 1% fetal bovine serum, 4 µM Fluo-3 AM and 2.5 mm probenecid for 60 minutes at 37° C. Cells used for such calcium assays can include human monocytes isolated as described by Weiner et al., *J. Immunol. Methods*, 36, 89-97 (1980) or cell lines which expresses the endogenous CCR2 receptor such as THP-1 and MonoMac-6. The cells are then washed three times in phosphate-buffered saline containing 0.1% bovine serum albumin, 20 mM HEPES, 5 mM glucose and 2.5 mM probenecid. The cells are resuspended in phosphate-buffered saline containing 0.5% bovine serum albumin, 20 mM HEPES and 2.5 mM probenecid at a final concentration of $2\text{-}4\times10^6$ cells/ml. Cells are plated into 96-well, black-wall microplates (100 µl/well) and the plates centrifuged at 200×g for 5 minutes. Various concentrations of compound are added to the wells (50 µl/well) and after 5 minutes, 50 µl/well of MCP-1 is added to give a final concentration of 10 nM. Calcium mobilization is detected by using a fluorescent-imaging plate reader. The cell monolayer is excited with an argon laser (488 nM) and cell-associated fluorescence measured for 3 minutes, (every second for the first 90 seconds and every 10 seconds for the next 90 seconds). Data are generated as arbitrary fluorescence units and the change in fluorescence for each well determined as the maximum-minimum differential. Compound-dependent inhibition is calculated relative to the response of MCP-1 alone.

Antagonism of MCP-1-induced Human PBMC Chemotaxis (Bacon et al., *Brit. J. Pharmacol.* 1988, 95, 966)

Compounds of the present invention have activity in the antagonism of MCP-1-induced human PBMC chemotaxis assay described here.

Neuroprobe MBA96-96-well chemotaxis chamber, Polyfiltronics MPC 96 well plate, and Neuroprobe polyvinylpyrrolidone-free polycarbonate PFD5 8-micron filters are warmed in a 37° C. incubator. Human Peripheral Blood Mononuclear Cells (PBMCs) (Boyum et al., *Scand. J. Clin. Lab Invest. Suppl.* 1968, 97, 31), freshly isolated via the standard ficoll density separation method, are suspended in DMEM at $1 \times 10^7$ c/ml and warmed at 37° C. A 60 nM solution of human MCP-1 is also warmed at 37° C. Dilutions of test compounds are made up at 2× the concentration needed in DMEM. The PBMC suspension and the 60 nm MCP-1 solution are mixed 1:1 in polypropylene tubes with prewarmed DMEM with or without a dilution of the test compounds. These mixtures are warmed in a 37° C. tube warmer. To start the assay, add the MCP-1/compound mixture into the wells of the Polyfiltronics MPC 96 well plate that has been placed into the bottom part of the Neuroprobe chemotaxis chamber. The approximate volume is 400 µl to each well and there should be a positive meniscus after dispensing. The 8 micron filter is placed gently on top of the 96 well plate, a rubber gasket is attached to the bottom of the upper chamber, and the chamber is assembled. A 200 µl volume of the cell suspension/compound mixture is added to the appropriate wells of the upper chamber. The upper chamber is covered with a plate sealer, and the assembled unit is placed in a 37° C. incubator for 45 minutes. After incubation, the plate sealer is removed and all the remaining cell suspension is aspirated off. The chamber is disassembled and the filter gently removed. While holding the filter at a 90 degree angle, unmigrated cells are washed away using a gentle stream of phosphate buffered saline and the top of the filter wiped with the tip of a rubber squeegee. Repeat this wash twice more. The filter is air dried and then immersed completely in Wright Geimsa stain for 45 seconds. The filter is then washed by soaking in distilled water for 7 minutes, and then a 15 second additional wash in fresh distilled water. The filter is again air dried. Migrated cells on the filter are quantified by visual microscopy.

Mammalian chemokine receptors provide a target for interfering with or promoting immune cell function in a mammal, such as a human. Compounds that inhibit or promote chemokine receptor function are particularly useful for modulating immune cell function for therapeutic purposes. Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (*Trichuriasis, Enterobiasis, Ascariasis*, Hookworm, *Strongyloidiasis, Trichinosis, filariasis*); trematodes (flukes) (*Schistosomiasis, Clonorchiasis*), cestodes (tape worms) (*Echinococcosis, Taeniasis saginata, Cysticercosis*); visceral worms, visceral larva migraines (e.g., *Toxocara*), eosinophilic gastroenteritis (e.g., *Anisaki* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases. In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

The compounds of the present invention are used to treat or prevent disorders selected from rheumatoid arthritis, osteoarthritis, septic shock, atherosclerosis, aneurism, fever, cardiovascular effects, haemodynamic shock, sepsis syndrom, post ischemic reperfusion injury, malaria, Crohn's disease, inflammatory bowel diseases, mycobacterial infection, meningitis, psoriasis, congestive heart failure, fibrotic diseases, cachexia, graft rejection, autoimmune diseases, skin inflammatory diseases, multiple sclerosis, radiation damage, hyperoxic alveolar injury, HIV, HIV dementia, non-insulin dependent diabetes melitus, asthma, allergic rhinitis, atopic dermatitis, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, cystic fibrosis, Churg-Strauss syndrome, lymphoma, Hodgkin's disease, colonic carcinoma, Felty's syndrome, sarcoidosis, uveitis, Alzheimer, Glomerulonephritis, and systemic lupus erythematosus.

In another aspect, the compounds are used to treat or prevent inflammatory disorders selected from from rheumatoid arthritis, osteoarthritis, atherosclerosis, aneurism, fever, cardiovascular effects, Crohn's disease, inflammatory bowel diseases, psoriasis, congestive heart failure, multiple sclerosis, autoimmune diseases, skin inflammatory diseases.

In another aspect, the compounds are used to treat or prevent inflammatory disorders selected from rheumatoid arthritis, osteoarthritis, atherosclerosis, Crohn's disease, inflammatory bowel diseases, and multiple sclerosis.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention may be used. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) integrin antagonists such as those for selecting, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102, 203), leukotriene biosynthesis inhibitors (zileuton, BAY-1005); (f) non-steroidal antiinflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (I) or (Ia) other antagonists of the chemokine receptors; (j) cholesterol lowering agents such as HMG-COA reductase inhibitors (lovastatin, simvastatin and pravastatin, fluvastatin, atorvsatatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone ad pioglitazone); (1) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (o) other compound such as 5-aminosalicylic acid an prodrugs thereof, antimetabolites such as azathioprine and 6-mercaptopurine, and cytotoxic cancer chemotherapeutic agents. The weight ratio of the compound of the present invention to the second active ingredient may be varied and will depend upon the effective doses of each ingredient.

Generally, an effective dose of each will be used. Thus, for example, when a compound of the present invention is combined with an NSAID the weight ratio of the compound of the present invention to the NSAID will generally range from about 1000:1 to about 1:1000, or alternatively from about 200:1 to about 1:200. Combinations of a compound of the present invention and other active ingredients will generally also be within the aforementioned range, but in each case, an effective dose of each active ingredient should be used.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, or between about 0.01 to 100 mg/kg of body weight per day, or alternativley, between about 1.0 to 20 mg/kg/day. Intravenously, the doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacylates, and crosslinked or amphipathic block copolymers of hydrogels. Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field. Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin. Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit. Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination. Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the appended claims, the invention may be practiced otherwise that as specifically described herein.

The invention claimed is:
1. A compound of Formula (I)

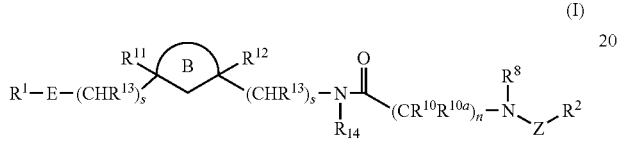

(I)

or a stereoisomer or a pharmaceutically acceptable salt thereof, wherein:

ring B is a heterocycle of 3 to 7 atoms wherein the heterocycle is saturated or partially unsaturated, the heterocycle containing a heteroatom selected from —O—, —S—, —S(=O)—, —S(=O)$_2$—, and —N(R$^4$)—, the heterocycle optionally containing a —C(O)—; ring B being substituted with 0-2 R$^5$;

Z is selected from a bond, —C(O)—, —C(O)NH—, —C(S)NH—, —SO$_2$—, and —SO$_2$NH—;

E is selected from —S(O)$_p$(CHR$^{15}$)—, —C(O)(CHR$^{15}$)—, —OC(O)NH—, —NHC(O)O—, and —NHC(O)NH—;

R$^1$ is selected from a C$_{6-10}$ aryl group substituted with 0-5 R$^6$ and a 5-10 membered heteroaryl system containing 1-4 heteroatoms selected from N, O, and S, substituted with 0-3 R$^6$;

R$^2$ is selected from a C$_{6-10}$ aryl group substituted with 0-5 R$^7$ and a 5-10 membered heteroaryl system containing 1-4 heteroatoms selected from N, O, and S, substituted with 0-3 R$^7$;

R$^4$ is selected from H, C$_{1-6}$ alkyl, C$_{3-8}$ alkenyl, C$_{3-8}$ alkynyl, (CRR)$_r$OH, (CRR)$_r$SH, (CRR)$_t$OR$^{4d}$, (CHR)$_r$SR$^{4d}$, (CRR)$_r$NR$^{4a}$R$^{4a}$, (CRR)$_q$C(O)OH, (CRR)$_r$C(O)R$^{4b}$, (CRR)$_r$C(O)NR$^{4a}$R$^{4a}$, (CRR)$_r$OC(O)NR$^{4a}$R$^{4a}$, (CRR)$_t$NR$^{4a}$C(O)OR$^{4d}$, (CRR)$_t$NR$^{4a}$C(O)R$^{4b}$, (CRR)$_r$C(O)OR$^{4b}$, (CRR)$_r$OC(O)R$^{4b}$, (CRR)$_r$S(O)$_p$R$^{4b}$, (CRR)$_r$S(O)$_2$NR$^{4a}$R$^{4a}$, (CRR)$_r$NR$^{4a}$S(O)$_2$R$^{4b}$, C$_{1-6}$ haloalkyl, a (CRR)$_r$—C$_{3-10}$ carbocyclic residue substituted with 0-3 R$^{4e}$, and a (CHR)$_r$-4-10 membered heterocyclic system containing 1-4 heteroatoms selected from N, O, and S, substituted with 0-2 R$^{4e}$;

R$^{4a}$, at each occurrence, is independently selected from H, methyl substituted with 0-1 R$^{4c}$, C$_{2-6}$ alkyl substituted with 0-3 R$^{4e}$, C$_{3-8}$ alkenyl substituted with 0-3 R$^{4e}$, C$_{3-8}$ alkynyl substituted with 0-3 R$^{4e}$, a (CH$_2$)$_r$—C$_{3-10}$ carbocyclic residue substituted with 0-4 R$^{4e}$, and a (CHR)$_r$-4-10 membered heterocyclic system containing 1-4 heteroatoms selected from N, O, and S, substituted with 0-2 R$^{4e}$;

R$^{4b}$, at each occurrence, is selected from H, C$_{1-6}$ alkyl substituted with 0-3 R$^{4e}$, C$_{3-8}$ alkenyl substituted with 0-3 R$^{4e}$, C$_{3-8}$ alkynyl substituted with 0-3 R$^{4e}$, a (CH$_2$)$_r$—C$_{3-6}$ carbocyclic residue substituted with 0-2 R$^{4e}$, and a (CHR)$_r$-4-10 membered heterocyclic system containing 1-4 heteroatoms selected from N, O, and S, substituted with 0-2 R$^{4e}$;

R$^{4c}$ is independently selected from —C(O)R$^{4b}$, —C(O)OR$^{4d}$, —C(O)NR$^{4f}$R$^{4f}$, and (CH$_2$)$_r$phenyl;

R$^{4d}$, at each occurrence, is selected from methyl, CF$_3$, C$_{1-6}$ alkyl substituted with 0-3 R$^{4e}$, C$_{3-8}$ alkenyl substituted with 0-3 R$^{4e}$, C$_{3-8}$ alkynyl substituted with 0-3 R$^{4e}$, and a C$_{3-10}$ carbocyclic residue substituted with 0-3 R$^{4e}$;

R$^{4e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{4f}$R$^{4f}$, —C(O)R$^{4i}$, —C(O)OR$^{4j}$, —C(O)NR$^{4h}$R$^{4h}$, —OC(O)NR$^{4h}$R$^{4h}$, —NR$^{4h}$C(O)NR$^{4h}$R$^{4h}$, —NR$^{4h}$C(O)OR$^{4j}$, and (CH$_2$)$_r$phenyl;

R$^{4f}$, at each occurrence, is selected from H, C$_{1-6}$ alkyl, C$_{3-6}$ cycloalkyl, and phenyl;

R$^{4h}$, at each occurrence, is independently selected from H, C$_{1-6}$ alkyl, C$_{3-8}$ alkenyl, C$_{3-8}$ alkynyl, and a (CH$_2$)$_r$—C$_{3-10}$ carbocyclic;

R$^{4i}$, at each occurrence, is selected from H, C$_{1-6}$ alkyl, C$_{3-8}$ alkenyl, C$_{3-8}$ alkynyl, and a (CH$_2$)$_r$—C$_{3-6}$ carbocyclic residue;

R$^{4j}$, at each occurrence, is selected from CF$_3$, C$_{1-6}$ alkyl, C$_{3-8}$ alkenyl, C$_{3-8}$ alkynyl, and a C$_{3-10}$ carbocyclic residue;

R$^5$, at each occurrence, is independently selected from H, =O, C$_{1-6}$ alkyl, N$_3$, C$_{2-8}$ alkenyl, C$_{2-8}$ alkynyl, (CRR)$_r$OH, (CRR)$_r$SH, (CRR)$_r$OR$^{5d}$, (CRR)$_r$SR$^{5d}$, (CRR)$_r$NR$^5$R$^{5a}$, (CRR)$_r$C(O)OH, (CRR)$_r$C(O)R$^{5b}$, (CRR)$_r$C(O)NR$^{5a}$R$^{5a}$, (CRR)$_r$NR$^{5a}$C(O)R$^{5b}$, (CRR)$_r$OC(O)NR$^{5a}$R$^{5a}$, (CRR)$_r$NR$^{5a}$C(O)OR$^{5d}$, (CRR)$_r$NR$^{5a}$C(O)NR$^{5a}$R$^{5a}$, (CRR)$_r$NR$^{5a}$C(O)H, (CRR)$_r$C(O)OR$^{5b}$, (CRR)$_r$OC(O)R$^{5b}$, (CRR)$_r$S(O)$_p$R$^{5b}$, (CRR)$_r$S(O)$_2$NR$^{5a}$R$^{5a}$, (CRR)$_r$NR$^{5a}$S(O)$_2$R$^{5b}$, (CRR)$_r$NR$^{5a}$S(O)$_2$NR$^{5a}$R$^{5a}$, (CRR)$_r$NR$^{5a}$C(=N)NR$^{5a}$R$^{5a}$, C$_{1-6}$ haloalkyl, a (CRR)$_r$—C$_{3-10}$ carbocyclic residue substituted with 0-3 R$^{5c}$, and a (CRR)$_r$-5-10 membered heterocyclic system containing 1-4 heteroatoms selected from N, O, and S, substituted with 0-2 R$^{5c}$;

R$^{5a}$, at each occurrence, is independently selected from H, methyl substituted with 0-1 R$^{5g}$, C$_{2-6}$ alkyl substituted with 0-2 R$^{5e}$, C$_{3-8}$ alkenyl substituted with 0-2 R$^{5e}$, C$_{3-8}$ alkynyl substituted with 0-2 R$^{5e}$, a (CH$_2$)$_r$—C$_{3-10}$ carbocyclic residue substituted with 0-5 R$^{5e}$, and a (CH$_2$)$_r$-5-10 membered heterocyclic system containing 1-4 heteroatoms selected from N, O, and S, substituted with 0-3 R$^{5e}$;

R$^{5b}$, at each occurrence, is selected from C$_{1-6}$ alkyl substituted with 0-3 R$^{5e}$, C$_{3-8}$ alkenyl substituted with 0-2 R$^{5e}$, C$_{3-8}$ alkynyl substituted with 0-2 R$^{5e}$, a (CH$_2$)$_r$—C$_{3-6}$ carbocyclic residue substituted with 0-2 R$^{5e}$, and a (CH$_2$)$_r$-5-6 membered heterocyclic system containing 1-4 heteroatoms selected from N, O, and S, substituted with 0-3 R$^{5e}$;

R$^{5c}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{5f}$R$^{5f}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{5b}$, (CH$_2$)$_r$C(O)NR$^{5f}$R$^{5f}$, (CH$_2$)$_r$NR$^{5f}$C(O)R$^{5b}$, (CH$_2$)$_r$C(O)OC$_{1-4}$ alkyl, (CH$_2$)$_r$OC(O)R$^{5b}$, (CH$_2$)$_r$C(=NR$^{5f}$)NR$^{5f}$R$^{5f}$, (CH$_2$)$_r$S(O)$_p$R$^{5b}$, (CH$_2$)$_r$NHC(=NR$^{5f}$)NR$^{5f}$R$^{5f}$, (CH$_2$)$_r$S(O)$_2$NR$^{5f}$R$^{5f}$, (CH$_2$)$_r$NR$^{5f}$S(O)$_2$R$^{5b}$, and (CH$_2$)$_r$phenyl substituted with 0-3 R$^{5e}$;

$R^{5d}$, at each occurrence, is selected from methyl, $CF_3$, $C_{2-6}$ alkyl substituted with 0-2 $R^{5e}$, $C_{3-8}$ alkenyl substituted with 0-2 $R^{5e}$, $C_{3-8}$ alkynyl substituted with 0-2 $R^{5e}$, and a $C_{3-10}$ carbocyclic residue substituted with 0-3 $R^{5e}$;

$R^{5e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{5f}R^{5f}$, and $(CH_2)_r$phenyl;

$R^{5f}$, at each occurrence, is selected from H, $C_{1-6}$ alkyl, and $C_{3-6}$ cycloalkyl;

$R^{5g}$ is independently selected from $-C(O)R^{5b}$, $-C(O)OR^{5d}$, $-C(O)NR^{5f}R^{5f}$, and $(CH_2)_r$phenyl;

R, at each occurrence, is selected from H, $C_{1-6}$ alkyl substituted with 0-3 $R^{5e}$, $C_{2-8}$ alkenyl, $C_{2-8}$ alkynyl, $(CH_2)_r$ $C_{3-6}$ cycloalkyl, and $(CH_2)_r$phenyl substituted with $R^{5e}$;

$R^6$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, (CR'R')$_r$NR$^{6a}$R$^{6a}$, (CR'R')$_r$OH, (CR'R')$_r$O(CR'R')$_r$R$^{6d}$, (CR'R')$_r$SH, (CR'R')$_r$C(O)H, (CR'R')$_r$S(CR'R')$_r$R$^{6d}$, (CR'R')$_r$SC(O)(CR'R')$_r$R$^{6b}$, (CR'R')$_r$C(O)OH, (CR'R')$_r$C(O)(CR'R')$_r$R$^{6b}$, (CR'R')$_r$NR$^{6a}$R$^{6a}$, (CR'R')$_r$C(O)NR$^{6a}$R$^{6a}$, (CR'R')$_r$NR$^{6f}$C(O)(CR'R')$_r$R$^{6b}$, (CR'R')$_r$C(O)O(CR'R')$_r$R$^{6d}$, (CR'R')$_r$OC(O)(CR'R')$_r$R$^{6b}$, (CR'R')$_r$OC(O)NR$^{6a}$(CR'R')$_r$R$^{6d}$, (CR'R')$_r$NR$^{6a}$C(O)NR$^{6a}$(CR'R')$_r$R$^{6d}$, (CR'R')$_r$NR$^{6a}$C(S)NR$^{6a}$(CR'R')$_r$R$^{6d}$, (CR'R')$_r$NR$^{6f}$C(O)O(CR'R')$_r$R$^{6b}$, (CR'R')$_r$C(=NR$^{6f}$)NR$^{6a}$R$^{6a}$, (CR'R')$_r$NHC(=NR$^{6f}$)NR$^{6f}$R$^{6f}$, (CR'R')$_r$S(O)$_p$(CR'R')$_r$R$^{6b}$, (CR'R')$_r$S(O)$_2$NR$^{6a}$R$^{6a}$, (CR'R')$_r$NR$^{6f}$S(O)$_2$NR$^{6a}$R$^{6a}$, (CR'R')$_r$NR$^{6f}$S(O)$_2$(CR'R')$_r$R$^{6b}$, $C_{1-6}$ haloalkyl, $C_{2-8}$ alkenyl substituted with 0-3 R', $C_{2-8}$ alkynyl substituted with 0-3 R', and (CR'R')$_r$phenyl substituted with 0-3 $R^{6e}$;

alternatively, two $R^6$ on adjacent atoms on $R^1$ may join to form a cyclic acetal;

$R^{6a}$, at each occurrence, is selected from H, methyl substituted with 0-1 $R^{6g}$, $C_{2-6}$ alkyl substituted with 0-2 $R^{6e}$, $C_{3-8}$ alkenyl substituted with 0-2 $R^{6e}$, $C_{3-8}$ alkynyl substituted with 0-2 $R^{6e}$, a $(CH_2)_r$—$C_{3-10}$ carbocyclic residue substituted with 0-5 $R^{6e}$, and a $(CH_2)_r$-5-10 membered heterocyclic system containing 1-4 heteroatoms selected from N, O, and S, substituted with 0-2 $R^{6e}$;

$R^{6b}$, at each occurrence, is selected from H, $C_{1-6}$ alkyl substituted with 0-2 $R^{6e}$, $C_{3-8}$ alkenyl substituted with 0-2 $R^{6e}$, $C_{3-8}$ alkynyl substituted with 0-2 $R^{6e}$, a $(CH_2)_r$ $C_{3-6}$ carbocyclic residue substituted with 0-3 $R^{6e}$, and a $(CH_2)_r$-5-6 membered heterocyclic system containing 1-4 heteroatoms selected from N, O, and S, substituted with 0-2 $R^{6e}$;

$R^{6d}$, at each occurrence, is selected from $C_{3-8}$ alkenyl substituted with 0-2 $R^{6e}$, $C_{3-8}$ alkynyl substituted with 0-2 $R^{6e}$, methyl, $CF_3$, $C_{2-6}$ alkyl substituted with 0-3 $R^{6e}$, a $(CH_2)_r$—$C_{3-10}$ carbocyclic residue substituted with 0-3 $R^{6e}$, and a $(CH_2)_r$-5-6 membered heterocyclic system containing 1-4 heteroatoms selected from N, O, and S, substituted with 0-3 $R^{6e}$;

$R^{6e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{6f}R^{6f}$, and $(CH_2)_r$phenyl;

$R^{6f}$, at each occurrence, is selected from H, $C_{1-5}$ alkyl, and $C_{3-6}$ cycloalkyl, and phenyl;

$R^{6g}$ is independently selected from $-C(O)R^{6b}$, $-C(O)OR^{6d}$, $-C(O)NR^{6f}R^{6f}$, and $(CH_2)_r$phenyl;

$R^7$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, (CR'R')$_r$NR$^{7a}$R$^{7a}$, (CR'R')$_r$OH, (CR'R')$_r$O(CR'R')$_r$R$^{7d}$, (CR'R')$_r$SH, (CR'R')$_r$C(O)H, (CR'R')$_r$S(CR'R')$_r$R$^{7d}$, (CR'R')$_r$C(O)OH, (CR'R')$_r$C(O)(CR'R')$_r$R$^{7b}$, (CR'R')$_r$C(O)NR$^{7a}$R$^{7a}$, (CR'R')$_r$NR$^{7f}$C(O)(CR'R')$_r$R$^{7b}$, (CR'R')$_r$C(O)O(CR'R')$_r$R$^{7d}$, (CR'R')$_r$OC(O)(CR'R')$_r$R$^{7a}$, (CR'R')$_r$R$^{7b}$, (CR'R')$_r$OC(O)NR$^{7a}$(CR'R')$_r$R$^{7a}$, (CR'R')$_r$NR$^{7a}$C(O)NR$^{7a}$(CR'R')$_r$R$^{7a}$, (CR'R')$_r$NR$^{7f}$C(O)O(CR'R')$_r$R$^{7b}$, (CR'R')$_r$C(=NR$^{7f}$)NR$^{7a}$R$^{7a}$, (CR'R')$_r$NHC(=NR$^{7f}$)NR$^{7f}$R$^{7f}$, (CR'R')$_r$S(O)$_p$(CR'R')$_r$R$^{7b}$, (CR'R')$_r$S(O)$_2$NR$^{7a}$R$^{7a}$, (CR'R')$_r$NR$^{7a}$S(O)$_2$NR$^{7a}$R$^{7a}$, (CR'R')$_r$NR$^{7f}$S(O)$_2$(CR'R')$_r$R$^{7b}$, $C_{1-6}$ haloalkyl, $C_{2-8}$ alkenyl substituted with 0-3 R', $C_{2-8}$ alkynyl substituted with 0-3 R', and (CR'R')$_r$phenyl substituted with 0-3 $R^{7e}$;

alternatively, two $R^7$ on adjacent atoms on $R^2$ may join to form a cyclic acetal;

$R^{7a}$, at each occurrence, is independently selected from H, methyl substituted with 0-1 $R^{7g}$, $C_{2-6}$ alkyl substituted with 0-2 $R^{7e}$, $C_{3-8}$ alkenyl substituted with 0-2 $R^{7e}$, $C_{3-8}$ alkynyl substituted with 0-2 $R^{7e}$, a $(CH_2)_r$—$C_{3-10}$ carbocyclic residue substituted with 0-5 $R^{7e}$, and a $(CH_2)_r$-5-10 membered heterocyclic system containing 1-4 heteroatoms selected from N, O, and S, substituted with 0-2 $R^{7e}$;

$R^{7b}$, at each occurrence, is selected from $C_{1-6}$ alkyl substituted with 0-3 $R^{7e}$, $C_{3-8}$ alkenyl substituted with 0-2 $R^{7e}$, $C_{3-8}$ alkynyl substituted with 0-2 $R^{7e}$, a $(CH_2)_rC_{3-6}$ carbocyclic residue substituted with 0-3 $R^{7e}$, and a $(CH_2)_r$-5-6 membered heterocyclic system containing 1-4 heteroatoms selected from N, O, and S, substituted with 0-2 $R^{7e}$;

$R^{7d}$, at each occurrence, is selected from $C_{3-8}$ alkenyl substituted with 0-2 $R^{7e}$, $C_{3-8}$ alkynyl substituted with 0-2 $R^{7e}$, methyl, $CF_3$, $C_{2-6}$ alkyl substituted with 0-3 $R^{7e}$, a $(CH_2)_r$—$C_{3-10}$ carbocyclic residue substituted with 0-3 $R^{7e}$, and a $(CH_2)_r$-5-6 membered heterocyclic system containing 1-4 heteroatoms selected from N, O, and S, substituted with 0-3 $R^{7e}$;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, C(O)$OC_{1-5}$ alkyl, $(CH_2)_rSC_{1-5}$ alkyl, $(CH_2)_rNR^{7f}R^{7f}$, and $(CH_2)_r$phenyl;

$R^{7f}$, at each occurrence, is selected from H, $C_{1-5}$ alkyl, and $C_{3-6}$ cycloalkyl, and phenyl;

$R^{7g}$ is independently selected from $-C(O)R^{7b}$, $-C(O)OR^{7d}$, $-C(O)NR^{7f}R^{7f}$, and $(CH_2)_r$phenyl;

R', at each occurrence, is selected from H, $C_{1-6}$ alkyl substituted with 0-3 $R^{6e}$, $C_{2-8}$ alkenyl, $C_{2-8}$ alkynyl, $(CH_2)_rC_{3-6}$ cycloalkyl, and $(CH_2)_r$phenyl substituted with $R^{6e}$;

$R^8$ is selected from H, $C_{1-4}$ alkyl, and $C_{3-4}$ cycloalkyl;

$R^{10}$ and $R^{10a}$ are independently selected from H, and $C_{1-4}$alkyl substituted with 0-1 $R^{10b}$, alternatively, $R^{10}$ and $R^{10a}$ can join to form a $C_{3-6}$ cycloalkyl;

$R^{10b}$, at each occurrence, is independently selected from $-OH$, $-SH$, $-NR^{10c}R^{10c}$, $-C(O)NR^{10c}R^{10c}$, and $-NHC(O)R^{10c}$;

$R^{10c}$ is selected from H, $C_{1-4}$ alkyl and $C_{3-6}$ cycloalkyl;

$R^{11}$ is selected from H, $C_{1-4}$ alkyl, (CHR)$_q$OH, (CHR)$_q$SH, (CHR)$_q$OR$^{11d}$, (CHR)$_q$S(O)$_p$R$^{11d}$, (CHR)$_r$C(O)R$^{11b}$, (CHR)$_r$NR$^{11a}$R$^{11a}$, (CHR)$_r$C(O)NR$^{11a}$R$^{11a}$, (CHR)$_r$C(O)NR$^{11a}$OR$^{11d}$, (CHR)$_q$NR$^{11a}$C(O)R$^{11b}$, (CHR)$_q$NR$^{11a}$C(O)OR$^{11d}$, (CHR)$_q$OC(O)NR$^{11a}$R$^{11a}$, (CHR)$_r$C(O)OR$^{11d}$, a(CHR)$_r$—$C_{3-6}$ carbocyclic residue substituted with 0-5 $R^{11e}$, and a (CHR)$_r$-5-10 membered heterocyclic system containing 1-4 heteroatoms selected from N, O, and S, substituted with 0-3 $R^{11e}$;

$R^{11a}$, at each occurrence, is independently selected from H, $C_{1-4}$ alkyl, $C_{3-4}$ alkenyl, $C_{3-4}$ alkynyl, $(CH_2)_rC_{3-6}$ cycloalkyl, a $(CH_2)_r$—$C_{3-6}$ carbocyclic residue substituted with 0-5 $R^{11e}$, and a $(CH_2)_r$-5-6 membered heterocyclic system containing 1-4 heteroatoms selected from N, O, and S, substituted with 0-3 $R^{11e}$;

$R^{11b}$, at each occurrence, is independently selected from $C_{1-4}$ alkyl, $C_{2-4}$ alkenyl, $C_{2-4}$ alkynyl, a $(CH_2)_r$—$C_{3-6}$ carbocyclic residue substituted with 0-2 $R^{11e}$, and a $(CH_2)_r$-5-6 membered heterocyclic system containing 1-4 heteroatoms selected from N, O, and S, substituted with 0-3 $R^{11e}$;

$R^{11d}$, at each occurrence, is independently selected from H, methyl, —$CF_3$, $C_{2-4}$ alkyl, $C_{3-6}$ alkenyl, $C_{3-6}$ alkynyl, a $C_{3-6}$ carbocyclic residue substituted with 0-3 $R^{11e}$, and a $(CH_2)_r$-5-6 membered heterocyclic system containing 1-4 heteroatoms selected from N, O, and S, substituted with 0-3 $R^{11e}$;

$R^{11e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{11f}R^{11f}$, and $(CH_2)_r$phenyl;

$R^{11f}$, at each occurrence, is selected from H, $C_{1-6}$ alkyl, and $C_{3-6}$ cycloalkyl;

$R^{12}$ is selected from H, $C_{1-4}$ alkyl, $(CHR)_qOH$, $(CHR)_qSH$, $(CHR)_qOR^{12d}$, $(CHR)_qS(O)_pR^{12d}$, $(CHR)_qC(O)R^{12b}$, $(CHR)_rNR^{12a}R^{12a}$, $(CHR)_rC(O)NR^{12a}R^{12a}$, $(CHR)_rC(O)NR^{12a}OR^{12d}$, $(CHR)_qNR^{12a}C(O)R^{12b}$, $(CHR)_qNR^{12a}C(O)OR^{12d}$, $(CHR)_qOC(O)NR^{12a}R^{12a}$, $(CHR)_rC(O)OR^{12d}$, a $(CHR)_r$—$C_{3-6}$ carbocyclic residue substituted with 0-5 $R^{12e}$, and a $(CHR)_r$-5-10 membered heterocyclic system containing 1-4 heteroatoms selected from N, O, and S, substituted with 0-3 $R^{12e}$;

$R^{12a}$, at each occurrence, is independently selected from H, $C_{1-4}$ alkyl, $C_{3-4}$ alkenyl, $C_{3-4}$ alkynyl, $(CH_2)_rC_{3-6}$ cycloalkyl, a $(CH_2)_r$—$C_{3-6}$ carbocyclic residue substituted with 0-5 $R^{12e}$, and a $(CH_2)_r$-5-6 membered heterocyclic system containing 1-4 heteroatoms selected from N, O, and S, substituted with 0-3 $R^{12e}$;

$R^{12b}$, at each occurrence, is independently selected from $C_{1-4}$ alkyl, $C_{2-4}$ alkenyl, $C_{2-4}$ alkynyl, a $(CH_2)_r$—$C_{3-6}$ carbocyclic residue substituted with 0-2 $R^{12e}$, and a $(CH_2)_r$-5-6 membered heterocyclic system containing 1-4 heteroatoms selected from N, O, and S, substituted with 0-3 $R^{12e}$;

$R^{12d}$, at each occurrence, is independently selected from H, methyl, —$CF_3$, $C_{2-4}$ alkyl, $C_{3-6}$ alkenyl, $C_{3-6}$ alkynyl, a $C_{3-6}$ carbocyclic residue substituted with 0-3 $R^{12e}$, and a $(CH_2)_r$-5-6 membered heterocyclic system containing 1-4 heteroatoms selected from N, O, and S, substituted with 0-3 $R^{12e}$;

$R^{12e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{12f}R^{12f}$ and $(CH_2)_r$phenyl;

$R^{12f}$, at each occurrence, is selected from H, $C_{1-6}$ alkyl, and $C_{3-6}$ cycloalkyl;

$R^{13}$, at each occurrence, is independently selected from methyl, $C_{2-4}$ alkyl substituted with 0-1 $R^{13b}$;

$R^{13b}$ is selected from —OH, —SH, —$NR^{13c}R^{13c}$, —C(O)$NR^{13c}R^{13c}$, and —NHC(O)$R^{13c}$;

$R^{13c}$ is selected from H, $C_{1-4}$ alkyl and $C_{3-6}$ cycloalkyl;

$R^{14}$ is selected from H, and $C_{1-3}$ alkyl;

$R^{15}$ is selected from H and $C_{1-3}$ alkyl;

n is selected from 1 and 2;

m is selected from 0 and 1;

p, at each occurrence, is independently selected from 0, 1, and 2;

q, at each occurrence, is independently selected from 1, 2, 3, and 4;

r, at each occurrence, is independently selected from 0, 1, 2, 3, and 4;

s, at each occurrence, is independently selected from 0 and 1; and t, at each occurrence, is independently selected from 2, 3, and 4.

2. The compound of claim 1, wherein the compound is of formula (Ia)

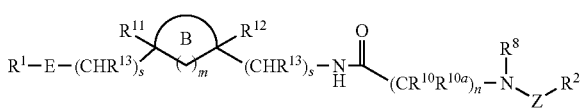

(Ia)

$R^4$ is selected from H, $C_{1-6}$ alkyl, $C_{3-8}$ alkenyl, $C_{3-8}$ alkynyl, $(CRR)_tOH$, $(CRR)_tSH$, $(CRR)_tOR^{4d}$, $(CHR)_tSR^{4d}$, $(CRR)_tNR^{4a}R^{4a}$, $(CRR)_qC(O)OH$, $(CRR)_tC(O)R^{4b}$, $(CRR)_tC(O)NR^{4a}R^{4a}$, $(CRR)_tOC(O)NR^{4a}R^{4a}$, $(CRR)_tNR^{4a}C(O)OR^{4d}$, $(CRR)_tNR^{4a}C(O)R^{4b}$, $(CRR)_tC(O)OR^{4b}$, $(CRR)_tOC(O)R^{4b}$, $(CRR)_tS(O)_pR^{4b}$, $(CRR)_tS(O)_2NR^{4a}R^{4a}$, $(CRR)_tNR^{4a}S(O)_2R^{4b}$, $C_{1-6}$ haloalkyl, a $(CRR)_r$—$C_{3-10}$ carbocyclic residue substituted with 0-3 $R^{4e}$, and a $(CHR)_r$-4-10 membered heterocyclic system containing 1-4 heteroatoms selected from N, O, and S, substituted with 0-2 $R^{4e}$;

$R^5$, at each occurrence, is independently selected from H, =O, $C_{1-6}$ alkyl, $C_{2-8}$ alkenyl, $C_{2-8}$ alkynyl, $(CRR)_rOH$, $(CRR)_rSH$, $(CRR)_rOR^{5d}$, $(CRR)_rSR^{5d}$, $(CRR)_rNR^{5a}R^{5a}$, $(CRR)_rC(O)OH$, $(CRR)_rC(O)R^{5b}$, $(CRR)_rC(O)NR^{5a}R^{5a}$, $(CRR)_rNR^{5a}C(O)R^{5b}$, $(CRR)_rOC(O)NR^{5a}R^{5a}$, $(CRR)_rNR^{5a}C(O)OR^{5d}$, $(CRR)_rNR^{5a}C(O)NR^{5a}R^{5a}$, $(CRR)_rNR^{5a}C(O)H$, $(CRR)_rC(O)OR^{5b}$, $(CRR)_rOC(O)R^{5b}$, $(CRR)_rS(O)_pR^{5b}$, $(CRR)_rS(O)_2NR^{5a}R^{5a}$, $(CRR)_rNR^{5a}S(O)_2R^{5b}$, $(CRR)_rNR^{5a}S(O)_2NR^{5a}R^{5a}$, $C_{1-6}$ haloalkyl, a $(CRR)_r$—$C_{3-10}$ carbocyclic residue substituted with 0-3 $R^{5c}$, and a $(CRR)_r$-5-10 membered heterocyclic system containing 1-4 heteroatoms selected from N, O, and S, substituted with 0-2 $R^{5c}$;

R, at each occurrence, is selected from H, $C_{1-6}$ alkyl substituted with 0-3 $R^{5e}$, $C_{2-8}$ alkenyl, $C_{2-8}$ alkynyl, $(CH_2)_rC_{3-6}$ cycloalkyl, and $(CH_2)_r$phenyl substituted with $R^{5e}$;

$R^{7b}$, at each occurrence, is selected from $C_{1-6}$ alkyl substituted with 0-2 $R^{7e}$, $C_{3-8}$ alkenyl substituted with 0-2 $R^{7e}$, $C_{3-8}$ alkynyl substituted with 0-2 $R^{7e}$, a $(CH_2)_rC_{3-6}$ carbocyclic residue substituted with 0-3 $R^{7e}$, and a $(CH_2)_r$-5-6 membered heterocyclic system containing 1-4 heteroatoms selected from N, O, and S, substituted with 0-2 $R^{7e}$;

R', at each occurrence, is selected from H, $C_{1-6}$ alkyl substituted with 0-3 $R^{6e}$, $C_{2-8}$ alkenyl, $C_{2-8}$ alkynyl, $(CH_2)_rC_{3-6}$ cycloalkyl, and $(CH_2)_r$phenyl substituted with $R^{6e}$.

3. The compound of claim 2, wherein:
ring B is selected from

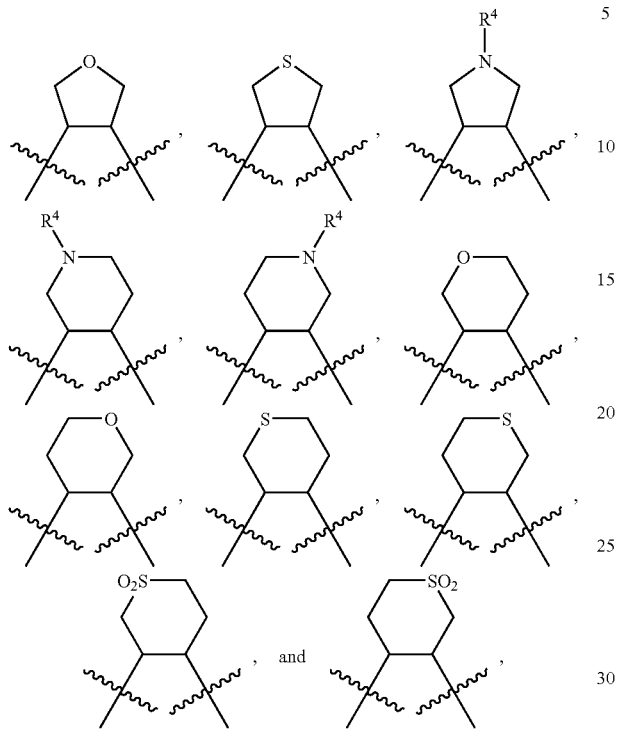

ring B being optionally substituted with 0-1 $R^5$; and $R^{11}$ and $R^{12}$ are H.

4. The compound of claim 3, wherein:
$R^5$, at each occurrence, is independently selected from H, $C_{1-6}$ alkyl, $C_{2-8}$ alkenyl, $C_{2-8}$ alkynyl, $(CRR)_rOH$, $(CRR)_rSH$, $(CRR)_rOR^{5d}$, $(CRR)_rSR^{5d}$, $(CRR)_rNR^{5a}R^{5a}$, $(CRR)_rC(O)OH$, $(CRR)_rC(O)R^{5b}$, $(CRR)_rC(O)NR^{5a}R^{5a}$, $(CRR)_rNR^{5a}C(O)R^{5b}$, $(CRR)_rNR^{5a}C(O)OR^{5d}$, $(CRR)_rOC(O)NR^{5a}R^{5a}$, $(CHR)_rNR^{5a}C(O)NR^{5a}R^{5a}$, $CRR(CRR)_rNR^{5a}C(O)H$, $(CRR)_rC(O)OR^{5b}$, $(CRR)_rOC(O)R^{5b}$, $(CRR)_rS(O)_pR^{5b}$, $(CRR)_rS(O)_2NR^{5a}R^{5a}$, $(CRR)_rNR^{5a}S(O)_2R^{5b}$, and $C_{1-6}$ haloalkyl;

$R^{5a}$, at each occurrence, is independently selected from H, methyl, $C_{2-6}$ alkyl substituted with 0-2 $R^{5e}$ wherein the alkyl is selected from ethyl, propyl, i-propyl, butyl, i-butyl, pentyl, hexyl, $C_3$ alkenyl substituted with 0-1 $R^{5e}$, wherein the alkenyl is selected from allyl, $C_3$ alkynyl substituted with 0-1 $R^{5e}$ wherein the alkynyl is selected from propynyl, and a $(CH_2)_r$—$C_{3-4}$ carbocyclic residue substituted with 0-5 $R^{5e}$, wherein the carbocyclic residue is selected from cyclopropyl, and cyclobutyl;

$R^{5b}$, at each occurrence, is selected from $C_{1-6}$ alkyl substituted with 0-3 $R^{5e}$, wherein the alkyl is selected from methyl, ethyl, propyl, i-propyl, butyl, i-butyl, pentyl, and hexyl, a $(CH_2)_r$—$C_{3-4}$ carbocyclic residue substituted with 0-2 $R^{5e}$, wherein the carbocyclic residue is selected from cyclopropyl, and cyclobutyl; and $R^{5d}$, at each occurrence, is selected from methyl, $CF_3$, $C_{2-6}$ alkyl substituted with 0-2 $R^{5e}$, wherein the alkyl is selected from methyl, ethyl, propyl, i-propyl, butyl, i-butyl, pentyl, and hexyl, $C_{3-8}$ alkenyl, $C_{3-8}$ alkynyl, and a $C_{3-10}$ carbocyclic residue substituted with 0-3 $R^{5e}$.

5. The compound of claim 4, wherein:
$R^4$ is selected from H, $C_{1-6}$ alkyl, $C_{3-8}$ alkenyl, $C_{3-8}$ alkynyl, $(CRR)_tOH$, $(CRR)_tSH$, $(CRR)_tOR^{4d}$, $(CRR)_tSR^{4d}$, $(CRR)_tNR^{4a}R^{4a}$, $(CRR)_qC(O)OH$, $(CRR)_rC(O)R^{4b}$, $(CRR)_rC(O)NR^{4a}R^{4a}$, $(CRR)_tNR^{4a}C(O)R^{4b}$, $(CRR)_tOC(O)NR^{4a}R^{4a}$, $(CRR)_tNR^{4a}C(O)OR^{4d}$, $(CRR)_tNR^{4a}C(O)R^{4b}$, $(CRR)_rC(O)OR^{4b}$, $(CRR)_tOC(O)R^{4b}$, $(CRR)_rS(O)_pR^{4b}$, $(CRR)_rS(O)_2NR^{4a}R^{4a}$, $(CRR)_rNR^{4a}S(O)OR^{4b}$;

R, at each occurrence, is independently selected from H, $C_{1-6}$ alkyl substituted with 0-3 $R^{5e}$, wherein the $C_{1-6}$ alkyl is selected from methyl, ethyl, propyl, allyl, propynyl, $(CH_2)_rC_{3-6}$ cycloalkyl, and $(CH_2)_r$phenyl substituted with $R^{6e}$;

$R^5$, at each occurrence, is independently selected from H, methyl, ethyl, propyl, i-propyl, butyl, i-butyl, allyl, propynyl, $(CH_2)_rOH$, $(CH_2)_rOR^{5d}$, $(CH_2)_rNR^{5a}R^{5a}$, $(CH_2)_rC(O)OH$, $(CH_2)_rC(O)R^{5b}$, $(CH_2)_rC(O)NR^{5a}R^{5a}$, $(CH_2)_rNR^{5a}C(O)R^{5b}$, $(CH_2)_rOC(O)NR^{5a}R^{5a}$, $(CH_2)_rNR^{5a}C(O)OR^{5d}$, $(CH_2)_rNR^{5a}C(O)R^{5b}$, $(CH_2)_rC(O)OR^{5b}$, $(CH_2)_rOC(O)R^{5b}$, $(CH_2)_rNR^{5a}S(O)_2R^{5b}$, and $C_{1-6}$ haloalkyl;

$R^{5a}$, at each occurrence, is independently selected from H, methyl, ethyl, propyl, i-propyl, butyl, i-butyl, pentyl, hexyl, cyclopropyl, cyclopropylmethyl, cyclobutyl, phenyl, and benzyl; and r, at each occurrence, is selected from 0, 1, and 2.

6. The compound of claim 5, wherein:
$R^1$ is selected from phenyl substituted with 0-2 $R^6$, naphthyl substituted with 0-2$R^6$, and a 5-10 membered heteroaryl system containing 1-4 heteroatoms selected from N, O, and S, substituted with 0-3 $R^6$ wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl;

$R^2$ is selected from phenyl substituted with 0-2 $R^7$, and a 5-10 membered heteroaryl system containing 1-4 heteroatoms selected from N, O, and S, substituted with 0-3 $R^7$ wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, phthalazinyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl;

$R^4$ is selected from H, methyl, ethyl, propyl, i-propyl, butyl, i-butyl, allyl, propynyl, $(CRR)_tOH$, $(CRR)_tSH$, $(CRR)_tOR^{4d}$, $(CRR)_tSR^{4d}$, $(CRR)_tNR^{4a}R^{4a}$, $(CRR)_qC(O)OH$, $(CRR)_rC(O)R^{4b}$, $(CRR)_rC(O)NR^{4a}R^{4a}$, $(CRR)_tNR^{4a}C(O)R^{4b}$, $(CRR)_tOC(O)NR^{4a}R^{4a}$, $(CRR)_tNR^{4a}C(O)OR^{4d}$, $(CRR)_tNR^{4a}C(O)R^{4b}$, $(CRR)_rC(O)OR^{4b}$, $(CRR)_tOC(O)R^{4b}$, $(CRR)_rS(O)_pR^{4b}$, $(CRR)_rS(O)_2NR^{4a}R^{4a}$, $(CRR)_rNR^{4a}S(O)_2R^{4b}$;

$R^{4a}$, at each occurrence, is independently selected from H, methyl substituted with 0-1 $R^{4c}$, $C_{2-6}$ alkyl substituted with 0-3 $R^{4e}$ wherein $C_{2-6}$ is selected from ethyl, propyl, i-propyl, butyl, i-butyl, t-butyl, pentyl and hexyl, and a $(CH_2)_r$—$C_{3-6}$ carbocyclic residue substituted with 0-4

R$^{4e}$ wherein the carbocyclic residue is selected from cyclopropyl, cyclohexyl, and phenyl;

R$^{4b}$ is selected from H, methyl, ethyl, propyl, i-propyl, butyl, i-butyl, t-butyl, pentyl, and cyclopropyl;

R$^{4d}$ is selected from methyl, ethyl, propyl, i-propyl, butyl, i-butyl, t-butyl, pentyl, and cyclopropyl; and R$^8$ is selected from H, methyl, ethyl, propyl, i-propyl, and cyclopropyl.

7. The compound of claim 6, wherein:

R$^6$, at each occurrence, is selected from C$_{1-8}$ alkyl, C$_{2-8}$ alkenyl, C$_{2-8}$ alkynyl, (CR'R')$_r$C$_{3-6}$ cycloalkyl, Cl, Br, I, F, NO$_2$, CN, (CR'R')$_r$NR$^{6a}$R$^{6a}$, (CR'R')$_r$OH, (CR'R')$_r$O (CR'R')$_r$R$^{6d}$, (CR'R')$_r$SH, (CRR)$_r$C(O)H, (CR'R')$_r$S (CR'R')$_r$R$^{6d}$, (CR'R')$_r$C(O)OH, (CR'R')$_r$C(O)(CR'R')$_r$R$^{6b}$, (CR'R')$_r$C(O)NR$^{6a}$R$^{6a}$, (CR'R')$_r$NR$^{6f}$C(O) (CR'R')$_r$R$^{6b}$, (CR'R')$_r$C(O)O(CR'R')$_r$R$^{6d}$, (CR'R')$_r$NR$^{6a}$C(O)NR$^{6a}$R$^{6a}$, (CR'R')$_r$NR$^{6a}$C(S)NR$^{6a}$R$^{6a}$, (CR'R')$_r$OC(O)(CR'R')$_r$R$^{6b}$, (CR'R')$_r$S(O)$_p$(CR'R')$_r$R$^{6b}$, (CR'R')$_r$S(O)$_2$NR$^{6a}$R$^{6a}$, (CR'R')$_r$NR$^{6f}$S(O)$_2$(CR'R')$_r$R$^{6b}$, (CR'R')$_r$NR$^{6f}$S(O)$_2$NR$^{6a}$R$^{6a}$, C$_{1-6}$ haloalkyl, and (CR'R')$_r$phenyl substituted with 0-3 R$^{6e}$;

R$^{6a}$, at each occurrence, is independently selected from H, methyl, ethyl, propyl, i-propyl, butyl, i-butyl, t-butyl, pentyl, hexyl, cyclopropyl and phenyl;

R$^{6b}$, at each occurrence, is selected from methyl, ethyl, propyl, i-propyl, butyl, i-butyl, t-butyl, pentyl, hexyl, cyclopropyl, and phenyl;

R$^{6d}$, at each occurrence, is selected from methyl, CF$_3$, ethyl, propyl, i-propyl, butyl, i-butyl, t-butyl, pentyl, hexyl, cyclopropyl, and phenyl;

R$^{6e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{6f}$R$^{6f}$, and (CH$_2$)$_r$phenyl;

R$^{6f}$, at each occurrence, is selected from H, methyl, ethyl, propyl, i-propyl, butyl, i-butyl, t-butyl, pentyl, hexyl, cyclopropyl, and phenyl;

R$^7$ is selected from methyl, ethyl, propyl, i-propyl, butyl, i-butyl, s-butyl, t-butyl, pentyl, hexyl, (CR'R')$_r$C$_{3-6}$ cycloalkyl, Cl, Br, I, F, NO$_2$, CN, (CR'R')$_r$NR$^{7a}$R$^{7a}$, (CR'R')$_r$OH, (CR'R')$_r$O(CH)$_r$R$^{7d}$, (CR'R')$_r$SH, (CR'R')$_r$C(O)H, (CR'R')$_r$S(CR'R')$_r$R$^{7d}$, (CR'R')$_r$C(O)OH, (CR'R')$_r$C(O)(CR'R')$_r$R$^{7b}$, (CR'R')$_r$C(O)NR$^{7a}$R$^{7a}$, (CR'R')$_r$NR$^{7f}$C(O)(CR'R')$_r$R$^{7b}$, (CR'R')$_r$C(O)O (CR'R')$_r$R$^{7d}$, (CR'R')$_r$OC(O)(CR'R')$_r$R$^{7b}$, (CR'R')$_r$NR$^{7a}$C(O)NR$^{7a}$R$^{7a}$, (CR'R')$_r$NR$^{7a}$C(O)O(CR'R')$_r$R$^{7d}$, (CR'R')$_r$S(O)$_p$(CR'R')$_r$R$^{7b}$, (CR'R')$_r$S(O)$_2$NR$^{7a}$R$^{7a}$, (CR'R')$_r$NR$^{7f}$S(O)$_2$(CR'R')$_r$R$^{7b}$, C$_{1-6}$ haloalkyl, and (CR'R')$_r$phenyl substituted with 0-3 R$^{7e}$;

R$^{7a}$, at each occurrence, is selected from H, methyl, ethyl, propyl, i-propyl, butyl, i-butyl, t-butyl, pentyl, hexyl, prop-2-enyl, 2-methyl-2-propenyl, cyclopropyl, cyclobutyl, cyclopentyl, cyclohexyl, CH$_2$cyclopropyl, and benzyl;

R$^{7b}$, at each occurrence, is selected from methyl, ethyl, propyl, i-propyl, butyl, i-butyl, t-butyl, pentyl, hexyl, cyclopropyl, cyclopentyl, CH$_2$-cyclopentyl, cyclohexyl, CH$_2$-cyclohexyl, CF$_3$, pyrrolidinyl, morpholinyl, piperizenyl substituted with 0-1 R$^{7e}$, and azetidinyl;

R$^{7d}$, at each occurrence, is selected from methyl, CF$_3$, ethyl, propyl, i-propyl, butyl, i-butyl, t-butyl, pentyl, hexyl, and cyclopropyl;

R$^{7e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, C(O) OC$_{1-5}$ alkyl, (CH$_2$)$_r$SC$_{1-5}$ alkyl, (CH$_2$)$_r$NR$^{7f}$R$^{7f}$, and (CH$_2$)$_r$phenyl;

R$^{7f}$, at each occurrence, is selected from H, methyl, ethyl, propyl, i-propyl, butyl, i-butyl, t-butyl, pentyl, hexyl, cyclopropyl, and phenyl; and r is 0 or 1.

8. The compound of claim 7, wherein

R$^7$ is selected from methyl, ethyl, propyl, i-propyl, butyl, i-butyl, s-butyl, pentyl, hexyl, Cl, Br, I, F, NO$_2$, NR$^{7a}$R$^{7a}$, NHC(O)NHR$^{7a}$, NR$^{7a}$C(O)R$^{7b}$, NR$^{7a}$C(O) OR$^{7d}$, CF$_3$, OCF$_3$, C(O)R$^{7b}$, C(O)OR$^{7d}$, NR$^{7f}$C(O) NR$^{7a}$R$^{7a}$, NHS(O)$_2$R$^{7b}$,

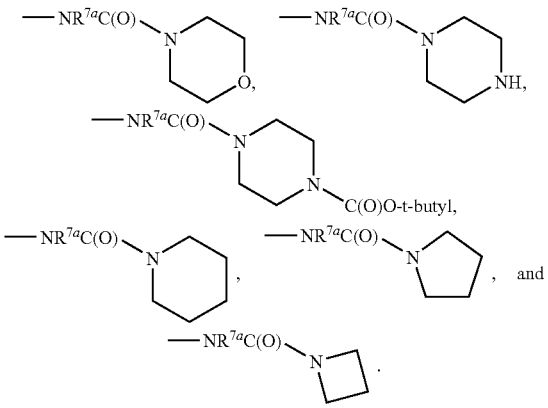

9. The compound of claim 8, wherein
ring B is selected from

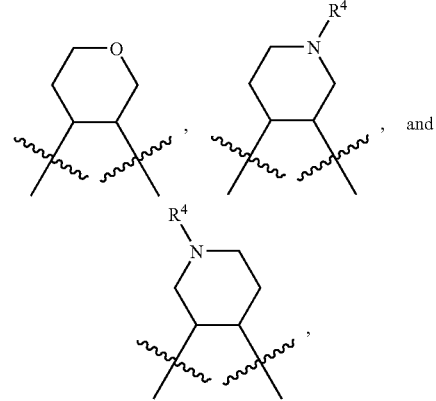

ring B being optionally substituted with 0-1 R$^5$;

Z is —C(O)—;

R$^1$ is selected from a C$_{6-10}$ aryl group substituted with 0-3 R$^6$ wherein the aryl group is selected from phenyl and naphthyl, and a 5-10 membered heteroaryl system containing 1-4 heteroatoms selected from N and O, substituted with 0-3 R$^6$ wherein the heteroaryl system is selected from indolyl and pyridinyl;

R$^2$ is phenyl substituted with 0-2 R$^7$;

R$^4$ is selected from H, methyl, ethyl, propyl, i-propyl, butyl, i-butyl, t-butyl, pentyl, hexyl, and (CH$_2$)$_r$C(O) R$^{4b}$;

R$^6$ is selected from methyl, ethyl, propyl, i-propyl, butyl, F, Cl, Br, I, NO$_2$, CN, O(CH$_2$)$_r$R$^{6d}$, C(O)H, SR$^{6d}$, NR$^{6a}$R$^{6a}$, NC(O)R$^{6b}$, OC(O)R$^{6b}$, S(O)$_p$R$^{6b}$, (CHR')$_r$S (O)$_2$NR$^{6a}$R$^{6a}$, CF$_3$;

R$^{6a}$ is H, methyl, or ethyl;

$R^{6b}$ is H, or methyl;
$R^{6d}$ is methyl, phenyl, $CF_3$, and $(CH_2)$-phenyl; and
r is 0 or 1.

10. The compound of claim 9, wherein:
ring B is selected from

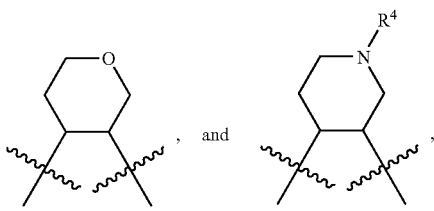

ring B is selected from ring B being substituted with 0-1 $R^5$;

$R^1$ is selected from a $C_{6-10}$ aryl group substituted with 0-3 $R^6$ wherein the aryl group is selected from phenyl, and a 5-10 membered heteroaryl system containing 1-4 heteroatoms selected from N and O, substituted with 0-3 $R^6$ wherein the heteroaryl system is selected from pyridinyl and indolyl;

$R^4$ is selected from H, methyl, ethyl, propyl, i-propyl, butyl, i-butyl, t-butyl, pentyl, hexyl, allyl and $(CH_2)_rC(O)R^{4b}$;

$R^5$ is selected from H, OH, $OCH_3$, and $NR^{5a}R^{5a}$;

$R^{5a}$ is selected from H, methyl, ethyl, propyl, i-propyl, butyl, s-butyl, i-butyl, t-butyl, pentyl, hexyl, allyl cyclopropyl, cyclopropylmethyl, acetyl, methysulfonyl, —C(O)CF$_3$, C(=N)NH$_2$, benzyl, and —C(O)O-t-butyl;

$R^6$ is selected from methyl, ethyl, propyl, i-propyl, butyl, vinyl, F, Cl, Br, I, C(O)H, $SR^{6d}$, $S(O)_pR^{6d}$, $CF_3$, and $CH_2OH$;

$R^{6d}$ is methyl;

$R^7$ is selected from methyl, ethyl, propyl, i-propyl, butyl, i-butyl, s-butyl, pentyl, hexyl, Cl, Br, I, F, $NO_2$, $NR^{7a}R^{7a}$, $NHC(O)NHR^{7a}$, $NR^{7a}C(O)R^{7b}$, $NR^{7a}C(O)OR^{7d}$, $CF_3$, $OCF_3$, $C(O)OR^{7d}$, $C(O)R^{7b}$, $NR^{7f}C(O)NR^{7a}R^{7a}$, $NHS(O)_2R^{7b}$,

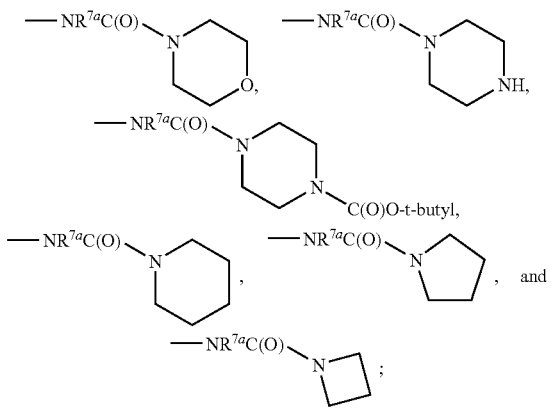

$R^{7a}$ is selected from H, methyl, ethyl, propyl, i-propyl, butyl, i-butyl, t-butyl, pentyl, neo-pentyl, cyclopropyl, cyclobutyl, cyclopentyl, and cyclohexyl;

$R^{7b}$ is selected from cyclohexyl and $CF_3$; and $R^{7d}$ is selected from methyl, ethyl, propyl, i-propyl, butyl, i-butyl, and t-butyl.

11. The compound of claim 10, wherein
E is $-S(O)_p(CHR^{15})-$.

12. The compound of claim 10, wherein
E is —NHC(O)NH—.

13. The compound of claim 7, wherein
Z is a bond; and
$R^2$ is a 5-10 membered heteroaryl system containing 1-4 heteroatoms selected from N, O, and S, substituted with 0-3 $R^7$ wherein the heteroaryl is selected from indolyl, naphthalenyl, phthalazinyl, cinnolinyl, quinolinyl, isoquinolinyl, indazolyl, and quinazolinyl, benzimidazolyl, benzofuranyl, benzothiofuranyl, benzoxazolyl, benzthiazolyl, benzisoxazolyl, and benzisothiazolyl.

14. The compound of claim 1, wherein:
$R^5$, at each occurrence, is independently selected from H, $C_{1-6}$ alkyl, $N_3$, $C_{2-8}$ alkenyl, $C_{2-8}$ alkynyl, $(CRR)_rOH$, $(CRR)_rSH$, $(CRR)_rOR^{5d}$, $(CRR)_rSR^{5d}$, $(CRR)_rNR^{5a}R^{5a}$, $(CRR)_rC(O)OH$, $(CRR)_rC(O)R^{5b}$, $(CRR)_rC(O)NR^{5a}R^{5a}$, $(CRR)_rNR^{5a}C(O)R^{5b}$, $(CRR)_rNR^{5a}C(O)OR^{5d}$, $(CRR)_rOC(O)NR^{5a}R^{5a}$, $(CHR)_rNR^{5a}C(O)NR^{5a}R^{5a}$, $CRR(CRR)_rNR^{5a}C(O)H$, $(CRR)_rC(O)OR^{5b}$, $(CRR)_rOC(O)R^{5b}$, $(CRR)_rS(O)_pR^{5b}$, $(CRR)_rS(O)_2NR^{5a}R^{5a}$, $(CRR)_rNR^{5a}S(O)_2R^{5b}$, $(CRR)_rNR^{5a}C(=N)NR^{5a}R^{5a}$, and $C_{1-6}$ haloalkyl, and a $(CH_2)_r$-5-10 membered heterocyclic system containing 1-4 heteroatoms selected from N, O, and S, substituted with 0-2 $R^{5c}$, wherein the heterocyclic system is selected from piperidinyl;

$R^{5a}$, at each occurrence, is independently selected from H, methyl, $C_{2-6}$ alkyl substituted with 0-2 $R^{5e}$ wherein the alkyl is selected from ethyl, propyl, i-propyl, butyl, i-butyl, pentyl, hexyl, $C_3$ alkenyl substituted with 0-1 $R^{5e}$, wherein the alkenyl is selected from allyl, $C_3$ alkynyl substituted with 0-1 $R^{5e}$ wherein the alkynyl is selected from propynyl, and a $(CH_2)_r-C_{3-4}$ carbocyclic residue substituted with 0-5 $R^{5e}$, wherein the carbocyclic residue is selected from cyclopropyl, cyclobutyl, cyclopentyl, cyclohexyl, and phenyl;

$R^{5b}$, at each occurrence, is selected from $C_{1-6}$ alkyl substituted with 0-3 $R^{5e}$, wherein the alkyl is selected from methyl, ethyl, propyl, i-propyl, butyl, i-butyl, pentyl, and hexyl, a $(CH_2)_r-C_{3-4}$ carbocyclic residue substituted with 0-2 $R^{5e}$, wherein the carbocyclic residue is selected from cyclopropyl, and cyclobutyl; and $R^{5d}$, at each occurrence, is selected from methyl, $CF_3$, $C_{2-6}$ alkyl substituted with 0-2 $R^{5e}$, wherein the alkyl is selected from methyl, ethyl, propyl, i-propyl, butyl, i-butyl, pentyl, and hexyl, $C_{3-8}$ alkenyl, $C_{3-8}$ alkynyl, and a $C_{3-10}$ carbocyclic residue substituted with 0-3 $R^{5e}$.

15. The compound of claim 14, wherein:
$R^4$ is selected from H, $C_{1-6}$ alkyl, $C_{3-8}$ alkenyl, $C_{3-8}$ alkynyl, $(CRR)_tOH$, $(CRR)_tSH$, $(CRR)_tOR^{4d}$, $(CRR)_tSR^{4d}$, $(CRR)_tNR^{4a}R^{4a}$, $(CRR)_qC(O)OH$, $(CRR)_tC(O)R^{4b}$, $(CRR)_tC(O)NR^{4a}R^{4a}$, $(CRR)_tNR^{4a}C(O)R^{4b}$, $(CRR)_tOC(O)NR^{4a}R^{4a}$, $(CRR)_tNR^{4a}C(O)OR^{4d}$, $(CRR)_tNR^{4a}C(O)R^{4b}$, $(CRR)_tC(O)OR^{4b}$, $(CRR)_tOC(O)R^{4b}$, $(CRR)_rS(O)_pR^{4b}$, $(CRR)_rS(O)_2NR^{4a}R^{4a}$, $(CRR)_rNR^{4a}S(O)_2R^{4b}$;

R, at each occurrence, is independently selected from H, $C_{1-6}$ alkyl substituted with 0-3 $R^{5e}$, wherein the $C_{1-6}$ alkyl is selected from methyl, ethyl, propyl, allyl, propynyl, $(CH_2)_rC_{3-6}$ cycloalkyl, and $(CH_2)_r$phenyl substituted with $R^{5e}$;

$R^5$, at each occurrence, is independently selected from H, methyl, ethyl, propyl, i-propyl, butyl, i-butyl, allyl, propynyl, $N_3$, $(CH_2)_rOH$, $(CH_2)_rOR^{5d}$, $(CH_2)_rNR^{5a}R^{5a}$, $(CH_2)_rC(O)OH$, $(CH_2)_rC(O)R^{5b}$, $(CH_2)_rC(O)NR^{5a}R^{5a}$, (CH$_2$)$_r$NR$^{5a}$C(O)R$^{5b}$, (CH$_2$)$_r$OC(O)NR$^{5a}$R$^{5a}$, (CH$_2$)$_r$NR$^{5a}$C(O)OR$^{5d}$, (CH$_2$)$_r$NR$^{5a}$C(O)R$^{5b}$, (CH$_2$)$_r$C(O)OR$^{5b}$, (CH$_2$)$_r$OC(O)R$^{5b}$, (CH$_2$)$_r$NR$^{5a}$S(O)$_2$R$^{5b}$, (CH$_2$)$_r$NR$^{5a}$C(=N)NR$^{5a}$R$^{5a}$, and C$_{1-6}$ haloalkyl, and a (CH$_2$)$_r$-5-10 membered heterocyclic system containing 1-4 heteroatoms selected from N, O, and S, substituted with 0-2 R$^{5c}$, wherein the heterocyclic system is selected from piperidinyl;

R$^{5a}$, at each occurrence, is independently selected from H, methyl, ethyl, propyl, i-propyl, butyl, i-butyl, pentyl, hexyl, cyclopropyl, and cyclobutyl; and r, at each occurrence, is selected from 0, 1, and 2.

16. The compound of claim 15, wherein:

R$^6$, at each occurrence, is selected from C$_{1-8}$ alkyl, C$_{2-8}$ alkenyl, C$_{2-8}$ alkynyl, (CHR')$_r$C$_{3-6}$ cycloalkyl, Cl, Br, I, F, NO$_2$, CN, (CHR')$_r$NR$^{6a}$R$^{6a}$, (CHR')$_r$OH, (CHR')$_r$OR$^{6d}$, (CHR')$_r$SH, (CHR')$_r$C(O)H, (CHR')$_r$SR$^{6d}$, (CHR')$_r$C(O)OH, (CHR')$_r$C(O)R$^{6b}$, (CHR')$_r$C(O)NR$^{6a}$R$^{6a}$, (CHR')$_r$NR$^{6f}$C(O)R$^{6b}$, (CHR')$_r$C(O)OR$^{6d}$, (CHR')$_r$NR$^{6a}$C(O)NR$^{6a}$R$_{6a}$, (CHR')$_r$NR$^{6a}$C(S)NR$^{6a}$R$^{6a}$, (CHR')$_r$OC(O)R$^{6b}$, (CHR')$_r$S(O)$_p$R$^{6b}$, (CHR')$_r$S(O)$_2$NR$^{6a}$R$^{6a}$, (CHR')$_r$NR$^{6f}$S(O)$_2$R$^{6b}$, (CHR')$_r$NR$^{6f}$S(O)$_2$NR$^{6a}$R$^{6a}$, C$_{1-6}$ haloalkyl, and (CHR')$_r$phenyl substituted with 0-3 R$^{6e}$;

R$^{6a}$, at each occurrence, is independently selected from H, methyl, ethyl, propyl, i-propyl, butyl, i-butyl, t-butyl, pentyl, hexyl, cyclopropyl and phenyl;

R$^{6b}$, at each occurrence, is selected from methyl, ethyl, propyl, i-propyl, butyl, i-butyl, t-butyl, pentyl, hexyl, —(CH$_2$)$_r$-cyclopropyl, and —(CH$_2$)$_r$phenyl;

R$^{6d}$, at each occurrence, is selected from methyl, CF$_3$, ethyl, propyl, i-propyl, butyl, i-butyl, t-butyl, pentyl, hexyl, —(CH$_2$)$_r$-cyclopropyl, and —(CH$_2$)$_r$-phenyl;

R$^{6e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{6f}$R$^{6f}$, and (CH$_2$)$_r$phenyl;

R$^{6f}$, at each occurrence, is selected from H, methyl, ethyl, propyl, i-propyl, butyl, i-butyl, t-butyl, pentyl, hexyl, cyclopropyl, and phenyl;

R$^7$ is selected from methyl, ethyl, propyl, i-propyl, butyl, i-butyl, s-butyl, t-butyl, pentyl, hexyl, (CRR)$_r$C$_{3-6}$ cycloalkyl, Cl, Br, I, F, NO$_2$, CN, (CHR')$_r$NR$^{7a}$R$^{7a}$, (CHR')$_r$OH, (CHR')$_r$O(CH)$_r$R$^{7d}$, (CHR')$_r$SH, (CHR')$_r$C(O)H, (CHR')$_r$SR$^{7d}$, (CHR')$_r$C(O)OH, (CHR')$_r$C(O)R$^{7b}$, (CHR')$_r$C(O)NR$^{7a}$R$^{7a}$, (CHR)$_r$NR$^{7f}$C(O)R$^{7b}$, (CHR')$_r$C(O)O(CRR)$_r$R$^{7d}$, (CHR')$_r$OC(O)R$^{7b}$, (CHR')$_r$NR$^{7a}$C(O)NR$^{7a}$R$^{7a}$, (CHR')$_r$NR$^{7a}$C(O)OR$^{7d}$, (CHR)$_r$S(O)$_p$(CRR)$_r$R$^{7b}$, (CHR')$_r$S(O)$_2$NR$^{7a}$R$^{7a}$, (CHR')$_r$NR$^{7f}$S(O)$_2$(CRR)$_r$R$^{7b}$, C$_{1-6}$ haloalkyl, and (CHR')$_r$phenyl substituted with 0-3 R$^{7e}$;

R$^{7a}$, at each occurrence, is selected from H, methyl, ethyl, propyl, i-propyl, butyl, i-butyl, t-butyl, pentyl, hexyl, prop-2-enyl, 2-methyl-2-propenyl, cyclopropyl, cyclobutyl, cyclopentyl, cyclohexyl, CH$_2$cyclopropyl, phenyl, and benzyl;

R$^{7b}$, at each occurrence, is selected from methyl, ethyl, propyl, i-propyl, butyl, i-butyl, t-butyl, pentyl, hexyl, cyclopropyl, cyclopentyl, CH$_2$-cyclopentyl, cyclohexyl, CH$_2$-cyclohexyl, CF$_3$, pyrrolidinyl, morpholinyl, piperizenyl substituted with 0-1 R$^{7e}$, and azetidinyl;

R$^{7d}$, at each occurrence, is selected from methyl, CF$_3$, ethyl, propyl, i-propyl, butyl, i-butyl, t-butyl, pentyl, hexyl, and cyclopropyl;

R$^{7e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, C(O) OC$_{1-5}$ alkyl, (CH$_2$)$_r$SC$_{1-5}$ alkyl, (CH$_2$)$_r$NR$^{7f}$R$^{7f}$, and (CH$_2$)$_r$phenyl;

R$^{7f}$, at each occurrence, is selected from H, methyl, ethyl, propyl, i-propyl, butyl, i-butyl, t-butyl, pentyl, hexyl, cyclopropyl, and phenyl; and r is 0 or 1.

17. The compound of claim 16, wherein
ring B is selected from

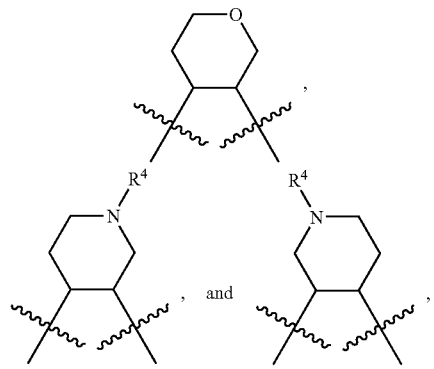

ring B being optionally substituted with 0-1 R$^5$;

Z is —C(O)—;

R$^1$ is selected from a C$_{6-10}$ aryl group substituted with 0-3 R$^6$ wherein the aryl group is selected from phenyl and naphthyl, and a 5-10 membered heteroaryl system containing 1-4 heteroatoms selected from N and O, substituted with 0-3 R$^6$ wherein the heteroaryl system is selected from benzothiazolyl, indolyl and pyridinyl;

R$^2$ is selected from phenyl substituted with 0-2 R$^7$;

R$^4$ is selected from H, methyl, ethyl, propyl, i-propyl, butyl, i-butyl, t-butyl, pentyl, hexyl, allyl, OH, C(O)OR$^{4d}$, and (CH$_2$)$_r$C(O)R$^{4b}$;

R$^6$ is selected from methyl, ethyl, propyl, i-propyl, butyl, vinyl, F, Cl, Br, I, NO$_2$, CN, O(CH$_2$)$_r$R$^{6d}$, C(O)H, (CH$_2$)OH, —CHOH—CH$_2$OH SR$^{6d}$, C(O)R$^{6b}$, NR$^{6a}$R$^{6a}$, NC(O)R$^{6b}$, OC(O)R$^{6b}$, S(O)$_p$R$^{6b}$, (CHR')$_r$S(O)$_2$NR$^{6a}$R$^{6a}$, CF$_3$;

R$^{6a}$ is H, methyl, or ethyl;

R$^{6b}$ is H, or methyl;

R$^{6d}$ is methyl, phenyl, CF$_3$, and (CH$_2$)-phenyl; and r is 0 or 1.

18. The compound of claim 17, wherein:
ring B is selected from

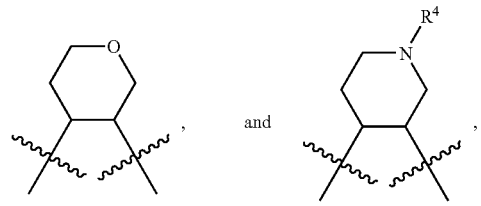

ring B being substituted with 0-1 R$^5$;

R$^1$ is selected from a C$_{6-10}$ aryl group substituted with 0-3 R$^6$ wherein the aryl group is selected from phenyl, and a 5-10 membered heteroaryl system containing 1-4 heteroatoms selected from N and O, substituted with 0-3 $R^6$ wherein the heteroaryl system is selected from benzothiazolyl;

$R^4$ is selected from H, methyl, ethyl, propyl, i-propyl, butyl, i-butyl, t-butyl, pentyl, hexyl, allyl and $(CH_2)_rC(O)R^{4b}$;

$R^5$ is selected from H, OH, $OCH_3$, $N_3$, $NHC(=NH)NH_2$, $NR^{5a}R^{5a}$, and piperidinyl;

$R^{5a}$ is selected from H, methyl, ethyl, propyl, i-propyl, butyl, s-butyl, i-butyl, t-butyl, pentyl, hexyl, allyl, propargyl, cyclopropyl, cyclopropylmethyl, acetyl, methysulfonyl, —$C(O)CF_3$, $C(=N)NH_2$, benzyl, and —$C(O)O$-t-butyl;

$R^7$ is selected from methyl, ethyl, propyl, i-propyl, butyl, i-butyl, s-butyl, pentyl, hexyl, Cl, Br, I, F, $NO_2$, $NR^{7a}R^{7a}$, $NHC(O)NHR^{7a}$, $NR^{7a}C(O)R^{7b}$, $NR^{7a}C(O)OR^{7d}$, $CF_3$, $OCF_3$, $C(O)OR^{7d}$, $C(O)R^{7b}$, $NR^{7f}C(O)NR^{7a}R^{7a}$, $NHS(O)_2R^{7b}$,

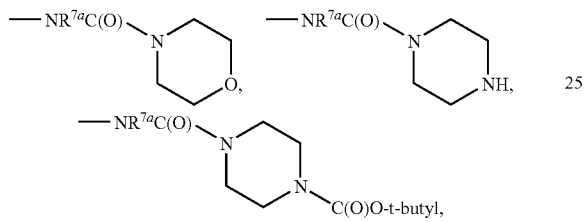

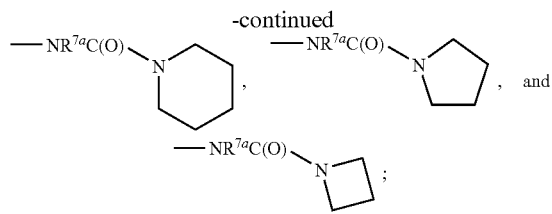

$R^{7a}$ is selected from H, methyl, ethyl, propyl, i-propyl, butyl, i-butyl, t-butyl, pentyl, neo-pentyl, cyclopropyl, cyclobutyl, cyclopentyl, and cyclohexyl;

$R^{7b}$ is selected from methyl, ethyl, propyl, i-propyl, butyl, cyclohexyl and $CF_3$;

$R^{7d}$ is selected from methyl, ethyl, propyl, i-propyl, butyl, i-butyl, and t-butyl; and $R^{14}$ is selected from H and methyl.

19. The compound of claim 16, wherein
Z is a bond; and
$R^2$ is a 5-10 membered heteroaryl system containing 1-4 heteroatoms selected from N, O, and S, substituted with 0-3 $R^7$ wherein the heteroaryl is selected from indolyl, naphthalenyl, phthalazinyl, cinnolinyl, quinolinyl, isoquinolinyl, indazolyl, and quinazolinyl, benzimidazolyl, benzofuranyl, benzothiofuranyl, benzoxazolyl, benzthiazolyl, benzisoxazolyl, and benzisothiazolyl.

20. The compound of claim 19, wherein,
$R^2$ is indazolyl.

* * * * *

UNITED STATES PATENT AND TRADEMARK OFFICE
CERTIFICATE OF CORRECTION

PATENT NO. : 7,776,884 B2
APPLICATION NO. : 11/351415
DATED : August 17, 2010
INVENTOR(S) : Robert J. Cherney It is certified that error appears in the above-identified patent and that said Letters Patent is hereby corrected as shown below:

On the Title Page:

Item (54), change "RECEPTORS" to "RECEPTOR".

Item (57), ABSTRACT:

Column 2 (structure), change

"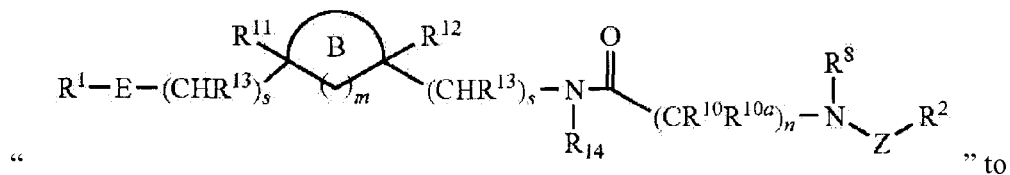 to

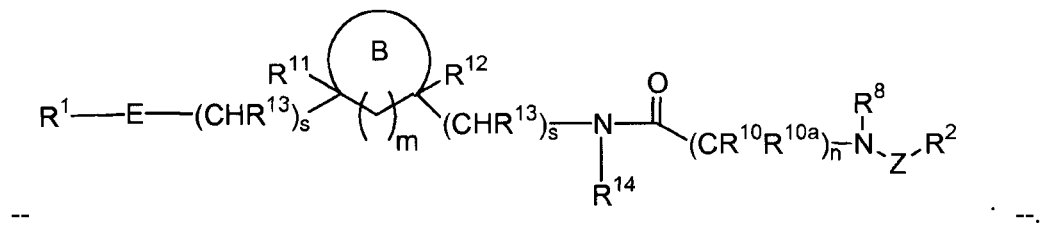 --.

In the Specification:

Column 1, line 2, change "RECEPTORS" to "RECEPTOR".

Column 1, lines 5 and 6, after "7,087,604," delete "now allowed,".

Signed and Sealed this
Twenty-ninth Day of November, 2011

David J. Kappos
*Director of the United States Patent and Trademark Office*

CERTIFICATE OF CORRECTION (continued)
U.S. Pat. No. 7,776,884 B2

In the Claims:

Claim 1:

Column 119, lines 20 to 23, change

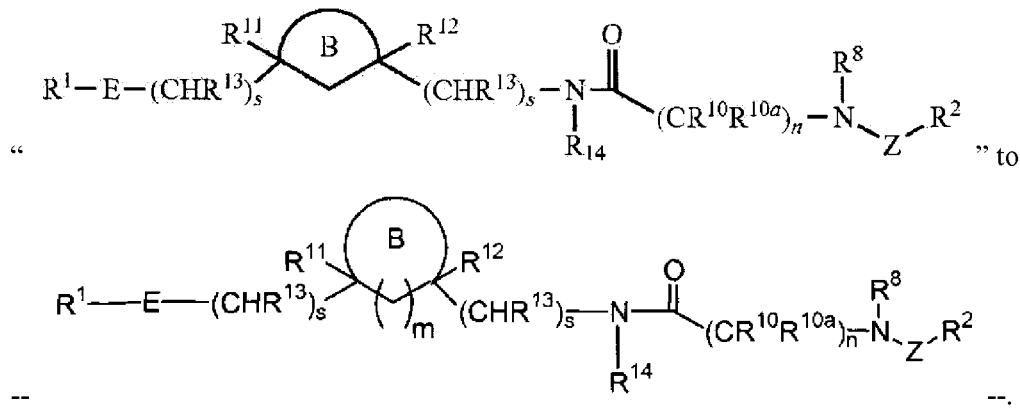

" to

-- --.

Column 122, line 2, change "(CR'R)" to -- (CR'R') --.

Column 123, line 57, after "$(CH_2)_rNR^{12f}R^{12f}$", insert -- , --.

Claim 5:

Column 126, line 9, change "$S(O)OR^{4b}$" to -- $S(O)_2R^{4b}$ --.

Claim 10:

Column 129, line 17, before "ring B being", delete "ring B is selected from".

Claim 14:

Column 130, line 17, change "$(CRR)^rSR^{5d}$" to -- $(CRR)_rSR^{5d}$ --.

Claim 15:

Column 130, line 63, change "$R^{5e}$" to -- $R^{6e}$ --.

Claim 16:

Column 131, line 20, change "$R_{6a}$" to -- $R^{6a}$ --.

Column 131, line 30, change "-$(CH_2)_r$phenyl" to -- -$(CH_2)_r$-phenyl --.

Column 131, line 47, change "(CHR)" to -- (CHR') --.

Column 131, line 49, change "(CHR)" to -- (CHR') --.